US012734176B2

(12) United States Patent
Shapiro et al.

(10) Patent No.: US 12,734,176 B2

(45) **Date of Patent: *Sep. 15, 2026**

(54) NON-CATALYTIC SUBSTRATE-SELECTIVE p38α-SPECIFIC MAPK INHIBITORS WITH ENDOTHELIAL-STABILIZING AND ANTI-INFLAMMATORY ACTIVITY, AND METHODS OF USE THEREOF

(71) Applicants: University of Maryland, Baltimore, Baltimore, MD (US); The United States of America as represented by the Department of Veterans Affairs, Washington, DC (US)

(72) Inventors: Paul S. Shapiro, Baltimore, MD (US); Alexander D. Mackerell, Jr., Baltimore, MD (US); Jeffrey D. Hasday, Timonium, MD (US)

(73) Assignees: University of Maryland, Baltimore, Baltimore, MD (US); The United States of America as represented by the Department of Veterans Affairs, Washington, DC (US)

(*) Notice: Subject to any disclaimer, the term of this patent is extended or adjusted under 35 U.S.C. 154(b) by 78 days.

This patent is subject to a terminal disclaimer.

(21) Appl. No.: 18/416,532

(22) Filed: Jan. 18, 2024

(65) Prior Publication Data

US 2024/0366619 A1 Nov. 7, 2024

Related U.S. Application Data

(63) Continuation of application No. 18/169,785, filed on Feb. 15, 2023, now Pat. No. 11,911,393, which is a continuation of application No. 17/740,248, filed on May 9, 2022, now Pat. No. 11,911,392, which is a continuation of application No. 17/231,598, filed on Apr. 15, 2021, now Pat. No. 11,357,781, which is a continuation of application No. 16/312,499, filed as application No. PCT/US2017/038697 on Jun. 22, 2017, now abandoned.

(60) Provisional application No. 62/469,913, filed on Mar. 10, 2017, provisional application No. 62/353,856, filed on Jun. 23, 2016.

(51) Int. Cl.

| | |
|---|---|
| ***A61K 31/5375*** | (2006.01) |
| ***A61K 31/18*** | (2006.01) |
| ***A61K 31/54*** | (2006.01) |
| ***A61P 19/02*** | (2006.01) |
| ***A61P 29/00*** | (2006.01) |
| ***A61P 31/00*** | (2006.01) |
| ***A61P 35/00*** | (2006.01) |

(52) U.S. Cl.

CPC .......... *A61K 31/5375* (2013.01); *A61K 31/18* (2013.01); *A61K 31/54* (2013.01); *A61P 19/02* (2018.01); *A61P 29/00* (2018.01); *A61P 31/00* (2018.01); *A61P 35/00* (2018.01)

(58) Field of Classification Search

CPC .................................................. A61K 31/5375

USPC ...................................................... 514/227.5

See application file for complete search history.

(56) References Cited

U.S. PATENT DOCUMENTS

| | | | | |
|---|---|---|---|---|
| 3,594,386 | A | 7/1971 | Regnier et al. | |
| 6,462,074 | B1 | 10/2002 | Stolle et al. | |
| 8,173,684 | B2 | 5/2012 | Kasahara et al. | |
| 10,632,114 | B2 | 4/2020 | Su | |
| 11,078,171 | B2 | 8/2021 | Shapiro et al. | |
| 11,286,260 | B2 | 3/2022 | Galan et al. | |
| 11,357,781 | B2 * | 6/2022 | Shapiro | A61P 31/00 |
| 11,440,918 | B2 | 9/2022 | Galan et al. | |
| 11,555,020 | B2 | 1/2023 | Galan et al. | |
| 11,911,392 | B2 * | 2/2024 | Shapiro | C07D 413/12 |
| 11,911,393 | B2 * | 2/2024 | Shapiro | C07D 263/32 |
| 2005/0256133 | A1 | 11/2005 | Lesur et al. | |
| 2007/0066616 | A1 | 3/2007 | Shapiro et al. | |
| 2007/0208015 | A1 | 9/2007 | Gill et al. | |
| 2010/0215618 | A1 | 8/2010 | Carter et al. | |
| 2012/0172375 | A1 | 7/2012 | Trapp et al. | |
| 2015/0357549 | A1 | 12/2015 | Muller et al. | |
| 2019/0151324 | A1 | 5/2019 | Shapiro et al. | |

FOREIGN PATENT DOCUMENTS

| | | | |
|---|---|---|---|
| CN | 101675034 | A | 3/2010 |
| CN | 105308004 | A | 2/2016 |
| CN | 109640970 | A | 4/2019 |
| DE | 19801646 | A1 | 7/1999 |
| EP | 3474835 | A1 | 5/2019 |
| GB | 2530598 | A | 3/2016 |
| JP | H11269146 | A | 10/1999 |
| JP | 2007/532615 | A | 11/2007 |
| JP | 2010/180234 | A | 8/2010 |
| JP | 2011/513288 | A | 4/2011 |
| JP | 7013453 | B | 1/2022 |
| WO | 2004/065351 | A1 | 8/2004 |

(Continued)

OTHER PUBLICATIONS

Biava et al. Medicinal Chemistry Research (1998),8(9),523-541. (Year: 1998).*

PubChem CID 899207, 4-chloro-N-[4-(piperidin-1-ylmethyl)phenyl]benzamide, created on Jul. 9, 2005, 1 page.

CAS STN Registry No. 2093620-87-0, N-[4-[(4-acetyl-1-piperazinyl)methyl]phenyl]-1-isoquinolinecarboxamide, searched on Apr. 8, 2025, entered on Apr. 28, 2017, p. 1 of 6.

CAS STN Registry No. 1389887-62-0, N-[4-[(4-ethyl-1-piperazinyl)methyl]phenyl]-4-quinolinecarboxamide, searched on Apr. 8, 2025, entered on Aug. 12, 2012, p. 1 of 6.

(Continued)

*Primary Examiner* — Kahsay Habte

(74) *Attorney, Agent, or Firm* — Sheppard Mullin Richter & Hampton LLP

(57) ABSTRACT

Compounds that inhibit p38α MAPK protein, and methods of using the same, are provided for treating or preventing diseases such as cancer or inflammatory diseases.

14 Claims, 8 Drawing Sheets

(56) References Cited

FOREIGN PATENT DOCUMENTS

| | | | |
|---|---|---|---|
| WO | 2004/072077 | A1 | 8/2004 |
| WO | 2005/100338 | A1 | 10/2005 |
| WO | 2008/140066 | A2 | 11/2008 |
| WO | 2009/106844 | A1 | 9/2009 |
| WO | 2010/082912 | A1 | 7/2010 |
| WO | 2010/094977 | A1 | 8/2010 |
| WO | 2015/121660 | A1 | 8/2015 |
| WO | 2016/051155 | A1 | 4/2016 |
| WO | 2016/073633 | A1 | 5/2016 |
| WO | 2017/223284 | A1 | 12/2017 |
| WO | 2018/085348 | A1 | 5/2018 |
| WO | 2018/119362 | A1 | 6/2018 |
| WO | 2020/118194 | A1 | 6/2020 |
| WO | 2021/183970 | A1 | 9/2021 |

OTHER PUBLICATIONS

CAS STN Registry No. 1389054-27-6, N-[4-[(4-methyl-1-piperidinyl)methyl]phenyl]-r-quinolinecaroxamide, searched on Apr. 8, 2025, entered on Aug. 12, 2012, p. 2 of 6.
CAS STN Registry No. 1388423-94-6, N-[4-[(4-methyl-1-piperidinyl)methyl]phenyl]-r-quinolinecaroxamide, searched on Apr. 8, 2025, entered on Aug. 9, 2012, p. 2 of 6.
CAS STN Registry No. 1295218-34-6, N-[4-[(4-methyyl-1-piperazinyul)methyl]phenyl]-2-quinolinecarboxamine, searched on Apr. 8, 2025, entered on May 15, 2011, p. 3 of 6.
CAS STN Registry No. 1280095-96-6, N-[4-[(4-ethyl-1-piperazinyl)methyl]phenyl]-5-quinolinecarboxamide, searched on Apr. 8, 2025, entered on Apr. 14, 2011, p. 3 of 6.
CAS STN Registry No. 1172737-06-2, N-[4-[[4-(2-furanylmethyl)-1-piperazinyl]methyl]phenyl]-8-quinolinesulfonamide, searched on Apr. 8, 2025, entered on Aug. 5, 2009, p. 4 of 6.
CAS STN Registry No. 117217-70-1, N-[4-[(4-methyl-1-piperazinyl)methyl]phenyl]-8-quinolinesulfonamide, searched on Apr. 8, 2025, entered on Jul. 31, 2009, p. 4 of 6.
CAS STN Registry No. 1111318-92-3, N-[4-[(4-methyl-1-piperidinyl)methyl]phenyl]-1-(1-piperidinyl)-4-isoquinolinecatoxamide, searched on Apr. 8, 2025, entered on Feb. 24, 2009, p. 5 of 6.
CAS STN Registry No. 1016156-06-1, 4-(1-piperidinylmethyl)-N-5-quinolinylbenzamide, searched on Apr. 8, 2025, entered on Apr. 21, 2008, p. 5 of 6.
CAS STN Registry No. 930048-56-9, 4-(4-morpholinylmethyl)-N-8-quinolinylbenzamide, searched on Apr. 8, 2025, entered on Apr. 13, 2007, p. 6 of 6.
CAS STN Registry No. 902700-86-1, N-[4-(1-piperidinylmethyl)phenyl]-8-quinolinesulfonamide, searched on Apr. 8, 2025, entered on Aug. 18, 2006, p. 6 of 6.
Biava et al., Antimycobacterial activity of new ortho-, meta- and para-toluidine derivatives, II Farmaco, 1999, vol. 54, pp. 721-727.
Biava et al., Synthesis and antimycobacterial activity of new amido derivatives of ortho-, meta- and para-toluidine, Medicinal Chemistry Research, 1998, 8(9), pp. 523-541.
Caira, Crystalline polymorphism of organic compounds, Topics in Current Chemistry, Jan. 1998, vol. 198, pp. 163-208.
Chemical Abstract STN Registry Database Record for RN 221058-13-5.
Chemical Abstract STN Registry Database Record for RN 1293859-67-2, benzamide, 4-chloro-N-[4-[(2,6-dimethyl-4-morphlinyl)sulfonyl]phenyl]- [online] Entered into STN Registry Database May 12, 2011, 1 page.
Chemical Abstract STN Registry Database Record for RN 1587574-74-0, 1-piperazineacetamide, N-[4-[(4-chlorobenzoyl)amino]phenyl]-2-oxo-hydrochloride [online] Entered into STN Registry Database Apr. 21, 2014, 1 page.
Chemical Abstract STN Registry Database Record for RN 2331174-12-8, benzaminde, N-[4-[[[2-(4-acetyl-1-piperazinyl)-2-oxoethyl]amino]carbonyl]phenyl]4-chloro- [online] Entered into STN Registry Database Jun. 12, 2019, 1 page.
Chemical Abstract STN Registry Database record for RN 2337349-33-2, 1-piperazinecarboxylic acid, 4-[2-[4-[(4-chlorobenzoyl)amino]phenyl]ethyl]-1,1-dimethylethyl ester [online] Entered into STN Registry Database Jun. 17, 2019, 1 page.
Chemical Abstract STN Registry Database Record for RN 2338713-47-4, benzaminde, N-[4-[(4-acetyl-1-piperazinyl)carbonyl]phenyl]-4-chloro- [online] Entered into STN Registry Database Jun. 18, 2019, 1 page.
Chemical Abstract STN Registry Database Record for RN 2347052-15-5, benzamide, N-[4-[2-(4-acetyl-1-piperazinyl)-2-oxoethyl]phenyl]-4-chloro- [online] Entered into STN Registry Database Jun. 27, 2019, 1 page.
Chemical Abstract STN Registry Database Record for RN 255713-96-3, [online] Entered into STN Registry Database Feb. 10, 2000, accessed on Jul. 19, 2021, 2 pages.
Chemical Abstract STN Registry Database Record for RN 697229-25-7, 4-chloro-N-{4-(1, 1-dioxido-4-thiomorpholinyl)methyl]phenyl]-benzamide [online] Entered into STN Registry Database Jun. 22, 2004, accessed on Jul. 19, 2021, 2 pages.
Chemical Abstract STN Registry Database Record for RN 851167-79-8, N-[4-[2-(4-acetyl-1-piperazinyl)-2-oxoethoxy]phenyl]-4-chlorobenzamide [online] Entered into STN Registry Database May 26, 2005, 1 page.
Chemical Abstract STN Registry Database Record for RN 1327798-32-2, 4-chloro-N-[4-[(3-methyl-4-morpholinyl) carbonyl]phenyl]benzamide, [online] Entered into STN Registry Database on Sep. 4, 2011, 1 page.
Cheng et al., Identification and optimization of new dual inhibitors of B-Raf and epidermal growth factor receptor kinases for overcoming resistance against vemurafenib, Journal of Medicinal Chemistry, 2014, vol. 57, pp. 2692-2703.
Haller et al., An updated patent review of p38 MAP kinase inhibitors (2014-2019), Expert Opinion on Therapeutics Patents, 2020, vol. 30, No. 6, pp. 453-466.
Kheiri et al., Role pf p38/MAPKs in Alzheimer's disease: implications for amyloid beta toxicity targeted therapy, Reviews in Neuroscience, 2018, vol. 30, No. 1, pp. 9-30.
Koroleva et al., Synthesis of new amides of the N-methylpiperazine series, Russian Journal of Organic Chemistry, Nauka/Interperiodica, Nov. 2011, vol. 47, No. 10, pp. 1556-1563.
Lee et al., Docketing-based 3D-QSAR study for 11β-HSD1 inhibitors, Bioorganic & Medicinal Chemistry Letters, 2008, vol. 18, pp. 2479-2490.
Mavropoulos et al., p38 mitogen-activated protein kinase (p38 MAPK)-mediated autoimmunity: Lessons to learn from ANCA vasculitis and pemphigus vulgaris, Autoimmunity Reviews, Mar. 2013, vol. 12, Issue 5, pp. 580-590.
Nagao et al., Synthesis and structure-activity relationships of novel, potent, orally active hypoxia-inducible factor-1 inhibitors, Bioorganic & Medicinal Chemistry, Jul. 2014, vol. 22, No. 19, pp. 5513-5529.
Pubchem Substance Database CID 899207, entered on Jul. 9, 2005, accessed Feb. 5, 2005, 7 pages.
Pubchem Substance Database SID 105140242, entered on Feb. 22, 2011, accessed on Aug. 8, 2017, accessed from https://pubchem.ncbi.nlm.nih.gov/substance/105140242, 6 pages.
Sasindran et al., *Mycobacterium tuberculosis* infection and inflammation: what is beneficial for the host and for the bacterium?, Frontiers in Microbiology, Jan. 2011, vol. 2, No. 2, 33 pages.
Segales et al., Regulation of muscle stem cell functions: A focus on the p38 MAPK signaling pathway, Frontiers in Cell and Developmental Biology, Aug. 2016, vol. 4, Article 91, 15 pages.
Shah et al., Novel noncatalytic substrate-selective p38[alpha]-specific MAPK Inhibitors with endothelial-Stabilizing and anti-Inflammatory activity, The Journal of Immunology, Mar. 2017, vol. 198, No. 8, pp. 3296-3306.
Wang et al., Chapter 2—A Structural atlas of kinases inhibited by clinically approved drugs, Methods of Enzymology, 2014, vol. 548, pp. 23-67.
Yong et al., The p38 MAPK inhibitors for the treatment of inflammatory diseases and cancer, Expert Opinion on Investigational Drugs, Oct. 2009, ISSN 1354-3784, vol. 18, No. 12, pp. 1893-1905.
Extended European Search Report for EP 17816192, Mar. 20, 2020, 5 pages.

(56) References Cited

OTHER PUBLICATIONS

International Search Report and Written Opinion for PCT International Application No. PCT/US2021/032487, dated Nov. 25, 2021, 16 pages.
International Preliminary Report on Patentability for PCT International Application No. PCT/US2021/032487 dated Dec. 1, 2022, 10 pages.
International Search Report and Written Opinion for PCT International Application No. PCT/US/2019/064960 dated Jun. 11, 2020, 7 pages.
International Preliminary Report on Patentability for PCT International Application No. PCT/US2019/064960 dated Jun. 17, 2021, 5 pages.
International Search Report and Written Opinion for PCT International Application No. PCT/US2017/038697 dated Dec. 28, 2017, 9 pages.
International Preliminary Report on Patentability for PCT International Application PCT/US2017/038697 dated Jan. 3, 2019, 8 pages.
International Search Report and Written Opinion for PCT International Application No. PCT/US2022/021181, dated Sep. 29, 2022, 11 pages.
International Preliminary Report on Patentability for PCT International Application PCT/US2022/021181 dated Sep. 12, 2023, 8 pages.
International Search Report and Written Opinion for PCT International Application No. PCT/US2021/055950, dated Jun. 28, 2022, 15 pages.
International Preliminary Report on Patentability for PCT International Application PCT/US2021/055950 dated May 11, 2023, 7 pages.
Non-final Office Action for U.S. Appl. No. 16/312,499 mailed on Feb. 13, 2020, 7 pages.
Final Office Action for U.S. Appl. No. 16/312,499 mailed on May 21, 2020, 10 pages.
Non-final Office Action for U.S. Appl. No. 16/312,499 mailed on Sep. 8, 2020, 8 pages.
Final Office Action for U.S. Appl. No. 16/312,499 mailed on Dec. 16, 2020, 7 pages.
Non-Final Office Action for U.S. Appl. No. 16/872,114 mailed on Dec. 7, 2020, 7 pages.
Notice of Allowance for U.S. Appl. No. 16/872,114 mailed on Mar. 17, 2021, 7 pages.
Non-Final Office Action for U.S. Appl. No. 17/231,598 mailed on Jun. 29, 2021, 6 pages.
Non-Final office Action for U.S. Appl. No. 17/231,598 mailed on Oct. 7, 2021, 6 pages.
Notice of Allowance for U.S. Appl. No. 17/231,598 mailed on Feb. 11, 2022, 5 pages.
Non-Final Office Action for U.S. Appl. No. 17/320,874 mailed on Aug. 11, 2021, 31 pages.
Notice of Allowance for U.S. Appl. No. 17/320,874 mailed on Jan. 15, 2022, 7 pages.
Non-Final Office Action for U.S. Appl. No. 17/349,468 mailed on Jan. 10, 2023, 8 pages.
Notice of Allowance for U.S. Appl. No. 17/349,468 mailed on Mar. 13, 2023, 5 pages.
Non-Final Office Action for U.S. Appl. No. 17/667,898 mailed on Apr. 14, 2022, 16 pages.
Notice of Allowance for U.S. Appl. No. 17/667,898 mailed on May 18, 2022, 12 pages.
Non-Final Office Action for U.S. Appl. No. 17/700,168 mailed on Jun. 30, 2022, 7 pages.
Final Office Action for U.S. Appl. No. 17/700,168 mailed on Jul. 28, 2022, 7 pages.
Non-Final Office Action for U.S. Appl. No. 17/700,168 mailed on Oct. 14, 2022, 7 pages.
Notice of Allowance for U.S. Appl. No. 17/700,168 mailed on Nov. 4, 2022, 9 pages.
Non-Final Office Action for U.S. Appl. No. 18/169,785 mailed on Jul. 18, 2023, 6 pages.
Notice of Allowance for U.S. Appl. No. 18/169,785 mailed on Nov. 1, 2023, 5 pages.
Non-Final Office Action for U.S. Appl. No. 17/740,248 mailed on Sep. 6, 2023, 6 pages.
Notice of Allowance for U.S. Appl. No. 17/740,248 mailed on Nov. 3, 2023, 5 pages.
Non-Final Office Action for U.S. Appl. No. 18/061,610 mailed on Oct. 4, 2023, 10 pages.
Non-Final Office Action for U.S. Appl. No. 17/813,382 mailed on Sep. 14, 2023, 17 pages.

* cited by examiner

Compound 2

Compound 3

Compound 4

Compound 5

Compound 8

Compound 13 Compound 16

Compound 23

Compound 29

Compound 31

Compound 43 Compound 55

Compound 60

Compound 63

Compound 69

Compound 101

Compound 115 Compound 141

Compound 146

Compound 150

NON-CATALYTIC SUBSTRATE-SELECTIVE p38α-SPECIFIC MAPK INHIBITORS WITH ENDOTHELIAL-STABILIZING AND ANTI-INFLAMMATORY ACTIVITY, AND METHODS OF USE THEREOF

CROSS-REFERENCE TO RELATED APPLICATIONS

This application is a continuation of U.S. application Ser. No. 18/169,785 filed on Feb. 15, 2023, issued as U.S. Pat. No. 11,911,393; which is a continuation of U.S. application Ser. No. 17/740,248 filed on May 9, 2022, issued as U.S. Pat. No. 11,911,392; which is a continuation of U.S. application Ser. No. 17/231,598 filed on Apr. 15, 2021, issued as U.S. Pat. No. 11,357,781, which is a continuation of U.S. application Ser. No. 16/312,499 filed on Dec. 21, 2018, which is a national phase filing under 35 U.S.C. § 371 of PCT International Application No. PCT/US2017/038697 filed on Jun. 22, 2017, which claims the benefit under 35 U.S.C. § 119(e) of U.S. Provisional Application No. 62/353,856, filed Jun. 23, 2016, and U.S. Provisional Application No. 62/469,913, filed Mar. 10, 2017. The contents of each of these applications are incorporated herein by reference in their entirety.

STATEMENT REGARDING FEDERALLY SPONSORED RESEARCH

This invention was made with government support under Grant Nos. CA120215 and HL069057 awarded by the National Institutes of Health. The government has certain rights in the invention.

FIELD OF THE INVENTION

The invention relates generally to compounds that are inhibitors of p38 Mitogen-Activated Protein Kinases (MAPKs) proteins, and more particularly, but not exclusively, to compounds that inhibit p38α MAPK protein by binding to a pocket near the ED substrate-docking site of p38α MAPK, and methods of using such compounds as treatments for disease.

BACKGROUND OF THE INVENTION p38 Mitogen-Activated Protein Kinases (MAPKs), contribute to pathogenesis of many diseases, but the currently available p38 catalytic inhibitors (e.g., SB203580) are poorly effective and cause toxicity possibly due to activity against non-inflammatory p38 isoforms (e.g., p38β) and loss of p38α-dependent counterregulatory responses (e.g., MSK1/2). Accordingly, new therapeutics and methods of treatment are needed in the field both to address selective inhibition of p38α MAPK and to selectively block certain p38α MAPK functions to preserve critical counterregulatory and homeostatic functions with application for the treatment of inflammatory and oncologic diseases.

SUMMARY OF THE INVENTION

In one embodiment, the invention relates to a pharmaceutical composition including a therapeutically effective amount of a p38α MAPK inhibitor for the treatment or prevention of a disease alleviated by inhibiting certain p38α MAPK activities in a patient in need thereof, or a pharmaceutically acceptable salt, solvate, hydrate, cocrystal, or prodrug thereof, and a physiologically compatible carrier medium, wherein the p38α MAPK inhibitor is a compound capable of binding to a pocket near the ED substrate-docking site of p38α MAPK. In one embodiment, the binding pocket is defined at least by residues R49, H107, L108, and K165 in p38α MAPK. In one embodiment, the binding pocket is defined by residues R49, H107, L108, M109, G110, A157, V158, E163, L164, and K165 in p38α MAPK.

In some embodiments, the p38α MAPK inhibitor is a compound of Formula 1 or Formula 2, or a pharmaceutically acceptable salt, solvate, hydrate, cocrystal, or prodrug thereof:

Formula 1

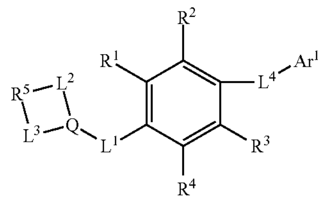

Formula 2

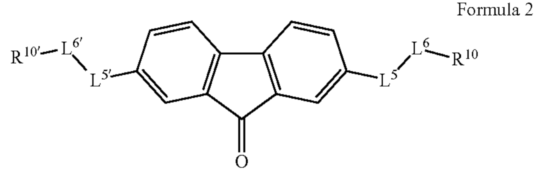

wherein in Formula 1 and Formula 2, Q is —CH— or N; each of $R^1$, $R^2$, $R^3$, and $R^4$ is independently hydrogen or optionally substituted alkyl, alkoxy, aryl, or heteroaryl; $R^5$ is —$SO_2$—, —CH(OH)—, —O—, or —$N(CH_3)$—; each of $R^{10}$ and $R^{10'}$ is independently —OH, —$NH_2$, or —SH; $L^1$ is —$CH_2$—, —$C(CH_3)_2$— or —$C(CH_2CH_2)$—; each of $L^2$ and $L^3$ is independently —$CH_2$—, —$CH_2CH_2$—, or —$CH_2CH_2CH_2$—; each of $L^4$, $L^5$, and $L^{5'}$ is independently —NHCO—, —CONH—, —$SO_2NH$—, —$NHSO_2$—, or —CH═CH—; each of $L^6$ and $L^{6'}$ is independently an optionally substituted $C_1$-$C_6$ alkyl chain; and $Ar^1$ is an optionally substituted aryl or heteroaryl ring. In some embodiments, $Ar^1$ is a six member ring.

In some embodiments, the p38α MAPK inhibitor is a compound of Formula 11, Formula 12, Formula 13, or Formula 14, or a pharmaceutically acceptable salt, solvate, hydrate, cocrystal, or prodrug thereof:

Formula 11

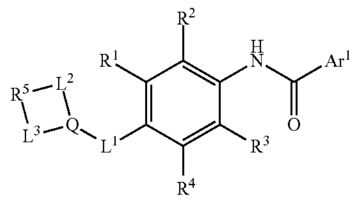

Formula 12

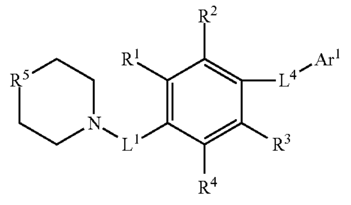

-continued

Formula 13

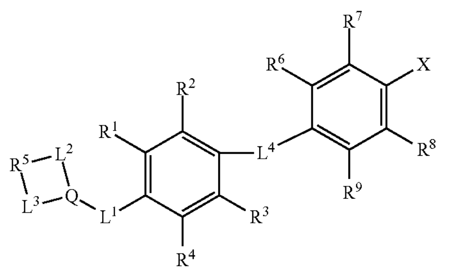

Formula 14

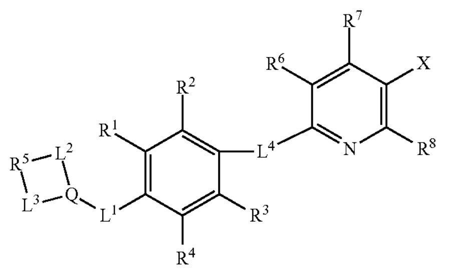

wherein in Formula 11, Formula 12, Formula 13, and Formula 14, Q is —CH— or N; each of $R^1$, $R^2$, $R^3$, $R^4$, $R^6$, $R^7$, $R^8$, and $R^9$ is independently hydrogen or optionally substituted alkyl, alkoxy, aryl, or heteroaryl; $R^5$ is $—SO_2—$, —CH(OH)—, —O—, or $—N(CH_3)—$; $L^1$ is $—CH_2—$, $—C(CH_3)_2$, or $—C(CH_2CH_2)—$; each of $L^2$ and $L^3$ is independently $—CH_2—$, $—CH_2CH_2—$, or $—CH_2CH_2CH_2—$; $L^4$ is —NHCO—, —CONH—, $—SO_2NH—$, $—NHSO_2—$, or —CH═CH—; $Ar^1$ is an optionally substituted aryl or heteroaryl ring; and X is a halogen. In some embodiments, $Ar^1$ is a six member ring.

In some embodiments, the p38α MAPK inhibitor is a compound of any one of Formulas 1001 to 1256 as defined in Table 1, or a pharmaceutically acceptable salt, solvate, hydrate, cocrystal, or prodrug thereof:

Formulas 1001 to 1256

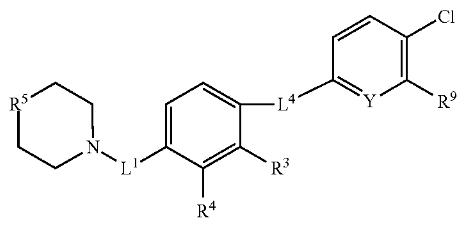

In some embodiments, the p38α MAPK inhibitor is a compound of Formula UM101, or a compound of Formula UM60:

Formula UM101

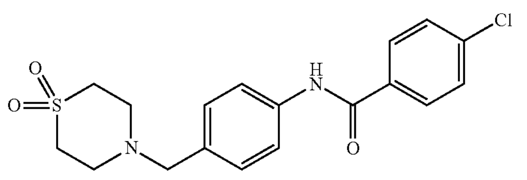

-continued

Formula UM60

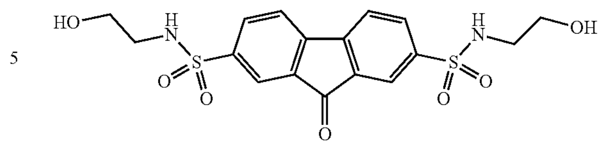

In one embodiment, the p38α MAPK inhibitor is a p38α MAPK selective inhibitor. In some embodiments, the disease is cancer or an inflammatory disease. In other embodiments, the disease is rheumatoid arthritis, a cardiovascular disease, multiple sclerosis, inflammatory bowel disease, chronic obstructive pulmonary disease (COPD), asthma, acute respiratory distress syndrome (ARDS), or acute lung injury (ALI). In some embodiments, the cancer can be acoustic neuroma, adenocarcinoma, angiosarcoma, astrocytoma, basal cell carcinoma, bile duct carcinoma, bladder carcinoma, brain cancer, breast cancer, bronchogenic carcinoma, cervical cancer, chordoma, choriocarcinoma, colon cancer, colorectal cancer, craniopharyngioma, cystadenocarcinoma, embryonal carcinoma, endotheliocarcinoma, ependymoma, epithelial carcinoma, esophageal cancer, Ewing's tumor, fibrosarcoma, gastric cancer, glioblastoma multiforme, glioma, head and neck cancer, hemangioblastoma, hepatoma, kidney cancer, leiomyosarcoma, liposarcoma, lung cancer, lymphangioendotheliosarcoma, lymphangiosarcoma, medullary carcinoma, medulloblastoma, melanoma, meningioma, mesothelioma, myxosarcoma, nasal cancer, neuroblastoma, oligodendroglioma, oral cancer, osteogenic sarcoma, ovarian cancer, pancreatic cancer, papillary adenocarcinoma, papillary carcinoma, pinealoma, prostate cancer, rabdomyosarcoma, rectal cancer, renal cell carcinoma, retinoblastoma, sarcoma, sebaceous gland carcinoma, seminoma, skin cancer, squamous cell carcinoma, stomach cancer, sweat gland carcinoma, synovioma, testicular cancer, small cell lung carcinoma, throat cancer, uterine cancer, Wilm's tumor, blood cancer, acute erythroleukemic leukemia, acute lymphoblastic B-cell leukemia, acute lymphoblastic T-cell leukemia, acute lymphoblastic leukemia, acute megakaryoblastic leukemia, acute monoblastic leukemia, acute myeloblastic leukemia, acute myelomonocytic leukemia, acute nonlymphocytic leukemia, acute promyelocytic leukemia, acute undifferentiated leukemia, chronic lymphocytic leukemia, chronic myelocytic leukemia, hairy cell leukemia, multiple myeloma, heavy chain disease, Hodgkin's disease, multiple myeloma, non-Hodgkin's lymphoma, polycythemia vera, or Waldenstrom's macroglobulinemia.

In one embodiment, the invention relates to a method of inhibiting p38α MAPK, the method including contacting the p38α MAPK with a compound capable of binding to a pocket near the ED substrate-docking site of p38α MAPK, or a pharmaceutically acceptable salt, solvate, hydrate, cocrystal, or prodrug thereof. In one embodiment, the binding pocket is defined at least by residues R49, H107, L108, and K165 in p38α MAPK. In one embodiment, the binding pocket is defined by residues R49, H107, L108, M109, G110, A157, V158, E163, L164, and K165 of p38α MAPK. In some embodiments, the compound is of Formula 1 or Formula 2, or a pharmaceutically acceptable salt, solvate, hydrate, cocrystal, or prodrug thereof, wherein in Formula 1 and Formula 2, Q is —CH— or N; each of $R^1$, $R^2$, $R^3$, and $R^4$ is independently hydrogen or optionally substituted alkyl, alkoxy, aryl, or heteroaryl; $R^5$ is $—SO_2—$, —CH(OH)—, —O—, or —N($CH_3$)—; each of $R^{10}$ and $R^{1'}$ is independently —OH, —$NH_2$, or —SH; $L^1$ is —$CH_2$—, —C($CH_3$)$_2$, or —C($CH_2CH_2$)—; each of $L^2$ and $L^3$ is independently —$CH_2$—, —$CH_2CH_2$—, or —$CH_2CH_2CH_2$—; each of $L^4$, $L^5$, and $L^{5'}$ is independently —NHCO—, —CONH—, —$SO_2$NH—, —NH$SO_2$—, or —CH═CH—; each of $L^6$ and $L^{6'}$ is independently an optionally substituted $C_1$-$C_6$ alkyl chain; and $Ar^1$ is an optionally substituted aryl or heteroaryl ring. In some embodiments, $Ar^1$ is a six member ring.

In other embodiments, the compound is of Formula 11, Formula 12, Formula 13, or Formula 14, or a pharmaceutically acceptable salt, solvate, hydrate, cocrystal, or prodrug thereof, wherein in Formula 11, Formula 12, Formula 13, and Formula 14, Q is —CH— or N; each of $R^1$, $R^2$, $R^3$, $R^4$, $R^6$, $R^7$, $R^8$, and $R^9$ is independently hydrogen or optionally substituted alkyl, alkoxy, aryl, or heteroaryl; $R^5$ is —$SO_2$—, —CH(OH)—, —O—, or —N($CH_3$)—; $L^1$ is —$CH_2$—, —C($CH_3$)$_2$, or —C($CH_2CH_2$)—; each of $L^2$ and $L^3$ is independently —$CH_2$—, —$CH_2CH_2$—, or —$CH_2CH_2CH_2$—; $L^4$ is —NHCO—, —CONH—, —$SO_2$NH—, —NH$SO_2$—, or —CH═CH—; $Ar^1$ is an optionally substituted aryl or heteroaryl ring; and X is a halogen. In some embodiments, $Ar^1$ is a six member ring. In some embodiments, the compound is of Formulas 1001 to 1256, or a pharmaceutically acceptable salt, solvate, hydrate, cocrystal, or prodrug thereof. In one embodiment, the compound is of Formula UM101, or a pharmaceutically acceptable salt, solvate, hydrate, cocrystal, or prodrug thereof. In another embodiment, the compound is of Formula UM60, or a pharmaceutically acceptable salt, solvate, hydrate, cocrystal, or prodrug thereof.

In one embodiment, the compound selectively inhibits p38α MAPK. In some embodiments, inhibition of p38α MAPK does not result in loss of a p38α-dependent counterregulatory response. In one embodiment, the p38α-dependent counterregulatory response relates to mitogen- and stress-activated protein kinase-1 (MSK1), or MSK2. In some embodiments, inhibiting p38α MAPK stabilizes an endothelial or epithelial barrier function. In other embodiments, inhibiting p38α MAPK reduces inflammation. In some embodiments, inhibiting p38α MAPK mitigates LPS-induced lung injury. In other embodiments, inhibiting p38α MAPK regulates leukocyte trafficking. In one embodiment, inhibiting p38α MAPK regulates cytokine expression.

In one embodiment, the invention relates to a method of treating or preventing a disease alleviated by inhibiting the p38α MAPK protein in a patient in need thereof, the method including administering to the patient a therapeutically effective amount of a p38α MAPK inhibitor, wherein the p38α MAPK inhibitor is a compound capable of binding to a pocket near the ED substrate-docking site of p38α MAPK, or a pharmaceutically acceptable salt, solvate, hydrate, cocrystal, or prodrug thereof. In one embodiment, the binding pocket is defined at least by residues R49, H107, L108, and K165 in p38α MAPK. In one embodiment, the binding pocket is defined by residues R49, H107, L108, M109, G110, A157, V158, E163, L164, and K165 in p38α MAPK. In some embodiments, the p38α MAPK inhibitor is a compound of Formula 1 or Formula 2, or a pharmaceutically acceptable salt, solvate, hydrate, cocrystal, or prodrug thereof, wherein in Formula 1 and Formula 2, Q is —CH— or N; each of $R^1$, $R^2$, $R^3$, and $R^4$ is independently hydrogen or optionally substituted alkyl, alkoxy, aryl, or heteroaryl; $R^5$ is —$SO_2$—, —CH(OH)—, —O—, or —N($CH_3$)—; each of $R^{10}$ and $R^{10'}$ is independently —OH, —$NH_2$, or —SH; $L^1$ is —$CH_2$—, —C($CH_3$)$_2$— or —C($CH_2CH_2$)—; each of $L^2$ and $L^3$ is independently —$CH_2$—, —$CH_2CH_2$—, or —$CH_2CH_2CH_2$—; each of $L^4$, $L^5$, and $L^{5'}$ is independently —NHCO—, —CONH—, —$SO_2$NH—, —NH$SO_2$—, or —CH═CH—; each of $L^6$ and $L^{6'}$ is independently an optionally substituted $C_1$-$C_6$ alkyl chain; and $Ar^1$ is an optionally substituted aryl or heteroaryl ring. In one embodiment, $Ar^1$ is a six member ring.

In some embodiments, the p38α MAPK inhibitor is a compound of Formula 11, Formula 12, Formula 13, or Formula 14, or a pharmaceutically acceptable salt, solvate, hydrate, cocrystal, or prodrug thereof, wherein in Formula 11, Formula 12, Formula 13, and Formula 14, Q is —CH— or N; each of $R^1$, $R^2$, $R^3$, $R^4$, $R^6$, $R^7$, $R^8$, and $R^9$ is independently hydrogen or optionally substituted alkyl, alkoxy, aryl, or heteroaryl; $R^5$ is —$SO_2$—, —CH(OH)—, —O—, or —N($CH_3$)—; $L^1$ is —$CH_2$—, —C($CH_3$)$_2$, or —C($CH_2CH_2$)—; each of $L^2$ and $L^3$ is independently —$CH_2$—, —$CH_2CH_2$—, or —$CH_2CH_2CH_2$—; $L^4$ is —NHCO—, —CONH—, —$SO_2$NH—, —NH$SO_2$—, or —CH═CH—; $Ar^1$ is an optionally substituted aryl or heteroaryl ring; and X is a halogen. In one embodiment, $Ar^1$ is a six member ring.

In other embodiments, the p38α MAPK inhibitor is a compound of Formulas 1001 to 1256, or a pharmaceutically acceptable salt, solvate, hydrate, cocrystal, or prodrug thereof. In one embodiment, the p38α MAPK inhibitor is a compound of Formula UM101, or a pharmaceutically acceptable salt, solvate, hydrate, cocrystal, or prodrug thereof. In another embodiment, the p38α MAPK inhibitor is a compound of Formula UM60, or a pharmaceutically acceptable salt, solvate, hydrate, cocrystal, or prodrug thereof. In one embodiment, the p38α MAPK inhibitor is a p38α MAPK selective inhibitor. In some embodiments, the p38α MAPK inhibitor is administered in a dosage unit form. In one embodiment, the dosage unit comprises a physiologically compatible carrier medium. In some embodiments, the disease is cancer or an inflammatory disease. In other embodiments, the disease is selected from the group consisting of rheumatoid arthritis, a cardiovascular disease, multiple sclerosis, inflammatory bowel disease, chronic obstructive pulmonary disease (COPD), asthma, acute respiratory distress syndrome (ARDS), and acute lung injury (ALI). In one embodiment, the cancer is selected from the group consisting of acoustic neuroma, adenocarcinoma, angiosarcoma, astrocytoma, basal cell carcinoma, bile duct carcinoma, bladder carcinoma, brain cancer, breast cancer, bronchogenic carcinoma, cervical cancer, chordoma, choriocarcinoma, colon cancer, colorectal cancer, craniopharyngioma, cystadenocarcinoma, embryonal carcinoma, endotheliocarcinoma, ependymoma, epithelial carcinoma, esophageal cancer, Ewing's tumor, fibrosarcoma, gastric cancer, glioblastoma multiforme, glioma, head and neck cancer, hemangioblastoma, hepatoma, kidney cancer, leiomyosarcoma, liposarcoma, lung cancer, lymphangioendotheliosarcoma, lymphangiosarcoma, medullary carcinoma, medulloblastoma, melanoma, meningioma, mesothelioma, myxosarcoma, nasal cancer, neuroblastoma, oligodendroglioma, oral cancer, osteogenic sarcoma, ovarian cancer, pancreatic cancer, papillary adenocarcinoma, papillary carcinoma, pinealoma, prostate cancer, rabdomyosarcoma, rectal cancer, renal cell carcinoma, retinoblastoma, sarcoma, sebaceous gland carcinoma, seminoma, skin cancer, squamous cell carcinoma, stomach cancer, sweat gland carcinoma, synovioma, testicular cancer, small cell lung carcinoma, throat cancer, uterine cancer, Wilm's tumor, blood cancer, acute erythroleukemic leukemia, acute lymphoblastic B-cell leukemia, acute lymphoblastic T-cell leukemia, acute lymphoblastic leukemia, acute megakaryoblastic leukemia, acute monoblastic leukemia, acute myeloblastic leukemia, acute myelomonocytic leukemia, acute nonlymphocytic leukemia, acute promyelocytic leukemia, acute undifferentiated leukemia, chronic lymphocytic leukemia, chronic myelocytic leukemia, hairy cell leukemia, multiple myeloma, heavy chain disease, Hodgkin's disease, multiple myeloma, non-Hodgkin's lymphoma, polycythemia vera, and Waldenstrom's macroglobulinemia.

BRIEF DESCRIPTION OF THE DRAWINGS

The foregoing summary, as well as the following detailed description of embodiments of the invention, will be better understood when read in conjunction with the appended drawings and figures.

FIG. 1*a* illustrates the structure of p38α showing CD, ED, DEF and activation site. FIG. 1*b* illustrates the comparison between the p38α and β structures; CD and ED sites are colored red and blue, and the CADD target yellow. Sequence comprising the CADD target on p38α and corresponding site on p38β differ in only three of ten amino acids (highlighted yellow). FIG. 1*c* illustrates the overlap of CADD target structure in apo- (PDB:1P38; green) and dual-phosphorylated (PDB:3PY3; yellow) mouse p38α. FIG. 1*d* illustrates the overview of CADD screening strategy. FIG. 1*e* illustrates the DSF screening of compounds added at 10, 25, 50, or 100 μM to recombinant p38α or ERK2 with binding indicated by increase in melting temperature. Compounds binding ERK2 and p38 α highlighted yellow. Those only binding to p38 α are highlighted in blue. FIG. if illustrates the chemical structure of UM60, UM101, and SB203580.

FIG. 2*a* and FIG. 2*b* illustrate the effect of 10 μM SB203580 (SB), or indicated concentration of UM60 or 101 on HMVECL permeability (FIG. 2*a*) and capacity for IL-8-directed neutrophil TEM (FIG. 2*b*). Cells were pretreated with DMSO or compounds for 1 h, then incubated with 10 ng/ml TNFα for 6 h prior to permeability assay (FIG. 2*a*) or at 39.5° C. without additional stimulus for 6 h prior to TEM assay (FIG. 2*b*). Mean±SE. * denotes $p<0.0001$ vs. DMSO, † $p<0.0001$ vs. SB, ‡ $p<0.005$ vs. 37° C. FIG. 2*c* and FIG. 2*d*. Male CD1 mice were pretreated with 1 mg SB or 0.1-1 mg UM101 prior to i.t. instillation of 50 μg LPS and hyperthermia exposure. * denotes $p<0.05$ vs. DMSO.

FIG. 3*a* and FIG. 3*b* illustrate the heat maps from RNASeq showing IPA pathways inhibited by SB203580 alone or SB203580 and UM101 or (FIG. 3*a*) and those only inhibited by UM101 (FIG. 3*b*). FIG. 3*c* illustrate the biochemical effects of substrate-selective p38 inhibitors on HeLa cells pre-treated with 50 μM UM101 or 10 μM SB203580 (SB) for 30 min, then treated with anisomycin for 10-60 min, and immunoblotted for phospho-MK2, Stat-1 and total p38. FIG. 3*d* illustrates the DSF analysis of UM101 and SB203580 (SB) binding to recombinant p38α and p380. Mean±SE of 4 experiments. *, †, and § denote $p<0.0001$ vs. p38α with DMSO, p380 with DMSO, and p38β with SB203580, respectively. $P<0.0001$ for difference between UM101 binding to p38α and p38β by MANOVA. FIG. 3*e* illustrates the DSF analysis of UM101 and SB203580 (SB) binding to recombinant wild-type p38α and a p38α mutant with 4 mutations in CADD-targeted pocket. Mean±SE of 4 experiments. * and †, denote $p<0.0001$ vs. wild-type with DMSO and mutant with DMSO, respectively. $P<0.0001$ for difference between UM101 binding to wild-type and mutant p38α by MANOVA. FIG. 3*f-k* illustrate STD-NMR performed with UM101 and p38α (FIG. 3*f* and FIG. 3*g*), p380 (FIG. 3*h* and FIG. 3*i*), and the p38α mutant (FIG. 3*j* and FIG. 3*k*). The 1D (FIG. 3*f*, FIG. 3*h*, and FIG. 3*j*) and STD spectra (FIG. 3*g*, FIG. 3*i*, and FIG. 3*k*) from the same sample are shown. The tentative peak assignments are indicated in FIG. 3*f*. The structure of UM101 with the protons labeled is shown in the insert.

DETAILED DESCRIPTION OF THE INVENTION

Figures 1A, 1B, 1C, 1D, 1E, 1F:
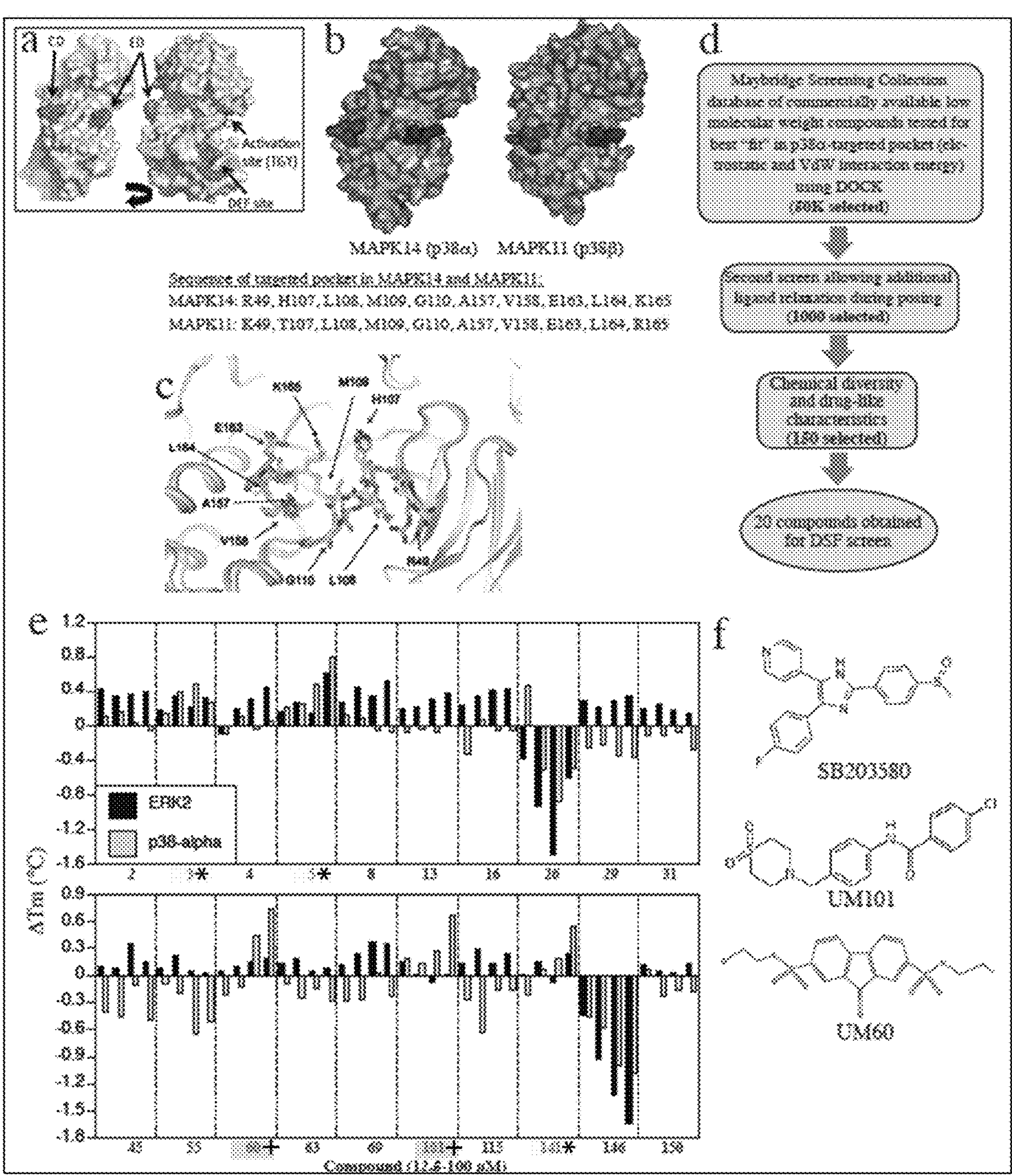
FIG. 1*a*-FIG. 1*f* illustrates the design of substrate-selective p38 inhibitors.

Unless defined otherwise, all technical and scientific terms used herein have the same meaning as is commonly understood by one of skill in the art to which this invention belongs. All patents and publications referred to herein are incorporated by reference in their entireties.

Definitions

As used herein, the terms "administer," "administration" or "administering" refer to (1) providing, giving, dosing, and/or prescribing by either a health practitioner or his authorized agent or under his or her direction according to the disclosure; and/or (2) putting into, taking or consuming by the mammal, according to the disclosure.

The terms "co-administration," "co-administering," "administered in combination with," "administering in combination with," "simultaneous," and "concurrent," as used herein, encompass administration of two or more active pharmaceutical ingredients to a subject so that both active pharmaceutical ingredients and/or their metabolites are present in the subject at the same time. Co-administration includes simultaneous administration in separate compositions, administration at different times in separate compositions, or administration in a composition in which two or more active pharmaceutical ingredients are present. Simultaneous administration in separate compositions and administration in a composition in which both agents are present are preferred.

The terms “active pharmaceutical ingredient” and “drug” include the p38α MAPK inhibitors described herein and, more specifically, the p38α MAPK inhibitors described by Formulas 1, 2, 11, 12, 13, 14, 1001 to 1256, UM60, and UM101. The terms “active pharmaceutical ingredient” and “drug” may also include those compounds described herein that bind p38α MAPK protein and thereby modulate p38α MAPK protein activity.

The term “isostere” refers to a group or molecule whose chemical and/or physical properties are similar to those of another group or molecule. A “bioisostere” is a type of isostere and refers to a group or molecule whose biological properties are similar to those of another group or molecule. For example, for the p38α MAPK inhibitors described herein, a carboxylic acid may be replaced by one of the following bioisosteres for carboxylic acids, including, without limitation, alkyl esters (COOR), acylsulfonamides ($CONR—SO_2R$), hydroxamic acids (CONR—OH), hydroxamates (CONR—OR), tetrazoles, hydroxyisoxazoles, isoxazol-3-ones, and sulfonamides ($SO_2NR$), where each R may independently represent hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

The term “in vivo” refers to an event that takes place in a subject’s body.

The term “in vitro” refers to an event that takes places outside of a subject’s body. In vitro assays encompass cell-based assays in which cells alive or dead are employed and may also encompass a cell-free assay in which no intact cells are employed.

The term “effective amount” or “therapeutically effective amount” refers to that amount of a compound or combination of compounds as described herein that is sufficient to effect the intended application including, but not limited to, disease treatment. A therapeutically effective amount may vary depending upon the intended application (in vitro or in vivo), or the subject and disease condition being treated (e.g., the weight, age and gender of the subject), the severity of the disease condition, the manner of administration, etc., which can readily be determined by one of ordinary skill in the art. The term also applies to a dose that will induce a particular response in target cells (e.g., the reduction of platelet adhesion and/or cell migration). The specific dose will vary depending on the particular compounds chosen, the dosing regimen to be followed, whether the compound is administered in combination with other compounds, timing of administration, the tissue to which it is administered, and the physical delivery system in which the compound is carried.

A “therapeutic effect” as that term is used herein, encompasses a therapeutic benefit and/or a prophylactic benefit. A prophylactic effect includes delaying or eliminating the appearance of a disease or condition, delaying or eliminating the onset of symptoms of a disease or condition, slowing, halting, or reversing the progression of a disease or condition, or any combination thereof.

As used herein, the terms “treat,” “treatment,” and/or “treating” may refer to the management of a disease, disorder, or pathological condition, or symptom thereof with the intent to cure, ameliorate, stabilize, and/or control the disease, disorder, pathological condition or symptom thereof. Regarding control of the disease, disorder, or pathological condition more specifically, “control” may include the absence of condition progression, as assessed by the response to the methods recited herein, where such response may be complete (e.g., placing the disease in remission) or partial (e.g., lessening or ameliorating any symptoms associated with the condition). As used herein, the terms “prevent,” “preventing,” and/or “prevention” may refer to reducing the risk of developing a disease, disorder, or pathaoligical condition.

As used herein, the terms “modulate” and “modulation” refer to a change in biological activity for a biological molecule (e.g., a protein, gene, peptide, antibody, and the like), where such change may relate to an increase in biological activity (e.g., increased activity, agonism, activation, expression, upregulation, and/or increased expression) or decrease in biological activity (e.g., decreased activity, antagonism, suppression, deactivation, downregulation, and/or decreased expression) for the biological molecule. For example, the compounds described herein may modulate (i.e., inhibit) p38α MAPK protein. In some embodiments, the compounds described herein may selectively modulate (i.e., selectively inhibit) p38α MAPK protein as compared to other MAPK or p38 MAPK proteins. In some embodiments, the compounds described herein may selectively modulate (i.e., selectively inhibit) p38α MAPK protein as compared to other MAPK or p38 MAPK proteins.

The terms “QD,” “qd,” or “q.d.” mean quaque die, once a day, or once daily. The terms “BID,” “bid,” or “b.i.d.” mean bis in die, twice a day, or twice daily. The terms “TID,” “tid,” or “t.i.d.” mean ter in die, three times a day, or three times daily. The terms “QID,” “qid,” or “q.i.d.” mean quater in die, four times a day, or four times daily.

The term “pharmaceutically acceptable salt” refers to salts derived from a variety of organic and inorganic counter ions known in the art. Pharmaceutically acceptable acid addition salts can be formed with inorganic acids and organic acids. Preferred inorganic acids from which salts can be derived include, for example, hydrochloric acid, hydrobromic acid, sulfuric acid, nitric acid and phosphoric acid. Preferred organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid and salicylic acid. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese and aluminum. Organic bases from which salts can be derived include, for example, primary, secondary, and tertiary amines, substituted amines including naturally occurring substituted amines, cyclic amines and basic ion exchange resins. Specific examples include isopropylamine, trimethylamine, diethylamine, triethylamine, tripropylamine, and ethanolamine. In some embodiments, the pharmaceutically acceptable base addition salt is chosen from ammonium, potassium, sodium, calcium, and magnesium salts. The term “cocrystal” refers to a molecular complex derived from a number of cocrystal formers known in the art. Unlike a salt, a cocrystal typically does not involve hydrogen transfer between the cocrystal and the drug, and instead involves intermolecular interactions, such as hydrogen bonding, aromatic ring stacking, or dispersive forces, between the cocrystal former and the drug in the crystal structure.

"Pharmaceutically acceptable carrier" or "pharmaceutically acceptable excipient" or "physiologically compatible" carrier or carrier medium is intended to include any and all solvents, dispersion media, coatings, antibacterial and antifungal agents, isotonic and absorption delaying agents, and inert ingredients. The use of such pharmaceutically acceptable carriers or pharmaceutically acceptable excipients for active pharmaceutical ingredients is well known in the art. Except insofar as any conventional pharmaceutically acceptable carrier or pharmaceutically acceptable excipient is incompatible with the active pharmaceutical ingredient, its use in the therapeutic compositions of the invention is contemplated. Additional active pharmaceutical ingredients, such as other drugs, can also be incorporated into the described compositions and methods.

A "prodrug" refers to a derivative of a compound described herein, the pharmacologic action of which results from the conversion by chemical or metabolic processes in vivo to the active compound. Prodrugs include compounds wherein an amino acid residue, or a polypeptide chain of two or more (e.g., two, three or four) amino acid residues is covalently joined through an amide or ester bond to a free amino, hydroxyl or carboxylic acid group of Formulas 1, 2, 11, 12, 13, 14, 1001 to 1256, UM60, and UM101. The amino acid residues include but are not limited to the 20 naturally occurring amino acids commonly designated by one or three letter symbols but also include, for example, 4-hydroxyproline, hydroxylysine, desmosine, isodesmosine, 3-methylhistidine, beta-alanine, gamma-aminobutyric acid, citrulline, homocysteine, homoserine, ornithine and methionine sulfone. Additional types of prodrugs are also encompassed. For instance, free carboxyl groups can be derivatized as amides or alkyl esters (e.g., methyl esters and acetoxy methyl esters). Prodrug esters as employed herein includes esters and carbonates formed by reacting one or more hydroxyls of compounds of the method of the invention with alkyl, alkoxy, or aryl substituted acylating agents employing procedures known to those skilled in the art to generate acetates, pivalates, methylcarbonates, benzoates and the like. As further examples, free hydroxyl groups may be derivatized using groups including but not limited to hemisuccinates, phosphate esters, dimethylaminoacetates, and phosphoryloxymethyloxycarbonyls, as outlined in Advanced Drug Delivery Reviews, 1996, 19, 115. Carbamate prodrugs of hydroxyl and amino groups are also included, as are carbonate prodrugs, sulfonate prodrugs, sulfonate esters and sulfate esters of hydroxyl groups. Free amines can also be derivatized to amides, sulfonamides or phosphonamides. All of the stated prodrug moieties may incorporate groups including but not limited to ether, amine and carboxylic acid functionalities. Moreover, any compound that can be converted in vivo to provide the bioactive agent (e.g., a compound of formula I, II, III, and IV) is a prodrug within the scope of the invention. Various forms of prodrugs are well known in the art. A comprehensive description of pro drugs and prodrug derivatives are described in: (a) The Practice of Medicinal Chemistry, Camille G. Wermuth et al., (Academic Press, 1996); (b) Design of Prodrugs, edited by H. Bundgaard, (Elsevier, 1985); (c) A Textbook of Drug Design and Development, P. Krogsgaard-Larson and H. Bundgaard, eds., (Harwood Academic Publishers, 1991). In general, prodrugs may be designed to improve the penetration of a drug across biological membranes in order to obtain improved drug absorption, to prolong duration of action of a drug (slow release of the parent drug from a prodrug, decreased first-pass metabolism of the drug), to target the drug action (e.g., organ or tumor-targeting, lymphocyte targeting), to modify or improve aqueous solubility of a drug (e.g., i.v. preparations and eyedrops), to improve topical drug delivery (e.g., dermal and ocular drug delivery), to improve the chemical/enzymatic stability of a drug, or to decrease off-target drug effects, and more generally in order to improve the therapeutic efficacy of the compounds utilized in the invention.

Unless otherwise stated, the chemical structures depicted herein are intended to include compounds which differ only in the presence of one or more isotopically enriched atoms. For example, compounds where one or more hydrogen atoms is replaced by deuterium or tritium, or wherein one or more carbon atoms is replaced by $^{13}C$- or $^{14}C$-enriched carbons, are within the scope of this invention.

When ranges are used herein to describe, for example, physical or chemical properties such as molecular weight or chemical formulae, all combinations and subcombinations of ranges and specific embodiments therein are intended to be included. Use of the term "about" when referring to a number or a numerical range means that the number or numerical range referred to is an approximation within experimental variability (or within statistical experimental error), and thus the number or numerical range may vary. The variation is typically from 0% to 15%, preferably from 0% to 10%, more preferably from 0% to 5% of the stated number or numerical range. The term "comprising" (and related terms such as "comprise" or "comprises" or "having" or "including") includes those embodiments such as, for example, an embodiment of any composition of matter, method or process that "consist of" or "consist essentially of" the described features.

"Alkyl" refers to a straight or branched hydrocarbon chain radical consisting solely of carbon and hydrogen atoms, containing no unsaturation, having from one to ten carbon atoms (e.g., $(C_{1-10})$alkyl or $C_{1-10}$ alkyl). Whenever it appears herein, a numerical range such as "1 to 10" refers to each integer in the given range, e.g., "1 to 10 carbon atoms" means that the alkyl group may consist of 1 carbon atom, 2 carbon atoms, 3 carbon atoms, etc., up to and including 10 carbon atoms, although the definition is also intended to cover the occurrence of the term "alkyl" where no numerical range is specifically designated. Typical alkyl groups include, but are in no way limited to, methyl, ethyl, propyl, isopropyl, n-butyl, isobutyl, sec-butyl isobutyl, tertiary butyl, pentyl, isopentyl, neopentyl, hexyl, septyl, octyl, nonyl and decyl. The alkyl moiety may be attached to the rest of the molecule by a single bond, such as for example, methyl (Me), ethyl (Et), n-propyl (Pr), 1-methylethyl (isopropyl), n-butyl, n-pentyl, 1,1-dimethylethyl (t-butyl) and 3-methylhexyl. Unless stated otherwise specifically in the specification, an alkyl group is optionally substituted by one or more of substituents which are independently heteroalkyl, acylsulfonamido, alkenyl, alkynyl, cycloalkyl, heterocycloalkyl, hydroxamate, aryl, arylalkyl, heteroaryl, heteroarylalkyl, hydroxy, halo, cyano, trifluoromethyl, trifluoromethoxy, nitro, trimethylsilanyl, $—OR^a$, $—SR^a$, $—S(O)_tR^a—$ (where t is 1 or 2), $—OC(O)—R^a$, $—N(R^a)_2$, $—C(O)R^a$, $—C(O)OR^a$, $—OC(O)N(R^a)_2$, $—C(O)N(R^a)_2$, $—N(R^a)C(O)OR^a$, $—N(R^a)C(O)R^a$, $—N(R^a)C(O)N(R^a)_2$, $N(R^a)C(NR^a)N(R^a)_2$, $—N(R^a)S(O)_tR^a$ (where t is 1 or 2), $—S(O)_tOR^a$ (where t is 1 or 2), $—S(O)_tN(R^a)_2$ (where t is 1 or 2), or $PO_3(R^a)_2$ where each $R^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Alkylaryl" refers to an -(alkyl)aryl radical where aryl and alkyl are as disclosed herein and which are optionally substituted by one or more of the substituents described as suitable substituents for aryl and alkyl respectively.

"Alkylhetaryl" refers to an -(alkyl)hetaryl radical where hetaryl and alkyl are as disclosed herein and which are optionally substituted by one or more of the substituents described as suitable substituents for aryl and alkyl respectively.

"Alkylheterocycloalkyl" refers to an -(alkyl) heterocyclic radical where alkyl and heterocycloalkyl are as disclosed herein and which are optionally substituted by one or more of the substituents described as suitable substituents for heterocycloalkyl and alkyl respectively.

An "alkene" moiety refers to a group consisting of at least two carbon atoms and at least one carbon-carbon double bond, and an "alkyne" moiety refers to a group consisting of at least two carbon atoms and at least one carbon-carbon triple bond. The alkyl moiety, whether saturated or unsaturated, may be branched, straight chain, or cyclic.

"Alkenyl" refers to a straight or branched hydrocarbon chain radical group consisting solely of carbon and hydrogen atoms, containing at least one double bond, and having from two to ten carbon atoms (i.e., $(C_{2-10})$alkenyl or $C_{2-10}$ alkenyl). Whenever it appears herein, a numerical range such as "2 to 10" refers to each integer in the given range—e.g., "2 to 10 carbon atoms" means that the alkenyl group may consist of 2 carbon atoms, 3 carbon atoms, etc., up to and including 10 carbon atoms. The alkenyl moiety may be attached to the rest of the molecule by a single bond, such as for example, ethenyl (i.e., vinyl), prop-1-enyl (i.e., allyl), but-1-enyl, pent-1-enyl and penta-1,4-dienyl. Unless stated otherwise specifically in the specification, an alkenyl group is optionally substituted by one or more substituents which are independently alkyl, heteroalkyl, acylsulfonamido, alkenyl, alkynyl, cycloalkyl, heterocycloalkyl, hydroxamate, aryl, arylalkyl, heteroaryl, heteroarylalkyl, hydroxy, halo, cyano, trifluoromethyl, trifluoromethoxy, nitro, trimethylsilanyl, —$OR^a$, —$SR^a$, —$S(O)_1R^a$— (where t is 1 or 2), —OC(O)—$R^a$, —$N(R^a)_2$, —$C(O)R^a$, —C(O)$OR^a$, —OC(O)$N(R^a)_2$, —C(O)$N(R^a)_2$, —$N(R^a)C(O)OR^a$, —$N(R^a)C(O)R^a$, —$N(R^a)C(O)N(R^a)_2$, $N(R^a)C(NR^a)N(R^a)_2$, —$N(R^a)S(O)_tR^a$ (where t is 1 or 2), —$S(O)_tOR^a$ (where t is 1 or 2), —$S(O)_tN(R^a)_2$ (where t is 1 or 2), or $PO_3(R^a)_2$, where each $R^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Alkenyl-cycloalkyl" refers to an -(alkenyl)cycloalkyl radical where alkenyl and cycloalkyl are as disclosed herein and which are optionally substituted by one or more of the substituents described as suitable substituents for alkenyl and cycloalkyl respectively.

"Alkynyl" refers to a straight or branched hydrocarbon chain radical group consisting solely of carbon and hydrogen atoms, containing at least one triple bond, having from two to ten carbon atoms (i.e., $(C_{2-10})$alkynyl or $C_{2-10}$ alkynyl). Whenever it appears herein, a numerical range such as "2 to 10" refers to each integer in the given range—e.g., "2 to 10 carbon atoms" means that the alkynyl group may consist of 2 carbon atoms, 3 carbon atoms, etc., up to and including 10 carbon atoms. The alkynyl may be attached to the rest of the molecule by a single bond, for example, ethynyl, propynyl, butynyl, pentynyl and hexynyl. Unless stated otherwise specifically in the specification, an alkynyl group is optionally substituted by one or more substituents which independently are: alkyl, heteroalkyl, alkenyl, alkynyl, cycloalkyl, heterocycloalkyl, hydroxamate, acylsulfonamido, aryl, arylalkyl, heteroaryl, heteroarylalkyl, hydroxy, halo, cyano, trifluoromethyl, trifluoromethoxy, nitro, trimethylsilanyl, —$OR^a$, —SR, —$S(O)_tR^a$— (where t is 1 or 2), —OC(O)—$R^a$, —$N(R^a)_2$, —$C(O)R^a$, —C(O)$OR^a$, —OC(O)$N(R^a)_2$, —C(O)$N(R^a)_2$, —$N(R^a)C(O)OR^a$, —$N(R^a)C(O)R^a$, —$N(R^a)C(O)N(R^a)_2$, $N(R^a)C(NR^a)N(R^a)_2$, —$N(R^a)S(O)_tR^a$ (where t is 1 or 2), —$S(O)OR^a$ (where t is 1 or 2), —$S(O)_tN(R^a)_2$ (where t is 1 or 2), or $PO_3(R^a)_2$, where each $R^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Alkynyl-cycloalkyl" refers to an -(alkynyl)cycloalkyl radical where alkynyl and cycloalkyl are as disclosed herein and which are optionally substituted by one or more of the substituents described as suitable substituents for alkynyl and cycloalkyl respectively.

"Acylsulfonamide" refers to the group —C(═O)$NR^a$—S(═O)$R^a$, where each $R^a$ is independently hydrogen, alkyl, fluoroalkyl, carbocyclyl, carbocyclylalkyl, aryl, aralkyl, heterocycloalkyl, heterocycloalkylalkyl, heteroaryl, or heteroarylalkyl.

"Carboxaldehyde" refers to a —(C═O)H radical.

"Carbonyl" refers to the group —C(═O)—. Carbonyl groups may be substituted with the following exemplary substituents: alkyl, heteroalkyl, alkenyl, alkynyl, cycloalkyl, heterocycloalkyl, hydroxamate, acylsulfonamido, aryl, arylalkyl, heteroaryl, heteroarylalkyl, hydroxy, halo, cyano, trifluoromethyl, trifluoromethoxy, nitro, trimethylsilanyl, —$OR^a$, —SR, —$S(O)_tR^a$— (where t is 1 or 2), —OC(O)—$R^a$, —$N(R^a)_2$, —$C(O)R^a$, —$NR^a$—$OR^a$—, —C(O)$OR^a$, OC(O)$N(R^a)_2$, —C(O)$N(R^a)_2$, —$N(R^a)C(O)OR^a$, —$N(R^a)C(O)R^a$, —$N(R^a)C(O)N(R^a)_2$, $N(R^a)C(NR^a)N(R^a)_2$, —$N(R^a)S(O)R^a$ (where t is 1 or 2), —$S(O)_tOR^a$ (where t is 1 or 2), —$S(O)_tN(R^a)_2$ (where t is 1 or 2), or $PO_3(R^a)_2$, where each $R^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Carboxyl" refers to a —(C═O)OH radical.

"Cyano" refers to a —CN radical.

"Cycloalkyl" refers to a monocyclic or polycyclic radical that contains only carbon and hydrogen, and may be saturated, or partially unsaturated. Cycloalkyl groups include groups having from 3 to 10 ring atoms (i.e., $(C_{3-10})$cycloalkyl or $C_{3-10}$ cycloalkyl). Whenever it appears herein, a numerical range such as "3 to 10" refers to each integer in the given range—e.g., "3 to 10 carbon atoms" means that the cycloalkyl group may consist of 3 carbon atoms, etc., up to and including 10 carbon atoms. Illustrative examples of cycloalkyl groups include, but are not limited to the following moieties: cyclopropyl, cyclobutyl, cyclopentyl, cyclopentenyl, cyclohexyl, cyclohexenyl, cycloheptyl, cyclooctyl, cyclononyl, cyclodecyl, norbornyl, and the like. Unless stated otherwise specifically in the specification, a cycloalkyl group is optionally substituted by one or more substituents which independently are: alkyl, heteroalkyl, alkenyl, alkynyl, cycloalkyl, acylsulfonamido, heterocycloalkyl, hydroxamate, aryl, arylalkyl, heteroaryl, heteroarylalkyl, hydroxy, halo, cyano, trifluoromethyl, trifluoromethoxy, nitro, trimethylsilanyl, —$OR^a$, —$SR^a$, —$S(O)_tR^a$— (where t is 1 or 2), —$S(O)R^a$— (where t is 1 or 2), —OC(O)—$R^a$, —$N(R^a)_2$, —$C(O)R^a$, —C(O)$OR^a$, —OC(O)$N(R^a)_2$, —C(O)$N(R^a)_2$, —$N(R^a)C(O)OR^a$, —$N(R^a)C(O)R^a$, —$N(R^a)C(O)N(R^a)_2$, $N(R^a)C(NR^a)N(R^a)_2$, —$N(R^a)S(O)_tR^a$ (where t is 1 or 2), —$S(O)_tOR^a$ (where t is 1 or 2), —$S(O)_tN(R^a)_2$ (where t is 1 or 2), or $PO_3(R^a)_2$, where each $R^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Cycloalkyl-alkenyl" refers to a -(cycloalkyl)alkenyl radical where cycloalkyl and alkenyl are as disclosed herein and which are optionally substituted by one or more of the substituents described as suitable substituents for cycloalkyl and alkenyl, respectively.

"Cycloalkyl-heterocycloalkyl" refers to a -(cycloalkyl) heterocycloalkyl radical where cycloalkyl and heterocycloalkyl are as disclosed herein and which are optionally substituted by one or more of the substituents described as suitable substituents for cycloalkyl and heterocycloalkyl, respectively.

"Cycloalkyl-heteroaryl" refers to a -(cycloalkyl)heteroaryl radical where cycloalkyl and heteroaryl are as disclosed herein and which are optionally substituted by one or more of the substituents described as suitable substituents for cycloalkyl and heteroaryl, respectively.

The term "alkoxy" refers to the group —O-alkyl, including from 1 to 8 carbon atoms of a straight, branched, cyclic configuration and combinations thereof attached to the parent structure through an oxygen. Examples include, but are not limited to, methoxy, ethoxy, propoxy, isopropoxy, cyclopropyloxy and cyclohexyloxy. "Lower alkoxy" refers to alkoxy groups containing one to six carbons.

The term "substituted alkoxy" refers to alkoxy wherein the alkyl constituent is substituted (i.e., —O-(substituted alkyl)). Unless stated otherwise specifically in the specification, the alkyl moiety of an alkoxy group is optionally substituted by one or more substituents which independently are: alkyl, heteroalkyl, alkenyl, acylsulfonamido, alkynyl, cycloalkyl, heterocycloalkyl, hydroxamate, aryl, arylalkyl, heteroaryl, heteroarylalkyl, hydroxy, halo, cyano, trifluoromethyl, trifluoromethoxy, nitro, trimethylsilanyl, —$OR^a$, —$SR^a$, —$S(O)_tR^a$— (where t is 1 or 2), —OC(O)—$R^a$, —$N(R^a)_2$, —C(O)$R^a$, —C(O)O$R^a$, —OC(O)$N(R^a)_2$, —C(O)$N(R^a)_2$, —$N(R^a)$C(O)O$R^a$, —$N(R^a)$C(O)$R^a$, —$N(R^a)$C(O)$N(R^a)_2$, $N(R^a)C(NR^a)N(R^a)_2$, —$N(R^a)S(O)_tR^a$ (where t is 1 or 2), —$S(O)_tOR^a$ (where t is 1 or 2), —$S(O)_tN(R^a)_2$ (where t is 1 or 2), or $PO_3(R^a)_2$, where each $R^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

The term "alkoxycarbonyl" refers to a group of the formula (alkoxy)(C═O)— attached through the carbonyl carbon wherein the alkoxy group has the indicated number of carbon atoms. Thus a $(C_{1-6})$alkoxycarbonyl group is an alkoxy group having from 1 to 6 carbon atoms attached through its oxygen to a carbonyl linker. "Lower alkoxycarbonyl" refers to an alkoxycarbonyl group wherein the alkoxy group is a lower alkoxy group.

The term "substituted alkoxycarbonyl" refers to the group (substituted alkyl)-O—C(O)— wherein the group is attached to the parent structure through the carbonyl functionality. Unless stated otherwise specifically in the specification, the alkyl moiety of an alkoxycarbonyl group is optionally substituted by one or more substituents which independently are: alkyl, heteroalkyl, acylsulfonamido, alkenyl, alkynyl, cycloalkyl, heterocycloalkyl, hydroxamate, aryl, arylalkyl, heteroaryl, heteroarylalkyl, hydroxy, halo, cyano, trifluoromethyl, trifluoromethoxy, nitro, trimethylsilanyl, —$OR^a$, —$SR^a$, —$S(O)_1R^a$— (where t is 1 or 2), —OC(O)—$R^a$, —$N(R^a)_2$, —C(O)$R^a$, —C(O)O$R^a$, —OC(O)$N(R^a)_2$, —C(O)$N(R^a)_2$, —$N(R^a)$C(O)O$R^a$, —$N(R^a)$C(O)$R^a$, —$N(R^a)$C(O)$N(R^a)_2$, $N(R^a)C(NR^a)N(R^a)_2$, —$N(R^a)S(O)_tR^a$ (where t is 1 or 2), —$S(O)_tOR^a$ (where t is 1 or 2), —$S(O)_tN(R^a)_2$ (where t is 1 or 2), or $PO_3(R^a)_2$, where each $R^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Acyl" refers to the groups (alkyl)-C(O)—, (aryl)-C(O)—, (heteroaryl)-C(O)—, (heteroalkyl)-C(O)— and (heterocycloalkyl)-C(O)—, wherein the group is attached to the parent structure through the carbonyl functionality. If the R radical is heteroaryl or heterocycloalkyl, the hetero ring or chain atoms contribute to the total number of chain or ring atoms. Unless stated otherwise specifically in the specification, the alkyl, aryl or heteroaryl moiety of the acyl group is optionally substituted by one or more substituents which are independently alkyl, heteroalkyl, acylsulfonamido, alkenyl, alkynyl, cycloalkyl, heterocycloalkyl, hydroxamate, aryl, arylalkyl, heteroaryl, heteroarylalkyl, hydroxy, halo, cyano, trifluoromethyl, trifluoromethoxy, nitro, trimethylsilanyl, —$OR^a$, —$SR^a$, —$S(O)_1R^a$— (where t is 1 or 2), —OC(O)—$R^a$, —$N(R^a)_2$, —C(O)$R^a$, —C(O)O$R^a$, —OC(O)$N(R^a)_2$, —C(O)$N(R^a)_2$, —$N(R^a)$C(O)O$R^a$, —$N(R^a)$C(O)$R^a$, —$N(R^a)$C(O)$N(R^a)_2$, $N(R^a)C(NR^a)N(R^a)_2$, —$N(R^a)S(O)_tR^a$ (where t is 1 or 2), —$S(O)_tOR^a$ (where t is 1 or 2), —$S(O)_tN(R^a)_2$ (where t is 1 or 2), or $PO_3(R^a)_2$, where each $R^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Acyloxy" refers to a R(C═O)O— radical wherein R is alkyl, aryl, heteroaryl, heteroalkyl or heterocycloalkyl, which are as described herein. If the R radical is heteroaryl or heterocycloalkyl, the hetero ring or chain atoms contribute to the total number of chain or ring atoms. Unless stated otherwise specifically in the specification, the R of an acyloxy group is optionally substituted by one or more substituents which independently are: alkyl, heteroalkyl, alkenyl, alkynyl, cycloalkyl, heterocycloalkyl, hydroxamate, aryl, arylalkyl, heteroaryl, heteroarylalkyl, hydroxy, halo, cyano, trifluoromethyl, trifluoromethoxy, nitro, trimethylsilanyl, —$OR^a$, —$SR^a$, —$S(O)_tR^a$— (where t is 1 or 2), —OC(O)—$R^a$, —$N(R^a)_2$, —C(O)$R^a$, —C(O)O$R^a$, —OC(O)$N(R^a)_2$, —C(O)$N(R^a)_2$, —$N(R^a)$C(O)O$R^a$, —$N(R^a)$C(O)$R^a$, —$N(R^a)$C(O)$N(R^a)_2$, $N(R^a)C(NR^a)N(R^a)_2$, —$N(R^a)$S(O)$R^a$ (where t is 1 or 2), —$S(O)_tOR^a$ (where t is 1 or 2), —$S(O)_tN(R^a)_2$ (where t is 1 or 2), or $PO_3(R^a)_2$, where each $R^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Amino" or "amine" refers to a —$N(R^a)_2$ radical group, where each $R^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl, unless stated otherwise specifically in the specification. When a —$N(R^a)_2$ group has two $R^a$ substituents other than hydrogen, they can be combined with the nitrogen atom to form a 4-, 5-, 6- or 7-membered ring. For example, —$N(R^a)_2$ is intended to include, but is not limited to, 1-pyrrolidinyl and 4-morpholinyl. Unless stated otherwise specifically in the specification, an amino group is optionally substituted by one or more substituents which independently are: alkyl, acylsulfonamido, heteroalkyl, alkenyl, alkynyl, cycloalkyl, heterocycloalkyl, hydroxamate, aryl, arylalkyl, heteroaryl, heteroarylalkyl, hydroxy, halo, cyano, trifluoromethyl, trifluoromethoxy, nitro, trimethylsilanyl, —$OR^a$, —$SR^a$, —$S(O)_tR^a$— (where t is 1 or 2), —OC(O)—$R^a$, —$N(R^a)_2$, —C(O)$R^a$, —C(O)O$R^a$, —OC(O)$N(R^a)_2$, —C(O)$N(R^a)_2$, —$N(R^a)$C(O)O$R^a$, —$N(R^a)$C(O)$R^a$, —$N(R^a)$C(O)$N(R^a)_2$, $N(R^a)C(NR^a)N(R^a)_2$, —$N(R^a)S(O)_tR^a$ (where t is 1 or 2), —$S(O)_tOR^a$ (where t is 1 or 2), —$S(O)_tN(R^a)_2$ (where t is 1 or 2), or $PO_3(R^a)_2$, where each $R^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

The term "substituted amino" also refers to N-oxides of the groups —NHR$^d$, and NR$^d$R$^d$ each as described above. N-oxides can be prepared by treatment of the corresponding amino group with, for example, hydrogen peroxide or m-chloroperoxybenzoic acid.

"Amide" or "amido" refers to a chemical moiety with formula —C(O)NR$^a$R$^b$ or —NR$^a$C(O)R$^b$, where R$^a$ and R$^b$ are selected from the group consisting of hydrogen, alkyl, cycloalkyl, aryl, heteroaryl (bonded through a ring carbon) and heteroalicyclic (bonded through a ring carbon), each of which moiety may itself be optionally substituted. The R$^a$ and R$^b$ of —C(O)NR$^a$R$^b$ amide may optionally be taken together with the nitrogen to which they are attached to form a 4-, 5-, 6- or 7-membered ring. Unless stated otherwise specifically in the specification, an amido group is optionally substituted independently by one or more of the substituents as described herein for alkyl, amino, cycloalkyl, aryl, heteroaryl, or heterocycloalkyl. An amide may be an amino acid or a peptide molecule attached to a compound disclosed herein, thereby forming a prodrug. The procedures and specific groups to make such amides are known to those of skill in the art and can readily be found in seminal sources such as Greene and Wuts, *Protective Groups in Organic Synthesis*, 3$^{rd}$ Ed., John Wiley & Sons, New York, N.Y., 1999, which is incorporated herein by reference in its entirety.

"Aromatic" or "aryl" or "Ar" refers to an aromatic radical with six to ten ring atoms (e.g., $C_6$-$C_{10}$ aromatic or $C_6$-$C_{10}$ aryl) which has at least one ring having a conjugated pi electron system which is carbocyclic (e.g., phenyl, fluorenyl, and naphthyl). Bivalent radicals formed from substituted benzene derivatives and having the free valences at ring atoms are named as substituted phenylene radicals. Bivalent radicals derived from univalent polycyclic hydrocarbon radicals whose names end in "-yl" by removal of one hydrogen atom from the carbon atom with the free valence are named by adding "-idene" to the name of the corresponding univalent radical, e.g., a naphthyl group with two points of attachment is termed naphthylidene. Whenever it appears herein, a numerical range such as "6 to 10" refers to each integer in the given range; e.g., "6 to 10 ring atoms" means that the aryl group may consist of 6 ring atoms, 7 ring atoms, etc., up to and including 10 ring atoms. The term includes monocyclic or fused-ring polycyclic (i.e., rings which share adjacent pairs of ring atoms) groups. Unless stated otherwise specifically in the specification, an aryl moiety is optionally substituted by one or more substituents which are independently alkyl, heteroalkyl, acylsulfonamido, alkenyl, alkynyl, cycloalkyl, heterocycloalkyl, hydroxamate, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —S(O)$_t$R$^a$— (where t is 1 or 2), —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Aralkyl" or "arylalkyl" refers to an (aryl)alkyl-radical where aryl and alkyl are as disclosed herein and which are optionally substituted by one or more of the substituents described as suitable substituents for aryl and alkyl respectively.

"Ester" refers to a chemical radical of formula —COOR, where R is selected from the group consisting of alkyl, cycloalkyl, aryl, heteroaryl (bonded through a ring carbon) and heteroalicyclic (bonded through a ring carbon). The procedures and specific groups to make esters are known to those of skill in the art and can readily be found in seminal sources such as Greene and Wuts, Protective Groups in Organic Synthesis, 3$^{rd}$ Ed., John Wiley & Sons, New York, N.Y., 1999, which is incorporated herein by reference in its entirety. Unless stated otherwise specifically in the specification, an ester group is optionally substituted by one or more substituents which independently are: alkyl, acylsulfonamido, heteroalkyl, alkenyl, alkynyl, cycloalkyl, heterocycloalkyl, hydroxamate, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —S(O)$_t$R$^a$— (where t is 1 or 2), —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Fluoroalkyl" refers to an alkyl radical, as defined above, that is substituted by one or more fluoro radicals, as defined above, for example, trifluoromethyl, difluoromethyl, 2,2,2-trifluoroethyl, 1-fluoromethyl-2-fluoroethyl, and the like. The alkyl part of the fluoroalkyl radical may be optionally substituted as defined above for an alkyl group.

"Halo," "halide," or, alternatively, "halogen" is intended to mean fluoro, chloro, bromo or iodo. The terms "haloalkyl," "haloalkenyl," "haloalkynyl," and "haloalkoxy" include alkyl, alkenyl, alkynyl and alkoxy structures that are substituted with one or more halo groups or with combinations thereof. For example, the terms "fluoroalkyl" and "fluoroalkoxy" include haloalkyl and haloalkoxy groups, respectively, in which the halo is fluorine.

"Heteroalkyl," "heteroalkenyl," and "heteroalkynyl" refer to optionally substituted alkyl, alkenyl and alkynyl radicals and which have one or more skeletal chain atoms selected from an atom other than carbon, e.g., oxygen, nitrogen, sulfur, phosphorus or combinations thereof. A numerical range may be given—e.g., $C_1$-$C_4$ heteroalkyl which refers to the chain length in total, which in this example is 4 atoms long. A heteroalkyl group may be substituted with one or more substituents which independently are: alkyl, heteroalkyl, alkenyl, alkynyl, acylsulfonamido, cycloalkyl, heterocycloalkyl, hydroxamate, aryl, arylalkyl, heteroaryl, heteroarylalkyl, hydroxy, halo, cyano, nitro, oxo, thioxo, trimethylsilanyl, —OR$^a$, —SR$^a$, —S(O)$_t$R$^a$— (where t is 1 or 2), —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Heteroalkylaryl" refers to an -(heteroalkyl)aryl radical where heteroalkyl and aryl are as disclosed herein and which are optionally substituted by one or more of the substituents described as suitable substituents for heteroalkyl and aryl, respectively.

"Heteroalkylheteroaryl" refers to an -(heteroalkyl)heteroaryl radical where heteroalkyl and heteroaryl are as disclosed herein and which are optionally substituted by one or more of the substituents described as suitable substituents for heteroalkyl and heteroaryl, respectively.

"Heteroalkylheterocycloalkyl" refers to an -(heteroalkyl) heterocycloalkyl radical where heteroalkyl and heterocycloalkyl are as disclosed herein and which are optionally substituted by one or more of the substituents described as suitable substituents for heteroalkyl and heterocycloalkyl, respectively.

"Heteroalkylcycloalkyl" refers to an -(heteroalkyl)cycloalkyl radical where heteroalkyl and cycloalkyl are as disclosed herein and which are optionally substituted by one or more of the substituents described as suitable substituents for heteroalkyl and cycloalkyl, respectively.

"Heteroaryl" or "heteroaromatic" or "HetAr" refers to a 5- to 18-membered aromatic radical (e.g., $C_5$-$C_{13}$ heteroaryl) that includes one or more ring heteroatoms selected from nitrogen, oxygen and sulfur, and which may be a monocyclic, bicyclic, tricyclic or tetracyclic ring system. Whenever it appears herein, a numerical range such as "5 to 18" refers to each integer in the given range—e.g., "5 to 18 ring atoms" means that the heteroaryl group may consist of 5 ring atoms, 6 ring atoms, etc., up to and including 18 ring atoms. Bivalent radicals derived from univalent heteroaryl radicals whose names end in "-yl" by removal of one hydrogen atom from the atom with the free valence are named by adding "-idene" to the name of the corresponding univalent radical—e.g., a pyridyl group with two points of attachment is a pyridylidene. A N-containing "heteroaromatic" or "heteroaryl" moiety refers to an aromatic group in which at least one of the skeletal atoms of the ring is a nitrogen atom. The polycyclic heteroaryl group may be fused or non-fused. The heteroatom(s) in the heteroaryl radical are optionally oxidized. One or more nitrogen atoms, if present, are optionally quaternized. The heteroaryl may be attached to the rest of the molecule through any atom of the ring(s). Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzoxazolyl, benzopyranyl, benzopyranonyl, benzofuranyl, benzofuranonyl, benzofurazanyl, benzothiazolyl, benzothienyl(benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furazanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, isoxazol-3-one, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyranyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, thiapyranyl, triazolyl, tetrazolyl, triazinyl, thieno[2,3-d]pyrimidinyl, thieno[3,2-d]pyrimidinyl, thieno[2,3-c]pyridinyl, and thiophenyl (i.e. thienyl). Unless stated otherwise specifically in the specification, a heteroaryl moiety is optionally substituted by one or more substituents which are independently: alkyl, acylsulfonamido, heteroalkyl, alkenyl, alkynyl, cycloalkyl, heterocycloalkyl, hydroxamate, aryl, arylalkyl, heteroaryl, heteroarylalkyl, hydroxy, halo, cyano, nitro, oxo, thioxo, trimethylsilanyl, —$OR^a$, —$SR^a$, —$S(O)_tR^a$— (where t is 1 or 2), —OC(O)—$R^a$, —$N(R^a)_2$, —$C(O)R^a$, —$C(O)OR^a$, —$OC(O)N(R^a)_2$, —$C(O)N(R^a)_2$, —$N(R^a)C(O)OR^a$, —$N(R^a)C(O)R^a$, —$N(R^a)C(O)N(R^a)_2$, $N(R^a)C(NR^a)N(R^a)_2$, —$N(R^a)S(O)_tR^a$ (where t is 1 or 2), —$S(O)_tOR^a$ (where t is 1 or 2), —$S(O)_tN(R^a)_2$ (where t is 1 or 2), or $PO_3(R^a)_2$, where each $R^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

Substituted heteroaryl also includes ring systems substituted with one or more oxide (—O—) substituents, such as, for example, pyridinyl N-oxides.

"Heteroarylalkyl" refers to a moiety having an aryl moiety, as described herein, connected to an alkylene moiety, as described herein, wherein the connection to the remainder of the molecule is through the alkylene group.

"Heterocycloalkyl" refers to a stable 3- to 18-membered non-aromatic ring radical that comprises two to twelve carbon atoms and from one to six heteroatoms selected from nitrogen, oxygen and sulfur. Whenever it appears herein, a numerical range such as "3 to 18" refers to each integer in the given range—e.g., "3 to 18 ring atoms" means that the heterocycloalkyl group may consist of 3 ring atoms, 4 ring atoms, etc., up to and including 18 ring atoms. Unless stated otherwise specifically in the specification, the heterocycloalkyl radical is a monocyclic, bicyclic, tricyclic or tetracyclic ring system, which may include fused or bridged ring systems. The heteroatoms in the heterocycloalkyl radical may be optionally oxidized. One or more nitrogen atoms, if present, are optionally quaternized. The heterocycloalkyl radical is partially or fully saturated. The heterocycloalkyl may be attached to the rest of the molecule through any atom of the ring(s). Examples of such heterocycloalkyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, a heterocycloalkyl moiety is optionally substituted by one or more substituents which independently are: alkyl, acylsulfonamido, heteroalkyl, alkenyl, alkynyl, cycloalkyl, heterocycloalkyl, hydroxamate, aryl, arylalkyl, heteroaryl, heteroarylalkyl, hydroxy, halo, cyano, nitro, oxo, thioxo, trimethylsilanyl, —$OR^a$, —$SR^a$, —$S(O)_tR^a$— (where t is 1 or 2), —OC(O)—$R^a$, —$N(R^a)_2$, —$C(O)R^a$, —$C(O)OR^a$, —$OC(O)N(R^a)_2$, —$C(O)N(R^a)_2$, —$N(R^a)C(O)OR^a$, —$N(R^a)C(O)R^a$, —$N(R^a)C(O)N(R^a)_2$, $N(R^a)C(NR^a)N(R^a)_2$, —$N(R^a)S(O)_tR^a$ (where t is 1 or 2), —$S(O)_tOR^a$ (where t is 1 or 2), —$S(O)_tN(R^a)_2$ (where t is 1 or 2), or $PO_3(R^a)_2$, where each $R^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Heterocycloalkyl" also includes bicyclic ring systems wherein one non-aromatic ring, usually with 3 to 7 ring atoms, contains at least 2 carbon atoms in addition to 1-3 heteroatoms independently selected from oxygen, sulfur, and nitrogen, as well as combinations comprising at least one of the foregoing heteroatoms; and the other ring, usually with 3 to 7 ring atoms, optionally contains 1-3 heteroatoms independently selected from oxygen, sulfur, and nitrogen and is not aromatic.

"Hydroxamate" refers to the —$C(O)NR^aOR^a$ moiety, where each $R^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Nitro" refers to the —$NO_2$ radical.

"Oxa" refers to the —O— radical.

"Oxo" refers to the =O radical.

"Isomers" are different compounds that have the same molecular formula. "Stereoisomers" are isomers that differ only in the way the atoms are arranged in space—i.e., having a different stereochemical configuration. "Enantiomers" are a pair of stereoisomers that are non-superimposable mirror images of each other. A 1:1 mixture of a pair of enantiomers is a "racemic" mixture. The term "(±)" is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon can be specified by either (R) or (S). Resolved compounds whose absolute configuration is unknown can be designated (+) or (−) depending on the direction (dextro- or levorotatory) which they rotate plane polarized light at the wavelength of the sodium D line. Certain of the compounds described herein contain one or more asymmetric centers and can thus give rise to enantiomers, diastereomers, and other stereoisomeric forms that can be defined, in terms of absolute stereochemistry, as (R) or (S). The present chemical entities, pharmaceutical compositions and methods are meant to include all such possible isomers, including racemic mixtures, optically pure forms and intermediate mixtures. Optically active (R)- and (S)-isomers can be prepared using chiral synthons or chiral reagents, or resolved using conventional techniques. When the compounds described herein contain olefinic double bonds or other centers of geometric asymmetry, and unless specified otherwise, it is intended that the compounds include both E and Z geometric isomers.

"Enantiomeric purity" as used herein refers to the relative amounts, expressed as a percentage, of the presence of a specific enantiomer relative to the other enantiomer. For example, if a compound, which may potentially have an (R)- or an (S)-isomeric configuration, is present as a racemic mixture, the enantiomeric purity is about 50% with respect to either the (R)- or (S)-isomer. If that compound has one isomeric form predominant over the other, for example, 80% (S)-isomer and 20% (R)-isomer, the enantiomeric purity of the compound with respect to the (S)-isomeric form is 80%. The enantiomeric purity of a compound can be determined in a number of ways known in the art, including but not limited to chromatography using a chiral support, polarimetric measurement of the rotation of polarized light, nuclear magnetic resonance spectroscopy using chiral shift reagents which include but are not limited to lanthanide containing chiral complexes or Pirkle's reagents, or derivatization of a compounds using a chiral compound such as Mosher's acid followed by chromatography or nuclear magnetic resonance spectroscopy.

In some embodiments, the enantiomerically enriched composition has a higher potency with respect to therapeutic utility per unit mass than does the racemic mixture of that composition. Enantiomers can be isolated from mixtures by methods known to those skilled in the art, including chiral high pressure liquid chromatography (HPLC) and the formation and crystallization of chiral salts; or preferred enantiomers can be prepared by asymmetric syntheses. See, for example, Jacques, et al., *Enantiomers, Racemates and Resolutions*, Wiley Interscience, New York (1981); E. L. Eliel, *Stereochemistry of Carbon Compounds*, McGraw-Hill, New York (1962); and E. L. Eliel and S. H. Wilen, *Stereochemistry of Organic Compounds*, Wiley-Interscience, New York (1994).

The terms "enantiomerically enriched" and "non-racemic," as used herein, refer to compositions in which the percent by weight of one enantiomer is greater than the amount of that one enantiomer in a control mixture of the racemic composition (e.g., greater than 1:1 by weight). For example, an enantiomerically enriched preparation of the (S)-enantiomer, means a preparation of the compound having greater than 50% by weight of the (S)-enantiomer relative to the (R)-enantiomer, such as at least 75% by weight, or such as at least 80% by weight. In some embodiments, the enrichment can be significantly greater than 80% by weight, providing a "substantially enantiomerically enriched" or a "substantially non-racemic" preparation, which refers to preparations of compositions which have at least 85% by weight of one enantiomer relative to other enantiomer, such as at least 90% by weight, or such as at least 95% by weight. The terms "enantiomerically pure" or "substantially enantiomerically pure" refers to a composition that comprises at least 98% of a single enantiomer and less than 2% of the opposite enantiomer.

"Moiety" refers to a specific segment or functional group of a molecule. Chemical moieties are often recognized chemical entities embedded in or appended to a molecule.

"Tautomers" are structurally distinct isomers that interconvert by tautomerization. "Tautomerization" is a form of isomerization and includes prototropic or proton-shift tautomerization, which is considered a subset of acid-base chemistry. "Prototropic tautomerization" or "proton-shift tautomerization" involves the migration of a proton accompanied by changes in bond order, often the interchange of a single bond with an adjacent double bond. Where tautomerization is possible (e.g., in solution), a chemical equilibrium of tautomers can be reached. An example of tautomerization is keto-enol tautomerization. A specific example of keto-enol tautomerization is the interconversion of pentane-2,4-dione and 4-hydroxypent-3-en-2-one tautomers. Another example of tautomerization is phenol-keto tautomerization. A specific example of phenol-keto tautomerization is the interconversion of pyridin-4-ol and pyridin-4(1H)-one tautomers.

A "leaving group or atom" is any group or atom that will, under selected reaction conditions, cleave from the starting material, thus promoting reaction at a specified site. Examples of such groups, unless otherwise specified, include halogen atoms and mesyloxy, p-nitrobenzensulphonyloxy and tosyloxy groups.

"Protecting group" is intended to mean a group that selectively blocks one or more reactive sites in a multifunctional compound such that a chemical reaction can be carried out selectively on another unprotected reactive site and the group can then be readily removed or deprotected after the selective reaction is complete. A variety of protecting groups are disclosed, for example, in T. H. Greene and P. G. M. Wuts, *Protective Groups in Organic Synthesis,* 3rd Edition, John Wiley & Sons, New York (1999).

"Solvate" refers to a compound in physical association with one or more molecules of a pharmaceutically acceptable solvent.

"Substituted" means that the referenced group may have attached one or more additional groups, radicals or moieties individually and independently selected from, for example, acyl, alkyl, alkylaryl, cycloalkyl, aralkyl, aryl, carbohydrate, carbonate, heteroaryl, heterocycloalkyl, hydroxamate, hydroxy, alkoxy, aryloxy, mercapto, alkylthio, arylthio, cyano, halo, carbonyl, ester, thiocarbonyl, isocyanato, thiocyanato, isothiocyanato, nitro, oxo, perhaloalkyl, perfluoroalkyl, phosphate, silyl, sulfinyl, sulfonyl, sulfonamidyl, sulfoxyl, sulfonate, urea, and amino, including mono- and di-substituted amino groups, and protected derivatives thereof. The substituents themselves may be substituted, for example, a cycloalkyl substituent may itself have a halide substituent at one or more of its ring carbons. The term "optionally substituted" means optional substitution with the specified groups, radicals or moieties.

"Sulfanyl" refers to groups that include —S-(optionally substituted alkyl), —S-(optionally substituted aryl), —S-(optionally substituted heteroaryl) and —S-(optionally substituted heterocycloalkyl).

"Sulfinyl" refers to groups that include —S(O)—H, —S(O)-(optionally substituted alkyl), —S(O)-(optionally substituted amino), —S(O)-(optionally substituted aryl), —S(O)-(optionally substituted heteroaryl) and —S(O)-(optionally substituted heterocycloalkyl).

"Sulfonyl" refers to groups that include —$S(O_2)$—H, —$S(O_2)$-(optionally substituted alkyl), —$S(O_2)$-(optionally substituted amino), —$S(O_2)$-(optionally substituted aryl), —$S(O_2)$-(optionally substituted heteroaryl), and —$S(O_2)$-(optionally substituted heterocycloalkyl).

"Sulfonamidyl" or "sulfonamido" refers to a —$S(=O)_2$—NRR radical, where each R is selected independently from the group consisting of hydrogen, alkyl, cycloalkyl, aryl, heteroaryl (bonded through a ring carbon) and heteroalicyclic (bonded through a ring carbon). The R groups in —NRR of the —$S(=O)_2$—NRR radical may be taken together with the nitrogen to which it is attached to form a 4-, 5-, 6- or 7-membered ring. A sulfonamido group is optionally substituted by one or more of the substituents described for alkyl, cycloalkyl, aryl, heteroaryl, respectively.

"Sulfoxyl" refers to a —$S(=O)_2OH$ radical.

"Sulfonate" refers to a —$S(=O)_2$—OR radical, where R is selected from the group consisting of alkyl, cycloalkyl, aryl, heteroaryl (bonded through a ring carbon) and heteroalicyclic (bonded through a ring carbon). A sulfonate group is optionally substituted on R by one or more of the substituents described for alkyl, cycloalkyl, aryl, heteroaryl, respectively.

Compounds of the invention also include crystalline and amorphous forms of those compounds, including, for example, polymorphs, pseudopolymorphs, solvates, hydrates, unsolvated polymorphs (including anhydrates), conformational polymorphs, and amorphous forms of the compounds, as well as mixtures thereof. "Crystalline form" and "polymorph" are intended to include all crystalline and amorphous forms of the compound, including, for example, polymorphs, pseudopolymorphs, solvates, hydrates, unsolvated polymorphs (including anhydrates), conformational polymorphs, and amorphous forms, as well as mixtures thereof, unless a particular crystalline or amorphous form is referred to.

p38 Mitogen-Activated Protein Kinases (MAPKs), Inhibition Thereof, and p38α Selective Inhibition The p38 mitogen-activated protein kinase (MAPKs) family of stress- and cytokine-activated kinases contribute to the pathogenesis of many human diseases, including cancer, rheumatoid arthritis, cardiovascular disease, multiple sclerosis, inflammatory bowel disease, chronic obstructive pulmonary disease (COPD), asthma, acute respiratory distress syndrome (ARDS), and acute lung injury (ALI). Among the many important biological processes regulated by p38 MAPKs, regulation of endothelial and epithelial barrier function, leukocyte trafficking, and cytokine expression are central to the pathogenesis of acute and chronic inflammatory disorders. While preclinical studies support pharmacologic inhibition of p38 as promising treatment for inflammatory diseases, p38 inhibitors have had very limited success in clinical testing because of dose-limiting toxicity and lack of efficacy. Of the 36 Phase II clinical trials of p38 inhibitors listed in www.clinicaltrials.gov, results of only 8 studies have been published or listed in ClinicalTrials.gov and showed little clinical benefit and moderate toxicity.

All available p38 inhibitors block catalytic activity either by directly competing for ATP binding or by allosterically causing conformational changes that preclude access of ATP to the catalytic site. Davidson et al. identified a purported p38α substrate-selective inhibitor, CMPD1, which selectively inhibited MK2 phosphorylation in in vitro kinase assays, but it bound near the p38α active site and was subsequently shown to lack substrate-selectivity in cells. Almost all available inhibitors are active against both p38α and p38β, and some are active against additional isoforms. Yet genetic and pharmacologic studies have identified p38α as the proinflammatory isoform, while other studies have demonstrated p38β signaling to be cytoprotective. Therefore, inhibition of p38β may contribute to both lack of efficacy and toxicity of non-isoform-selective p38 inhibitors. However, the extensive structural conservation of the catalytic module across most protein kinases presents a challenge to developing catalytic inhibitors with high selectivity, especially for individual p38 isoforms.

Even if the catalytic inhibitors were absolutely selective for p38α, these compounds by design would block all p38α signaling events, many of which are essential for reestablishing and maintaining homeostasis. For example, p38α not only activates expression of proinflammatory cytokines, it also activates anti-inflammatory cytokines and counterregulatory dual specificity protein phosphatase-2 (DUSP2) through the p38α substrate, MSK1/2. The transient decrease and subsequent rebound of serum C-reactive protein (CRP) levels seen in clinical trials of p38 catalytic inhibitors might be caused by loss of the MSK1/2-dependent anti-inflammatory signaling.

As an alternative to the catalytic inhibitors, the compounds and methods of the invention target the substrate binding groove of p38α, which stretches between two acidic patches, the CD and ED domains, and is distinct from the DEF substrate-binding pocket. Downstream substrates, upstream activating kinases, and possibly scaffolding molecules, all interact with p38 through these sites. Computer-aided drug design (CADD) was used in order to target low molecular weight compounds to a pocket near the p38α ED substrate binding site, which is required for phosphorylation of MAPK-activated protein kinase-2 (MAPKAPK2; MK2), a p38α substrate known to mediate endothelial permeability and neutrophil transendothelial migration (TEM) in vitro, and pulmonary edema in a mouse lung injury model; whereas anti-inflammatory MSK1/2 binds to the CD site. Using this algorithm, p38α-binding compounds with high efficiency were identified, including the lead compound UM101 that selectively bounds p38α and not p38β, stabilizes endothelial barrier function in human lung microvascular endothelial cells (HMVECLs), inhibits LPS-induced proinflammatory gene expression in THP1 cells, and is well tolerated and more potent than SB203580 in mitigating experimental ALI.

Acute Lung Injury Treated by the p38α MAPK Inhibitors and Methods Described Herein Acute respiratory distress syndrome (ARDS) is a common cause of respiratory failure, which has 30-40% mortality and no effective therapeutic options. p38 signaling is important in ARDS pathogenesis, but clinical trials of p38 inhibitors, all of which inactivate the p38 catalytic site and block phosphorylation of all p38 substrates, have been disappointing due to dose-limiting toxicity.

Acute respiratory distress syndrome (ARDS) is characterized by acute onset of non-hydrostatic pulmonary edema caused predominantly by neutrophil-mediated injury to the alveolar epithelium and capillary endothelial barrier dysfunction. A complex network of pro- and anti-inflammatory mediators activated in association with ARDS is critical to the pathogenesis of acute lung injury (ALI) as well as the multiple organ failure that often accompanies ARDS. However, therapeutic agents that target proinflammatory mediators have proven to be ineffective in ARDS. Injury to lung parenchyma causes reduced compliance, intrapulmonary shunting, and mismatched ventilation-perfusion that usually necessitates mechanical ventilation. However, the cyclical recruitment/de-recruitment of alveoli and overdistension caused by mechanical ventilation can itself cause neutrophil-dependent inflammation and lung injury even to previously normal lungs. Appreciation of this mechanism led to a Phase III randomized clinical trial demonstrating that mechanical ventilation with low tidal volumes improves survival in patients with ARDS. Two additional supportive maneuvers have been shown to improve mortality in patients with severe ARDS, neuromuscular blockade and prone positioning. A third intervention, conservative fluid management, was shown to decrease duration of mechanical ventilation and ICU length of stay, but not mortality. Despite these improvements in supportive care, mortality in patients with ARDS remains 30-40% with about 74,500 deaths per year in the United States, underscoring the importance of developing new therapeutics that target the relevant pathogenic mechanisms.

The p38 mitogen-activated protein kinases (MAPKs) are a family of stress- and cytokine-activated kinases that are activated by many of the pathogenic signals associated with ARDS, including inflammatory mediators, febrile-range hyperthermia (FRH), and cyclic stretch. Since p38 MAPK is activated in patients at-risk for ARDS and, as discussed below, p38 MAPK participates in multiple processes that contribute to the pathogenesis of ARDS, this family of MAPKs presents an intriguing therapeutic target in ARDS. As proof of this concept, the prototypical pyridinyl imidazole compound SB203580, which inhibits kinase activity of p38α and p, but not p387 or 6 has been shown to block multiple processes that contribute to the pathogenesis of ARDS. Endothelial p38 signaling is activated by neutrophil binding and required for neutrophil transendothelial migration (TEM). Cross-linking ICAM-1 on human umbilical vein endothelial cells (HUVECs) stimulates p38α activation, HSP27 phosphorylation, F-actin rearrangement, ICAM-1 aggregation, and cell stiffening, and increases migration of neutrophils to HUVEC intercellular junctions, all of which is blocked by SB203580. Cross-linking E-selectin on HUVECs activates p38 and p38-dependent cytoskeleton rearrangement, stress fiber formation and neutrophil TEM. Similarly, ICAM-1 ligation of 82 integrins on neutrophils activates neutrophil p38 and p38-dependent chemokinesis and chemotaxis. Pretreatment with p38 inhibitor was protective in a mouse model of ventilator-induced lung injury, complement-induced lung injury, and lung injury associated with a cecal-ligation and puncture model of sepsis, but not hemorrhage and endotoxemia-induced lung injury. Our own laboratory has shown that the exaggerated endothelial barrier dysfunction caused by FRH (2-3° C. increase in core temperature) in experimental ALI is associated with p38 activation and blocked by SB203580. The effectiveness of SB203580 in mitigating multiple pathogenic processes that contribute to acute lung injury and the relatively high expression of p38α and R in human lung supports a central role for these two p38 isoforms in the pathogenesis of ARDS.

Despite these persuasive preclinical data there has been only one clinical trial that begins to evaluate p38 inhibition as a therapeutic strategy in ARDS. This early phase IIa trial of SB-681323/dilmapimod in patients at-risk for ARDS (clinicaltrials.gov no. NCT00996840) showed dilmapimod was safe at the doses administered and modestly reduced serum C-reactive protein (CRP) levels, but was not powered to analyze effects on ARDS incidence or severity. There are currently a total of 74 clinical trials of p38 inhibitors listed in www.clinicaltrials.gov, including 26 Phase I, 47 Phase II, and one Phase III trial. Phase II and III trials tested safety and efficacy of ten different p38 catalytic inhibitors for 13 different disease/indications including analgesia (6 trials), osteoarthritis (2 trials), rheumatoid arthritis (13 trials), Alzheimer's disease (2 trials), ankylosing spondylitis (1 trial), cardiomyopathy (1 trial), psoriasis (2 trials), atherosclerosis (5 trials), depression (2 trials), COPD (8 trials), at-risk ARDS (1 trial), cancer (4 trials), and glomerulosclerosis (1 trial). Although only a portion of the data is in the public domain, the failure of most of these drugs seems to have been due to adverse side-effect profiles or lack of effectiveness at the doses used. Of the 48 Phase II and III trials 36 have been completed and 3 terminated early, but results of only 8 studies have been published or listed in ClinicalTrials.gov. Two trials of VX-702 in rheumatoid arthritis showed small increases in proportion of treated subjects with ACR20 symptom score vs. placebo. Of two published studies of p38 inhibitors for pain, one reported modest reduction in pain and the other no effect. Of two published studies of p38 inhibitors in COPD, one showed no effect and the other showed a 100 ml increase in FEV1 and a decrease in serum CRP levels in the treatment group, but with associated toxicity (rash, pharyngitis, prolonged QTc). GW85655 (losmapimod), improved vascular relaxation and reduced serum CRP in patients with hypercholesterolemia. In a ninth clinical trial, which was not listed in clinicaltrials.gov, BIRB 796 (doramapimod) had no clinical effect in patients with Crohn's disease but transiently reduced serum CRP levels. Collectively, these studies demonstrate the therapeutic potential of p38 inhibition in a broad range of human disease, but underscore the limited efficacy of the currently available p38 inhibitors at doses that can be safely administered to humans.

The p38 MAPKs, like most protein kinases, share a conserved bi-lobed structure and a catalytic site, with its hydrophobic ATP-binding pocket, located between the N-terminal and C-terminal lobes. Most available protein kinase inhibitors compete with ATP for binding to the ATP-binding pocket of the catalytic site, but the extensive structural conservation of the catalytic module across most protein kinases presents a challenge to developing catalytic p38 inhibitors with high specificity. Since the pyridinyl imidazole inhibitor SB203580 binds the ATP-binding site of p38α and p, but its access to the ATP binding site of p387 and 6 is blocked by a bulky methionine, it is used as a specific inhibitor of p38α and p. However, proteomic analysis identified several additional kinases that were inhibited by SB203580 with sub-micromolar $IC_{50}$, including Rip-like interacting caspase-like apoptosis-regulatory protein kinase (RICK/Rip2), casein kinase (CK)-16, and cyclin G-associated kinase (GAK).

A new class of diaryl urea compounds was discovered in a high throughput biochemical screen for p38 inhibitors. Rather than bind directly to the ATP binding pocket, these compounds bind to an allosteric site that induces a conformational change in p38 that precludes access of ATP to its binding pocket in the catalytic site. Three allosteric p38 inhibitors, BIRB 796/dormapimod, GW856553/losmapimod, and SB-681323/dilmapimod have entered clinical testing, but like the ATP-competitive, have not progressed beyond phase II testing except for the LATITUDE study, an ongoing Phase III trial of losmapimod in patients with acute coronary syndrome (clinicaltrials.gov no. NCT02145468). Since the allosteric inhibitors are not affected by the presence of the gatekeeper methionine, these compounds inhibit all four p38 isoforms, but BIRB 796 also potently inhibits Jnk2α2 with $IC_{50}$ of 0.1 μM and c-Raf-1 with $IC_{50}$ 1.4 μM. The lack of specificity of the ATP-competitive and allosteric p38 inhibitors is likely a major source of off-target toxicity.

An equally important source of p38 inhibitor toxicity likely derives from the broad range of functions of each p38 MAPK isoform. Since both types of inhibitors block the p38 catalytic site, the ATP-competitive and allosteric inhibitors block all p38 phosphorylation events. Since p38 phosphorylates at least 66 recognized substrates with important biological activity, dose-limiting toxicity may be unavoidable with these agents.

MAPK p38 and ERK family members share a structural feature, a substrate binding groove located on the C-terminal lobe of the protein on the side opposite the catalytic domain. The binding groove stretches between two acidic patches, the CD and ED domains. This region of p38 not only binds p38 substrates but also binds upstream kinases and scaffolding proteins. Our group has previously developed a new class of ERK1/2 MAPK inhibitors with improved toxicity profile by using computer-aided drug design (CADD) to identify small molecules that target the substrate binding groove rather than the catalytic module of ERK2. As described herein, a similar strategy may be employed to identify low molecular weight compounds targeting a pocket near the p38α ED substrate binding site, which is required for phosphorylation of MK2, a p38 substrate known to mediate pulmonary endothelial permeability in vitro and pulmonary edema in a mouse lung injury model. Using CADD to search a database of commercially available compounds, 150 low molecular weight compounds predicted to bind to the targeted pocket near the ED binding site of p38α target have been identified. Twenty structurally distinct compounds from this list were obtained, screened for selective binding to p38α but not ERK2 by differential scanning fluorimetry (DSF), then analyzed for capacity to reduce pathogenic endothelial barrier changes in human lung microvascular endothelial cells (HMVECLs) and cytokine expression in THP1 monocytes in vitro, and to mitigate ALI induced in mice. Of the 20 CADD-selected compounds tested, five bound to p38α with sufficient affinity to detect by DSF, two bound selectively to p38α but not ERK2 and were more effective than SB203580 in stabilizing endothelial barrier function in vitro, and one of these compounds was well tolerated and more potent than SB203580 in mitigating experimental ALI.

In certain embodiments, the p38α MAPK inhibitors described herein may be used in the treatment of acute respiratory distress syndrome (ARDS) and/or acute lung injury (ALI).

p38α MAPK Inhibitors and Methods of Inhibiting p38α MAPK

In an embodiment, the invention includes compounds that may be p38α MAPK inhibitors and/or modulators of p38α MAPK protein activity, for example compounds capable of binding to a pocket near the ED substrate-docking site of p38α MAPK, or a pharmaceutically acceptable salt, solvate, hydrate, cocrystal, or prodrug thereof. In one embodiment, the p38α MAPK inhibitor is a p38α MAPK selective inhibitor. In an embodiment, the p38α MAPK inhibitor binds p38α MAPK near the substrate binding groove of p38α MAPK, which stretches between two acidic patches, the CD and ED domains. In other embodiments, the p38α MAPK inhibitor causes inhibition of MK2 phosphorylation.

In one embodiment, a lead p38α MAPK inhibitor compound has been identified, that has favorable biological effects in human cell culture models and in a mouse model of inflammatory lung injury. In one embodiment, a p38α MAPK inhibitor has been identified by means of a CADD strategy. The CADD-targeted pocket in p38α differed from the corresponding pocket in p380 in 3 of 10 amino acids, which provided an opportunity for p38α-selectivity. In some embodiments, the sequence of the targeted pocket at least includes amino acids R49, H107, L108, and K165 in p38α MAPK. In some embodiments, the sequence of the targeted pocket is R49, H107, L108, M109, G110, A157, V158, E163, L164, and K165 in p38α MAPK.

In one embodiment, the p38α MAPK inhibitor is a compound of Formula 1 or Formula 2, or a pharmaceutically acceptable salt, solvate, hydrate, cocrystal, or prodrug thereof:

Formula 1

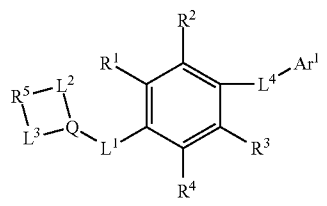

Formula 2

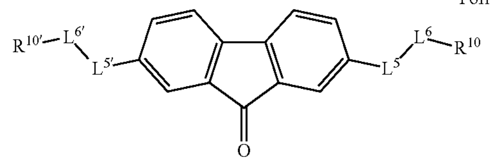

wherein in Formula 1 and Formula 2, Q is —CH— or N; each of $R^1$, $R^2$, $R^3$, and $R^4$ is independently hydrogen or optionally substituted alkyl, alkoxy, aryl, or heteroaryl; $R^5$ is —$SO_2$—, —CH(OH)—, —O—, or —$N(CH_3)$—; each of $R^{10}$ and $R^{10'}$ is independently —OH, —$NH_2$, or —SH; $L^1$ is —$CH_2$—, —$C(CH_3)_2$— or —$C(CH_2CH_2)$—; each of $L^2$ and $L^3$ is independently —$CH_2$—, —$CH_2CH_2$—, or —$CH_2CH_2CH_2$—; each of $L^4$, $L^5$, and $L^{5'}$ is independently —NHCO—, —CONH—, —$SO_2NH$—, —$NHSO_2$—, or —CH═CH—; each of $L^6$ and $L^{6'}$ is independently an optionally substituted $C_1$-$C_6$ alkyl chain; and $Ar^1$ is an optionally substituted aryl or heteroaryl ring. In some embodiments, $Ar^1$ is a six member ring.

In some embodiments, the p38α MAPK inhibitor is a compound of Formula 11, Formula 12, Formula 13, or Formula 14, or a pharmaceutically acceptable salt, solvate, hydrate, cocrystal, or prodrug thereof:

Formula 11

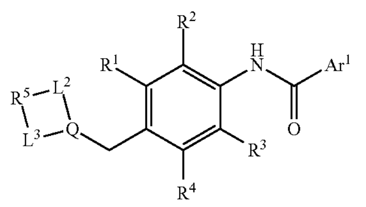

Formula 12

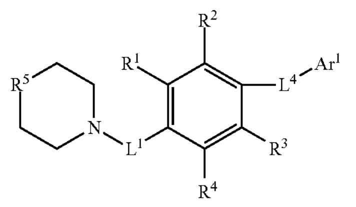

Formula 13

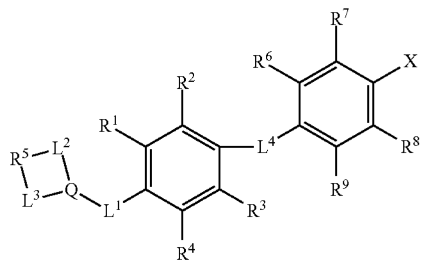

-continued

Formula 14

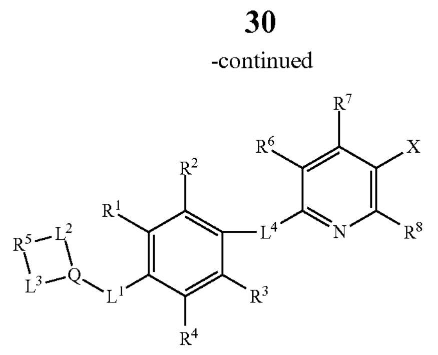

wherein in Formula 11, Formula 12, Formula 13, and Formula 14, Q is —CH— or N; each of $R^1$, $R^2$, $R^3$, $R^4$, $R^6$, $R^7$, $R^8$, and $R^9$ is independently hydrogen or optionally substituted alkyl, alkoxy, aryl, or heteroaryl; $R^5$ is —$SO_2$—, —CH(OH)—, —O—, or —$N(CH_3)$—; $L^1$ is —$CH_2$—, —$C(CH_3)_2$, or —$C(CH_2CH_2)$—; each of $L^2$ and $L^3$ is independently —$CH_2$—, —$CH_2CH_2$—, or —$CH_2CH_2CH_2$—; $L^4$ is —NHCO—, —CONH—, —$SO_2NH$—, —$NHSO_2$—, or —CH═CH—; $Ar^1$ is an optionally substituted aryl or heteroaryl ring; and X is a halogen. In some embodiments, $Ar^1$ is a six member ring.

In some embodiments, the p38α MAPK inhibitor is a compound of any one of Formulas 1001 to 1256 as defined in Table 1, or a pharmaceutically acceptable salt, solvate, hydrate, cocrystal, or prodrug thereof:

Formulas 1001 to 1256

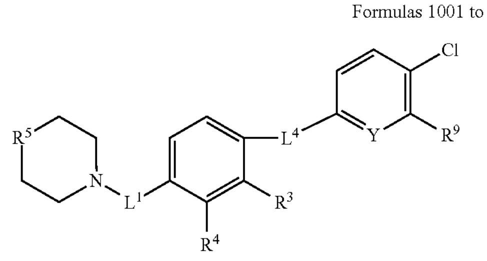

TABLE 1

| Formula | $R^3$ | $R^4$ | $R^5$ | $R^9$ | $L^1$ | $L^4$ | Y |
|---|---|---|---|---|---|---|---|
| 1001 | H | H | —$SO_2$— | H | —$CH_2$— | —NHCO— | CH |
| 1002 | —OEt | H | —$SO_2$— | H | —$CH_2$— | —NHCO— | CH |
| 1003 | H | Ph | —$SO_2$— | H | —$CH_2$— | —NHCO— | CH |
| 1004 | —OEt | Ph | —$SO_2$— | H | —$CH_2$— | —NHCO— | CH |
| 1005 | H | H | —$SO_2$— | H | —$C(CH_2CH_2)$— | —NHCO— | CH |
| 1006 | —OEt | H | —$SO_2$— | H | —$C(CH_2CH_2)$— | —NHCO— | CH |
| 1007 | H | Ph | —$SO_2$— | H | —$C(CH_2CH_2)$— | —NHCO— | CH |
| 1008 | —OEt | Ph | —$SO_2$— | H | —$C(CH_2CH_2)$— | —NHCO— | CH |
| 1009 | H | H | —$SO_2$— | 4-oxazolyl | —$CH_2$— | —NHCO— | CH |
| 1010 | —OEt | H | —$SO_2$— | 4-oxazolyl | —$CH_2$— | —NHCO— | CH |
| 1011 | H | Ph | —$SO_2$— | 4-oxazolyl | —$CH_2$— | —NHCO— | CH |
| 1012 | —OEt | Ph | —$SO_2$— | 4-oxazolyl | —$CH_2$— | —NHCO— | CH |
| 1013 | H | H | —$SO_2$— | 4-oxazolyl | —$C(CH_2CH_2)$— | —NHCO— | CH |
| 1014 | —OEt | H | —$SO_2$— | 4-oxazolyl | —$C(CH_2CH_2)$— | —NHCO— | CH |
| 1015 | H | Ph | —$SO_2$— | 4-oxazolyl | —$C(CH_2CH_2)$— | —NHCO— | CH |
| 1016 | —OEt | Ph | —$SO_2$— | 4-oxazolyl | —$C(CH_2CH_2)$— | —NHCO— | CH |
| 1017 | H | H | —CH(OH)— | H | —$CH_2$— | —NHCO— | CH |
| 1018 | —OEt | H | —CH(OH)— | H | —$CH_2$— | —NHCO— | CH |

TABLE 1-continued

| Formula | $R^3$ | $R^4$ | $R^5$ | $R^9$ | $L^1$ | $L^4$ | Y |
|---|---|---|---|---|---|---|---|
| 1019 | H | Ph | —CH(OH)— | H | $—CH_2—$ | —NHCO— | CH |
| 1020 | —OEt | Ph | —CH(OH)— | H | $—CH_2—$ | —NHCO— | CH |
| 1021 | H | H | —CH(OH)— | H | $—C(CH_2CH_2)—$ | —NHCO— | CH |
| 1022 | —OEt | H | —CH(OH)— | H | $—C(CH_2CH_2)—$ | —NHCO— | CH |
| 1023 | H | Ph | —CH(OH)— | H | $—C(CH_2CH_2)—$ | —NHCO— | CH |
| 1024 | —OEt | Ph | —CH(OH)— | H | $—C(CH_2CH_2)—$ | —NHCO— | CH |
| 1025 | H | H | —CH(OH)— | 4-oxazolyl | $—CH_2—$ | —NHCO— | CH |
| 1026 | —OEt | H | —CH(OH)— | 4-oxazolyl | $—CH_2—$ | —NHCO— | CH |
| 1027 | H | Ph | —CH(OH)— | 4-oxazolyl | $—CH_2—$ | —NHCO— | CH |
| 1028 | —OEt | Ph | —CH(OH)— | 4-oxazolyl | $—CH_2—$ | —NHCO— | CH |
| 1029 | H | H | —CH(OH)— | 4-oxazolyl | $—C(CH_2CH_2)—$ | —NHCO— | CH |
| 1030 | —OEt | H | —CH(OH)— | 4-oxazolyl | $—C(CH_2CH_2)—$ | —NHCO— | CH |
| 1031 | H | Ph | —CH(OH)— | 4-oxazolyl | $—C(CH_2CH_2)—$ | —NHCO— | CH |
| 1032 | —OEt | Ph | —CH(OH)— | 4-oxazolyl | $—C(CH_2CH_2)—$ | —NHCO— | CH |
| 1033 | H | H | —O— | H | $—CH_2—$ | —NHCO— | CH |
| 1034 | —OEt | H | —O— | H | $—CH_2—$ | —NHCO— | CH |
| 1035 | H | Ph | —O— | H | $—CH_2—$ | —NHCO— | CH |
| 1036 | —OEt | Ph | —O— | H | $—CH_2—$ | —NHCO— | CH |
| 1037 | H | H | —O— | H | $—C(CH_2CH_2)—$ | —NHCO— | CH |
| 1038 | —OEt | H | —O— | H | $—C(CH_2CH_2)—$ | —NHCO— | CH |
| 1039 | H | Ph | —O— | H | $—C(CH_2CH_2)—$ | —NHCO— | CH |
| 1040 | —OEt | Ph | —O— | H | $—C(CH_2CH_2)—$ | —NHCO— | CH |
| 1041 | H | H | —O— | 4-oxazolyl | $—CH_2—$ | —NHCO— | CH |
| 1042 | —OEt | H | —O— | 4-oxazolyl | $—CH_2—$ | —NHCO— | CH |
| 1043 | H | Ph | —O— | 4-oxazolyl | $—CH_2—$ | —NHCO— | CH |
| 1044 | —OEt | Ph | —O— | 4-oxazolyl | $—CH_2—$ | —NHCO— | CH |
| 1045 | H | H | —O— | 4-oxazolyl | $—C(CH_2CH_2)—$ | —NHCO— | CH |
| 1046 | —OEt | H | —O— | 4-oxazolyl | $—C(CH_2CH_2)—$ | —NHCO— | CH |
| 1047 | H | Ph | —O— | 4-oxazolyl | $—C(CH_2CH_2)—$ | —NHCO— | CH |
| 1048 | —OEt | Ph | —O— | 4-oxazolyl | $—C(CH_2CH_2)—$ | —NHCO— | CH |
| 1049 | H | H | $—N(CH_3)—$ | H | $—CH_2—$ | —NHCO— | CH |
| 1050 | —OEt | H | $—N(CH_3)—$ | H | $—CH_2—$ | —NHCO— | CH |
| 1051 | H | Ph | $—N(CH_3)—$ | H | $—CH_2—$ | —NHCO— | CH |
| 1052 | —OEt | Ph | $—N(CH_3)—$ | H | $—CH_2—$ | —NHCO— | CH |
| 1053 | H | H | $—N(CH_3)—$ | H | $—C(CH_2CH_2)—$ | —NHCO— | CH |
| 1054 | —OEt | H | $—N(CH_3)—$ | H | $—C(CH_2CH_2)—$ | —NHCO— | CH |
| 1055 | H | Ph | $—N(CH_3)—$ | H | $—C(CH_2CH_2)—$ | —NHCO— | CH |
| 1056 | —OEt | Ph | $—N(CH_3)—$ | H | $—C(CH_2CH_2)—$ | —NHCO— | CH |
| 1057 | H | H | $—N(CH_3)—$ | 4-oxazolyl | $—CH_2—$ | —NHCO— | CH |
| 1058 | —OEt | H | $—N(CH_3)—$ | 4-oxazolyl | $—CH_2—$ | —NHCO— | CH |
| 1059 | H | Ph | $—N(CH_3)—$ | 4-oxazolyl | $—CH_2—$ | —NHCO— | CH |
| 1060 | —OEt | Ph | $—N(CH_3)—$ | 4-oxazolyl | $—CH_2—$ | —NHCO— | CH |
| 1061 | H | H | $—N(CH_3)—$ | 4-oxazolyl | $—C(CH_2CH_2)—$ | —NHCO— | CH |
| 1062 | —OEt | H | $—N(CH_3)—$ | 4-oxazolyl | $—C(CH_2CH_2)—$ | —NHCO— | CH |
| 1063 | H | Ph | $—N(CH_3)—$ | 4-oxazolyl | $—C(CH_2CH_2)—$ | —NHCO— | CH |
| 1064 | —OEt | Ph | $—N(CH_3)—$ | 4-oxazolyl | $—C(CH_2CH_2)—$ | —NHCO— | CH |
| 1065 | H | H | $—SO_2—$ | H | $—CH_2—$ | —CH═CH— | CH |
| 1066 | —OEt | H | $—SO_2—$ | H | $—CH_2—$ | —CH═CH— | CH |
| 1067 | H | Ph | $—SO_2—$ | H | $—CH_2—$ | —CH═CH— | CH |
| 1068 | —OEt | Ph | $—SO_2—$ | H | $—CH_2—$ | —CH═CH— | CH |
| 1069 | H | H | $—SO_2—$ | H | $—C(CH_2CH_2)—$ | —CH═CH— | CH |
| 1070 | —OEt | H | $—SO_2—$ | H | $—C(CH_2CH_2)—$ | —CH═CH— | CH |
| 1071 | H | Ph | $—SO_2—$ | H | $—C(CH_2CH_2)—$ | —CH═CH— | CH |
| 1072 | —OEt | Ph | $—SO_2—$ | H | $—C(CH_2CH_2)—$ | —CH═CH— | CH |
| 1073 | H | H | $—SO_2—$ | 4-oxazolyl | $—CH_2—$ | —CH═CH— | CH |
| 1074 | —OEt | H | $—SO_2—$ | 4-oxazolyl | $—CH_2—$ | —CH═CH— | CH |
| 1075 | H | Ph | $—SO_2—$ | 4-oxazolyl | $—CH_2—$ | —CH═CH— | CH |
| 1076 | —OEt | Ph | $—SO_2—$ | 4-oxazolyl | $—CH_2—$ | —CH═CH— | CH |
| 1077 | H | H | $—SO_2—$ | 4-oxazolyl | $—C(CH_2CH_2)—$ | —CH═CH— | CH |
| 1078 | —OEt | H | $—SO_2—$ | 4-oxazolyl | $—C(CH_2CH_2)—$ | —CH═CH— | CH |
| 1079 | H | Ph | $—SO_2—$ | 4-oxazolyl | $—C(CH_2CH_2)—$ | —CH═CH— | CH |
| 1080 | —OEt | Ph | $—SO_2—$ | 4-oxazolyl | $—C(CH_2CH_2)—$ | —CH═CH— | CH |
| 1081 | H | H | —CH(OH)— | H | $—CH_2—$ | —CH═CH— | CH |
| 1082 | —OEt | H | —CH(OH)— | H | $—CH_2—$ | —CH═CH— | CH |
| 1083 | H | Ph | —CH(OH)— | H | $—CH_2—$ | —CH═CH— | CH |
| 1084 | —OEt | Ph | —CH(OH)— | H | $—CH_2—$ | —CH═CH— | CH |
| 1085 | H | H | —CH(OH)— | H | $—C(CH_2CH_2)—$ | —CH═CH— | CH |
| 1086 | —OEt | H | —CH(OH)— | H | $—C(CH_2CH_2)—$ | —CH═CH— | CH |
| 1087 | H | Ph | —CH(OH)— | H | $—C(CH_2CH_2)—$ | —CH═CH— | CH |
| 1088 | —OEt | Ph | —CH(OH)— | H | $—C(CH_2CH_2)—$ | —CH═CH— | CH |
| 1089 | H | H | —CH(OH)— | 4-oxazolyl | $—CH_2—$ | —CH═CH— | CH |
| 1090 | —OEt | H | —CH(OH)— | 4-oxazolyl | $—CH_2—$ | —CH═CH— | CH |
| 1091 | H | Ph | —CH(OH)— | 4-oxazolyl | $—CH_2—$ | —CH═CH— | CH |
| 1092 | —OEt | Ph | —CH(OH)— | 4-oxazolyl | $—CH_2—$ | —CH═CH— | CH |
| 1093 | H | H | —CH(OH)— | 4-oxazolyl | $—C(CH_2CH_2)—$ | —CH═CH— | CH |
| 1094 | —OEt | H | —CH(OH)— | 4-oxazolyl | $—C(CH_2CH_2)—$ | —CH═CH— | CH |
| 1095 | H | Ph | —CH(OH)— | 4-oxazolyl | $—C(CH_2CH_2)—$ | —CH═CH— | CH |
| 1096 | —OEt | Ph | —CH(OH)— | 4-oxazolyl | $—C(CH_2CH_2)—$ | —CH═CH— | CH |

TABLE 1-continued

| Formula | $R^3$ | $R^4$ | $R^5$ | $R^9$ | $L^1$ | $L^4$ | Y |
|---|---|---|---|---|---|---|---|
| 1097 | H | H | —O— | H | —$CH_2$— | —CH═CH— | CH |
| 1098 | —OEt | H | —O— | H | —$CH_2$— | —CH═CH— | CH |
| 1099 | H | Ph | —O— | H | —$CH_2$— | —CH═CH— | CH |
| 1100 | —OEt | Ph | —O— | H | —$CH_2$— | —CH═CH— | CH |
| 1101 | H | H | —O— | H | —$C(CH_2CH_2)$— | —CH═CH— | CH |
| 1102 | —OEt | H | —O— | H | —$C(CH_2CH_2)$— | —CH═CH— | CH |
| 1103 | H | Ph | —O— | H | —$C(CH_2CH_2)$— | —CH═CH— | CH |
| 1104 | —OEt | Ph | —O— | H | —$C(CH_2CH_2)$— | —CH═CH— | CH |
| 1105 | H | H | —O— | 4-oxazolyl | —$CH_2$— | —CH═CH— | CH |
| 1106 | —OEt | H | —O— | 4-oxazolyl | —$CH_2$— | —CH═CH— | CH |
| 1107 | H | Ph | —O— | 4-oxazolyl | —$CH_2$— | —CH═CH— | CH |
| 1108 | —OEt | Ph | —O— | 4-oxazolyl | —$CH_2$— | —CH═CH— | CH |
| 1109 | H | H | —O— | 4-oxazolyl | —$C(CH_2CH_2)$— | —CH═CH— | CH |
| 1110 | —OEt | H | —O— | 4-oxazolyl | —$C(CH_2CH_2)$— | —CH═CH— | CH |
| 1111 | H | Ph | —O— | 4-oxazolyl | —$C(CH_2CH_2)$— | —CH═CH— | CH |
| 1112 | —OEt | Ph | —O— | 4-oxazolyl | —$C(CH_2CH_2)$— | —CH═CH— | CH |
| 1113 | H | H | —$N(CH_3)$— | H | —$CH_2$— | —CH═CH— | CH |
| 1114 | —OEt | H | —$N(CH_3)$— | H | —$CH_2$— | —CH═CH— | CH |
| 1115 | H | Ph | —$N(CH_3)$— | H | —$CH_2$— | —CH═CH— | CH |
| 1116 | —OEt | Ph | —$N(CH_3)$— | H | —$CH_2$— | —CH═CH— | CH |
| 1117 | H | H | —$N(CH_3)$— | H | —$C(CH_2CH_2)$— | —CH═CH— | CH |
| 1118 | —OEt | H | —$N(CH_3)$— | H | —$C(CH_2CH_2)$— | —CH═CH— | CH |
| 1119 | H | Ph | —$N(CH_3)$— | H | —$C(CH_2CH_2)$— | —CH═CH— | CH |
| 1120 | —OEt | Ph | —$N(CH_3)$— | H | —$C(CH_2CH_2)$— | —CH═CH— | CH |
| 1121 | H | H | —$N(CH_3)$— | 4-oxazolyl | —$CH_2$— | —CH═CH— | CH |
| 1122 | —OEt | H | —$N(CH_3)$— | 4-oxazolyl | —$CH_2$— | —CH═CH— | CH |
| 1123 | H | Ph | —$N(CH_3)$— | 4-oxazolyl | —$CH_2$— | —CH═CH— | CH |
| 1124 | —OEt | Ph | —$N(CH_3)$— | 4-oxazolyl | —$CH_2$— | —CH═CH— | CH |
| 1125 | H | H | —$N(CH_3)$— | 4-oxazolyl | —$C(CH_2CH_2)$— | —CH═CH— | CH |
| 1126 | —OEt | H | —$N(CH_3)$— | 4-oxazolyl | —$C(CH_2CH_2)$— | —CH═CH— | CH |
| 1127 | H | Ph | —$N(CH_3)$— | 4-oxazolyl | —$C(CH_2CH_2)$— | —CH═CH— | CH |
| 1128 | —OEt | Ph | —$N(CH_3)$— | 4-oxazolyl | —$C(CH_2CH_2)$— | —CH═CH— | CH |
| 1129 | H | H | —$SO_2$— | H | —$CH_2$— | —NHCO— | N |
| 1130 | —OEt | H | —$SO_2$— | H | —$CH_2$— | —NHCO— | N |
| 1131 | H | Ph | —$SO_2$— | H | —$CH_2$— | —NHCO— | N |
| 1132 | —OEt | Ph | —$SO_2$— | H | —$CH_2$— | —NHCO— | N |
| 1133 | H | H | —$SO_2$— | H | —$C(CH_2CH_2)$— | —NHCO— | N |
| 1134 | —OEt | H | —$SO_2$— | H | —$C(CH_2CH_2)$— | —NHCO— | N |
| 1135 | H | Ph | —$SO_2$— | H | —$C(CH_2CH_2)$— | —NHCO— | N |
| 1136 | —OEt | Ph | —$SO_2$— | H | —$C(CH_2CH_2)$— | —NHCO— | N |
| 1137 | H | H | —$SO_2$— | 4-oxazolyl | —$CH_2$— | —NHCO— | N |
| 1138 | —OEt | H | —$SO_2$— | 4-oxazolyl | —$CH_2$— | —NHCO— | N |
| 1139 | H | Ph | —$SO_2$— | 4-oxazolyl | —$CH_2$— | —NHCO— | N |
| 1140 | —OEt | Ph | —$SO_2$— | 4-oxazolyl | —$CH_2$— | —NHCO— | N |
| 1141 | H | H | —$SO_2$— | 4-oxazolyl | —$C(CH_2CH_2)$— | —NHCO— | N |
| 1142 | —OEt | H | —$SO_2$— | 4-oxazolyl | —$C(CH_2CH_2)$— | —NHCO— | N |
| 1143 | H | Ph | —$SO_2$— | 4-oxazolyl | —$C(CH_2CH_2)$— | —NHCO— | N |
| 1144 | —OEt | Ph | —$SO_2$— | 4-oxazolyl | —$C(CH_2CH_2)$— | —NHCO— | N |
| 1145 | H | H | —CH(OH)— | H | —$CH_2$— | —NHCO— | N |
| 1146 | —OEt | H | —CH(OH)— | H | —$CH_2$— | —NHCO— | N |
| 1147 | H | Ph | —CH(OH)— | H | —$CH_2$— | —NHCO— | N |
| 1148 | —OEt | Ph | —CH(OH)— | H | —$CH_2$— | —NHCO— | N |
| 1149 | H | H | —CH(OH)— | H | —$C(CH_2CH_2)$— | —NHCO— | N |
| 1150 | —OEt | H | —CH(OH)— | H | —$C(CH_2CH_2)$— | —NHCO— | N |
| 1151 | H | Ph | —CH(OH)— | H | —$C(CH_2CH_2)$— | —NHCO— | N |
| 1152 | —OEt | Ph | —CH(OH)— | H | —$C(CH_2CH_2)$— | —NHCO— | N |
| 1153 | H | H | —CH(OH)— | 4-oxazolyl | —$CH_2$— | —NHCO— | N |
| 1154 | —OEt | H | —CH(OH)— | 4-oxazolyl | —$CH_2$— | —NHCO— | N |
| 1155 | H | Ph | —CH(OH)— | 4-oxazolyl | —$CH_2$— | —NHCO— | N |
| 1156 | —OEt | Ph | —CH(OH)— | 4-oxazolyl | —$CH_2$— | —NHCO— | N |
| 1157 | H | H | —CH(OH)— | 4-oxazolyl | —$C(CH_2CH_2)$— | —NHCO— | N |
| 1158 | —OEt | H | —CH(OH)— | 4-oxazolyl | —$C(CH_2CH_2)$— | —NHCO— | N |
| 1159 | H | Ph | —CH(OH)— | 4-oxazolyl | —$C(CH_2CH_2)$— | —NHCO— | N |
| 1160 | —OEt | Ph | —CH(OH)— | 4-oxazolyl | —$C(CH_2CH_2)$— | —NHCO— | N |
| 1161 | H | H | —O— | H | —$CH_2$— | —NHCO— | N |
| 1162 | —OEt | H | —O— | H | —$CH_2$— | —NHCO— | N |
| 1163 | H | Ph | —O— | H | —$CH_2$— | —NHCO— | N |
| 1164 | —OEt | Ph | —O— | H | —$CH_2$— | —NHCO— | N |
| 1165 | H | H | —O— | H | —$C(CH_2CH_2)$— | —NHCO— | N |
| 1166 | —OEt | H | —O— | H | —$C(CH_2CH_2)$— | —NHCO— | N |
| 1167 | H | Ph | —O— | H | —$C(CH_2CH_2)$— | —NHCO— | N |
| 1168 | —OEt | Ph | —O— | H | —$C(CH_2CH_2)$— | —NHCO— | N |
| 1169 | H | H | —O— | 4-oxazolyl | —$CH_2$— | —NHCO— | N |
| 1170 | —OEt | H | —O— | 4-oxazolyl | —$CH_2$— | —NHCO— | N |
| 1171 | H | Ph | —O— | 4-oxazolyl | —$CH_2$— | —NHCO— | N |
| 1172 | —OEt | Ph | —O— | 4-oxazolyl | —$CH_2$— | —NHCO— | N |
| 1173 | H | H | —O— | 4-oxazolyl | —$C(CH_2CH_2)$— | —NHCO— | N |
| 1174 | —OEt | H | —O— | 4-oxazolyl | —$C(CH_2CH_2)$— | —NHCO— | N |

TABLE 1-continued

| Formula | $R^3$ | $R^4$ | $R^5$ | $R^9$ | $L^1$ | $L^4$ | Y |
|---|---|---|---|---|---|---|---|
| 1175 | H | Ph | —O— | 4-oxazolyl | —C($CH_2CH_2$)— | —NHCO— | N |
| 1176 | —OEt | Ph | —O— | 4-oxazolyl | —C($CH_2CH_2$)— | —NHCO— | N |
| 1177 | H | H | —N($CH_3$)— | H | —$CH_2$— | —NHCO— | N |
| 1178 | —OEt | H | —N($CH_3$)— | H | —$CH_2$— | —NHCO— | N |
| 1179 | H | Ph | —N($CH_3$)— | H | —$CH_2$— | —NHCO— | N |
| 1180 | —OEt | Ph | —N($CH_3$)— | H | —$CH_2$— | —NHCO— | N |
| 1181 | H | H | —N($CH_3$)— | H | —C($CH_2CH_2$)— | —NHCO— | N |
| 1182 | —OEt | H | —N($CH_3$)— | H | —C($CH_2CH_2$)— | —NHCO— | N |
| 1183 | H | Ph | —N($CH_3$)— | H | —C($CH_2CH_2$)— | —NHCO— | N |
| 1184 | —OEt | Ph | —N($CH_3$)— | H | —C($CH_2CH_2$)— | —NHCO— | N |
| 1185 | H | H | —N($CH_3$)— | 4-oxazolyl | —$CH_2$— | —NHCO— | N |
| 1186 | —OEt | H | —N($CH_3$)— | 4-oxazolyl | —$CH_2$— | —NHCO— | N |
| 1187 | H | Ph | —N($CH_3$)— | 4-oxazolyl | —$CH_2$— | —NHCO— | N |
| 1188 | —OEt | Ph | —N($CH_3$)— | 4-oxazolyl | —$CH_2$— | —NHCO— | N |
| 1189 | H | H | —N($CH_3$)— | 4-oxazolyl | —C($CH_2CH_2$)— | —NHCO— | N |
| 1190 | —OEt | H | —N($CH_3$)— | 4-oxazolyl | —C($CH_2CH_2$)— | —NHCO— | N |
| 1191 | H | Ph | —N($CH_3$)— | 4-oxazolyl | —C($CH_2CH_2$)— | —NHCO— | N |
| 1192 | —OEt | Ph | —N($CH_3$)— | 4-oxazolyl | —C($CH_2CH_2$)— | —NHCO— | N |
| 1193 | H | H | —$SO_2$— | H | —$CH_2$— | —CH═CH— | N |
| 1194 | —OEt | H | —$SO_2$— | H | —$CH_2$— | —CH═CH— | N |
| 1195 | H | Ph | —$SO_2$— | H | —$CH_2$— | —CH═CH— | N |
| 1196 | —OEt | Ph | —$SO_2$— | H | —$CH_2$— | —CH═CH— | N |
| 1197 | H | H | —$SO_2$— | H | —C($CH_2CH_2$)— | —CH═CH— | N |
| 1198 | —OEt | H | —$SO_2$— | H | —C($CH_2CH_2$)— | —CH═CH— | N |
| 1199 | H | Ph | —$SO_2$— | H | —C($CH_2CH_2$)— | —CH═CH— | N |
| 1200 | —OEt | Ph | —$SO_2$— | H | —C($CH_2CH_2$)— | —CH═CH— | N |
| 1201 | H | H | —$SO_2$— | 4-oxazolyl | —$CH_2$— | —CH═CH— | N |
| 1202 | —OEt | H | —$SO_2$— | 4-oxazolyl | —$CH_2$— | —CH═CH— | N |
| 1203 | H | Ph | —$SO_2$— | 4-oxazolyl | —$CH_2$— | —CH═CH— | N |
| 1204 | —OEt | Ph | —$SO_2$— | 4-oxazolyl | —$CH_2$— | —CH═CH— | N |
| 1205 | H | H | —$SO_2$— | 4-oxazolyl | —C($CH_2CH_2$)— | —CH═CH— | N |
| 1206 | —OEt | H | —$SO_2$— | 4-oxazolyl | —C($CH_2CH_2$)— | —CH═CH— | N |
| 1207 | H | Ph | —$SO_2$— | 4-oxazolyl | —C($CH_2CH_2$)— | —CH═CH— | N |
| 1208 | —OEt | Ph | —$SO_2$— | 4-oxazolyl | —C($CH_2CH_2$)— | —CH═CH— | N |
| 1209 | H | H | —CH(OH)— | H | —$CH_2$— | —CH═CH— | N |
| 1210 | —OEt | H | —CH(OH)— | H | —$CH_2$— | —CH═CH— | N |
| 1211 | H | Ph | —CH(OH)— | H | —$CH_2$— | —CH═CH— | N |
| 1212 | —OEt | Ph | —CH(OH)— | H | —$CH_2$— | —CH═CH— | N |
| 1213 | H | H | —CH(OH)— | H | —C($CH_2CH_2$)— | —CH═CH— | N |
| 1214 | —OEt | H | —CH(OH)— | H | —C($CH_2CH_2$)— | —CH═CH— | N |
| 1215 | H | Ph | —CH(OH)— | H | —C($CH_2CH_2$)— | —CH═CH— | N |
| 1216 | —OEt | Ph | —CH(OH)— | H | —C($CH_2CH_2$)— | —CH═CH— | N |
| 1217 | H | H | —CH(OH)— | 4-oxazolyl | —$CH_2$— | —CH═CH— | N |
| 1218 | —OEt | H | —CH(OH)— | 4-oxazolyl | —$CH_2$— | —CH═CH— | N |
| 1219 | H | Ph | —CH(OH)— | 4-oxazolyl | —$CH_2$— | —CH═CH— | N |
| 1220 | —OEt | Ph | —CH(OH)— | 4-oxazolyl | —$CH_2$— | —CH═CH— | N |
| 1221 | H | H | —CH(OH)— | 4-oxazolyl | —C($CH_2CH_2$)— | —CH═CH— | N |
| 1222 | —OEt | H | —CH(OH)— | 4-oxazolyl | —C($CH_2CH_2$)— | —CH═CH— | N |
| 1223 | H | Ph | —CH(OH)— | 4-oxazolyl | —C($CH_2CH_2$)— | —CH═CH— | N |
| 1224 | —OEt | Ph | —CH(OH)— | 4-oxazolyl | —C($CH_2CH_2$)— | —CH═CH— | N |
| 1225 | H | H | —O— | H | —$CH_2$— | —CH═CH— | N |
| 1226 | —OEt | H | —O— | H | —$CH_2$— | —CH═CH— | N |
| 1227 | H | Ph | —O— | H | —$CH_2$— | —CH═CH— | N |
| 1228 | —OEt | Ph | —O— | H | —$CH_2$— | —CH═CH— | N |
| 1229 | H | H | —O— | H | —C($CH_2CH_2$)— | —CH═CH— | N |
| 1230 | —OEt | H | —O— | H | —C($CH_2CH_2$)— | —CH═CH— | N |
| 1231 | H | Ph | —O— | H | —C($CH_2CH_2$)— | —CH═CH— | N |
| 1232 | —OEt | Ph | —O— | H | —C($CH_2CH_2$)— | —CH═CH— | N |
| 1233 | H | H | —O— | 4-oxazolyl | —$CH_2$— | —CH═CH— | N |
| 1234 | —OEt | H | —O— | 4-oxazolyl | —$CH_2$— | —CH═CH— | N |
| 1235 | H | Ph | —O— | 4-oxazolyl | —$CH_2$— | —CH═CH— | N |
| 1236 | —OEt | Ph | —O— | 4-oxazolyl | —$CH_2$— | —CH═CH— | N |
| 1237 | H | H | —O— | 4-oxazolyl | —C($CH_2CH_2$)— | —CH═CH— | N |
| 1238 | —OEt | H | —O— | 4-oxazolyl | —C($CH_2CH_2$)— | —CH═CH— | N |
| 1239 | H | Ph | —O— | 4-oxazolyl | —C($CH_2CH_2$)— | —CH═CH— | N |
| 1240 | —OEt | Ph | —O— | 4-oxazolyl | —C($CH_2CH_2$)— | —CH═CH— | N |
| 1241 | H | H | —N($CH_3$)— | H | —$CH_2$— | —CH═CH— | N |
| 1242 | —OEt | H | —N($CH_3$)— | H | —$CH_2$— | —CH═CH— | N |
| 1243 | H | Ph | —N($CH_3$)— | H | —$CH_2$— | —CH═CH— | N |
| 1244 | —OEt | Ph | —N($CH_3$)— | H | —$CH_2$— | —CH═CH— | N |
| 1245 | H | H | —N($CH_3$)— | H | —C($CH_2CH_2$)— | —CH═CH— | N |
| 1246 | —OEt | H | —N($CH_3$)— | H | —C($CH_2CH_2$)— | —CH═CH— | N |
| 1247 | H | Ph | —N($CH_3$)— | H | —C($CH_2CH_2$)— | —CH═CH— | N |
| 1248 | —OEt | Ph | —N($CH_3$)— | H | —C($CH_2CH_2$)— | —CH═CH— | N |
| 1249 | H | H | —N($CH_3$)— | 4-oxazolyl | —$CH_2$— | —CH═CH— | N |
| 1250 | —OEt | H | —N($CH_3$)— | 4-oxazolyl | —$CH_2$— | —CH═CH— | N |
| 1251 | H | Ph | —N($CH_3$)— | 4-oxazolyl | —$CH_2$— | —CH═CH— | N |
| 1252 | —OEt | Ph | —N($CH_3$)— | 4-oxazolyl | —$CH_2$— | —CH═CH— | N |

TABLE 1-continued

| Formula | $R^3$ | $R^4$ | $R^5$ | $R^9$ | $L^1$ | $L^4$ | Y |
|---|---|---|---|---|---|---|---|
| 1253 | H | H | $—N(CH_3)—$ | 4-oxazolyl | $—C(CH_2CH_2)—$ | —CH═CH— | N |
| 1254 | —OEt | H | $—N(CH_3)—$ | 4-oxazolyl | $—C(CH_2CH_2)—$ | —CH═CH— | N |
| 1255 | H | Ph | $—N(CH_3)—$ | 4-oxazolyl | $—C(CH_2CH_2)—$ | —CH═CH— | N |
| 1256 | —OEt | Ph | $—N(CH_3)—$ | 4-oxazolyl | $—C(CH_2CH_2)—$ | —CH═CH— | N |

In some embodiments, the p38ac MAPK inhibitor is a compound of Formula UM101, or a compound of Formula UM60:

Formula UM101

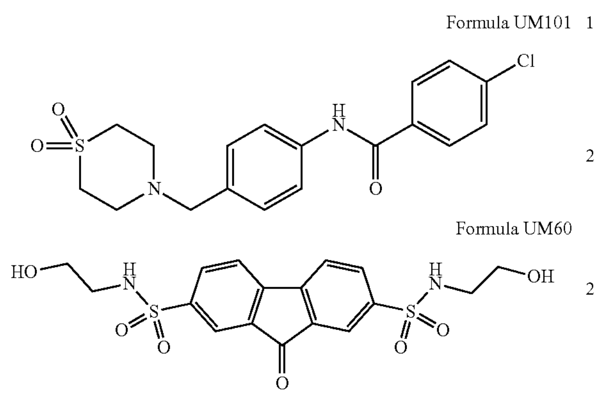

Formula UM60

Figures 3A, 3B, 3C, 3D, 3E, 3F, 3G, 3H, 3I, 3J, 3K:
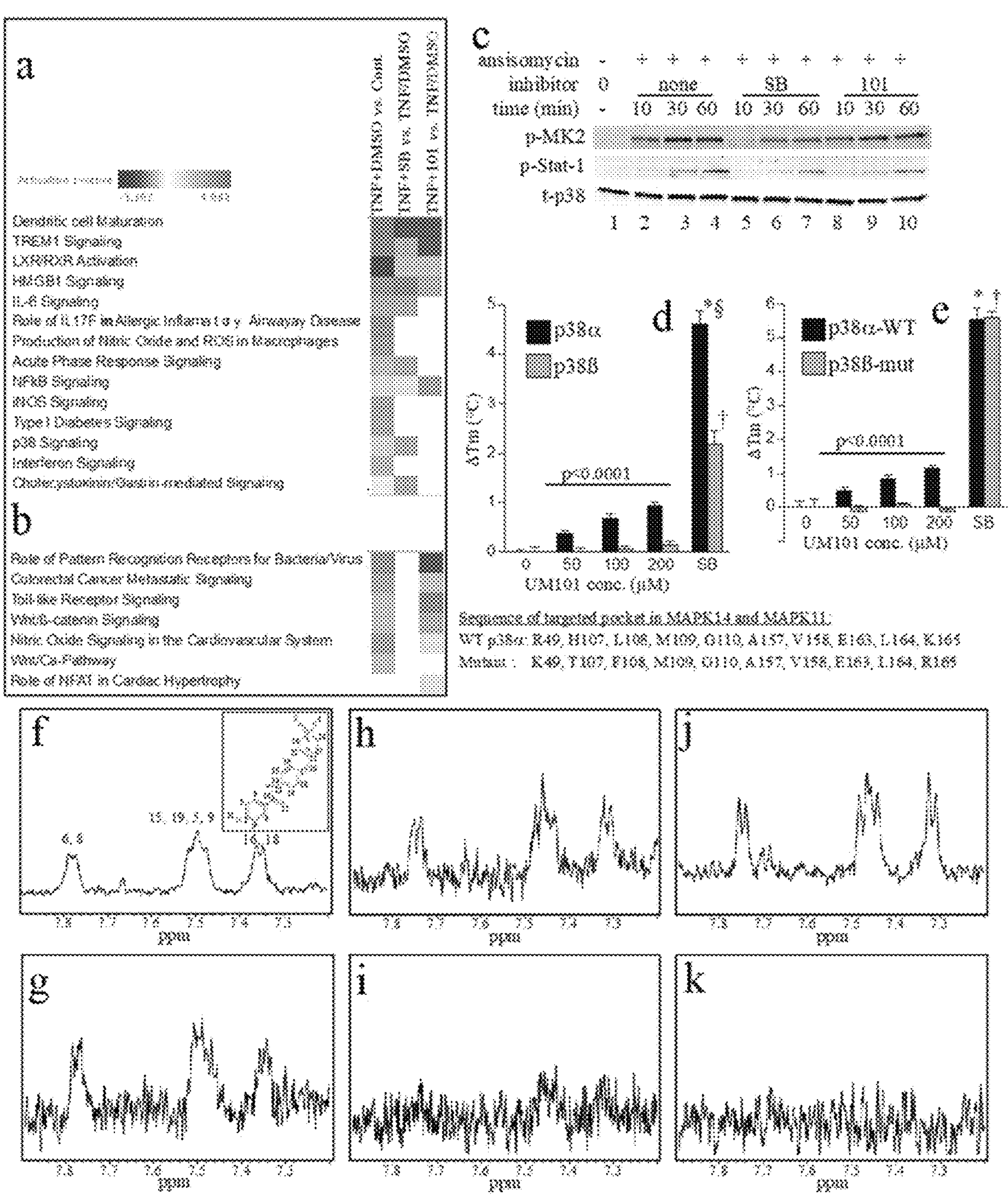
FIG. 3*a*-FIG. 3*k* illustrates the biochemical effects of substrate-selective p38 inhibitors.

Selective binding of UM101 to p38α was confirmed using complementary technologies. DSF, which detects ligand-induced protein stabilization showed UM101 to cause a concentration-dependent increase in melting temperature of p38α but not p380 (FIG. 3*d*). The smaller effect of UM101 compared with SB203580 on p38α melting suggests lower p38α binding affinity of substrate-selective vs. catalytic inhibitors, which is similar substrate-selective ERK inhibitors. The smaller effect of SB203580 on p380 than p38α is consistent with the known ~10-fold higher binding affinity of SB203580 for p38α. STD-NMR, which measures low affinity protein:ligand binding via non-scalar magnetization transfer from protein to ligand protons, confirmed specific UM101 binding to p38α and localized the interaction to its aromatic rings. UM101 binding to its CADD target was also confirmed by showing that mutating four of ten amino acids in the targeted pocket abrogated UM101 binding while SB203580 binding was preserved.

In some embodiments, the p38α MAPK inhibitor causes a concentration-dependent increase in melting temperature of p38α MAPK. The difference in melting temperature ΔTm (° C.) is measured at a p38α MAPK inhibitor concentration of between 1 nM and 1000 μM. In one embodiment, the difference in melting temperature ΔTm (° C.) is measured at a p38α MAPK inhibitor concentration of 100 μM. In one embodiment, ΔTm is between about 0.1 and about 2° C. In one embodiment, ΔTm is between about 0.01 and about 0.05° C. In one embodiment, ΔTm is between about 0.01 and about 0.1° C. In one embodiment, ΔTm is between about 0.03 and about 0.7° C. In one embodiment, ΔTm is between about 0.06 and about 1.5° C. In one embodiment, ΔTm is between about 1° C. and about 2° C. In one embodiment, ΔTm is between about 1.5 and about 2° C. In one embodiment, ΔTm is about 0.1° C. In one embodiment, ΔTm is about 0.2° C. In one embodiment, ΔTm is about 0.3° C. In one embodiment, ΔTm is about 0.4° C. In one embodiment, ΔTm is about 0.5° C. In one embodiment, ΔTm is about 0.6° C. In one embodiment, ΔTm is about 0.7° C. In one embodiment, ΔTm is about 0.8° C. In one embodiment, ΔTm is about 0.9° C. In one embodiment, ΔTm is about 1° C. In one embodiment, ΔTm is about 1.1° C. In one embodiment, ΔTm is about 1.2° C. In one embodiment, ΔTm is about 1.3° C. In one embodiment, ΔTm is about 1.4° C. In one embodiment, ΔTm is about 1.5° C. In one embodiment, ΔTm is about 1.6° C. In one embodiment, ΔTm is about 1.7° C. In one embodiment, ΔTm is about 1.8° C. In one embodiment, ΔTm is about 1.9° C. In one embodiment, ΔTm is about 2° C. In one embodiment, ΔTm is about 0.735° C. In one embodiment, ΔTm is about 0.667° C.

In some embodiments, the p38α MAPK inhibitor has a molecular weight (MW) between about 200 and about 2000 Da. In some embodiments, the p38α MAPK inhibitor has a molecular weight (MW) between about 200 and about 500 Da. In one embodiment, the p38α MAPK inhibitor has a MW between about 250 and about 450 Da. In one embodiment, the p38α MAPK inhibitor has a MW between about 300 and about 435 Da. In one embodiment, the p38α MAPK inhibitor has a MW of about 300 Da. In one embodiment, the p38α MAPK inhibitor has a MW of about 310 Da. In one embodiment, the p38α MAPK inhibitor has a MW of about 320 Da. In one embodiment, the p38α MAPK inhibitor has a MW of about 330 Da. In one embodiment, the p38α MAPK inhibitor has a MW of about 340 Da. In one embodiment, the p38α MAPK inhibitor has a MW of about 350 Da. In one embodiment, the p38α MAPK inhibitor has a MW of about 360 Da. In one embodiment, the p38α MAPK inhibitor has a MW of about 370 Da. In one embodiment, the p38α MAPK inhibitor has a MW of about 380 Da. In one embodiment, the p38α MAPK inhibitor has a MW of about 390 Da. In one embodiment, the p38α MAPK inhibitor has a MW of about 400 Da. In one embodiment, the p38α MAPK inhibitor has a MW of about 410 Da. In one embodiment, the p38α MAPK inhibitor has a MW of about 420 Da. In one embodiment, the p38α MAPK inhibitor has a MW of about 430 Da. In one embodiment, the p38α MAPK inhibitor has a MW of about 378 Da. In one embodiment, the p38α MAPK inhibitor has a MW of about 426 Da.

In some embodiments, the p38α MAPK inhibitor has a log P between about −5 and about 10. In some embodiments, the p38α MAPK inhibitor has a log P between about −3 and about 8. In some embodiments, the p38α MAPK inhibitor has a log P between about 0 and about 5. In some embodiments, the p38α MAPK inhibitor has a log P between about 0.1 and about 3. log P is a measure of drug solubility, and is defined as the logarithm of the octanol/water partition coefficient of the drug. In one embodiment, the p38α MAPK inhibitor has a log P between about 0.1 and about 1. In one embodiment, the p38α MAPK inhibitor has a log P between about 0.5 and about 1.5. In one embodiment, the p38α MAPK inhibitor has a log P between about 0.75 and about 2. In one embodiment, the p38α MAPK inhibitor has a log P between about 1 and about 2.5. In one embodiment, the p38α MAPK inhibitor has a log P between about 1.75 and about 3. In one embodiment, the p38α MAPK inhibitor has a log P of about 0.1. In one embodiment, the p38α MAPK inhibitor has a log P of about 0.25. In one embodiment, the p38α MAPK inhibitor has a log P of about 0.5. In one embodiment, the p38α MAPK inhibitor has a log P of about 0.75. In one embodiment, the p38α MAPK inhibitor has a log P of about 1. In one embodiment, the p38α MAPK inhibitor has a log P of about 1.25. In one embodiment, the p38α MAPK inhibitor has a log P of about 1.5. In one embodiment, the p38α MAPK inhibitor has a log P of about 1.75. In one embodiment, the p38α MAPK inhibitor has a log P of about 2. In one embodiment, the p38α MAPK inhibitor has a log P of about 2.25. In one embodiment, the p38α MAPK inhibitor has a log P of about 2.5. In one embodiment, the p38α MAPK inhibitor has a log P of about 2.75. In one embodiment, the p38α MAPK inhibitor has a log P of about 3. In one embodiment, the p38α MAPK inhibitor has a log P of about 0.28. In one embodiment, the p38α MAPK inhibitor has a log P of about 2.31.

Phosphorylation of MK2 requires binding to the ED site adjacent to the CADD target pocket in p38α MAPK. In some embodiments, the target pocket is at least defined by amino acids R49, H107, L108, and K165 in p38α MAPK. In some embodiments, the target pocket is defined by amino acids selected from the group consisting of R49, H107, L108, M109, G110, A157, V158, E163, L164, and K165 in p38α MAPK, and combinations thereof. In some embodiments, the target pocket is defined by the amino acids R49, H107, L108, M109, G110, A157, V158, E163, L164, and K165 in p38α MAPK. Western blotting confirmed partial inhibition of MK2 phosphorylation in anisomycin-stimulated HeLa cells by UM101, but less compared with 10 μM SB203580. SB203580 at a concentration 200- and 20-fold higher than the $IC_{50}$ for p38α and p380, respectively failed to completely block MK2 phosphorylation, which may reflect a contribution from p387 or 6 as both isoforms are expressed in HeLa cells.

In one embodiment, the invention relates to a method of inhibiting p38α MAPK where inhibiting p38α MAPK stabilizes an endothelial or epithelial barrier function. Both of the selective p38α binding compounds, UM60 and UM101, exerted SB203580-like endothelial-barrier-stabilizing and macrophage-cytokine-modifying effects, thereby validating the ED-targeting strategy. UM101 more effectively stabilized endothelial barriers than SB203580 (FIG. 2a and FIG. 2b) despite having less effect on MK2 phosphorylation. In one embodiment, endothelial barrier permeability can be measured by separate or combined exposure to TNFα and hyperthermia, followed by measurement of permeability for 10 kDa dextran. In one embodiment, endothelial barrier stabilization is assessed by pretreating with a compound of the invention, preceded and followed by permeability measurements, where stabilization is expressed as a % reduction in the before and after pretreatment permeability increase. Pretreatment with a p38α MAPK inhibitor can be done at various concentrations, for example at 10, 25, 50, or 100 μM. In one embodiment, the permeability increase for 10 kDa dextran can be reduced by between 5% to more than 100%. In one embodiment, the permeability increase is reduced by about 5%. In one embodiment, the permeability increase is reduced by about 10%. In one embodiment, the permeability increase is reduced by about 20%. In one embodiment, the permeability increase is reduced by about 30%. In one embodiment, the permeability increase is reduced by about 40%. In one embodiment, the permeability increase is reduced by about 50%. In one embodiment, the permeability increase is reduced by about 60%. In one embodiment, the permeability increase is reduced by about 70%. In one embodiment, the permeability increase is reduced by about 80%. In one embodiment, the permeability increase is reduced by about 90%. In one embodiment, the permeability increase is reduced by about 100%. In one embodiment, the permeability increase is reduced by about more than 100%. In one embodiment, the permeability increase is reduced by about 71%. In one embodiment, the permeability increase is reduced by about 74%. In one embodiment, the permeability increase is reduced by about 89%. In one embodiment, the permeability increase is reduced by about 100%.

Since UM101 more effectively stabilized endothelial barriers than SB203580 (FIG. 2a and FIG. 2b) despite having less effect on MK2 phosphorylation (FIG. 3c), additional molecular actions were evaluated by comparing the effects of UM101 and SB203580 on global gene expression using RNASeq in TNFα-treated HMVECLs. TNFα increased expression of 511 genes by ≥2-fold, of which 61 were reduced and 38 increased by pretreatment with 10 μM SB203580. Despite using a concentration of UM101 that was >10-fold higher than required to stabilize HMVECL barrier functions (FIG. 2a and FIG. 2b), UM101 modified expression of only 38 of the 99 SB203580-modified genes. PathwayNet analysis showed UM101 to block only 7 of the 15 SB203580-blocked transcription factors. MSK1/2 was among those spared by UM101, which is consistent with the targeting strategy for UM101 for the ED site, and in an advantageous way, given the anti-inflammatory actions of MSK1/2.

The partial functional overlap of UM101 and SB203580 revealed by RNASeq is consistent with the design of UM101 as a non-catalytic substrate-selective inhibitor, but might also be the result of off-target effects of SB203580, which include Receptor-interacting Protein Kinase-2, cyclin G-associated kinase, and casein kinase-1δ. However, none of the SB203580-inhibited transcription factors identified by the PathwayNet analysis are known substrates for these kinases as analyzed using PhosphoNetworks.

Although the high concentration of UM101 used in this initial analysis may have caused some p38-independent actions, the data described herein support a conclusion that UM101 exerts its biological effects predominantly by modifying p38α: (1) DSF and STD-NMR show p38α-specific binding of UM101; (2) p38α binding of UM101 was abrogated by mutating 4 of 10 target pocket amino acids; (3) UM60 and 101 both bind p38α and exert effects on endothelial function similar to SB203580; (4) UM101 partially blocked phosphorylation of the p38 substrates MK2 and Stat-1 in TNFα-stimulated HeLa cells; and (5) UM101 inhibited expression of about half the genes inhibited by SB203580. UM101 may be more effective than SB203580 in stabilizing endothelial barrier because of its selective sparing of potential counterregulatory genes, such as GM-CSF, MSK1/2-dependent anti-inflammatory genes, and p38β-dependent pro-survival genes.

In one embodiment, the invention relates to a method of inhibiting p38α MAPK, including contacting the p38α MAPK with a compound capable of binding to a pocket near the ED substrate-docking site of p38α MAPK, or a pharmaceutically acceptable salt, solvate, hydrate, cocrystal, or prodrug thereof. In one embodiment, the compound selectively inhibits p38α MAPK. In an embodiment, the p38α MAPK inhibitor binds p38α MAPK near the substrate binding groove of p38α MAPK, which stretches between two acidic patches, the CD and ED domains. In one embodiment, the binding pocket is defined at least by residues R49, H107, L108, and K165 in p38α MAPK. In one embodiment, the binding pocket is defined by residues R49, H107, L108, M109, G110, A157, V158, E163, L164, and K165 in p38α MAPK. In some embodiments, the p38α MAPK inhibitor causes a concentration-dependent increase in melting temperature of p38α MAPK. In other embodiments, the p38α MAPK inhibitor causes inhibition of MK2 phosphorylation. In one embodiment, the compound is of Formula 1 or Formula 2, or a pharmaceutically acceptable salt, solvate, hydrate, cocrystal, or prodrug thereof, wherein in Formula 1 and Formula 2, Q is —CH— or N; each of $R^1$, $R^2$, $R^3$, and $R^4$ is independently hydrogen or optionally substituted alkyl, alkoxy, aryl, or heteroaryl; $R^5$ is —$SO_2$—, —CH(OH)—, —O—, or —$N(CH_3)$—; each of $R^{10}$ and $R^{10'}$ is independently —OH, —$NH_2$, or —SH; $L^1$ is —$CH_2$—, —$C(CH_3)_2$, or —$C(CH_2CH_2)$—; each of $L^2$ and $L^3$ is independently —$CH_2$—, —$CH_2CH_2$—, or —$CH_2CH_2CH_2$—; each of $L^4$, $L^5$, and $L^{5'}$ is independently —NHCO—, —CONH—, —$SO_2NH$—, —$NHSO_2$—, or —CH═CH—; each of $L^6$ and $L^{6'}$ is independently an optionally substituted $C_1$-$C_6$ alkyl chain; and $Ar^1$ is an optionally substituted aryl or heteroaryl ring. In one embodiment, $Ar^1$ is a six member ring. In some embodiments, the compound is of Formula 11, Formula 12, Formula 13, or Formula 14, or a pharmaceutically acceptable salt, solvate, hydrate, cocrystal, or prodrug thereof, wherein in Formula 11, Formula 12, Formula 13, and Formula 14, Q is —CH— or N; each of $R^1$, $R^2$, $R^3$, $R^4$, $R^6$, $R^7$, $R^8$, and $R^9$ is independently hydrogen or optionally substituted alkyl, alkoxy, aryl, or heteroaryl; $R^5$ is —$SO_2$—, —CH(OH)—, —O—, or —$N(CH_3)$—; $L^1$ is —$CH_2$—, —$C(CH_3)_2$, or —$C(CH_2CH_2)$—; each of $L^2$ and $L^3$ is independently —$CH_2$—, —$CH_2CH_2$—, or —$CH_2CH_2CH_2$—; $L^4$ is —NHCO—, —CONH—, —$SO_2NH$—, —$NHSO_2$—, or —CH═CH—; $Ar^1$ is an optionally substituted aryl or heteroaryl ring; and X is a halogen. In some embodiments, the compound is of Formulas 1001 to 1256, or a pharmaceutically acceptable salt, solvate, hydrate, cocrystal, or prodrug thereof, wherein Formulas 1001 to 1256 are as defined in Table 1. In one embodiment, the compound is of Formula UM101, or a pharmaceutically acceptable salt, solvate, hydrate, cocrystal, or prodrug thereof, or of Formula UM60, or a pharmaceutically acceptable salt, solvate, hydrate, cocrystal, or prodrug thereof.

In one embodiment, the invention relates to a method of inhibiting p38α MAPK where inhibition of p38α MAPK does not result in loss of p38α-dependent counterregulatory responses. In some embodiments, the p38α-dependent counterregulatory response relates to mitogen- and stress-activated protein kinase-1 (MSK1), or MSK2. In targeting a pocket near the ED substrate-docking site of p38α, the inhibitors described herein avoid interfering with CD-specific substrates, including MSK1/2, thus limiting inflammation through expression of IL-10 and DUSP2. Among the effects of MSK1/2 deletion in mice is increased and prolonged LPS-induced expression of the CRP-regulator, IL-6, suggesting a possible mechanism of the rebound in serum CRP observed in some clinical trials of catalytic p38 inhibitors.

In one embodiment, the invention relates to a method of inhibiting p38α MAPK where inhibiting p38α MAPK reduces inflammation. In one embodiment, the effects of a p38α MAPK inhibitor on inflammatory cytokine expression are compared by pretreating PMA-differentiated THP1 cells with a p38α MAPK inhibitor, then stimulating with LPS, and harvesting RNA a period of time later for analysis by PCR-based cytokine array. In some embodiments, a p38α MAPK inhibitor inhibits expression of various genes, such as IL-1A, IL-8, TNFSF8, CXCL5, CCL7, CCL17, TNFSF9, IL-1B, CXCL1, TNFSF15, CCL5, CCL4, CCL20, CXCL2, TNF, or BMP6. In some embodiments, a p38α MAPK inhibitor inhibits expression of Smad3, which drives differentiation of Foxp3 T regulatory cells and suppresses interferon-gamma. The p38α MAPK inhibitor can be used in any appropriate concentration, for example 10, 25, 50, or 100 μM. In one embodiment, inflammation reduction is measured by comparing the fold change mRNA levels vs. unstimulated PMA-differentiated THP1 cells at various concentrations of p38α MAPK inhibitor.

In some embodiments, a p38α MAPK inhibitor modulates TNFα-induced gene expression in HMVECLs, as evidenced using RNASeq. In one embodiment, HMVECLs were pretreated for a period of time with a p38α MAPK inhibitor at an appropriate concentration, for example 10 μM or 100 μM, and then stimulated with TNFα for a period of time. A p38α MAPK inhibitor of the invention inhibits genes such as PRRG4, TSLP, CCL17, EXOC3L4, MMP9, IDO1, CXCL10, CD200, SLC15A3, VDR, IL1B, GPR88, CD207, TCHH, HAS3, GBP1P1, MUC4, ELOVL7, CXCL11, GBP4, PLA1A, or CXCL5.

Figures 2A, 2B, 2C, 2D:
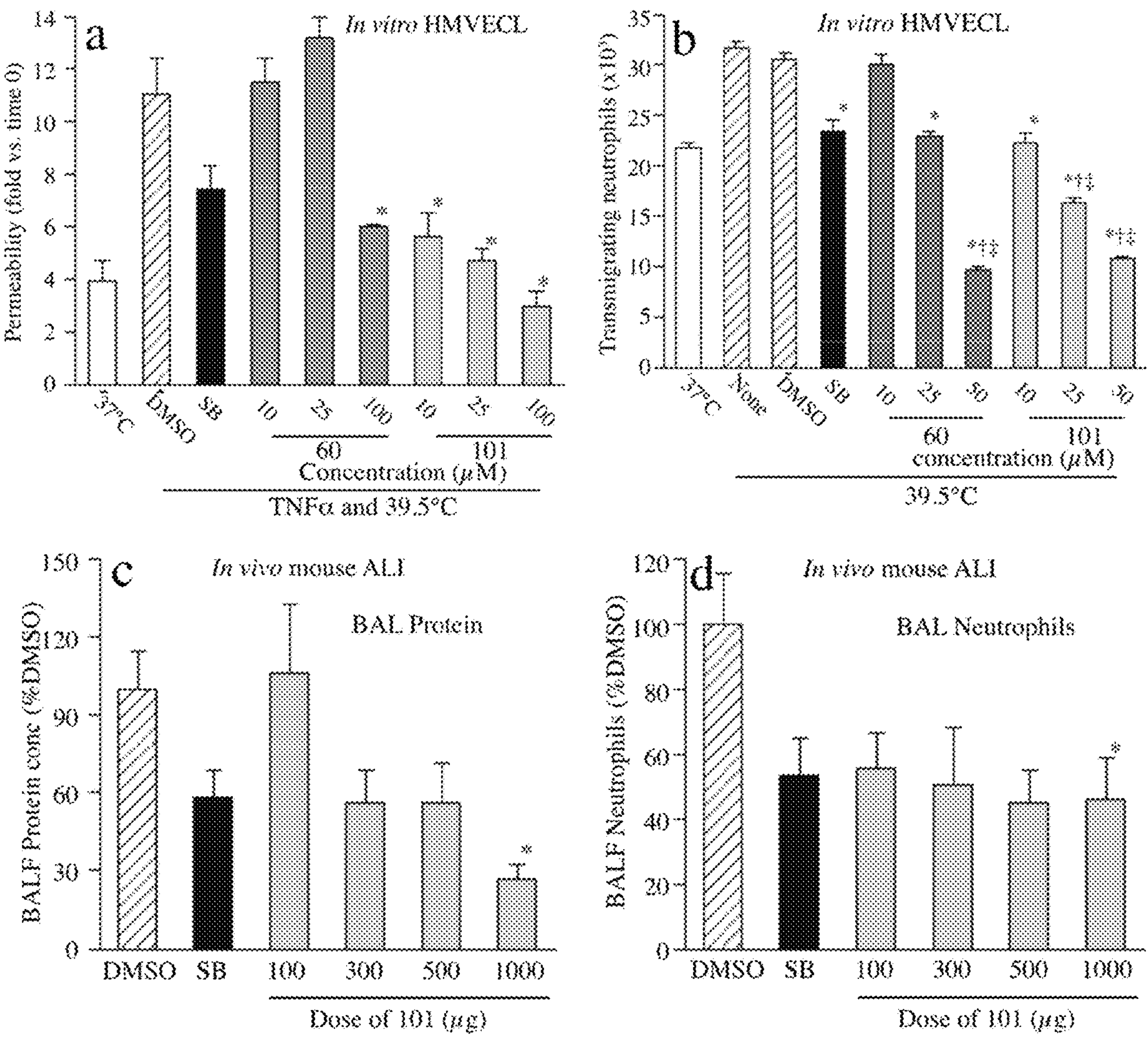
FIG. 2*a*-FIG. 2*d* illustrates the biological effects of p38 inhibitors.

In one embodiment, the invention relates to a method of inhibiting p38α MAPK where inhibiting p38α MAPK mitigates LPS-induced lung injury in a subject. In one embodiment, the effectiveness of a p38α MAPK inhibitor in mitigating transalveolar protein and neutrophil extravasation in a mouse model of LPS/hyperthermia-induced ALI was compared (FIG. 2*c* and FIG. 2*d*). In one embodiment, subjects receive intraperitoneal injection(s) of a p38α MAPK inhibitor at concentrations such as 100, 250, 300, 400, 500, 750, 1000 μg, or the like, in an appropriate carrier, for example DMSO, a period of time prior to intratracheal instillation of LPS, and/or transfer to hyperthermic chambers. Lung lavage from subjects are measured for protein and/or neutrophils. Compared with control subjects, lavage protein concentration and neutrophil content in subjects pretreated with a p38α MAPK inhibitor are reduced. In some embodiments, the reduction is between about 5% and about 100%. In one embodiment, the reduction is greater than about 5%. In one embodiment, the reduction is greater than about 10%. In one embodiment, the reduction is greater than about 20%. In one embodiment, the reduction is greater than about 30%. In one embodiment, the reduction is greater than about 40%. In one embodiment, the reduction is greater than about 50%. In one embodiment, the reduction is greater than about 60%. In one embodiment, the reduction is greater than about 70%. In one embodiment, the reduction is greater than about 80%. In one embodiment, the reduction is greater than about 90%. In one embodiment, the reduction is about 100%. In one embodiment, the reduction is less than about 10%. In one embodiment, the reduction is less than about 20%. In one embodiment, the reduction is less than about 30%. In one embodiment, the reduction is less than about 40%. In one embodiment, the reduction is less than about 50%. In one embodiment, the reduction is less than about 60%. In one embodiment, the reduction is less than about 70%. In one embodiment, the reduction is less than about 80%. In one embodiment, the reduction is less than about 90%. In one embodiment, the reduction is about 100%. In one embodiment, the reduction is about 44.1%. In one embodiment, the reduction is about 43.9%. In one embodiment, the reduction is about 92.9%. In one embodiment, the reduction is about 44.4%. In one embodiment, the reduction is about 49.5%. In one embodiment, the reduction is about 55.3%. In one embodiment, the reduction is about 54%.

In one embodiment, the invention relates to a method of inhibiting p38α MAPK where inhibiting p38α MAPK regulates leukocyte trafficking.

In one embodiment, the invention relates to a method of inhibiting p38α MAPK where inhibiting p38α MAPK regulates cytokine expression.

Methods of Treatment

The compounds and compositions described herein can be used in methods for treating diseases. In some embodiments, the compounds and compositions described herein can be used in methods for treating diseases associated with the up- and/or downregulation of the p38α MAPK protein.

In one embodiment, the invention relates to a method of treating a disease alleviated by inhibiting the p38α MAPK protein in a patient in need thereof, including administering to the patient a therapeutically effective amount of a p38α MAPK inhibitor, wherein the p38α MAPK inhibitor is a compound capable of binding to a pocket near the ED substrate-docking site of p38α MAPK, or a pharmaceutically acceptable salt, solvate, hydrate, cocrystal, or prodrug thereof. In one embodiment, the binding pocket is defined at least by residues R49, H107, L108, and K165 in p38α MAPK. In one embodiment, the binding pocket is defined by residues R49, H107, L108, M109, G110, A157, V158, E163, L164, and K165 in p38α MAPK. In one embodiment, the p38α MAPK inhibitor is a compound of Formula 1 or Formula 2, or a pharmaceutically acceptable salt, solvate, hydrate, cocrystal, or prodrug thereof, wherein in Formula 1 and Formula 2, Q is —CH— or N; each of $R^1$, $R^2$, $R^3$, and $R^4$ is independently hydrogen or optionally substituted alkyl, alkoxy, aryl, or heteroaryl; $R^5$ is —$SO_2$—, —CH(OH)—, —O—, or —$N(CH_3)$—; each of $R^{10}$ and $R^{10'}$ is independently —OH, —$NH_2$, or —SH; $L^1$ is —$CH_2$—, —$C(CH_3)_2$— or —$C(CH_2CH_2)$—; each of $L^2$ and $L^3$ is independently —$CH_2$—, —$CH_2CH_2$—, or —$CH_2CH_2CH_2$—; each of $L^4$, $L^5$, and $L^{5'}$ is independently —NHCO—, —CONH—, —$SO_2NH$—, —$NHSO_2$—, or —CH═CH—; each of $L^6$ and $L^{6'}$ is independently an optionally substituted $C_1$-$C_6$ alkyl chain; and $Ar^1$ is an optionally substituted aryl or heteroaryl ring. In one embodiment, $Ar^1$ is a six member ring. In one embodiment, the p38α MAPK inhibitor is a compound of Formula 11, Formula 12, Formula 13, or Formula 14, or a pharmaceutically acceptable salt, solvate, hydrate, cocrystal, or prodrug thereof, wherein in Formula 11, Formula 12, Formula 13, and Formula 14, Q is —CH— or N; each of $R^1$, $R^2$, $R^3$, $R^4$, $R^6$, $R^7$, $R^8$, and $R^9$ is independently hydrogen or optionally substituted alkyl, alkoxy, aryl, or heteroaryl; $R^5$ is —$SO_2$—, —CH(OH)—, —O—, or —$N(CH_3)$—; $L^1$ is —$CH_2$—, —$C(CH_3)_2$, or —$C(CH_2CH_2)$—; each of $L^2$ and $L^3$ is independently —$CH_2$—, —$CH_2CH_2$—, or —$CH_2CH_2CH_2$—; $L^4$ is —NHCO—, —CONH—, —$SO_2NH$—, —$NHSO_2$—, or —CH═CH—; $Ar^1$ is an optionally substituted aryl or heteroaryl ring; and X is a halogen. In some embodiments, the p38α MAPK inhibitor is a compound of Formulas 1001 to 1256, or a pharmaceutically acceptable salt, solvate, hydrate, cocrystal, or prodrug thereof, wherein Formulas 1001 to 1256 are as defined in Table 1. In one embodiment, the p38α MAPK inhibitor is a compound of Formula UM101, or a pharmaceutically acceptable salt, solvate, hydrate, cocrystal, or prodrug thereof, or a compound of Formula UM60, or a pharmaceutically acceptable salt, solvate, hydrate, cocrystal, or prodrug thereof. In one embodiment, the p38α MAPK inhibitor is a p38α MAPK selective inhibitor.

In one embodiment, the invention relates to a method of treating a disease alleviated by inhibiting the p38α MAPK protein in a patient in need thereof, including administering to the patient a therapeutically effective amount of a p38α MAPK inhibitor in a dosage unit form. In one embodiment, the dosage unit comprises a physiologically compatible carrier medium.

In one embodiment, the invention relates to a method of treating a disease alleviated by inhibiting the p38α MAPK protein in a patient in need thereof, including administering to the patient a therapeutically effective amount of a p38α MAPK inhibitor, wherein the disease is cancer or an inflammatory disease. In some embodiments, the disease is rheumatoid arthritis, a cardiovascular disease, multiple sclerosis, inflammatory bowel disease, chronic obstructive pulmonary disease (COPD), asthma, acute respiratory distress syndrome (ARDS), or acute lung injury (ALI). In one embodiment, the disease is a hyperproliferative diseases. In some embodiments, the hyperproliferative disorder is cancer. In some embodiments, the cancer is pancreatic cancer, breast cancer, prostate cancer, lymphoma, skin cancer, colon cancer, melanoma, malignant melanoma, ovarian cancer, brain cancer, primary brain carcinoma, head-neck cancer, glioma, glioblastoma, liver cancer, bladder cancer, non-small cell lung cancer, head or neck carcinoma, breast carcinoma, ovarian carcinoma, lung carcinoma, small-cell lung carcinoma, Wilms' tumor, cervical carcinoma, testicular carcinoma, bladder carcinoma, pancreatic carcinoma, stomach carcinoma, colon carcinoma, prostatic carcinoma, genitourinary carcinoma, thyroid carcinoma, esophageal carcinoma, myeloma, multiple myeloma, adrenal carcinoma, renal cell carcinoma, endometrial carcinoma, adrenal cortex carcinoma, malignant pancreatic insulinoma, malignant carcinoid carcinoma, choriocarcinoma, mycosis fungoides, malignant hypercalcemia, cervical hyperplasia, leukemia, acute lymphocytic leukemia, chronic lymphocytic leukemia, acute myelogenous leukemia, chronic myelogenous leukemia, chronic granulocytic leukemia, acute granulocytic leukemia, hairy cell leukemia, neuroblastoma, rhabdomyosarcoma, Kaposi's sarcoma, polycythemia vera, essential thrombocytosis, Hodgkin's disease, non-Hodgkin's lymphoma, soft-tissue sarcoma, osteogenic sarcoma, primary macroglobulinemia, or retinoblastoma, and the like. In other embodiments, the cancer is acoustic neuroma, adenocarcinoma, angiosarcoma, astrocytoma, basal cell carcinoma, bile duct carcinoma, bladder carcinoma, brain cancer, breast cancer, bronchogenic carcinoma, cervical cancer, chordoma, choriocarcinoma, colon cancer, colorectal cancer, craniopharyngioma, cystadenocarcinoma, embryonal carcinoma, endotheliocarcinoma, ependymoma, epithelial carcinoma, esophageal cancer, Ewing's tumor, fibrosarcoma, gastric cancer, glioblastoma multiforme, glioma, head and neck cancer, hemangioblastoma, hepatoma, kidney cancer, leiomyosarcoma, liposarcoma, lung cancer, lymphangioendotheliosarcoma, lymphangiosarcoma, medullary carcinoma, medulloblastoma, melanoma, meningioma, mesothelioma, myxosarcoma, nasal cancer, neuroblastoma, oligodendroglioma, oral cancer, osteogenic sarcoma, ovarian cancer, pancreatic cancer, papillary adenocarcinoma, papillary carcinoma, pinealoma, prostate cancer, rabdomyosarcoma, rectal cancer, renal cell carcinoma, retinoblastoma, sarcoma, sebaceous gland carcinoma, seminoma, skin cancer, squamous cell carcinoma, stomach cancer, sweat gland carcinoma, synovioma, testicular cancer, small cell lung carcinoma, throat cancer, uterine cancer, Wilm's tumor, blood cancer, acute erythroleukemic leukemia, acute lymphoblastic B-cell leukemia, acute lymphoblastic T-cell leukemia, acute lymphoblastic leukemia, acute megakaryoblastic leukemia, acute monoblastic leukemia, acute myeloblastic leukemia, acute myelomonocytic leukemia, acute nonlymphocytic leukemia, acute promyelocytic leukemia, acute undifferentiated leukemia, chronic lymphocytic leukemia, chronic myelocytic leukemia, hairy cell leukemia, multiple myeloma, heavy chain disease, Hodgkin's disease, multiple myeloma, non-Hodgkin's lymphoma, polycythemia vera, or Waldenstrom's macroglobulinemia.

In some embodiments, the hyperproliferative disorder (e.g., cancer) treated by the compounds and compositions described herein includes cells having p38α MAPK protein and/or p38α MAPK related protein expression.

In one embodiment, the invention relates to a method of treating a disease alleviated by inhibiting the p38α MAPK protein in a patient in need thereof, including administering to the patient a therapeutically effective amount of a p38α MAPK inhibitor, wherein the p38α MAPK inhibitor is a compound capable of binding to a pocket near the ED substrate-docking site of p38α MAPK, or a pharmaceutically acceptable salt, solvate, hydrate, cocrystal, or prodrug thereof, and one or more additional therapeutic agents, including chemotherapeutic and/or immunotherapeutic agents.

Efficacy of the compounds and combinations of compounds described herein in treating the indicated diseases or disorders can be tested using various models known in the art, and described herein, which provide guidance for treatment of human disease. Any and all of the described methods of treatment may include medical follow-up to determine the therapeutic or prophylactic effect brought about in the subject undergoing treatment with the compound(s) and/or composition(s) described herein.

Pharmaceutical Compositions

In an embodiment, an active pharmaceutical ingredient or combination of active pharmaceutical ingredients, such as any of the p38α MAPK inhibitors of the invention, is provided as a pharmaceutically acceptable composition.

In one embodiment, the invention relates to a pharmaceutical composition including a therapeutically effective amount of a p38α MAPK inhibitor for the treatment of a disease alleviated by inhibiting p38α MAPK activity in a patient in need thereof, or a pharmaceutically acceptable salt, solvate, hydrate, cocrystal, or prodrug thereof; and a physiologically compatible carrier medium; wherein the p38α MAPK inhibitor is a compound capable of binding to a pocket near the ED substrate-docking site of p38α MAPK. In one embodiment, the binding pocket is defined at least by residues R49, H107, L108, and K165 in p38α MAPK. In one embodiment, the binding pocket is defined by residues R49, H107, L108, M109, G110, A157, V158, E163, L164, and K165 in p38α MAPK. In one embodiment, the p38α MAPK inhibitor is a compound of Formula 1 or Formula 2, or a pharmaceutically acceptable salt, solvate, hydrate, cocrystal, or prodrug thereof, wherein in Formula 1 and Formula 2, Q is —CH— or N; each of $R^1$, $R^2$, $R^3$, and $R^4$ is independently hydrogen or optionally substituted alkyl, alkoxy, aryl, or heteroaryl; $R^5$ is $—SO_2—$, —CH(OH)—, —O—, or $—N(CH_3)—$; each of $R^{10}$ and $R^{10'}$ is independently —OH, $—NH_2$, or —SH; $L^1$ is $—CH_2—$, $—C(CH_3)_2—$ or $—C(CH_2CH_2)—$; each of $L^2$ and $L^3$ is independently $—CH_2—$, $—CH_2CH_2—$, or $—CH_2CH_2CH_2—$; each of $L^4$, $L^5$, and $L^{5'}$ is independently —NHCO—, —CONH—, $—SO_2NH—$, $—NHSO_2—$, or —CH═CH—; each of $L^6$ and $L^{6'}$ is independently an optionally substituted $C_1$-$C_6$ alkyl chain; and $Ar^1$ is an optionally substituted aryl or heteroaryl ring. In one embodiment, $Ar^1$ is a six member ring. In one embodiment, the p38α MAPK inhibitor is a compound of Formula 11, Formula 12, Formula 13, or Formula 14, or a pharmaceutically acceptable salt, solvate, hydrate, cocrystal, or prodrug thereof, wherein in Formula 11, Formula 12, Formula 13, and Formula 14, Q is —CH— or N; each of $R^1$, $R^2$, $R^3$, $R^4$, $R^6$, $R^7$, $R^8$, and $R^9$ is independently hydrogen or optionally substituted alkyl, alkoxy, aryl, or heteroaryl; $R^5$ is $—SO_2—$, —CH(OH)—, —O—, or $—N(CH_3)—$; $L^1$ is $—CH_2—$, $—C(CH_3)_2$, or $—C(CH_2CH_2)—$; each of $L^2$ and $L^3$ is independently $—CH_2—$, $—CH_2CH_2—$, or $—CH_2CH_2CH_2—$; $L^4$ is —NHCO—, —CONH—, $—SO_2NH—$, $—NHSO_2—$, or —CH═CH—; $Ar^1$ is an optionally substituted aryl or heteroaryl ring; and X is a halogen. In one embodiment, the p38α MAPK inhibitor is a compound of any one of Formulas 1001 to 1256, or a pharmaceutically acceptable salt, solvate, hydrate, cocrystal, or prodrug thereof, wherein Formulas 1001 to 1256 are as defined in Table 1. In one embodiment, the p38α MAPK inhibitor is a compound of Formula UM101, or, a compound of Formula UM60. In one embodiment, the p38α MAPK inhibitor is a p38α MAPK selective inhibitor.

In one embodiment, the invention relates to a pharmaceutical composition including a therapeutically effective amount of a p38α MAPK inhibitor for the treatment of a disease alleviated by inhibiting p38α MAPK activity in a patient in need thereof, or a pharmaceutically acceptable salt, solvate, hydrate, cocrystal, or prodrug thereof; and a physiologically compatible carrier medium, wherein the disease is cancer or an inflammatory disease. In one embodiment, the disease is rheumatoid arthritis, a cardiovascular disease, multiple sclerosis, inflammatory bowel disease, chronic obstructive pulmonary disease (COPD), asthma, acute respiratory distress syndrome (ARDS), or acute lung injury (ALI). In one embodiment, the diseases is a cancer such as acoustic neuroma, adenocarcinoma, angiosarcoma, astrocytoma, basal cell carcinoma, bile duct carcinoma, bladder carcinoma, brain cancer, breast cancer, bronchogenic carcinoma, cervical cancer, chordoma, choriocarcinoma, colon cancer, colorectal cancer, craniopharyngioma, cystadenocarcinoma, embryonal carcinoma, endotheliocarcinoma, ependymoma, epithelial carcinoma, esophageal cancer, Ewing's tumor, fibrosarcoma, gastric cancer, glioblastoma multiforme, glioma, head and neck cancer, hemangioblastoma, hepatoma, kidney cancer, leiomyosarcoma, liposarcoma, lung cancer, lymphangioendotheliosarcoma, lymphangiosarcoma, medullary carcinoma, medulloblastoma, melanoma, meningioma, mesothelioma, myxosarcoma, nasal cancer, neuroblastoma, oligodendroglioma, oral cancer, osteogenic sarcoma, ovarian cancer, pancreatic cancer, papillary adenocarcinoma, papillary carcinoma, pinealoma, prostate cancer, rabdomyosarcoma, rectal cancer, renal cell carcinoma, retinoblastoma, sarcoma, sebaceous gland carcinoma, seminoma, skin cancer, squamous cell carcinoma, stomach cancer, sweat gland carcinoma, synovioma, testicular cancer, small cell lung carcinoma, throat cancer, uterine cancer, Wilm's tumor, blood cancer, acute erythroleukemic leukemia, acute lymphoblastic B-cell leukemia, acute lymphoblastic T-cell leukemia, acute lymphoblastic leukemia, acute megakaryoblastic leukemia, acute monoblastic leukemia, acute myeloblastic leukemia, acute myelomonocytic leukemia, acute nonlymphocytic leukemia, acute promyelocytic leukemia, acute undifferentiated leukemia, chronic lymphocytic leukemia, chronic myelocytic leukemia, hairy cell leukemia, multiple myeloma, heavy chain disease, Hodgkin's disease, multiple myeloma, non-Hodgkin's lymphoma, polycythemia vera, or Waldenstrom's macroglobulinemia.

In some embodiments, the concentration of each of the active pharmaceutical ingredients provided in the pharmaceutical compositions of the invention, such as any of the p38α MAPK inhibitors of the invention, is less than, for example, 100%, 90%, 80%, 70%, 60%, 50%, 40%, 30%, 20%, 19%, 18%, 17%, 16%, 15%, 14%, 13%, 12%, 11%, 10% 9%, 8%, 7%, 6%, 5%, 4%, 3%, 2%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002% or 0.0001% w/w, w/v, or v/v of the pharmaceutical composition.

In some embodiments, the concentration of each of the active pharmaceutical ingredients provided in the pharmaceutical compositions of the invention, such as any of the p38α MAPK inhibitors of the invention, is greater than 90%, 80%, 70%, 60%, 50%, 40%, 30%, 20%, 19.75%, 19.50%, 19.25% 19%, 18.75%, 18.50%, 18.25% 18%, 17.75%, 17.50%, 17.25% 17%, 16.75%, 16.50%, 16.25% 16%, 15.75%, 15.50%, 15.25% 15%, 14.75%, 14.50%, 14.25% 14%, 13.75%, 13.50%, 13.25% 13%, 12.75%, 12.50%, 12.25% 12%, 11.75%, 11.50%, 11.25% 11%, 10.75%, 10.50%, 10.25% 10%, 9.75%, 9.50%, 9.25% 9%, 8.75%, 8.50%, 8.25% 8%, 7.75%, 7.50%, 7.25% 7%, 6.75%, 6.50%, 6.25% 6%, 5.75%, 5.50%, 5.25% 5%, 4.75%, 4.50%, 4.25%, 4%, 3.75%, 3.50%, 3.25%, 3%, 2.75%, 2.50%, 2.25%, 2%, 1.75%, 1.50%, 125%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002% or 0.0001% w/w, w/v, or v/v of the pharmaceutical composition.

In some embodiments, the concentration of each of the active pharmaceutical ingredients provided in the pharmaceutical compositions of the invention, such as any of the p38α MAPK inhibitors of the invention, is in the range from about 0.0001% to about 50%, about 0.001% to about 40%, about 0.01% to about 30%, about 0.02% to about 29%, about 0.03% to about 28%, about 0.04% to about 27%, about 0.05% to about 26%, about 0.06% to about 25%, about 0.07% to about 24%, about 0.08% to about 23%, about 0.09% to about 22%, about 0.1% to about 21%, about 0.2% to about 20%, about 0.3% to about 19%, about 0.4% to about 18%, about 0.5% to about 17%, about 0.6% to about 16%, about 0.7% to about 15%, about 0.8% to about 14%, about 0.9% to about 12% or about 1% to about 10% w/w, w/v, or v/v of the pharmaceutical composition.

In some embodiments, the concentration of each of the active pharmaceutical ingredients provided in the pharmaceutical compositions of the invention, such as any of the p38α MAPK inhibitors of the invention, is in the range from about 0.001% to about 10%, about 0.01% to about 5%, about 0.02% to about 4.5%, about 0.03% to about 4%, about 0.04% to about 3.5%, about 0.05% to about 3%, about 0.06% to about 2.5%, about 0.07% to about 2%, about 0.08% to about 1.5%, about 0.09% to about 1%, about 0.1% to about 0.9% w/w, w/v, or v/v of the pharmaceutical composition.

In some embodiments, the amount of each of the active pharmaceutical ingredients provided in the pharmaceutical compositions of the invention, such as any of the foregoing p38α MAPK inhibitors of the invention, is equal to or less than 10 g, 9.5 g, 9.0 g, 8.5 g, 8.0 g, 7.5 g, 7.0 g, 6.5 g, 6.0 g, 5.5 g, 5.0 g, 4.5 g, 4.0 g, 3.5 g, 3.0 g, 2.5 g, 2.0 g, 1.5 g, 1.0 g, 0.95 g, 0.9 g, 0.85 g, 0.8 g, 0.75 g, 0.7 g, 0.65 g, 0.6 g, 0.55 g, 0.5 g, 0.45 g, 0.4 g, 0.35 g, 0.3 g, 0.25 g, 0.2 g, 0.15 g, 0.1 g, 0.09 g, 0.08 g, 0.07 g, 0.06 g, 0.05 g, 0.04 g, 0.03 g, 0.02 g, 0.01 g, 0.009 g, 0.008 g, 0.007 g, 0.006 g, 0.005 g, 0.004 g, 0.003 g, 0.002 g, 0.001 g, 0.0009 g, 0.0008 g, 0.0007 g, 0.0006 g, 0.0005 g, 0.0004 g, 0.0003 g, 0.0002 g, or 0.0001 g.

In some embodiments, the amount of each of the active pharmaceutical ingredients provided in the pharmaceutical compositions of the invention, such as any of the p38α MAPK inhibitors of the invention, is more than 0.0001 g, 0.0002 g, 0.0003 g, 0.0004 g, 0.0005 g, 0.0006 g, 0.0007 g, 0.0008 g, 0.0009 g, 0.001 g, 0.0015 g, 0.002 g, 0.0025 g, 0.003 g, 0.0035 g, 0.004 g, 0.0045 g, 0.005 g, 0.0055 g, 0.006 g, 0.0065 g, 0.007 g, 0.0075 g, 0.008 g, 0.0085 g, 0.009 g, 0.0095 g, 0.01 g, 0.015 g, 0.02 g, 0.025 g, 0.03 g, 0.035 g, 0.04 g, 0.045 g, 0.05 g, 0.055 g, 0.06 g, 0.065 g, 0.07 g, 0.075 g, 0.08 g, 0.085 g, 0.09 g, 0.095 g, 0.1 g, 0.15 g, 0.2 g, 0.25 g, 0.3 g, 0.35 g, 0.4 g, 0.45 g, 0.5 g, 0.55 g, 0.6 g, 0.65 g, 0.7 g, 0.75 g, 0.8 g, 0.85 g, 0.9 g, 0.95 g, 1 g, 1.5 g, 2 g, 2.5, 3 g, 3.5, 4 g, 4.5 g, 5 g, 5.5 g, 6 g, 6.5 g, 7 g, 7.5 g, 8 g, 8.5 g, 9 g, 9.5 g, or 10 g.

Each of the active pharmaceutical ingredients according to the invention is effective over a wide dosage range. For example, in the treatment of adult humans, dosages independently range from 0.01 to 1000 mg, from 0.5 to 100 mg, from 1 to 50 mg per day, and from 5 to 40 mg per day are examples of dosages that may be used. The exact dosage will depend upon the route of administration, the form in which the compound is administered, the gender and age of the subject to be treated, the body weight of the subject to be treated, and the preference and experience of the attending physician. The clinically-established dosages of the p38α MAPK inhibitors of the invention may also be used if appropriate.

In an embodiment, the molar ratio of two active pharmaceutical ingredients in the pharmaceutical compositions is in the range from 10:1 to 1:10, preferably from 2.5:1 to 1:2.5, and more preferably about 1:1. In an embodiment, the weight ratio of the molar ratio of two active pharmaceutical ingredients in the pharmaceutical compositions is selected from the group consisting of 20:1, 19:1, 18:1, 17:1, 16:1, 15:1, 14:1, 13:1, 12:1, 11:1, 10:1, 9:1, 8:1, 7:1, 6:1, 5:1, 4:1, 3:1, 2:1, 1:1, 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, and 1:20. In an embodiment, the weight ratio of the molar ratio of two active pharmaceutical ingredients in the pharmaceutical compositions is selected from the group consisting of 20:1, 19:1, 18:1, 17:1, 16:1, 15:1, 14:1, 13:1, 12:1, 11:1, 10:1, 9:1, 8:1, 7:1, 6:1, 5:1, 4:1, 3:1, 2:1, 1:1, 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, and 1:20.

In an embodiment, the pharmaceutical compositions described herein, such as any of the p38α MAPK inhibitors of the invention, are for use in the treatment of an inflammatory disease. In an embodiment, the pharmaceutical compositions described herein, such as any of the p38α MAPK inhibitors of the invention, are for use in the treatment of rheumatoid arthritis, a cardiovascular disease, multiple sclerosis, inflammatory bowel disease, chronic obstructive pulmonary disease (COPD), asthma, acute respiratory distress syndrome (ARDS), or acute lung injury (ALI).

In an embodiment, the pharmaceutical compositions described herein, such as any of the p38α MAPK inhibitors of the invention, are for use in the treatment of hyperproliferative disorders associated with the overexpression or up- and/or downregulation p38α MAPK protein. In a some embodiments, the pharmaceutical compositions described herein are for use in the treatment of a cancer associated with overexpression or up- and/or downregulation of p38α MAPK protein, such as pancreatic cancer, breast cancer, prostate cancer, lymphoma, skin cancer, colon cancer, melanoma, malignant melanoma, ovarian cancer, brain cancer, primary brain carcinoma, head-neck cancer, glioma, glioblastoma, liver cancer, bladder cancer, non-small cell lung cancer, head or neck carcinoma, breast carcinoma, ovarian carcinoma, lung carcinoma, small-cell lung carcinoma, Wilms' tumor, cervical carcinoma, testicular carcinoma, bladder carcinoma, pancreatic carcinoma, stomach carcinoma, colon carcinoma, prostatic carcinoma, genitourinary carcinoma, thyroid carcinoma, esophageal carcinoma, myeloma, multiple myeloma, adrenal carcinoma, renal cell carcinoma, endometrial carcinoma, adrenal cortex carcinoma, malignant pancreatic insulinoma, malignant carcinoid carcinoma, choriocarcinoma, mycosis fungoides, malignant hypercalcemia, cervical hyperplasia, leukemia, acute lymphocytic leukemia, chronic lymphocytic leukemia, acute myelogenous leukemia, chronic myelogenous leukemia, chronic granulocytic leukemia, acute granulocytic leukemia, hairy cell leukemia, neuroblastoma, rhabdomyosarcoma, Kaposi's sarcoma, polycythemia vera, essential thrombocytosis, Hodgkin's disease, non-Hodgkin's lymphoma, soft-tissue sarcoma, osteogenic sarcoma, primary macroglobulinemia, or retinoblastoma.

Described below are non-limiting pharmaceutical compositions and methods for preparing the same.

Pharmaceutical Compositions for Oral Administration

In an embodiment, the invention provides a pharmaceutical composition for oral administration containing the active pharmaceutical ingredient or combination of active pharmaceutical ingredients, such as the p38α MAPK inhibitors described herein, and a pharmaceutical excipient suitable for oral administration.

In some embodiments, the invention provides a solid pharmaceutical composition for oral administration containing: (i) an effective amount of an active pharmaceutical ingredient or combination of active pharmaceutical ingredients, and (ii) a pharmaceutical excipient suitable for oral administration. In selected embodiments, the composition further contains (iii) an effective amount of a third active pharmaceutical ingredient, and optionally (iv) an effective amount of a fourth active pharmaceutical ingredient.

In some embodiments, the pharmaceutical composition may be a liquid pharmaceutical composition suitable for oral consumption. Pharmaceutical compositions of the invention suitable for oral administration can be presented as discrete dosage forms, such as capsules, sachets, or tablets, or liquids or aerosol sprays each containing a predetermined amount of an active ingredient as a powder or in granules, a solution, or a suspension in an aqueous or non-aqueous liquid, an oil-in-water emulsion, a water-in-oil liquid emulsion, powders for reconstitution, powders for oral consumptions, bottles (including powders or liquids in a bottle), orally dissolving films, lozenges, pastes, tubes, gums, and packs. Such dosage forms can be prepared by any of the methods of pharmacy, but all methods include the step of bringing the active ingredient(s) into association with the carrier, which constitutes one or more necessary ingredients. In general, the compositions are prepared by uniformly and intimately admixing the active ingredient(s) with liquid carriers or finely divided solid carriers or both, and then, if necessary, shaping the product into the desired presentation. For example, a tablet can be prepared by compression or molding, optionally with one or more accessory ingredients. Compressed tablets can be prepared by compressing in a suitable machine the active ingredient in a free-flowing form such as powder or granules, optionally mixed with an excipient such as, but not limited to, a binder, a lubricant, an inert diluent, and/or a surface active or dispersing agent. Molded tablets can be made by molding in a suitable machine a mixture of the powdered compound moistened with an inert liquid diluent.

The invention further encompasses anhydrous pharmaceutical compositions and dosage forms since water can facilitate the degradation of some compounds. For example, water may be added (e.g., 5%) in the pharmaceutical arts as a means of simulating long-term storage in order to determine characteristics such as shelf-life or the stability of formulations over time. Anhydrous pharmaceutical compositions and dosage forms of the invention can be prepared using anhydrous or low moisture containing ingredients and low moisture or low humidity conditions. Pharmaceutical compositions and dosage forms of the invention which contain lactose can be made anhydrous if substantial contact with moisture and/or humidity during manufacturing, packaging, and/or storage is expected. An anhydrous pharmaceutical composition may be prepared and stored such that its anhydrous nature is maintained. Accordingly, anhydrous compositions may be packaged using materials known to prevent exposure to water such that they can be included in suitable formulary kits. Examples of suitable packaging include, but are not limited to, hermetically sealed foils, plastic or the like, unit dose containers, blister packs, and strip packs.

Each of the active pharmaceutical ingredients can be combined in an intimate admixture with a pharmaceutical carrier according to conventional pharmaceutical compounding techniques. The carrier can take a wide variety of forms depending on the form of preparation desired for administration. In preparing the compositions for an oral dosage form, any of the usual pharmaceutical media can be employed as carriers, such as, for example, water, glycols, oils, alcohols, flavoring agents, preservatives, coloring agents, and the like in the case of oral liquid preparations (such as suspensions, solutions, and elixirs) or aerosols; or carriers such as starches, sugars, micro-crystalline cellulose, diluents, granulating agents, lubricants, binders, and disintegrating agents can be used in the case of oral solid preparations, in some embodiments without employing the use of lactose. For example, suitable carriers include powders, capsules, and tablets, with the solid oral preparations. If desired, tablets can be coated by standard aqueous or nonaqueous techniques.

Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, microcrystalline cellulose, and mixtures thereof.

Examples of suitable fillers for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof.

Disintegrants may be used in the compositions of the invention to provide tablets that disintegrate when exposed to an aqueous environment. Too much of a disintegrant may produce tablets which disintegrate in the bottle. Too little may be insufficient for disintegration to occur, thus altering the rate and extent of release of the active ingredients from the dosage form. Thus, a sufficient amount of disintegrant that is neither too little nor too much to detrimentally alter the release of the active ingredient(s) may be used to form the dosage forms of the compounds disclosed herein. The amount of disintegrant used may vary based upon the type of formulation and mode of administration, and may be readily discernible to those of ordinary skill in the art. About 0.5 to about 15 weight percent of disintegrant, or about 1 to about 5 weight percent of disintegrant, may be used in the pharmaceutical composition. Disintegrants that can be used to form pharmaceutical compositions and dosage forms of the invention include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums or mixtures thereof.

Lubricants which can be used to form pharmaceutical compositions and dosage forms of the invention include, but are not limited to, calcium stearate, magnesium stearate, sodium stearyl fumarate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethylaureate, agar, or mixtures thereof. Additional lubricants include, for example, a syloid silica gel, a coagulated aerosol of synthetic silica, silicified microcrystalline cellulose, or mixtures thereof. A lubricant can optionally be added in an amount of less than about 0.5% or less than about 1% (by weight) of the pharmaceutical composition.

When aqueous suspensions and/or elixirs are desired for oral administration, the active pharmaceutical ingredient(s) may be combined with various sweetening or flavoring agents, coloring matter or dyes and, if so desired, emulsifying and/or suspending agents, together with such diluents as water, ethanol, propylene glycol, glycerin and various combinations thereof.

The tablets can be uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Surfactants which can be used to form pharmaceutical compositions and dosage forms of the invention include, but are not limited to, hydrophilic surfactants, lipophilic surfactants, and mixtures thereof. That is, a mixture of hydrophilic surfactants may be employed, a mixture of lipophilic surfactants may be employed, or a mixture of at least one hydrophilic surfactant and at least one lipophilic surfactant may be employed.

A suitable hydrophilic surfactant may generally have an HLB value of at least 10, while suitable lipophilic surfactants may generally have an HLB value of or less than about 10. An empirical parameter used to characterize the relative hydrophilicity and hydrophobicity of non-ionic amphiphilic compounds is the hydrophilic-lipophilic balance ("HLB" value). Surfactants with lower HLB values are more lipophilic or hydrophobic, and have greater solubility in oils, while surfactants with higher HLB values are more hydrophilic, and have greater solubility in aqueous solutions. Hydrophilic surfactants are generally considered to be those compounds having an HLB value greater than about 10, as well as anionic, cationic, or zwitterionic compounds for which the HLB scale is not generally applicable. Similarly, lipophilic (i.e., hydrophobic) surfactants are compounds having an HLB value equal to or less than about 10. However, HLB value of a surfactant is merely a rough guide generally used to enable formulation of industrial, pharmaceutical and cosmetic emulsions.

Hydrophilic surfactants may be either ionic or non-ionic. Suitable ionic surfactants include, but are not limited to, alkylammonium salts; fusidic acid salts; fatty acid derivatives of amino acids, oligopeptides, and polypeptides; glyceride derivatives of amino acids, oligopeptides, and polypeptides; lecithins and hydrogenated lecithins; lysolecithins and hydrogenated lysolecithins; phospholipids and derivatives thereof; lysophospholipids and derivatives thereof; carnitine fatty acid ester salts; salts of alkylsulfates; fatty acid salts; sodium docusate; acyl-lactylates; mono- and di-acetylated tartaric acid esters of mono- and di-glycerides; succinylated mono- and di-glycerides; citric acid esters of mono- and di-glycerides; and mixtures thereof.

Within the aforementioned group, ionic surfactants include, by way of example: lecithins, lysolecithin, phospholipids, lysophospholipids and derivatives thereof; carnitine fatty acid ester salts; salts of alkylsulfates; fatty acid salts; sodium docusate; acylactylates; mono- and di-acetylated tartaric acid esters of mono- and di-glycerides; succinylated mono- and di-glycerides; citric acid esters of mono- and di-glycerides; and mixtures thereof.

Ionic surfactants may be the ionized forms of lecithin, lysolecithin, phosphatidylcholine, phosphatidylethanolamine, phosphatidylglycerol, phosphatidic acid, phosphatidylserine, lysophosphatidylcholine, lysophosphatidylethanolamine, lysophosphatidylglycerol, lysophosphatidic acid, lysophosphatidylserine, PEG-phosphatidylethanolamine, PVP-phosphatidylethanolamine, lactylic esters of fatty acids, stearoyl-2-lactylate, stearoyl lactylate, succinylated monoglycerides, mono/diacetylated tartaric acid esters of mono/diglycerides, citric acid esters of mono/diglycerides, cholylsarcosine, caproate, caprylate, caprate, laurate, myristate, palmitate, oleate, ricinoleate, linoleate, linolenate, stearate, lauryl sulfate, teracecyl sulfate, docusate, lauroyl carnitines, palmitoyl carnitines, myristoyl carnitines, and salts and mixtures thereof.

Hydrophilic non-ionic surfactants may include, but not limited to, alkylglucosides; alkylmaltosides; alkylthioglucosides; lauryl macrogolglycerides; polyoxyalkylene alkyl ethers such as polyethylene glycol alkyl ethers; polyoxyalkylene alkylphenols such as polyethylene glycol alkyl phenols; polyoxyalkylene alkyl phenol fatty acid esters such as polyethylene glycol fatty acids monoesters and polyethylene glycol fatty acids diesters; polyethylene glycol glycerol fatty acid esters; polyglycerol fatty acid esters; polyoxyalkylene sorbitan fatty acid esters such as polyethylene glycol sorbitan fatty acid esters; hydrophilic transesterification products of a polyol with at least one member of the group consisting of glycerides, vegetable oils, hydrogenated vegetable oils, fatty acids, and sterols; polyoxyethylene sterols, derivatives, and analogs thereof, polyoxyethylated vitamins and derivatives thereof, polyoxyethylene-polyoxypropylene block copolymers; and mixtures thereof; polyethylene glycol sorbitan fatty acid esters and hydrophilic transesterification products of a polyol with at least one member of the group consisting of triglycerides, vegetable oils, and hydrogenated vegetable oils. The polyol may be glycerol, ethylene glycol, polyethylene glycol, sorbitol, propylene glycol, pentaerythritol, or a saccharide.

Other hydrophilic-non-ionic surfactants include, without limitation, PEG-10 laurate, PEG-12 laurate, PEG-20 laurate, PEG-32 laurate, PEG-32 dilaurate, PEG-12 oleate, PEG-15 oleate, PEG-20 oleate, PEG-20 dioleate, PEG-32 oleate, PEG-200 oleate, PEG-400 oleate, PEG-15 stearate, PEG-32 distearate, PEG-40 stearate, PEG-100 stearate, PEG-20 dilaurate, PEG-25 glyceryl trioleate, PEG-32 dioleate, PEG-20 glyceryl laurate, PEG-30 glyceryl laurate, PEG-20 glyceryl stearate, PEG-20 glyceryl oleate, PEG-30 glyceryl oleate, PEG-30 glyceryl laurate, PEG-40 glyceryl laurate, PEG-40 palm kernel oil, PEG-50 hydrogenated castor oil, PEG-40 castor oil, PEG-35 castor oil, PEG-60 castor oil, PEG-40 hydrogenated castor oil, PEG-60 hydrogenated castor oil, PEG-60 corn oil, PEG-6 caprate/caprylate glycerides, PEG-8 caprate/caprylate glycerides, polyglyceryl-10 laurate, PEG-30 cholesterol, PEG-25 phyto sterol, PEG-30 soya sterol, PEG-20 trioleate, PEG-40 sorbitan oleate, PEG-80 sorbitan laurate, polysorbate 20, polysorbate 80, POE-9 lauryl ether, POE-23 lauryl ether, POE-10 oleyl ether, POE-20 oleyl ether, POE-20 stearyl ether, tocopheryl PEG-100 succinate, PEG-24 cholesterol, polyglyceryl-10 oleate, Tween 40, Tween 60, sucrose monostearate, sucrose monolaurate, sucrose monopalmitate, PEG 10-100 nonyl phenol series, PEG 15-100 octyl phenol series, and poloxamers.

Suitable lipophilic surfactants include, by way of example only: fatty alcohols; glycerol fatty acid esters; acetylated glycerol fatty acid esters; lower alcohol fatty acids esters; propylene glycol fatty acid esters; sorbitan fatty acid esters; polyethylene glycol sorbitan fatty acid esters; sterols and sterol derivatives; polyoxyethylated sterols and sterol derivatives; polyethylene glycol alkyl ethers; sugar esters; sugar ethers; lactic acid derivatives of mono- and di-glycerides; hydrophobic transesterification products of a polyol with at least one member of the group consisting of glycerides, vegetable oils, hydrogenated vegetable oils, fatty acids and sterols; oil-soluble vitamins/vitamin derivatives; and mixtures thereof. Within this group, preferred lipophilic surfactants include glycerol fatty acid esters, propylene glycol fatty acid esters, and mixtures thereof, or are hydrophobic transesterification products of a polyol with at least one member of the group consisting of vegetable oils, hydrogenated vegetable oils, and triglycerides.

In an embodiment, the composition may include a solubilizer to ensure good solubilization and/or dissolution of the compound of the present invention and to minimize precipitation of the compound of the present invention. This can be especially important for compositions for non-oral use—e.g., compositions for injection. A solubilizer may also be added to increase the solubility of the hydrophilic drug and/or other components, such as surfactants, or to maintain the composition as a stable or homogeneous solution or dispersion.

Examples of suitable solubilizers include, but are not limited to, the following: alcohols and polyols, such as ethanol, isopropanol, butanol, benzyl alcohol, ethylene glycol, propylene glycol, butanediols and isomers thereof, glycerol, pentaerythritol, sorbitol, mannitol, transcutol, dimethyl isosorbide, polyethylene glycol, polypropylene glycol, polyvinylalcohol, hydroxypropyl methylcellulose and other cellulose derivatives, cyclodextrins and cyclodextrin derivatives; ethers of polyethylene glycols having an average molecular weight of about 200 to about 6000, such as tetrahydrofurfuryl alcohol PEG ether (glycofurol) or methoxy PEG; amides and other nitrogen-containing compounds such as 2-pyrrolidone, 2-piperidone, ε-caprolactam, N-alkylpyrrolidone, N-hydroxyalkylpyrrolidone, N-alkylpiperidone, N-alkylcaprolactam, dimethylacetamide and polyvinylpyrrolidone; esters such as ethyl propionate, tributylcitrate, acetyl triethylcitrate, acetyl tributyl citrate, triethylcitrate, ethyl oleate, ethyl caprylate, ethyl butyrate, triacetin, propylene glycol monoacetate, propylene glycol diacetate, ε-caprolactone and isomers thereof, 8-valerolactone and isomers thereof, β-butyrolactone and isomers thereof; and other solubilizers known in the art, such as dimethyl acetamide, dimethyl isosorbide, N-methyl pyrrolidones, monooctanoin, diethylene glycol monoethyl ether, and water.

Mixtures of solubilizers may also be used. Examples include, but not limited to, triacetin, triethylcitrate, ethyl oleate, ethyl caprylate, dimethylacetamide, N-methylpyrrolidone, N-hydroxyethylpyrrolidone, polyvinylpyrrolidone, hydroxypropyl methylcellulose, hydroxypropyl cyclodextrins, ethanol, polyethylene glycol 200-100, glycofurol, transcutol, propylene glycol, and dimethyl isosorbide. Particularly preferred solubilizers include sorbitol, glycerol, triacetin, ethyl alcohol, PEG-400, glycofurol and propylene glycol.

The amount of solubilizer that can be included is not particularly limited. The amount of a given solubilizer may be limited to a bioacceptable amount, which may be readily determined by one of skill in the art. In some circumstances, it may be advantageous to include amounts of solubilizers far in excess of bioacceptable amounts, for example to maximize the concentration of the drug, with excess solubilizer removed prior to providing the composition to a patient using conventional techniques, such as distillation or evaporation. Thus, if present, the solubilizer can be in a weight ratio of 10%, 25%, 50%, 100%, or up to about 200% by weight, based on the combined weight of the drug, and other excipients. If desired, very small amounts of solubilizer may also be used, such as 5%, 2%, 1% or even less. Typically, the solubilizer may be present in an amount of about 1% to about 100%, more typically about 5% to about 25% by weight.

The composition can further include one or more pharmaceutically acceptable additives and excipients. Such additives and excipients include, without limitation, detackifiers, anti-foaming agents, buffering agents, polymers, antioxidants, preservatives, chelating agents, viscomodulators, tonicifiers, flavorants, colorants, odorants, opacifiers, suspending agents, binders, fillers, plasticizers, lubricants, and mixtures thereof.

In addition, an acid or a base may be incorporated into the composition to facilitate processing, to enhance stability, or for other reasons. Examples of pharmaceutically acceptable bases include amino acids, amino acid esters, ammonium hydroxide, potassium hydroxide, sodium hydroxide, sodium hydrogen carbonate, aluminum hydroxide, calcium carbonate, magnesium hydroxide, magnesium aluminum silicate, synthetic aluminum silicate, synthetic hydrocalcite, magnesium aluminum hydroxide, diisopropylethylamine, ethanolamine, ethylenediamine, triethanolamine, triethylamine, triisopropanolamine, trimethylamine, tris(hydroxymethyl) aminomethane (TRIS) and the like. Also suitable are bases that are salts of a pharmaceutically acceptable acid, such as acetic acid, acrylic acid, adipic acid, alginic acid, alkanesulfonic acid, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid, and the like. Salts of polyprotic acids, such as sodium phosphate, disodium hydrogen phosphate, and sodium dihydrogen phosphate can also be used. When the base is a salt, the cation can be any convenient and pharmaceutically acceptable cation, such as ammonium, alkali metals and alkaline earth metals. Example may include, but not limited to, sodium, potassium, lithium, magnesium, calcium and ammonium.

Suitable acids are pharmaceutically acceptable organic or inorganic acids. Examples of suitable inorganic acids include hydrochloric acid, hydrobromic acid, hydriodic acid, sulfuric acid, nitric acid, boric acid, phosphoric acid, and the like. Examples of suitable organic acids include acetic acid, acrylic acid, adipic acid, alginic acid, alkanesulfonic acids, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, methanesulfonic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid and uric acid.

Pharmaceutical Compositions for Injection

In some embodiments, a pharmaceutical composition is provided for injection containing an active pharmaceutical ingredient or combination of active pharmaceutical ingredients, such as a p38α MAPK inhibitor, and a pharmaceutical excipient suitable for injection.

The forms in which the compositions of the present invention may be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles.

Aqueous solutions in saline are also conventionally used for injection. Ethanol, glycerol, propylene glycol and liquid polyethylene glycol (and suitable mixtures thereof), cyclodextrin derivatives, and vegetable oils may also be employed. The proper fluidity can be maintained, for example, by the use of a coating, such as lecithin, for the maintenance of the required particle size in the case of dispersion and by the use of surfactants. The prevention of the action of microorganisms can be brought about by various antibacterial and antifungal agents, for example, parabens, chlorobutanol, phenol, sorbic acid, and thimerosal.

Sterile injectable solutions are prepared by incorporating an active pharmaceutical ingredient or combination of active pharmaceutical ingredients in the required amounts in the appropriate solvent with various other ingredients as enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, certain desirable methods of preparation are vacuum-drying and freeze-drying techniques which yield a powder of the active ingredient plus any additional desired ingredient from a previously sterile-filtered solution thereof.

Pharmaceutical Compositions for Topical Delivery

In some embodiments, a pharmaceutical composition is provided for transdermal delivery containing an active pharmaceutical ingredient or combination of active pharmaceutical ingredients, such as p38α MAPK inhibitors described herein, and a pharmaceutical excipient suitable for transdermal delivery.

Compositions of the present invention can be formulated into preparations in solid, semi-solid, or liquid forms suitable for local or topical administration, such as gels, water soluble jellies, creams, lotions, suspensions, foams, powders, slurries, ointments, solutions, oils, pastes, suppositories, sprays, emulsions, saline solutions, dimethylsulfoxide (DMSO)-based solutions. In general, carriers with higher densities are capable of providing an area with a prolonged exposure to the active ingredients. In contrast, a solution formulation may provide more immediate exposure of the active ingredient to the chosen area.

The pharmaceutical compositions also may comprise suitable solid or gel phase carriers or excipients, which are compounds that allow increased penetration of, or assist in the delivery of, therapeutic molecules across the stratum corneum permeability barrier of the skin. There are many of these penetration-enhancing molecules known to those trained in the art of topical formulation. Examples of such carriers and excipients include, but are not limited to, humectants (e.g., urea), glycols (e.g., propylene glycol), alcohols (e.g., ethanol), fatty acids (e.g., oleic acid), surfactants (e.g., isopropyl myristate and sodium lauryl sulfate), pyrrolidones, glycerol monolaurate, sulfoxides, terpenes (e.g., menthol), amines, amides, alkanes, alkanols, water, calcium carbonate, calcium phosphate, various sugars, starches, cellulose derivatives, gelatin, and polymers such as polyethylene glycols.

Another exemplary formulation for use in the methods of the present invention employs transdermal delivery devices ("patches"). Such transdermal patches may be used to provide continuous or discontinuous infusion of an active pharmaceutical ingredient or combination of active pharmaceutical ingredients in controlled amounts, either with or without another active pharmaceutical ingredient.

The construction and use of transdermal patches for the delivery of pharmaceutical agents is well known in the art. See, e.g., U.S. Pat. Nos. 5,023,252; 4,992,445; and 5,001,139, the entirety of which are incorporated herein by reference. Such patches may be constructed for continuous, pulsatile, or on demand delivery of pharmaceutical agents.

Pharmaceutical Compositions for Inhalation

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra and the p38α MAPK inhibitors described herein. Preferably the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a face mask tent, or intermittent positive pressure breathing machine. Solution, suspension, or powder compositions may be administered, preferably orally or nasally, from devices that deliver the formulation in an appropriate manner. Dry powder inhalers may also be used to provide inhaled delivery of the compositions.

Other Pharmaceutical Compositions

Pharmaceutical compositions of the p38α MAPK inhibitors described herein may also be prepared from compositions described herein and one or more pharmaceutically acceptable excipients suitable for sublingual, buccal, rectal, intraosseous, intraocular, intranasal, epidural, or intraspinal administration. Preparations for such pharmaceutical compositions are well-known in the art. See, e.g., Anderson, Philip O.; Knoben, James E.; Troutman, William G, eds., Handbook of Clinical Drug Data, Tenth Edition, McGraw-Hill, 2002; and Pratt and Taylor, eds., Principles of Drug Action, Third Edition, Churchill Livingston, N.Y., 1990, each of which is incorporated by reference herein in its entirety.

Administration of an active pharmaceutical ingredient or combination of active pharmaceutical ingredients or a pharmaceutical composition thereof can be effected by any method that enables delivery of the compounds to the site of action. These methods include oral routes, intraduodenal routes, parenteral injection (including intravenous, intraarterial, subcutaneous, intramuscular, intravascular, intraperitoneal or infusion), topical (e.g., transdermal application), rectal administration, via local delivery by catheter or stent or through inhalation. The active pharmaceutical ingredient or combination of active pharmaceutical ingredients can also be administered intraadiposally or intrathecally.

Exemplary parenteral administration forms include solutions or suspensions of active compound in sterile aqueous solutions, for example, aqueous propylene glycol or dextrose solutions. Such dosage forms can be suitably buffered, if desired.

Kits

The invention also provides kits. The kits include an active pharmaceutical ingredient or combination of active pharmaceutical ingredients, either alone or in combination in suitable packaging, and written material that can include instructions for use, discussion of clinical studies and listing of side effects. Such kits may also include information, such as scientific literature references, package insert materials, clinical trial results, and/or summaries of these and the like, which indicate or establish the activities and/or advantages of the composition, and/or which describe dosing, administration, side effects, drug interactions, or other information useful to the health care provider. Such information may be based on the results of various studies, for example, studies using experimental animals involving in vivo models and studies based on human clinical trials. The kit may further contain another active pharmaceutical ingredient. In selected embodiments, an active pharmaceutical ingredient or combination of active pharmaceutical ingredients are provided as separate compositions in separate containers within the kit. In selected embodiments, an active pharmaceutical ingredient or combination of active pharmaceutical ingredients are provided as a single composition within a container in the kit. Suitable packaging and additional articles for use (e.g., measuring cup for liquid preparations, foil wrapping to minimize exposure to air, and the like) are known in the art and may be included in the kit. Kits described herein can be provided, marketed and/or promoted to health providers, including physicians, nurses, pharmacists, formulary officials, and the like. Kits may also, in selected embodiments, be marketed directly to the consumer.

In some embodiments, the invention provides a kit comprising a composition comprising a therapeutically effective amount of an active pharmaceutical ingredient (e.g., a p38α MAPK inhibitor) or combination of active pharmaceutical ingredients or a pharmaceutically acceptable salt, solvate, hydrate, cocrystal, or prodrug thereof. These compositions are typically pharmaceutical compositions. The kit is for co-administration of the active pharmaceutical ingredient or combination of active pharmaceutical ingredients, either simultaneously or separately.

In some embodiments, the invention provides a kit comprising (1) a composition comprising a therapeutically effective amount of an active pharmaceutical ingredient (e.g., a p38α MAPK inhibitor) or combination of active pharmaceutical ingredients or a pharmaceutically acceptable salt, solvate, hydrate, cocrystal, or prodrug thereof, and (2) a diagnostic test for determining whether a patient's cancer is a particular subtype of a cancer. Any of the foregoing diagnostic methods may be utilized in the kit.

The kits described above are preferably for use in the treatment of the diseases and conditions described herein. In some embodiments, the kits are for use in the treatment of an inflammatory disease. In some embodiments, the kits are for use in the treatment of rheumatoid arthritis, a cardiovascular disease, multiple sclerosis, inflammatory bowel disease, chronic obstructive pulmonary disease (COPD), asthma, acute respiratory distress syndrome (ARDS), or acute lung injury (ALI). In a particular embodiment, the kits are for use in the treatment of hyperproliferative disorders, such as cancer.

In a particular embodiment, the kits described herein are for use in the treatment of cancer. In some embodiments, the kits described herein are for use in the treatment of a cancer selected from the group consisting of pancreatic cancer, breast cancer, prostate cancer, lymphoma, skin cancer, colon cancer, melanoma, malignant melanoma, ovarian cancer, brain cancer, primary brain carcinoma, head-neck cancer, glioma, glioblastoma, liver cancer, bladder cancer, non-small cell lung cancer, head or neck carcinoma, breast carcinoma, ovarian carcinoma, lung carcinoma, small-cell lung carcinoma, Wilms' tumor, cervical carcinoma, testicular carcinoma, bladder carcinoma, pancreatic carcinoma, stomach carcinoma, colon carcinoma, prostatic carcinoma, genitourinary carcinoma, thyroid carcinoma, esophageal carcinoma, myeloma, multiple myeloma, adrenal carcinoma, renal cell carcinoma, endometrial carcinoma, adrenal cortex carcinoma, malignant pancreatic insulinoma, malignant carcinoid carcinoma, choriocarcinoma, mycosis fungoides, malignant hypercalcemia, cervical hyperplasia, leukemia, acute lymphocytic leukemia, chronic lymphocytic leukemia, acute myelogenous leukemia, chronic myelogenous leukemia, chronic granulocytic leukemia, acute granulocytic leukemia, hairy cell leukemia, neuroblastoma, rhabdomyosarcoma, Kaposi's sarcoma, polycythemia vera, essential thrombocytosis, Hodgkin's disease, non-Hodgkin's lymphoma, soft-tissue sarcoma, osteogenic sarcoma, primary macroglobulinemia, and retinoblastoma. In particular embodiments, the kits described herein are for use in the treatment of malignant melanoma.

Dosages and Dosing Regimens

The amounts of the pharmaceutical compositions administered using the methods herein, such as the dosages of p38α MAPK inhibitors, will be dependent on the human or mammal being treated, the severity of the disorder or condition, the rate of administration, the disposition of the active pharmaceutical ingredients and the discretion of the prescribing physician. However, an effective dosage is in the range of about 0.001 to about 100 mg per kg body weight per day, such as about 1 to about 35 mg/kg/day, in single or divided doses. For a 70 kg human, this would amount to about 0.05 to 7 g/day, such as about 0.05 to about 2.5 g/day. In some instances, dosage levels below the lower limit of the aforesaid range may be more than adequate, while in other cases still larger doses may be employed without causing any harmful side effect—e.g., by dividing such larger doses into several small doses for administration throughout the day. The dosage of the pharmaceutical compositions and active pharmaceutical ingredients may be provided in units of mg/kg of body mass or in mg/$m^2$ of body surface area.

In some embodiments, the invention includes methods of treating a cancer in a human subject suffering from the cancer in which cancer cells overexpress p38α MAPK, the method comprising the steps of administering a therapeutically effective dose of an active pharmaceutical ingredient that is a p38α MAPK inhibitor to the human subject.

In some embodiments, the invention includes methods of treating a cancer in a human subject suffering from the cancer in which cancer cells overexpress p38α MAPK, the method comprising the steps of administering a therapeutically effective dose of an active pharmaceutical ingredient that is a p38α MAPK inhibitor to the human subject to inhibit or decrease the activity of p38α MAPK protein.

In some embodiments, a pharmaceutical composition or active pharmaceutical ingredient is administered in a single dose. Such administration may be by injection, e.g., intravenous injection, in order to introduce the active pharmaceutical ingredient quickly. However, other routes, including the preferred oral route, may be used as appropriate. A single dose of a pharmaceutical composition may also be used for treatment of an acute condition.

In some embodiments, a pharmaceutical composition or active pharmaceutical ingredient is administered in multiple doses. In an embodiment, a pharmaceutical composition is administered in multiple doses. Dosing may be once, twice, three times, four times, five times, six times, or more than six times per day. Dosing may be once a month, once every two weeks, once a week, or once every other day. In other embodiments, a pharmaceutical composition is administered about once per day to about 6 times per day. In some embodiments, a pharmaceutical composition is administered once daily, while in other embodiments, a pharmaceutical composition is administered twice daily, and in other embodiments a pharmaceutical composition is administered three times daily.

Administration of the active pharmaceutical ingredients may continue as long as necessary. In selected embodiments, a pharmaceutical composition is administered for more than 1, 2, 3, 4, 5, 6, 7, 14, or 28 day(s). In some embodiments, a pharmaceutical composition is administered for less than 28, 14, 7, 6, 5, 4, 3, 2, or 1 day(s). In some embodiments, a pharmaceutical composition is administered chronically on an ongoing basis—e.g., for the treatment of chronic effects. In some embodiments, the administration of a pharmaceutical composition continues for less than about 7 days. In yet another embodiment the administration continues for more than about 6, 10, 14, 28 days, two months, six months, or one year. In some cases, continuous dosing is achieved and maintained as long as necessary.

In some embodiments, an effective dosage of an active pharmaceutical ingredient disclosed herein is in the range of about 1 mg to about 500 mg, about 10 mg to about 300 mg, about 20 mg to about 250 mg, about 25 mg to about 200 mg, about 10 mg to about 200 mg, about 20 mg to about 150 mg, about 30 mg to about 120 mg, about 10 mg to about 90 mg, about 20 mg to about 80 mg, about 30 mg to about 70 mg, about 40 mg to about 60 mg, about 45 mg to about 55 mg, about 48 mg to about 52 mg, about 50 mg to about 150 mg, about 60 mg to about 140 mg, about 70 mg to about 130 mg, about 80 mg to about 120 mg, about 90 mg to about 110 mg, about 95 mg to about 105 mg, about 150 mg to about 250 mg, about 160 mg to about 240 mg, about 170 mg to about 230 mg, about 180 mg to about 220 mg, about 190 mg to about 210 mg, about 195 mg to about 205 mg, or about 198 to about 202 mg. In some embodiments, an effective dosage of an active pharmaceutical ingredient disclosed herein is less than about 25 mg, less than about 50 mg, less than about 75 mg, less than about 100 mg, less than about 125 mg, less than about 150 mg, less than about 175 mg, less than about 200 mg, less than about 225 mg, or less than about 250 mg. In some embodiments, an effective dosage of an active pharmaceutical ingredient disclosed herein is greater than about 25 mg, greater than about 50 mg, greater than about 75 mg, greater than about 100 mg, greater than about 125 mg, greater than about 150 mg, greater than about 175 mg, greater than about 200 mg, greater than about 225 mg, or greater than about 250 mg.

In some embodiments, an effective dosage of an active pharmaceutical ingredient disclosed herein is in the range of about 0.01 mg/kg to about 200 mg/kg, or about 0.1 to 100 mg/kg, or about 1 to 50 mg/kg.

In some embodiments, an active pharmaceutical ingredient is administered at a dosage of 10 to 200 mg BID, including 50, 60, 70, 80, 90, 100, 150, or 200 mg BID. In some embodiments, an active pharmaceutical ingredient is administered at a dosage of 10 to 500 mg BID, including 1, 5, 10, 15, 25, 50, 75, 100, 150, 200, 300, 400, or 500 mg BID.

In some instances, dosage levels below the lower limit of the aforesaid ranges may be more than adequate, while in other cases still larger doses may be employed without causing any harmful side effect, e.g., by dividing such larger doses into several small doses for administration throughout the day. Of course, as those skilled in the art will appreciate, the dosage actually administered will depend upon the condition being treated, the age, health and weight of the recipient, the type of concurrent treatment, if any, and the frequency of treatment. Moreover, the effective dosage amount may be determined by one skilled in the art on the basis of routine empirical activity testing to measure the bioactivity of the compound(s) in a bioassay, and thus establish the appropriate dosage to be administered.

An effective amount of the combination of the active pharmaceutical ingredient may be administered in either single or multiple doses by any of the accepted modes of administration of agents having similar utilities, including rectal, buccal, intranasal and transdermal routes, by intra-arterial injection, intravenously, intraperitoneally, parenterally, intramuscularly, subcutaneously, orally, topically, or as an inhalant.

In some embodiments, the compositions described herein further include controlled-release, sustained release, or extended-release therapeutic dosage forms for administration of the compounds described herein, which involves incorporation of the compounds into a suitable delivery system in the formation of certain compositions. This dosage form controls release of the compound(s) in such a manner that an effective concentration of the compound(s) in the bloodstream may be maintained over an extended period of time, with the concentration in the blood remaining relatively constant, to improve therapeutic results and/or minimize side effects. Additionally, a controlled-release system would provide minimum peak to trough fluctuations in blood plasma levels of the compound.

The following examples describe the invention in further detail. These examples are provided for illustrative purposes only, and should in no way be considered as limiting the invention.

EXAMPLES

Materials and Methods

Chemicals, recombinant proteins and antibodies: Mouse anti-human p38α and rabbit anti-phospho-MK2 (T222) and phospho-Stat-1 (S727) were purchased from Cell Signaling Technology (Danvers, MA). The coding sequences for human p38α variant 2 and p38β (with N-terminal HA tag) were amplified by PCR and cloned into pRSetA (Thermo Fisher). Mutations were introduced into p38α using Quikchange (Stratagene) and confirmed by bidirectional sequencing. Plasmids were transformed in *E. coli* BL21 and proteins were purified using cobalt columns (TALON™; Clontech Laboratories; Mountain View, CA) and confirmed by SDS-PAGE and Western blotting. The compounds identified in the CADD screen were purchased from Maybridge Chemical Co. (Belgium).

CADD identification of lead compounds (FIG. 1*d*): Based on the X-ray crystal structure of mouse p38α/MAPK14 (PDB ID: 1P38), a step-wise iterative CADD process was used to screen an in silico database of small molecule compounds available from Maybridge Chemical Screening Collection for the potential to bind in a pocket near the ED substrate binding site (FIG. 1*a* and FIG. 1*b*). In silico preparation of p38α conformation was performed using CHARMM36 and general (CGenFF) force field with the Nanoscale Molecular Dynamics (NAMD) program, to identify local potential ligand-binding pockets. Protein structures were subjected to clustering to identify 20 representative protein conformations to account for protein flexibility. Screening was performed in the following stages: (1) potential inhibitor binding sites were identified; (2) compounds were ranked based on their van der Waals (VDW) and electrostatic interaction energies with the protein binding pockets using the program DOCK with size-based score normalization; (3) the top 50,000 compounds were subjected to a second in silico screen with additional relaxation of the ligands during simulated binding and the top 1,000 compounds were selected based on total interaction energy including score normalization based on ligand size; (4) chemical fingerprint-based cluster analysis of the top scoring compounds using the program MOE (Chemical Computing Group) was performed to identify chemically diverse compounds and the final list of potential p38α-interacting compounds were selected based on a scalar bioavailability metric, 4DBA, that accounts for the physiochemical descriptors in Lipinski's Rule of Five.

Mouse unphosphorylated p38α/MAPK14 variant-1 differs from its human variant-2 by only two amino acids, H48L and A263T and from mouse variant-2 and human variant-1 by only 14 amino acids between residues 230 and 254. Neither these amino differences nor the phosphorylation state of p38α (FIG. 1*c*) are predicted to significantly alter the structure of the CD or ED sites or our CADD targeted, thereby validating the use of mouse unphosphorylated p38α variant-1 for the CADD search and unphosphorylated recombinant human p38α variant-2 protein for the DSF screen.

Figure 7:
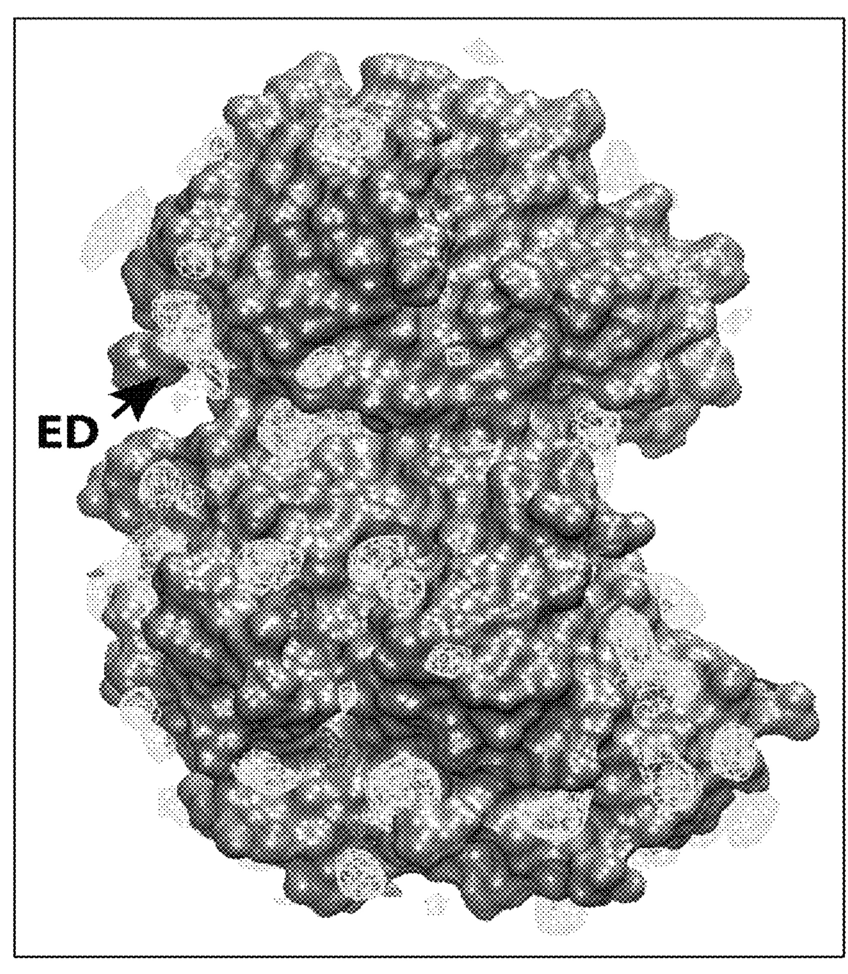
FIG. 7 is the SILCS FragMap of p38α. Nonpolar maps (green) indicate putative binding pockets, with the location of the ED site indicated. H-bond donor (blue) and acceptor (red) maps are shown.

Site Identification by Ligand Competitive Saturation (SILCS): An in silico map of all potential ligand-binding pockets in p38α has been completed, including the ED site target, using the Site Identification by Ligand Competitive Saturation (SILCS) method (FIG. 7, potential binding sites in green). The SILCS method creates a free energy map (grid free energy; GFE FragMaps) of the functional group interaction pattern of p38α that allows for identification of putative binding sites and rapid free energy estimates of ligand binding to the various p38α sites (ligand GFE or LGFE). The SILCS GFE FragMaps account for protein flexibility, protein desolvation, functional group desolvation, as well as functional group-protein interactions, thereby yielding highly accurate mapping of the protein for use in database screen and lead compound optimization. Each stepwise in silico CADD screen of any compound database starts with the SILCS pharmacophore approach, which takes into account protein flexibility. The secondary screen is based on the MC SILCS approach from which relative free energies of binding are calculated. A final screen based on chemical diversity, physiochemical properties that maximize absorption, distribution, metabolism, and excretion (ADME) characteristics and potential for chemical optimization, generates a list of compounds for testing of selective p38α binding and biological activity. Additional rounds of screening are performed using CADD strategies modified based on the proteomic and structural analyses of lead compounds. Searches of the database for structural analogs of lead compounds from earlier rounds are performed using the program MOE (Chemical Computing Group).

Alternative CADD methodology: The program Dock can be used with scoring based on the Dock van der Waals (vdW) interaction energy normalized for molecular weight (MW). This method identifies compounds that sterically fit the binding site while biasing towards low MW compounds. Additional ranking of compounds use generalized linear response methods and include free energy of solvation based on the implicit solvent Generalized Born (GB) model.

Alternative p38α targets: the search strategy can be changed to target the CD, or the DEF sites. Since formation of the DEF pocket requires p38α activation, dual-phosphorylated p38α is used for its DSF screen.

Differential Scanning Fluorimetry (DSF): Binding of CADD selected compounds to p38α and R isoforms was tested experimentally using DSF, which evaluates changes in the target protein melting temperature (ΔTm) due to interactions with test compound. SYPRO orange (Invitrogen; diluted 1:1000 in 10 mM HEPES, 150 mM NaCl, pH 7.5) and 1 μM unphosphorylated recombinant human p38α were added to 96-well PCR plates, then 50 nM to 200 μM test compound in 100% DMSO (2% final DMSO concentration) was added, the plates mixed, sealed, centrifuged at 1000 rpm for 1 min, and melting curve performed using an Applied Biosystems real time PCR instrument. The melting point was determined from the first derivative curve. In addition, p38β, or target-disrupted p38α mutant are used as well.

Although DSF is less sensitive than other assays of ligand:protein binding, it is low-cost and has relatively high throughput. DSF detected p38α binding by 25% of the CADD-identified compounds screened and selective p38α binding by 10%, demonstrating good efficiency of both the CADD and DSF screening strategies. The 10% hit rate of the CADD search for substrate-selective p38α inhibitors was similar to the search for substrate-selective ERK inhibitors, and much greater than the usual 0.1-0.01% hit rate using experimental screening alone.

Cell culture: HMVECLs were purchased from Promocell (Heidelberg, DE), maintained in Endothelial Cell Growth Medium MV2, used at passage 3 to 10, and studied at postconfluence according to the supplier's protocol. The THP1 human monocyte cell line (American Type Culture Collection/ATCC no. TIB202) was maintained in RPMI 1640 supplemented with 2 mM L-glutamine, 1 mM sodium pyruvate, 10 mM HEPES buffer, pH 7.3, penicillin, streptomycin, 0.05 mM β-mercaptoethanol and 10% defined fetal bovine serum (FBS; Gibco, Life Technologies, Grand Island, NY). HeLa cells (ATCC no. CCL-2) were cultured in DMEM with 4.5 g/L glucose, 1 mM sodium pyruvate, 2 mM L-glutamine, penicillin, streptomycin, and 10% FBS. Prior to experimental exposures, THP1 cells were differentiated by treating with 5 ng/ml Phorbol 12-myristate 13-acetate (PMA, Sigma-Aldrich) for 24 h, washing with PBS, and culturing at 37° C. in PMA-free media for an additional 24 h.

Endothelial permeability assay: Permeability of HMVECL monolayers was assessed by measuring transendothelial flux of 10 kDa dextran conjugated to Cascade blue fluorescent dye for 30 min at 37° C. in Matrigel-coated 3 μm pore size Transwell plates.

Cells are treated with test compound at 1-100 μM, 10 μM SB203580, or DMSO for 1 h, then with 10 ng/ml rhTNFα at 39.5° C. for 6 h and permeability is assessed by adding 100 μg/ml Cascade-blue-conjugated 10 kDa dextran to the bottom well for 30 min at 37° C. and analyzing fluorescence (400/420 nm) in the upper well.

Neutrophil transendothelial migration (TEM) assay: Neutrophils were isolated from heparinized venous blood that was collected from healthy volunteers using a protocol approved by the University of Maryland Institutional Review Board and TEM of calcein-labeled neutrophils through HMVECLs was measured.

Cytotoxicity of HMVECL exposed to 10-100 μM of each compound is analyzed by MTS assay (Promega), LDH release (Promega), and immunoblotting for activated caspase-3 (Cell Signaling).

Macrophage cytokine expression: The capacity of test compounds to block LPS-induced cytokine expression is assessed in PMA-differentiated THP1 cells using qRT-PCR and Luminex-based immunoassays (UMB Cytokine Core Lab). THP1 cells differentiated with 5 ng/ml PMA for 24 h, are treated with 1-100 μM test compound, 10 μM SB203580, or DMSO for 1 h, then with 100 ng/ml ultrapure *E. coli* 0111:B4 LPS (InvivoGen) for 3 h (qRT-PCR; Real Time Primers) or 24 h (supernatants for immunoassays).

Mouse acute lung injury Model: Male CD-1 mice weighing 25-30 g were purchased from Charles River and housed in the Baltimore Veterans Administration Medical Center Animal Care Facility under AALAC-approved conditions. All protocols were approved by the University of Maryland Baltimore IACUC. Inhibitors were tested in a mouse i.t. LPS/FRH-induced ALI model. Mice were pretreated with SB203580 or putative p38 inhibitors in ≤2% DMSO via 0.5 ml i.p. injection 1 h prior to i.t. instillation of 50 μg LPS and switch to a 37° C. incubator, which increases core temperature to ~39.5° C. Mice were euthanized after 24 h, the lungs lavaged with a total of 2 ml PBS, the cells counted and the cell free lavage fluid analyzed for protein content using the Bradford method (Biorad).

Animals are anesthetized with inhaled isoflurane during surgery to implant intraperitoneal thermistors. Mice receive 0.05-0.1 mg/kg buprenorphine analgesia s.c. Q12h for 2 postoperative days. If significant distress occurs during the ALI model buprenorphine analgesia is administered. LPS is administered in 50 μl PBS via instillation in the posterior oropharynx during anesthesia with isoflurane. p38 inhibitors are administered via i.p. injection with a 25 g needle with the mouse conscious and lightly restrained.

The combination of FRH and intratracheal LPS induces robust pulmonary neutrophil influx, cytokine expression, and protein leak by 12-24 h and 50% mortality beginning at 48 h. UM101 was more potent than SB203580 in reducing neutrophil and protein accumulation in BAL in this model. Thus, to minimize the number of mice required for this screen, lung injury, lung and extrapulmonary inflammation, and drug toxicity are measured at a single 24 h time point, including BAL protein, neutrophil, and proinflammatory cytokine content, serum levels of IL-6, creatinine and AST (Abcam), and Cardiac Troponin I (MyBiosource). Novel compounds are tested at doses of 4, 12, and 40 mg/kg and compared with vehicle (DMSO)- and SB203580 (40 mg/kg)-treated controls. All vehicle- and drug-treated mice are exposed to i.t. LPS/FRH and compared with naïve mice. 4 mice per group can be used.

Generally, screening is done in prevention models and final candidates are also evaluated in a treatment model.

Inhibition of substrate phosphorylation: A functional analysis of UM101 to block p38-dependent phosphorylation of MK2 and Stat-1 was performed in HeLa cells. The cells were pre-treated with SB203580 or UM101 for 30 min and then activated with 10 μM anisomycin for 30 min. Cell extracts prepared in RIPA buffer containing protease and phosphatase inhibitors were resolved by SDS-PAGE, transferred to PVDF membrane, blocked with 5% nonfat dry milk, probed with primary antibodies against phosphorylated MK2 and Stat-1, and total p38α as a loading control. Bands were detected using secondary antibodies conjugated to infrared fluorophores and infrared fluorescence imaging (Odyssey; LICOR).

Cytotoxicity assay: Cytotoxicity was monitored in parallel HMVEC-L monolayers established in 96-well culture plates using a colorimetric assay that measured reduction of 3-(4,5-dimethylthiazol-2-yl)-5-(3-carboxymethoxyphenyl)-2-(4-sulfophenyl)-2H-tetrazolium (MTS) to a formazan dye (CellTiter 96™; Promega; Madison, WI) according to the manufacturer's protocol and quantifying product formation by measuring absorption at 490 nm.

Gene Expression: RNA integrity was confirmed by Agilent Bioanalyzer 2100 and all samples were confirmed to have RNA integrity scores (RIN) of 10 prior to further analysis. Poly(A)-enriched samples were reverse transcribed and sequenced using the Illumina HiSeq platform to generate at least 90 million reads per sample. Intergenic sequence accounted for less than 0.7% of all reads indicating minimal genomic DNA contamination. Raw data were analyzed using the TopHat read alignment tool and *Homo sapiens* genomic reference sequence (Ensembl version GRCh38.78). Differential gene expression was analyzed using the DESeq R package (Bioconductor) and the negative binomial model. Criteria for significant differences in gene expression were (1) false discovery rate (FDR)<0.05, (2) expression level >$10^{th}$ percentile, and (3)≥2-fold change. The differential gene expression patterns were further analyzed using the PathwayNet (Troyanskaya Lab, Princeton) and Ingenuity™ Pathway Analysis (Qiagen) tools. Cytokine gene expression in THP1 cells was analyzed by quantitative RT-PCR using primers in a commercially available PCR array (HCA-II array; Real Time Primers; Elkins Park, PA) and SYBR-green reaction mix (Biorad), and a BioRad iCycler IQ Optical Module according to the supplier's protocol. Data were quantified using the Gene Expression Ct Difference method, and standardized to levels of the housekeeping gene, GAPDH, using Ct values automatically determined by the thermocycler.

Saturation Transfer Difference Nuclear Magnetic Resonance (STD-NMR): A 40 mM stock solution of UM101 was made in d6-DMSO. STD-NMR samples contained 150 mM NaCl, 50 mM phosphate, pH 7, 200 μM UM101, and 5 μM p38 protein in D20. Spectra were recorded on an Agilent DD2 500-MHz spectrometer equipped with a 5-mm inverse HFCN probe head at 300 K. During each transient, the protein was saturated with a series of 58 GAUSSIAN-shaped pulses (50 ms, 1 ms delay between pulses) using the vendor-supplied STD-ES pulse sequence, for a total saturation time of 3 seconds. The on-resonance irradiation of protein was done at 0.5 ppm and off-resonance irradiation at 30 ppm. The vendor-supplied WATERGATE pulse sequence was used to suppress the water signal in the STD spectrum. The on-resonance and off-resonance pulse sequences were subtracted internally. A total of 16,384 transients were collected for each STD experiment with a 1 second delay between acquisitions, 6000 Hz spectral width, and 1.3 second acquisition time.

Comparative proteome and phosphopeptide expression profiling by mass spectrometry (MS): Protein expression and the percentage of phosphorylation of specific proteins is quantified in a label-free manner using mass spectrometry-based techniques. Specifically, the effects of compounds of the invention are compared with SB203580 on protein phosphorylation pattern and proteome expression in TNFα-stimulated HMVECLs and LPS-stimulated THP1 cells using LC-MS/MS. Cells are pretreated for 30 min with 10 μM SB203580 or test compound at $EC_{50}$ and $EC_{90}$ (based on HMVECL permeability and THP1 IL-8 expression assays). For phosphopeptide analysis, cells are stimulated for 0.5, 1.5, and 4 h. Tryptic phosphopeptides are enriched using a commercially available $TiO_2$ enrichment protocol (Pierce), then analyzed on a nanoUPLC coupled Thermo Orbitrap Fusion Tribrid Mass Spectrometer using three strategies: (1) hybrid Electron-Transfer (ETD)/Higher-Energy Collision (HCD) Dissociation (EThcD); (2) data-dependent decision tree (DDDT) logic; (3) HCD product-dependent ETD (HCD-pd-ETD); and/or (4) nanoUPLC coupled Waters Synapt G2S Mass Spectrometer, using ion mobility linked parallel MS ($UDMS^e$). For comparative proteome expression analysis, cells are stimulated for 4 and 12 h and lysates analyzed on the nanoUPLC coupled Waters Synapt G2S and/or nanoUPLC coupled Thermo Orbitrap Fusion Tribrid using $UDMS^E$ and ADAPT-DDA, respectively. Relative peptide abundance is measured by comparing the MS1 peak area of peptide ions, whose identities and phosphorylation events are confirmed by MS2 sequencing using the different fragmentation strategies described above (EThcD, DDDT, HCD-pd-ETD and $UDMS^e$). An aligned AMRT (accurate mass and retention time) cluster quantification algorithm as described is used for label free quantification.

Immunoblot analysis: Changes in total in vivo proteome and the phosphoproteome are confirmed by immunoblotting using commercial antibodies and infrared fluorescence imaging (Odyssey; LICOR). In vitro kinase assays is performed in reactions containing recombinant active p38α and one or more recombinant substrate proteins and analyzed by immunoblotting with phosphospecific antibodies.

X-ray crystallography: Higher resolution analysis of compound binding to p38α is provided by x-ray crystallography. The primary approach to growing p38α includes co-crystallization of compound crystals with a 2:1 compound:p38α molar ratio. Alternatively, compounds are soaked into preformed p38α crystals. Diffraction quality protein crystals are grown and screened using an automated system comprising an Alchemist DT screen maker, Gryphon drop setter with LCP module, and Minstrel DT UV/Vis automated visualization system (Rigaku). These structures are solved by molecular replacement methods using known p38α structures and standard crystallographic analysis software (SBGrid).

Analysis of p38-binding kinetics: The KD for the compounds of the invention are estimated by DSF. ITC is performed to refine the KD calculation of compounds and produce thermodynamic information to facilitate ligand optimization. Data is collected on an Auto ITC HT Microcalorimeter (MicroCal). Recombinant p38α (10 μM) and stock concentration of test compounds (200 μM) are prepared in identical buffers containing low ionization energy (e.g., 50 mM phosphate or citrate with 50 mM NaCl) and degassed. Heat generation/absorption during titration of compound are measured and analyzed with MicroCal software.

Pharmacokinetic/pharmacodynamic (PK/PD) analysis of lead compounds: Compounds are comprehensively analyzed for in vivo toxicity and effectiveness as both prevention and treatment in the intratracheal LPS+FRH-induced mouse ALI model. This model is a short-term model of human ARDS, amenable to parenteral dosing of therapeutic agents, characterized by extensive endothelial permeability, neutrophil accumulation, proinflammatory cytokine and chemokine expression, epithelial injury, and ~50% mortality beginning after 48 h. The results are generalizable to other inflammatory diseases. Compounds are solubilized in a final concentration of ≤1% DMSO and administered as a single intraperitoneal injection. Maximal tolerated dose (MTD) is determined by monitoring mice for 24 h for signs of distress (including change in locomotor activity, weight loss, reduced grooming, and ruffled fur), creatinine, BUN, aspartate transaminase (AST), and cardiac troponin. Inhibitors are administered either 30 min prior to or 8 h after LPS+FRH as models of prevention or treatment, respectively.

Animal number and sex: All testing is performed in CD1 mice, a robust strain in which ALI and pneumonia models have been validated. Dose escalation uses 2 mice per dose and 24 h observation according to published guidelines. Survival differences are tested in groups of 20 mice (to detect differences in survival of 75% vs. 25%; $\alpha$=0.05; $\beta$=0.2). Group sizes of 6 mice for BAL and plasma analysis of injury/inflammation and lung homogenates for analysis of apoptotic signaling and groups of 4 mice for histology are used. Survival experiments are performed in equal numbers of male and female mice and differences compared by 2-way ANOVA. Additional experiments are added to analyze any unexpected gender differences found in drug effects. In some embodiments, experiments will use male mice.

Maximal Tolerated Dose of most potent, structurally distinct compounds is determined by measuring toxicity of 20, 40, and 80 mg/kg i.p.in 2 mice per dose, monitored for 24 h and euthanized. Serum is analyzed for markers of hepatic, renal, and cardiac toxicity. Kidney, heart, liver and lung (inflated) are fixed, paraffin-embedded, H&E-stained, and examined for inflammation and injury. Control mice receive vehicle (1% DMSO). Toxic compounds are replaced by the next structurally distinct compound on the list of candidates.

Activity of Inhibitors in blocking FRH augmented LPS-induced ALI: Compounds are tested at the MTD in the LPS+FRH-induced ALI model.

Effect of pretreatment on survival: Effectiveness of pretreatment with test compounds at the MTD on survival in LPS/FRH-challenged mice is compared with 40 mg/kg SB203580 and vehicle (1% DMSO) in groups of 20 mice. Mice receive pretreatment as a single 0.5 ml injection and 30 min later receive 50 μg LPS via i.t. instillation and placed in 37° C. ambient temperature. This exposure increases core temperature from 36.5° C. to 39.5° C., but is confirmed in some mice using telemetric temperature monitoring (Data Sciences International; St. Paul, MN). Mice are monitored for survival using moribundity as a surrogate for death. Those compounds showing survival advantage vs. DMSO are further analyzed for efficacy when given 24 h post-LPS. Ineffective compounds are replaced by the next compound from the candidate list. Effective compounds are further tested at 10% and 30% of the MTD.

Effect of post-LPS dosing on survival: Compounds that are effective as pretreatment are analyzed for effectiveness at the same doses using the same protocol except delaying dosing until 8 h after LPS instillation and initiation of FRH. Compounds conferring survival advantage vs. SB203580 are analyzed for biological effects and PK. Ineffective compounds are replaced by the next compound on the list.

Effect of compounds on inflammation, lung injury, and permeability: The most effective compounds in the survival experiments are further analyzed for effects on lung injury and inflammation in the LPS+FRH ALI model. Mice are pretreated with each compound at its ED50 based on the survival experiments, 40 mg/kg SB203580, or DMSO 30 min prior to or 8 h-after LPS/FRH challenge and euthanized 24 h post-LPS. In 6 mice per group, BALF is collected and analyzed for neutrophil content by counting modified-Giemsa-stained cytopreps, total protein by Bradford method, and levels of cytokines by Luminex-based immunoassay (UMB Cytokine Core Lab). After lavage, lungs are excised, snap-frozen in liquid nitrogen and homogenates prepared for immunoblotting of candidate p38α substrates to confirm substrate inhibitor effects found in vitro. Lungs from 4 mice per group are inflation/fixed at 20 cm $H_2O$ with Prefer™, paraffin embedded, H&E stained, or GR-1 immunostained to analyze lung injury and neutrophil infiltration, and TUNEL staining and immunostaining for active caspase-3 to assess apoptosis. Serum IL-6 is measured as an indicator of systemic inflammation.

Pharmacokinetics of novel p38 modifiers: PK of effective compounds in mice is characterized. First, a bioanalytical method for each compound is developed and validated according to FDA Guidance. PK studies are then conducted to determine lung uptake and key PK parameters that characterize each compound (i.e., clearance (CL), volume of distribution (Vd), maximum plasma conc. ($C_{max}$), time to reach $C_{max}$ ($T_{max}$), area under the plasma concentration curve (AUC) and half-life ($t_{1/2}$)). The PK parameters are used to estimate the time needed to reach steady state plasma concentration (equivalent to five half-lives), and to guide dose selection for further PD studies. In addition, these studies help rank the tested p38 modifiers in terms of their lung/plasma conc. ratios. For each study, CD1 mice (n=30) are treated with a single i.p. dose (10-50 mg/kg) of the selected p38 modifier (dose range for each p38 modifier is dependent on the outcome of studies outlined above. In some embodiments, mice (n=3/time point) are euthanized at a pre-dose and at 5, 15, 30, 60, 120, 240, 360, 600, 720 min post dose. Blood and lung samples are analyzed using validated HPLC methods.

Data Analysis: Pathways modified by compounds of the invention as compared with SB203580 are deduced-by: (1) analyzing comparative proteome expression using Ingenuity Pathway Analysis and PathwayNet, similarly to RNASeq data from UM101; and (2) analyzing the comparative phosphoproteome by quantitative approaches and bioinformatics. The mass spectrometry results are confirmed by analyzing phosphorylation of candidate substrates in cells and in vitro kinase assays by immunoblotting. Off-target binding suggested by the proteomics data is evaluated over a broad concentration range of test compound by DSF and STD-NMR and by phosphoimmunoblotting for specific substrates and confirmed in in vitro kinase reactions. By identifying common pathways modified by multiple lead compounds and their interactions with p38α, the common p38α effects required for their favorable biological activity are deduced and incorporated into the CADD algorithm for subsequent searches and lead compound optimization.

Since the objective of this invention is, in one embodiment, to identify and characterize the PD/PK properties of novel anti-inflammatory compounds, these compounds are tested in one embodiment, in order of activity based on functional screens, and compounds that fail toxicity or efficacy in survival studies are replaced with the next most potent and structurally dissimilar compound. Compounds are compared with vehicle alone and SB203580 using one-way ANOVA/Fisher PLSD. The PK data is analyzed by the naive averaging method. Compartmental modeling is used to estimate various pharmacokinetic parameters using Phoenix platform (ver. 1.3, Pharsight, Sunnyvale, CA). Several compartmental models are evaluated to determine the best-fit model. A variety of weighting schemes are used including equal weight, 1/y, $1/\hat{y}$, $1/y^2$, and $1/\hat{y}^2$, where y is the observed drug conc., and $\hat{y}$ is the model-predicted drug conc. In some embodiments, a final model is selected based on goodness-of-fit plots, weighted residual sum of squares, random distribution of residuals, precision of parameter estimates, Akaike's information criteria, and Schwarz criteria. After the final model is developed, estimates of the PK parameters are reported including plasma CL, Vd, $C_{max}$, $T_{max}$, AUC, and $t_{1/2}$. Lung uptake is represented as a lung/plasma (L/P) conc. ratio.

Alternative Approaches: If phosphospecific antibodies are not available and phosphorylation does not cause detectable shifts on immunoblots, cell lysates can be enriched using TiO2 prior to immunoblotting. Incubation times can be adjusted, as needed, based on in vitro and in vivo proteomics and immunoblot results. Low protein abundance could preclude phosphoprotein detection in cell lysates despite maximum starting material or using isolated cell fractions. In this case, the in vivo cellular phosphoproteome analysis can be augmented by using LC-MS-MS to comprehensively analyze the effects of inhibitors on phosphopeptide patterns in p38α in vitro kinase assays using cell lysates as substrate after inactivating endogenous kinases with 5'-4-fluorosulphonylbenzoyladenosine (FSBA). Stable isotope dimethyl labeling can be used in case of ambiguous label-free results. Other back-up technologies include deuterium-hydrogen exchange mass spectroscopy and NMR, and DSF/STD-NMR-assessed binding to wild-type p38α and CADD-target-mutants. Surface plasmon resonance (SPR) (Biacore T200 Core) can be evaluated as an alternative to ITC to reduce the protein/compound requirements.

Statistical methods: Data are presented as mean±SE. Differences among >2 groups were analyzed by applying a Tukey Honestly Significant Difference test to a one-way analysis of variance (ANOVA). Differences between dose-response curves was analyzed by multivariate ANOVA (MANOVA) Differences with $p<0.05$ were considered significant.

Example 1: CADD Modeling of p38 MAPK Substrate-Docking Site, Compound Identification, and Screening Compounds for Direct, Selective Interaction with p38α

The inhibitors and methods of the invention relate to a CADD-based strategy to identify low molecular weight compounds predicted to bind near the ED substrate-docking site of mouse unphosphorylated p38α (MAPK14 variant-1; PDB:1P38), which is >99% identical with human p38α (variant-2) (FIG. 1*a*). The ED and CD sites in p38α are located at either end of a substrate-binding cleft located on the opposite side of the protein from the catalytic site (FIG. 1*a*). A pocket near the ED binding site comprising 10 amino acids, only 7 of which were identical in p38α and p380, was identified (FIG. 1*b*). Overlay of structures of mouse unphosphorylated (PDB:1P38) and dual-phosphorylated p38α (PDB:3PY3) revealed near-superimposition of the targeted pocket in the two forms (FIG. 1*c*).

Figure 4:
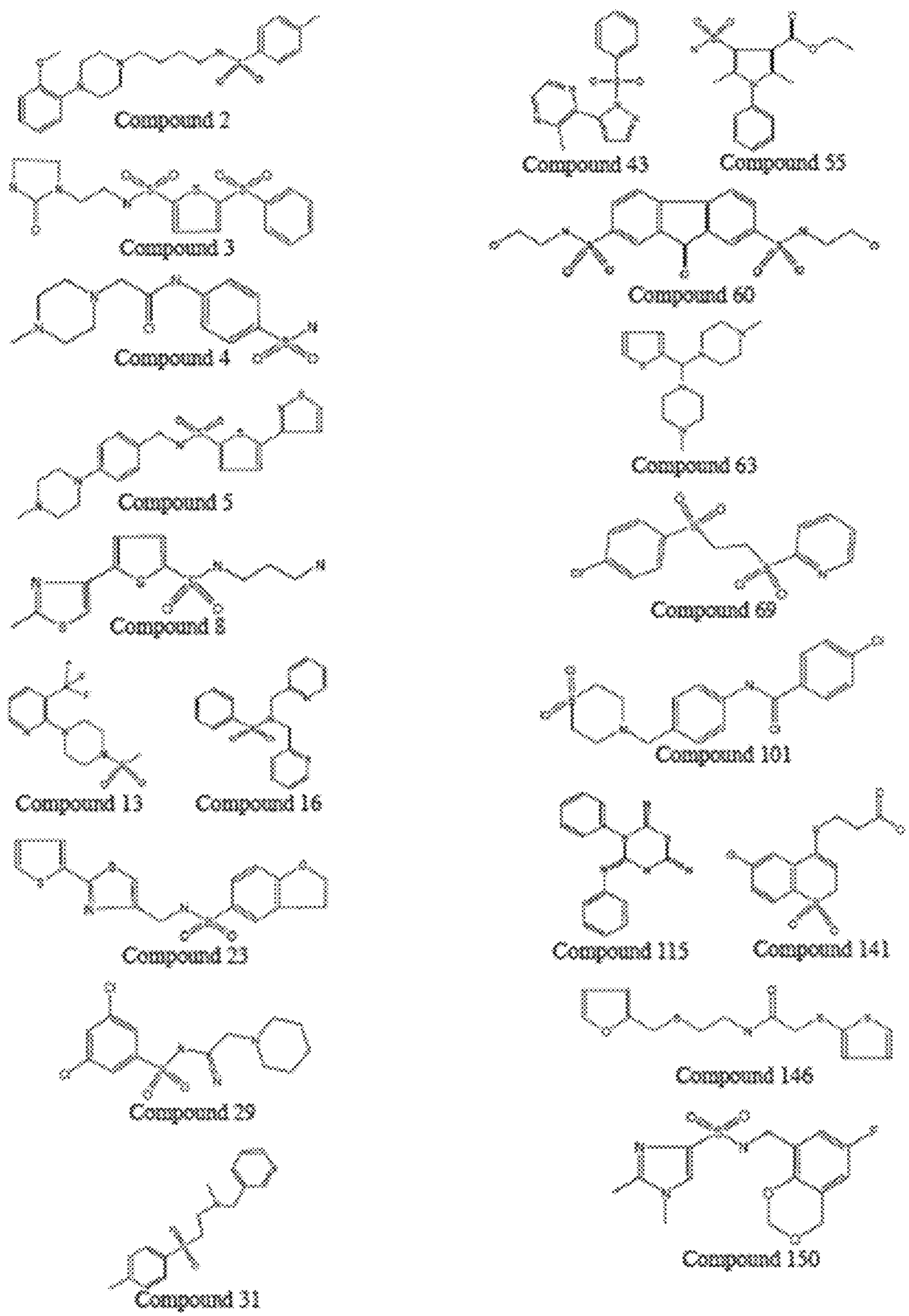
FIG. 4 illustrates the chemical structures of 20 compounds selected from a list of 150 CADD selected compounds and screened by DSF from the Maybridge catalogue.

An overview of the CADD screening and compound testing protocols is shown in FIG. 1*d*. The compounds in the Maybridge Screening Collection were analyzed for binding to the targeted p38α pocket based on Van Der Waals (VDW) and electrostatic interaction energies, chemical diversity by chemical fingerprint-based cluster analysis, solubility, molecular weight and number of hydrogen bonding functional groups that maximize bioavailability. Twenty structurally dissimilar compounds were selected for functional analysis (Table 2, FIG. 4), out of a panel of 150 diverse compounds (Table 3) which were selected for potential biological testing.

TABLE 2

CADD-identified p38α ED site-binding candidates screened for p38α binding

| CADD no. | Compound ID[1] | MW | logP[2] | p38α ΔTm (° C.) @100 μM[3] | ERK2 ΔTm (° C.) @100 μM[3] |
|---|---|---|---|---|---|
| 2 | SEW 06373 | 417 | 3.19 | −0.05 | 0.412 |
| 3 | HTS 02798 | 415 | 0.67 | 0.282 | 0.337 |
| 4 | HTS 13333 | 312 | −1.10 | 0.065 | 0.452 |
| 5 | SCR 00846 | 418 | 2.22 | 0.808 | 0.628 |
| 8 | AW 00509 | 317 | 1.13 | −0.07 | 0.531 |
| 13 | SEW 06264 | 309 | 0.28 | 0.005 | 0.390 |
| 16 | SCR 00610 | 339 | 1.69 | −0.052 | 0.444 |
| 23 | SCR 01200 | 378 | 2.79 | −0.488 | −0.598 |
| 29 | BTB 05645 | 350 | 3.07 | −0.353 | 0.342 |
| 31 | KM 04113 | 304 | 1.83 | −0.278 | 0.153 |
| 43 | CD 11992 | 300 | 1.16 | −0.485 | 0.151 |
| 55 | SP 01164 | 2.11 | 1.92 | −0.506 | 0.022 |
| 60 | BTB 13869 | 426 | 0.28 | 0.735 | 0.195 |
| 63 | PD 00612 | 294 | 0.61 | −0.287 | 0.075 |
| 69 | KM 00081 | 345 | 1.68 | −0.233 | 0.361 |
| 101 | HTS 05732 | 378 | 2.31 | 0.667 | 0.0175 |
| 115 | NRB 03986 | 278 | 3.88 | −0.156 | 0.246 |
| 141 | SEW 02182 | 318 | 2.46 | 0.554 | 0.238 |
| 146 | KM 10445 | 313 | 2.55 | −1.084 | −1.632 |
| 150 | HTS 03239 | 341 | 1.68 | −0.171 | 0.133 |

[1]Compound ID from Maybridge portfolio.

[2]logP is the logarithm of the estimated octanol/water partition coefficient, a measure of compound solubility

[3]Change in melting temperature relative to DMSO control in DSF assay

TABLE 3

Top 150 CADD-identified p38α ED site-binding candidates

| CADD no. | Compound ID[1] | MW | logP[2] |
|---|---|---|---|
| 1 | AW 1221 | 442 | 3.84 |
| 2 | SEW 06373 | 417 | 3.19 |
| 3 | HTS 02798 | 415 | 0.67 |
| 4 | HTS 13333 | 312 | −1.10 |
| 5 | SCR 00846 | 418 | 2.22 |
| 6 | HTS 01830 | 400 | 4.15 |
| 7 | KM11105 | 409 | 1.27 |
| 8 | AW 00509 | 317 | 1.13 |
| 9 | SCR 01457 | 401 | 2.12 |
| 10 | KM 09878 | 362 | 2.45 |
| 11 | BTB 10384 | 434 | 2.32 |
| 12 | HTS 03243 | 419 | 3.46 |
| 13 | SEW 06264 | 309 | 0.28 |
| 14 | CD 06142 | 382 | 3.29 |
| 15 | KM 08516 | 382 | 2.03 |
| 16 | SCR 00610 | 339 | 1.69 |
| 17 | KM 09250 | 364 | 0.87 |
| 18 | SCR 01462 | 344 | −0.25 |
| 19 | KM 08262 | 375 | 1.34 |
| 20 | SCR 01164 | 430 | 3.44 |
| 21 | HTS 05992 | 360 | 2.65 |
| 22 | CD 00735 | 390 | 1.72 |
| 23 | SCR 01200 | 378 | 2.79 |
| 24 | SCR 01160 | 390 | 0.69 |
| 25 | SCR 00883 | 398 | 2.09 |
| 26 | AW 01002 | 331 | 1.49 |
| 27 | KM 10346 | 339 | 1.52 |
| 28 | KM 09924 | 374 | 2.25 |
| 29 | BTB 05645 | 350 | 3.07 |
| 30 | HTS 01722 | 401 | 3.5 |
| 31 | KM 04113 | 304 | 1.83 |
| 32 | SCR 00662 | 338 | 2.62 |
| 33 | RJC 02765 | 348 | 1.21 |
| 34 | HTS 08093 | 330 | 0.50 |
| 35 | KM 09335 | 352 | 1.08 |
| 36 | HTS 06913 | 355 | 1.52 |
| 37 | KM 07646 | 296 | 0.23 |
| 38 | KM 06447 | 355 | 2.44 |
| 39 | HTS 01903 | 444 | 2.51 |
| 40 | KM 06789 | 333 | 1.38 |
| 41 | EN 00285 | 380 | 2.34 |
| 42 | JFD 01748 | 321 | 2.74 |
| 43 | CD 11992 | 300 | 1.16 |
| 44 | KM 03098 | 455 | 2.56 |
| 45 | RJF 01988 | 450 | 3.99 |
| 46 | RH 00635 | 402 | 4.14 |

TABLE 3-continued

Top 150 CADD-identified p38α ED site-binding candidates

| CADD no. | Compound ID[1] | MW | logP[2] |
|---|---|---|---|
| 47 | GK 02919 | 363 | 1.17 |
| 48 | KM 02331 | 451 | 3.96 |
| 49 | GK 01789 | 360 | 2.91 |
| 50 | GK 03735 | 376 | 1.38 |
| 51 | HTS 05862 | 364 | 1.97 |
| 52 | KM 07197 | 337 | 0.40 |
| 53 | BTB 02067 | 305 | 1.94 |
| 54 | JFD 01679 | 357 | 3.55 |
| 55 | SP 01164 | 2.11 | 1.92 |
| 56 | KM 00730 | 450 | 1.92 |
| 57 | HTS 03184 | 407 | 3.33 |
| 58 | HTS 01701 | 397 | 4.06 |
| 59 | HTS 11459 | 409 | −1.37 |
| 60 | BTB 13869 | 426 | 0.28 |
| 61 | RJC 00192 | 360 | 3.85 |
| 62 | HTS 06577 | 367 | 3.73 |
| 63 | PD 00612 | 294 | 0.61 |
| 64 | HTS 09813 | 453 | 2.98 |
| 65 | RJC 02517 | 404 | 1.93 |
| 66 | DP 01615 | 356 | 4.00 |
| 67 | DP 01320 | 385 | 3.74 |
| 68 | JFD 01765 | 352 | 3.24 |
| 69 | KM 00081 | 345 | 1.68 |
| 70 | RDR 03171 | 419 | 2.14 |
| 71 | HTS 04127 | 398 | 2.82 |
| 72 | AW 00409 | 403 | 2.36 |
| 73 | BTB 06009 | 413 | 2.14 |
| 74 | KM 10383 | 443 | 2.81 |
| 75 | HTS 05233 | 369 | 0.82 |
| 76 | KM 05297 | 428 | 0.00 |
| 77 | CD 11533 | 373 | 3.22 |
| 78 | KM 04839 | 441 | 3.01 |
| 79 | CD 09639 | 460 | 3.00 |
| 80 | HTS 04160 | 414 | 2.73 |
| 81 | KM 07794 | 358 | 3.70 |
| 82 | CD 04864 | 420 | 3.51 |
| 83 | RDR 02594 | 397 | 3.10 |
| 84 | DP 01806 | 435 | 3.43 |
| 85 | HTS 03190 | 388 | 3.29 |
| 86 | KM 09808 | 405 | 3.70 |
| 87 | CD 09308 | 396 | 2.27 |
| 88 | SPB 01817 | 416 | 3.99 |
| 89 | KM 07150 | 411 | 2.05 |
| 90 | KM 09339 | 381 | 0.91 |
| 91 | RDR 01132 | 415 | 3.32 |
| 92 | SS 00046 | 322 | 3.63 |
| 93 | HTS 02914 | 351 | 1.98 |
| 94 | KM 02270 | 381 | 4.08 |
| 95 | CD 09636 | 366 | 1.15 |
| 96 | KBK 00012 | 364 | 3.69 |
| 97 | HTS 13527 | 337 | 0.78 |
| 98 | BB 06821 | 389 | 3.99 |
| 99 | AW 01218 | 343 | 2.37 |
| 100 | PD 00703 | 303 | 0.33 |
| 101 | HTS 05732 | 378 | 2.31 |
| 102 | HTS 03187 | 357 | 0.79 |
| 103 | HTS 05493 | 427 | 1.73 |
| 104 | RJF 01945 | 356 | 3.81 |
| 105 | CD 05416 | 378 | 3.30 |
| 106 | CD 08365 | 285 | 1.37 |
| 107 | SPB 02947 | 372 | 3.15 |
| 108 | SCR 01004 | 357 | 0.95 |
| 109 | HTS 05491 | 429 | 3.03 |
| 110 | HTS 02224 | 372 | 0.33 |
| 111 | KM 05869 | 421 | 1.45 |
| 112 | KM 02112 | 388 | 3.19 |
| 113 | KM 07452 | 347 | 0.49 |
| 114 | RJC 02844 | 302 | 2.65 |
| 115 | NRB 03986 | 278 | 3.88 |
| 116 | SEW 06625 | 373 | 3.05 |
| 117 | SCR 0170 | 320 | −0.70 |
| 118 | SPB 06098 | 373 | 4.07 |
| 119 | FM 00079 | 382 | 3.19 |
| 120 | BTB 03095 | 350 | 1.91 |
| 121 | KM 08272 | 382 | 1.99 |
| 122 | BTB 07326 | 458 | 3.97 |
| 123 | HTS 10719 | 386 | 3.71 |
| 124 | JFD 01751 | 375 | 1.21 |
| 125 | HTS 05737 | 366 | 0.34 |
| 126 | BTB 02557 | 300 | −0.17 |
| 127 | KM 01947 | 386 | 3.26 |
| 128 | KM 04674 | 340 | 2.99 |
| 129 | BTB 14836 | 358 | 1.88 |
| 130 | KM 07275 | 346 | 3.43 |
| 131 | RH 02254 | 321 | 1.27 |
| 132 | S 07734 | 274 | 2.06 |
| 133 | KM 03963 | 308 | 2.90 |
| 134 | KM 01163 | 377 | 2.95 |
| 135 | SEW 05535 | 324 | −1.08 |
| 136 | RDR 02622 | 321 | 2.97 |
| 137 | AW 00695 | 338 | −0.37 |
| 138 | RJC 03556 | 323 | 1.30 |
| 139 | SP 00787 | 415 | 2.74 |
| 140 | JFD 02020 | 322 | 0.84 |
| 141 | SEW 02182 | 318 | 2.46 |
| 142 | SEW 00427 | 350 | 1.64 |
| 143 | HTS 00966 | 311 | 3.43 |
| 144 | HTS 02841 | 339 | −0.16 |
| 145 | KM 06585 | 371 | 2.32 |
| 146 | KM 10445 | 313 | 2.55 |
| 147 | KM 03965 | 356 | 3.97 |
| 148 | AW 00554 | 345 | 0.36 |
| 149 | HTS 01470 | 371 | 2.01 |
| 150 | HTS 03239 | 341 | 1.68 |

[1]Compound ID from Maybridge portfolio.

[2]logP is the logarithm of the octanol/water partition coefficient, a measure of drug solubility.

Test compounds at 10-100 μM were screened for binding to recombinant p38α and ERK2 using DSF (FIG. 1*e*, Table 1). Five compounds caused concentration-dependent stabilization of p38α, indicating binding. Three of these also stabilized ERK2 (3, 5, and 141 highlighted yellow (with "*")) and two (highlighted blue (with "+")), UM60 (N2,N7-di(2-hydroxyethyl)-9-oxo-9H-2,7-fluorenedisulfonamide) and UM101 (4-chloro-N-{4-[(1,1-dioxo-1lambda~6~,4-thiazinan-4-yl)methyl]phenyl}benzamide), stabilized p38α but not ERK2. These two structurally dissimilar compounds (FIG. 1*f*), added at 100 μM, increased the melting temperature of p38α by ~0.7° C., compared with a 6° C. increase with SB203580.

Figure 8:
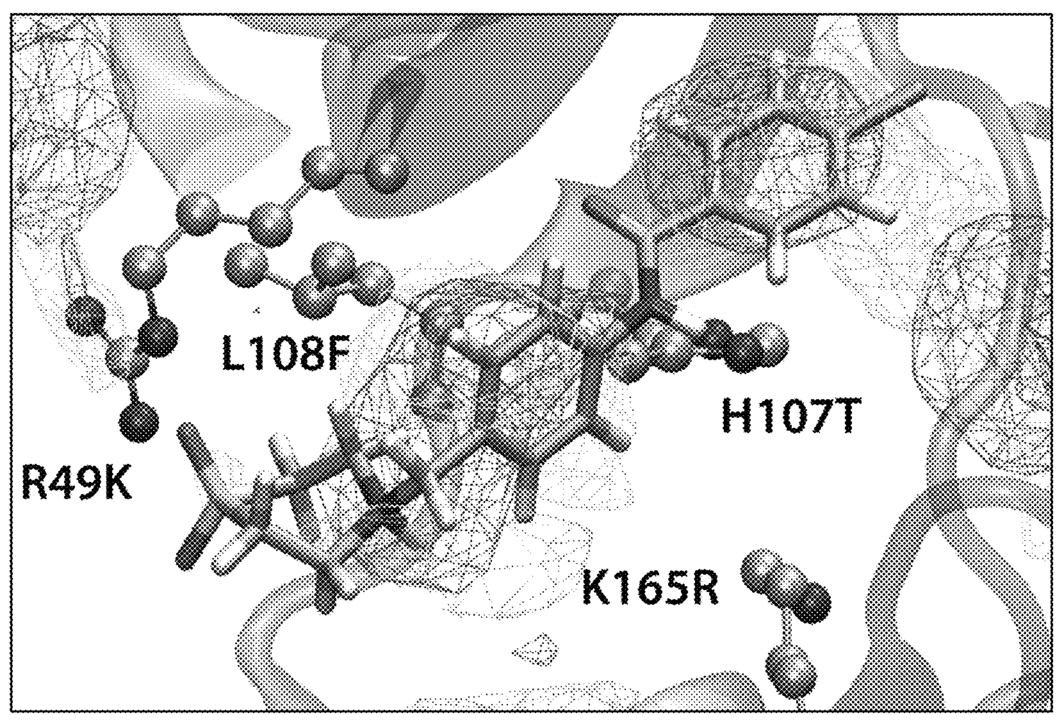
FIG. 8 illustrates compound UM101 overlaid on SILCS FragMaps shown in wireframe at contours of −1.0 kcal/mol for aromatic (purple), aliphatic (green), positive (cyan), H-bond acceptor (red) and H-bond donor (blue) functional groups on the p38α backbone, with sidechains of the four residues mutated in our CADD-site-disrupted mutant indicated. Spatial distributions of FragMaps indicate where respective functional groups make favorable contributions to binding.

MC SILCS docking of UM101 to the ED site and GFE FragMap analysis has identified several structural features that can be modified to improve selectivity and potency (FIG. 8). The modifiable sites on UM101 correspond to those identified as interacting with the p38α in the NMR STD analysis (FIG. 3*f*-3*k*).

Example 2: Effects of Compounds on Endothelial Barrier Functions

The capacity of UM60 and UM101 to stabilize endothelial barriers to macromolecules and neutrophils in TNFα- and hyperthermia-stressed HMVECL monolayers was tested (FIG. 2). Combined exposure to 1 ng/ml TNFα and hyperthermia (39.5° C.) for 6 h increased permeability for 10 kDa dextran 2.8-fold, compared with untreated 37° C. cells. Pretreating with 10 μM SB203580 for 30 min reduced TNFα/hyperthermia-induced permeability by 50% (FIG. 2*a*). Pretreatment with UM60 at 10 and 25 μM had no effect on permeability, but 100 μM UM60 reduced the TNFα/hyperthermia-induced permeability increase by 71% while UM101 at 10, 25, and 100 μM reduced the TNFα/hyperthermia-induced permeability increase by 74%, 89% and >100%, respectively.

Preincubating HMVECLs at 39.5° C. for 6 h increased subsequent IL-8-directed neutrophil TEM from 22.8±0.45×$10^3$ to 31.8±0.54×$10^3$ neutrophils (FIG. 2*b*). Pretreatment with 10 μM SB203580 reduced hyperthermia-augmented neutrophil TEM by 84%. UM60 at 10 and 25 μM and UM101 at 10 μM reduced hyperthermia-augmented increase in TEM by 18%, 89%, and 95%. UM60 at 50 μM and UM101 at 25 and 50 μM reduced TEM to less than baseline levels. Neither compound was toxic in LDH release and MTS assays when added to HMVECLs at 100 μM for 48 h.

Example 3: Comparing Effectiveness of SB203580 and UM101 in Mouse ALI

The effectiveness of UM60, UM101, and SB203580 in mitigating transalveolar protein and neutrophil extravasation in a mouse model of LPS/hyperthermia-induced ALI was compared (FIG. 2*c* and FIG. 2*d*). Mice received a single intraperitoneal injection of 100, 300, 500, or 1000 μg UM101, 1000 μg UM60, or 1000 μg SB203580 in 0.5 ml 2% DMSO 30 min prior to intratracheal instillation of 50 μg LPS and transfer to hyperthermic chambers. Control mice received DMSO. Four of six UM60-treated, one of six SB203580-treated, and one of eleven DMSO-treated control mice died within 24 h. All sixteen UM101-pretreated mice survived. Lung lavage from DMSO-pretreated, LPS/hyperthermia-challenged mice contained 1.09±0.19 mg/ml protein and 3.97±1.07×$10^6$ neutrophils. Compared with DMSO-treated controls, lavage protein concentration and neutrophil content in mice pretreated with 1000 μg SB203580 were reduced by 42% and 46.8%, respectively. Lavage protein concentration in mice pretreated with 100 μg, 300 μg, 500 μg, and 1000 μg UM101 was reduced by 0, 44.1%, 43.9%, and 92.9%, respectively and lavage neutrophil content was reduced by 44.4%, 49.5%, 55.3 and 54%, respectively.

Example 4: Effect of SB203580 and UM101 on LPS-Induced Gene Expression in Human THP1 Promonocytes The effects of UM101 and SB203580 on inflammatory cytokine expression were compared by pretreating PMA-differentiated THP1 cells with 25 μM SB203580 or 10, 25, or 100 μM UM101 for 30 min, then stimulating with 100 ng/ml LPS, and harvesting RNA 4 h later for analysis by PCR-based cytokine array. Of 16 LPS-stimulated genes in the array, SB203580 inhibited expression of seven, IL-la, IL-8, TNFSF8 (CD30 ligand), TNFSF9 (CD137 ligand), CXCL5, CCL7, and CCL17 (Table 4). UM101 inhibited expression of all SB203580-inhibited genes except TNFSF9, and inhibited four SB203580-insensitive genes, IL-10, CXCL1, TNFSF15, and CCL5.

TABLE 4

Effects of SB203580 and UM101 on LPS-induced cytokine expression in THP1 cells[1]

| Gene | DMSO[2] | ANOVA[3] | SB203580 25 μM | P vs. LPS[4] | UM101 10 μM | P vs. LPS[4] | UM101 25 μM | P vs. LPS | UM101 100 μM | P vs. LPS[4] |
|---|---|---|---|---|---|---|---|---|---|---|
| IL-1A | 453 ± 24 | <0.0001 | 141 ± 9.2 | <0.0001 | 424 ± 22.6 | 0.74 | 339 ± 13.5 | 0.041 | 88 ± 3.33 | <0.0001 |
| IL-8 | 56.5 ± 3.3 | 0.0026 | 9.6 ± 0.1 | 0.002 | 35.6 ± 0.7 | 0.40 | 26.7 ± 4.1 | 0.564 | 19.7 ± 1.8 | 0.015 |
| TNFSF8 | 60.5 ± 5.5 | 0.0073 | 20.6 ± 8.8 | 0.024 | 23.5 ± 8.3 | 0.37 | 10.5 ± 3.9 | 0.006 | 20.7 ± 9.5 | 0.025 |
| CXCL5 | 49.7 ± 2.9 | <0.0001 | 3.2 ± 1.0 | <0.0001 | 23.2 ± 3.7 | 0.0002 | 8.7 ± 2.9 | <0.0001 | 3.1 ± 0.2 | <0.0001 |
| CCL7 | 12.8 ± 1.2 | <0.0001 | 4.2 ± 0.3 | <0.0001 | 7.7 ± 0.3 | 0.0036 | 6.2 ± 0.9 | 0.0036 | 4 ± 0.4 | <0.0001 |
| CCL17 | 56.9 ± 6.1 | <0.0001 | 21.5 ± 3.7 | 0.001 | 30.4 ± 4.7 | 0.008 | 11 ± 1.0 | 0.0004 | 2.5 ± 0.33 | <0.0001 |
| TNFSF9 | 50.8 ± 6.1 | 0.0046 | 20.7 ± 3.1 | 0.0054 | 48 ± 2.1 | 0.99 | 38.2 ± 6.9 | 0.334 | 32 ± 1.12 | 0.086 |
| IL-1B | 171 ± 9.0 | 0.0089 | 187 ± 7.4 | 0.988 | 104 ± 21 | 0.382 | 88 ± 9.0 | 0.204 | 51.6 ± 5.2 | 0.033 |
| CXCL1 | 24.5 ± 0.5 | <0.0001 | 28.2 ± 1.9 | 0.577 | 19.8 ± 1.8 | 0.36 | 12.8 ± 2.5 | 0.005 | 5.2 ± 1.0 | <0.0001 |
| TNFSF15 | 9.6 ± 1.1 | 0.0012 | 10 ± 1.1 | 0.998 | 7.6 ± 0.9 | 0.544 | 5.4 ± 0.8 | 0.053 | 2.9 ± 0.6 | 0.003 |
| CCL5 | 7.6 ± 0.9 | 0.0045 | 3.6 ± 0.8 | 0.26 | 3 ± 0.5 | 0.018 | 2.7 ± 0.2 | 0.008 | 2.6 ± 1.2 | 0.006 |
| CCL4 | 188 ± 12 | 0.9519 | 188 ± 16 | ns | 174 ± 41 | ns | 191 ± 57 | ns | 217 ± 51 | ns |
| CCL20 | 82.5 ± 27.8 | 0.1189 | 106 ± 15.1 | ns | 63 ± 3.1 | ns | 63.4 ± 1.0 | ns | 42.7 ± 12.7 | ns |
| CXCL2 | 122 ± 11.0 | 0.9887 | 125 ± 4.6 | ns | 128 ± 20.0 | ns | 132 ± 22.9 | ns | 130 ± 6.4 | ns |
| TNF | 115 ± 13/1 | 0.6112 | 66.4 ± 9.6 | ns | 87 ± 12.4 | ns | 95.9 ± 21.2 | ns | 80 ± 14.5 | ns |
| BMP6 | 8.1 ± 1.8 | 0.1195 | 4.1 ± 1.1 | ns | 8.9 ± 1.7 | ns | 7.8 ± 1.1 | ns | 3.9 ± 0.5 | ns |

[1]All values are fold change mRNA levels vs. unstimulated PMA-differentiated THP1 cells

[2]Cells were preincubated with 0.4% DMSO or inhibitors for 1 h, then stimulated with 100 ng/ml LPS for 2 h.

[3]P-values from one-way ANOVA.

[4]P-values from Tukey Honestly Significant Difference post hoc test.

Figure 5:
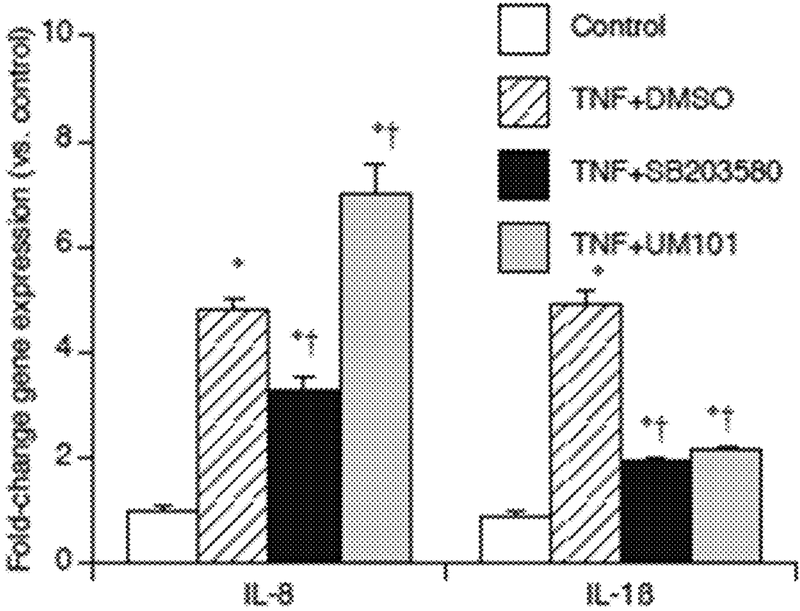
FIG. 5 illustrates the preliminary analysis of IL-8 and IL-1B mRNA by qRT-PCR prior to RNASeq. HMVECLs were preincubated with 0.4% DMSO, 10 μM SB203580, or 100 μM UM101 for 1 h, then stimulated with 10 ng/ml TNFα for 4 h and total RNA was collected, reverse transcribed, analyzed by qRT-PCR and fold change relative to unstimulated control cells calculated using the delta-delta method and GAPDH as the housekeeping gene.

Example 5: Comparing Effects of SB203580 and UM101 on TNFα-Induced Gene Expression in HMVECLs The effects ofUMO and SB203580 on TNFα-induced gene expression in HMVECLs using RNASeq were compared. HMVECLs were pretreated for h with 10 M SB203580 or 100 μM UM101, and then stimulated with 10 ng/ml TNF for 3 h. A U101 concentration 10-fold higher than its biologically effective dose in HMVECL barrier assays was used, to ensure identifying any partial overlap with Syb203580. The TNF concentration and duration of stimulation used were based on previously published studies and confirmed by preliminary qRT-PCR analysis of IL8-8 and IL-1β mRNA expression (FIG. 5). After filtering the RNASeq results for genes having ≥10 reads in at least one sample per experiment, 511 genes that were upregulated and 520 downregulated by ≥2-fold by TNFα treatment were found (Table 5).

TABLE 5

| RNASeq results filtered for genes with at least 10 reads in one sample per set | | | | | |
|---|---|---|---|---|---|
| | Log (base 2) fold-change | | | | |
| Gene | UM101 vs. control | SB203580 vs. control | bin | Gene Symbol | Gene Name |
| ENSG00000006468 | 1.14697638 | 1.42107626 | 1 | ETV1 | ets variant 1 [Source: HGNC Symbol; Acc: HGNC: 3490] |
| ENSG00000128917 | 1.25167179 | 1.33201352 | 1 | DLL4 | delta-like 4 (*Drosophila*) [Source: HGNC Symbol; Acc: HGNC: 2910] |
| ENSG00000196872 | 1.10366409 | 1.62514778 | 1 | KIAA1211L | KIAA1211-like [Source: HGNC Symbol; Acc: HGNC: 33454] |
| ENSG00000108984 | 1.34524718 | 1.27752638 | 1 | MAP2K6 | mitogen-activated protein kinase kinase 6 [Source: HGNC Symbol; Acc: HGNC: 6846] |
| ENSG00000229953 | 1.63323083 | 1.70115175 | 1 | RP11-284F21.7 | |
| ENSG00000255690 | 1.81451563 | 1.5932836 | 1 | TRIL | TLR4 interactor with leucine-rich repeats [Source: HGNC Symbol; Acc: HGNC: 22200] |
| ENSG00000095739 | 1.11321658 | 1.12281058 | 1 | BAMBI | BMP and activin membrane-bound inhibitor [Source: HGNC Symbol; Acc: HGNC: 30251] |
| ENSG00000137872 | 2.48510888 | 1.90449301 | 1 | SEMA6D | sema domain, transmembrane domain (TM), and cytoplasmic domain, (semaphorin) 6D [Source: HGNC Symbol; Acc: HGNC: 16770] |
| ENSG00000184185 | 1.18112212 | 1.55055314 | 1 | KCNJ12 | potassium channel, inwardly rectifying subfamily J, member 12 [Source: HGNC Symbol; Acc: HGNC: 6258] |
| ENSG00000125848 | 1.25784422 | 1.46432561 | 1 | FLRT3 | fibronectin leucine rich transmembrane protein 3 [Source: HGNC Symbol; Acc: HGNC: 3762] |
| ENSG00000196664 | −1.5535936 | 1.21794414 | 2 | TLR7 | toll-like receptor 7 [Source: HGNC Symbol; Acc: HGNC: 15631] |
| ENSG00000119714 | −1.3040616 | 1.22615088 | 2 | GPR68 | G protein-coupled receptor 68 [Source: HGNC Symbol; Acc: HGNC: 4519] |
| ENSG00000165379 | −1.4439353 | 2.06145291 | 2 | LRFN5 | leucine rich repeat and fibronectin type III domain containing 5 [Source: HGNC Symbol; Acc: HGNC: 20360] |
| ENSG00000135378 | −1.1984882 | −1.78258053 | 3 | PRRG4 | proline rich Gla (G-carboxyglutamic acid) 4 (transmembrane) [Source: HGNC Symbol; Acc: HGNC: 30799] |
| ENSG00000145777 | −1.3366525 | −1.65143959 | 3 | TSLP | thymic stromal lymphopoietin [Source: HGNC Symbol; Acc: HGNC: 30743] |
| ENSG00000102970 | −2.7303098 | −1.83414345 | 3 | CCL17 | chemokine (C-C motif) ligand 17 [Source: HGNC Symbol; Acc: HGNC: 10615] |
| ENSG00000259717 | −1.4952254 | −1.6963101 | 3 | LINC00677 | long intergenic non-protein coding RNA 677 [Source: HGNC Symbol; Acc: HGNC: 20121] |
| ENSG00000205436 | −1.160471 | −1.47916318 | 3 | EXOC3L4 | exocyst complex component 3-like 4 [Source: HGNC Symbol; Acc: HGNC: 20120] |
| ENSG00000100985 | −1.0911796 | −1.15709135 | 3 | MMP9 | matrix metallopeptidase 9 (gelatinase B, 92 kDa gelatinase, 92 kDa type IV collagenase) [Source: HGNC Symbol; Acc: HGNC: 7176] |
| ENSG00000131203 | −3.5679874 | −3.51063293 | 3 | IDO1 | indoleamine 2,3-dioxygenase 1 [Source: HGNC Symbol; Acc: HGNC: 6059] |
| ENSG00000276408 | −3.0213604 | −2.36477309 | 3 | RP11-490B18.5 | |

TABLE 5-continued

| RNASeq results filtered for genes with at least 10 reads in one sample per set | | | | | |
|---|---|---|---|---|---|
| | Log (base 2) fold-change | | | | |
| Gene | UM101 vs. control | SB203580 vs. control | bin | Gene Symbol | Gene Name |
| ENSG00000169245 | −4.3698367 | −3.10091556 | 3 | CXCL10 | chemokine (C-X-C motif) ligand 10 [Source: HGNC Symbol; Acc: HGNC: 10637] |
| ENSG00000091972 | −1.5381554 | −1.72928565 | 3 | CD200 | CD200 molecule [Source: HGNC Symbol; Acc: HGNC: 7203] |
| ENSG00000110446 | −1.7310589 | −1.00338842 | 3 | SLC15A3 | solute carrier family 15 (oligopeptide transporter), member 3 [Source: HGNC Symbol; Acc: HGNC: 18068] |
| ENSG00000111424 | −1.1973169 | −1.16718631 | 3 | VDR | vitamin D (1,25-dihydroxyvitamin D3) receptor [Source: HGNC Symbol; Acc: HGNC: 12679] |
| ENSG00000125538 | −1.1725305 | −1.40158693 | 3 | IL1B | interleukin 1, beta [Source: HGNC Symbol; Acc: HGNC: 5992] |
| ENSG00000279805 | −1.4538855 | −1.28507313 | 3 | CTA-212A2.1 | |
| ENSG00000202533 | −2.8157077 | −1.96733528 | 3 | Y_RNA | Y RNA [Source: RFAM; Acc: RF00019] |
| ENSG00000181656 | −2.1505992 | −1.39708375 | 3 | GPR88 | G protein-coupled receptor 88 [Source: HGNC Symbol; Acc: HGNC: 4539] |
| ENSG00000116031 | −3.3824373 | −1.54775729 | 3 | CD207 | CD207 molecule, langerin [Source: HGNC Symbol; Acc: HGNC: 17935] |
| ENSG00000159450 | −1.5476653 | −1.50495809 | 3 | TCHH | trichohyalin [Source: HGNC Symbol; Acc: HGNC: 11791] |
| ENSG00000103044 | −1.1243396 | −1.43377734 | 3 | HAS3 | hyaluronan synthase 3 [Source: HGNC Symbol; Acc: HGNC: 4820] |
| ENSG00000225492 | −1.7557061 | −1.3632872 | 3 | GBP1P1 | guanylate binding protein 1, interferon-inducible pseudogene 1 [Source: HGNC Symbol; Acc: HGNC: 39561] |
| ENSG00000145113 | −1.0573157 | −2.85949188 | 3 | MUC4 | mucin 4, cell surface associated [Source: HGNC Symbol; Acc: HGNC: 7514] |
| ENSG00000164181 | −1.3810632 | −1.34093337 | 3 | ELOVL7 | ELOVL fatty acid elongase 7 [Source: HGNC Symbol; Acc: HGNC: 26292] |
| ENSG00000169248 | −4.1363549 | −1.37790594 | 3 | CXCL11 | chemokine (C-X-C motif) ligand 11 [Source: HGNC Symbol; Acc: HGNC: 10638] |
| ENSG00000162654 | −2.8359479 | −1.25928308 | 3 | GBP4 | guanylate binding protein 4 [Source: HGNC Symbol; Acc: HGNC: 20480] |
| ENSG00000144837 | −1.5006334 | −1.27452433 | 3 | PLA1A | phospholipase A1 member A [Source: HGNC Symbol; Acc: HGNC: 17661] |
| ENSG00000222365 | −1.7462552 | −2.69898993 | 3 | SNORD12B | small nucleolar RNA, C/D box 12B [Source: HGNC Symbol; Acc: HGNC: 33573] |
| ENSG00000237988 | −3.7376706 | −1.08751395 | 3 | OR2I1P | olfactory receptor, family 2, subfamily I, member 1 pseudogene [Source: HGNC Symbol; Acc: HGNC: 8258] |
| ENSG00000163735 | −1.4683077 | −1.01742785 | 3 | CXCL5 | chemokine (C-X-C motif) ligand 5 [Source: HGNC Symbol; Acc: HGNC: 10642] |
| ENSG00000277105 | 1.8720451 | −1.66179692 | 4 | FP236383.10 | |
| ENSG00000259498 | 1.51730088 | 0 | 5 | RP11-244F12.3 | |
| ENSG00000079841 | 1.1627696 | 0 | 5 | RIMS1 | regulating synaptic membrane exocytosis 1 [Source: HGNC Symbol; Acc: HGNC: 17282] |
| ENSG00000104081 | 1.87839947 | 0 | 5 | BMF | Bcl2 modifying factor [Source: HGNC Symbol; Acc: HGNC: 24132] |

TABLE 5-continued

| RNASeq results filtered for genes with at least 10 reads in one sample per set | | | | | |
|---|---|---|---|---|---|
| | Log (base 2) fold-change | | | | |
| Gene | UM101 vs. control | SB203580 vs. control | bin | Gene Symbol | Gene Name |
| ENSG00000128011 | 1.21234677 | 0 | 5 | LRFN1 | leucine rich repeat and fibronectin type III domain containing 1 [Source: HGNC Symbol; Acc: HGNC: 29290] |
| ENSG00000102760 | 2.39873086 | 0 | 5 | RGCC | regulator of cell cycle [Source: HGNC Symbol; Acc: HGNC: 20369] |
| ENSG00000272918 | 2.02570082 | 0 | 5 | CTB-152G17.6 | |
| ENSG00000158715 | 1.09721113 | 0 | 5 | SLC45A3 | solute carrier family 45, member 3 [Source: HGNC Symbol; Acc: HGNC: 8642] |
| ENSG00000169247 | 1.22087519 | 0 | 5 | SH3TC2 | SH3 domain and tetratricopeptide repeats 2 [Source: HGNC Symbol; Acc: HGNC: 29427] |
| ENSG00000163235 | 1.00798575 | 0 | 5 | TGFA | transforming growth factor, alpha [Source: HGNC Symbol; Acc: HGNC: 11765] |
| ENSG00000138311 | 1.68539518 | 0 | 5 | ZNF365 | zinc finger protein 365 [Source: HGNC Symbol; Acc: HGNC: 18194] |
| ENSG00000263426 | 1.90751532 | 0 | 5 | RN7SL471P | RNA, 7SL, cytoplasmic 471, pseudogene [Source: HGNC Symbol; Acc: HGNC: 46487] |
| ENSG00000203883 | 3.1401464 | 0 | 5 | SOX18 | SRY (sex determining region Y)-box 18 [Source: HGNC Symbol; Acc: HGNC: 11194] |
| ENSG00000152213 | 2.11880858 | 0 | 5 | ARL11 | ADP-ribosylation factor-like 11 [Source: HGNC Symbol; Acc: HGNC: 24046] |
| ENSG00000115641 | 1.20543525 | 0 | 5 | FHL2 | four and a half LIM domains 2 [Source: HGNC Symbol; Acc: HGNC: 3703] |
| ENSG00000163884 | 1.31377126 | 0 | 5 | KLF15 | Kruppel-like factor 15 [Source: HGNC Symbol; Acc: HGNC: 14536] |
| ENSG00000171223 | 1.07792014 | 0 | 5 | JUNB | jun B proto-oncogene [Source: HGNC Symbol; Acc: HGNC: 6205] |
| ENSG00000137875 | 1.24981 | 0 | 5 | BCL2L10 | BCL2-like 10 (apoptosis facilitator) [Source: HGNC Symbol; Acc: HGNC: 993] |
| ENSG00000119630 | 1.02473901 | 0 | 5 | PGF | placental growth factor [Source: HGNC Symbol; Acc: HGNC: 8893] |
| ENSG00000157404 | 1.98981566 | 0 | 5 | KIT | v-kit Hardy-Zuckerman 4 feline sarcoma viral oncogene homolog [Source: HGNC Symbol; Acc: HGNC: 6342] |
| ENSG00000004799 | 2.74875752 | 0 | 5 | PDK4 | pyruvate dehydrogenase kinase, isozyme 4 [Source: HGNC Symbol; Acc: HGNC: 8812] |
| ENSG00000104903 | 1.17436711 | 0 | 5 | LYL1 | lymphoblastic leukemia associated hematopoiesis regulator 1 [Source: HGNC Symbol; Acc: HGNC: 6734] |
| ENSG00000164683 | 2.56462289 | 0 | 5 | HEY1 | hes-related family bHLH transcription factor with YRPW motif 1 [Source: HGNC Symbol; Acc: HGNC: 4880] |
| ENSG00000229436 | 2.97587733 | 0 | 5 | AC073850.6 | |
| ENSG00000074590 | 1.86606392 | 0 | 5 | NUAK1 | NUAK family, SNF1-like kinase, 1 [Source: HGNC Symbol; Acc: HGNC: 14311] |
| ENSG00000163121 | 1.17777496 | 0 | 5 | NEURL3 | neuralized E3 ubiquitin protein ligase 3 [Source: HGNC Symbol; Acc: HGNC: 25162] |

TABLE 5-continued

| RNASeq results filtered for genes with at least 10 reads in one sample per set | | | | | |
|---|---|---|---|---|---|
| | Log (base 2) fold-change | | | | |
| Gene | UM101 vs. control | SB203580 vs. control | bin | Gene Symbol | Gene Name |
| ENSG00000171435 | 2.0275154 | 0 | 5 | KSR2 | kinase suppressor of ras 2 [Source: HGNC Symbol; Acc: HGNC: 18610] |
| ENSG00000225213 | 2.78814593 | 0 | 5 | RP11-197M22.2 | |
| ENSG00000175556 | 2.1400816 | 0 | 5 | LONRF3 | LON peptidase N-terminal domain and ring finger 3 [Source: HGNC Symbol; Acc: HGNC: 21152] |
| ENSG00000172031 | 1.46275504 | 0 | 5 | EPHX4 | epoxide hydrolase 4 [Source: HGNC Symbol; Acc: HGNC: 23758] |
| ENSG00000164284 | 1.60799521 | 0 | 5 | GRPEL2 | GrpE-like 2, mitochondrial (*E. coli*) [Source: HGNC Symbol; Acc: HGNC: 21060] |
| ENSG00000198774 | 1.92290695 | 0 | 5 | RASSF9 | Ras association (RalGDS/AF-6) domain family (N-terminal) member 9 [Source: HGNC Symbol; Acc: HGNC: 15739] |
| ENSG00000109452 | 1.25820227 | 0 | 5 | INPP4B | inositol polyphosphate-4-phosphatase, type II, 105 kDa [Source: HGNC Symbol; Acc: HGNC: 6075] |
| ENSG00000071282 | 1.2458539 | 0 | 5 | LMCD1 | LIM and cysteine-rich domains 1 [Source: HGNC Symbol; Acc: HGNC: 6633] |
| ENSG00000163545 | 1.15652631 | 0 | 5 | NUAK2 | NUAK family, SNF1-like kinase, 2 [Source: HGNC Symbol; Acc: HGNC: 29558] |
| ENSG00000125968 | 2.63377664 | 0 | 5 | ID1 | inhibitor of DNA binding 1, dominant negative helix-loop-helix protein [Source: HGNC Symbol; Acc: HGNC: 5360] |
| ENSG00000099260 | 1.50498454 | 0 | 5 | PALMD | palmdelphin [Source: HGNC Symbol; Acc: HGNC: 15846] |
| ENSG00000176641 | 1.2877484 | 0 | 5 | RNF152 | ring finger protein 152 [Source: HGNC Symbol; Acc: HGNC: 26811] |
| ENSG00000139874 | 1.37617951 | 0 | 5 | SSTR1 | somatostatin receptor 1 [Source: HGNC Symbol; Acc: HGNC: 11330] |
| ENSG00000137834 | 2.51438228 | 0 | 5 | SMAD6 | SMAD family member 6 [Source: HGNC Symbol; Acc: HGNC: 6772] |
| ENSG00000259721 | 1.0709029 | 0 | 5 | RP11-758N13.1 | |
| ENSG00000181800 | 2.42803687 | 0 | 5 | CELF2-AS1 | CELF2 antisense RNA 1 [Source: HGNC Symbol; Acc: HGNC: 23515] |
| ENSG00000184523 | 2.14599043 | 0 | 5 | PTGER4P2 | prostaglandin E receptor 4 (subtype EP4) pseudogene 2 [Source: HGNC Symbol; Acc: HGNC: 9598] |
| ENSG00000101187 | 1.12788457 | 0 | 5 | SLCO4A1 | solute carrier organic anion transporter family, member 4A1 [Source: HGNC Symbol; Acc: HGNC: 10953] |
| ENSG00000237512 | 1.72226772 | 0 | 5 | UNC5B-AS1 | UNC5B antisense RNA 1 [Source: HGNC Symbol; Acc: HGNC: 45096] |
| ENSG00000156463 | 1.43711148 | 0 | 5 | SH3RF2 | SH3 domain containing ring finger 2 [Source: HGNC Symbol; Acc: HGNC: 26299] |
| ENSG00000137672 | 1.41739616 | 0 | 5 | TRPC6 | transient receptor potential cation channel, subfamily C, member 6 [Source: HGNC Symbol; Acc: HGNC: 12338] |
| ENSG00000138135 | 2.4356406 | 0 | 5 | CH25H | cholesterol 25-hydroxylase [Source: HGNC Symbol; Acc: HGNC: 1907] |
| ENSG00000183691 | 1.18113108 | 0 | 5 | NOG | noggin [Source: HGNC Symbol; Acc: HGNC: 7866] |

TABLE 5-continued

| RNASeq results filtered for genes with at least 10 reads in one sample per set | | | | | |
|---|---|---|---|---|---|
| | Log (base 2) fold-change | | | | |
| Gene | UM101 vs. control | SB203580 vs. control | bin | Gene Symbol | Gene Name |
| ENSG00000139174 | 2.23155754 | 0 | 5 | PRICKLE1 | prickle homolog 1 (*Drosophila*) [Source: HGNC Symbol; Acc: HGNC: 17019] |
| ENSG00000188305 | 1.46592995 | 0 | 5 | C19orf35 | chromosome 19 open reading frame 35 [Source: HGNC Symbol; Acc: HGNC: 24793] |
| ENSG00000082497 | 3.01359039 | 0 | 5 | SERTAD4 | SERTA domain containing 4 [Source: HGNC Symbol; Acc: HGNC: 25236] |
| ENSG00000134215 | 1.69084 | 0 | 5 | VAV3 | vav 3 guanine nucleotide exchange factor [Source: HGNC Symbol; Acc: HGNC: 12659] |
| ENSG00000242902 | 1.87508823 | 0 | 5 | RP11-309L24.2 | |
| ENSG00000027075 | 1.03323842 | 0 | 5 | PRKCH | protein kinase C, eta [Source: HGNC Symbol; Acc: HGNC: 9403] |
| ENSG00000203280 | 1.22563855 | 0 | 5 | CTA-221G9.12 | |
| ENSG00000006459 | 1.00029861 | 0 | 5 | KDM7A | lysine (K)-specific demethylase 7A [Source: HGNC Symbol; Acc: HGNC: 22224] |
| ENSG00000171408 | 3.15161753 | 0 | 5 | PDE7B | phosphodiesterase 7B [Source: HGNC Symbol; Acc: HGNC: 8792] |
| ENSG00000162981 | 1.53241836 | 0 | 5 | FAM84A | family with sequence similarity 84, member A [Source: HGNC Symbol; Acc: HGNC: 20743] |
| ENSG00000118946 | 1.93243268 | 0 | 5 | PCDH17 | protocadherin 17 [Source: HGNC Symbol; Acc: HGNC: 14267] |
| ENSG00000146376 | 1.27126839 | 0 | 5 | ARHGAP18 | Rho GTPase activating protein 18 [Source: HGNC Symbol; Acc: HGNC: 21035] |
| ENSG00000204086 | 2.05144911 | 0 | 5 | RPA4 | replication protein A4, 30 kDa [Source: HGNC Symbol; Acc: HGNC: 30305] |
| ENSG00000221887 | 1.05893107 | 0 | 5 | HMSD | histocompatibility (minor) serpin domain containing [Source: HGNC Symbol; Acc: HGNC: 23037] |
| ENSG00000196196 | 1.26354255 | 0 | 5 | HRCT1 | histidine rich carboxyl terminus 1 [Source: HGNC Symbol; Acc: HGNC: 33872] |
| ENSG00000172548 | 2.84971177 | 0 | 5 | NIPAL4 | NIPA-like domain containing 4 [Source: HGNC Symbol; Acc: HGNC: 28018] |
| ENSG00000156804 | 2.04515428 | 0 | 5 | FBXO32 | F-box protein 32 [Source: HGNC Symbol; Acc: HGNC: 16731] |
| ENSG00000203684 | 1.5984677 | 0 | 5 | IBA57-AS1 | IBA57 antisense RNA 1 (head to head) [Source: HGNC Symbol; Acc: HGNC: 32062] |
| ENSG00000205502 | 1.63750711 | 0 | 5 | C2CD4B | C2 calcium-dependent domain containing 4B [Source: HGNC Symbol; Acc: HGNC: 33628] |
| ENSG00000163734 | 1.26141193 | 0 | 5 | CXCL3 | chemokine (C-X-C motif) ligand 3 [Source: HGNC Symbol; Acc: HGNC: 4604] |
| ENSG00000181444 | 1.48713949 | 0 | 5 | ZNF467 | zinc finger protein 467 [Source: HGNC Symbol; Acc: HGNC: 23154] |
| ENSG00000275342 | 1.45192287 | 0 | 5 | SGK223 | Tyrosine-protein kinase SgK223 [Source: UniProtKB/Swiss-Prot; Acc: Q86YV5] |
| ENSG00000214944 | 1.43116765 | 0 | 5 | ARHGEF28 | Rho guanine nucleotide exchange factor (GEF) 28 [Source: HGNC Symbol; Acc: HGNC: 30322] |

TABLE 5-continued

| RNASeq results filtered for genes with at least 10 reads in one sample per set | | | | | |
|---|---|---|---|---|---|
| | Log (base 2) fold-change | | | | |
| Gene | UM101 vs. control | SB203580 vs. control | bin | Gene Symbol | Gene Name |
| ENSG00000198795 | 1.37664308 | 0 | 5 | ZNF521 | zinc linger protein 521 [Source: HGNC Symbol; Acc: HGNC: 24605] |
| ENSG00000108932 | 1.95156031 | 0 | 5 | SLC16A6 | solute carrier family 16, member 6 [Source: HGNC Symbol; Acc: HGNC: 10927] |
| ENSG00000145990 | 1.18764084 | 0 | 5 | GFOD1 | glucose-fructose oxidoreductase domain containing 1 [Source: HGNC Symbol; Acc: HGNC: 21096] |
| ENSG00000179546 | 1.7287987 | 0 | 5 | HTR1D | 5-hydroxytryptamine (serotonin) receptor 1D, G protein-coupled [Source: HGNC Symbol; Acc: HGNC: 5289] |
| ENSG00000186472 | 1.73331066 | 0 | 5 | PCLO | piccolo presynaptic cytomatrix protein [Source: HGNC Symbol; Acc: HGNC: 13406] |
| ENSG00000138678 | 1.55650245 | 0 | 5 | AGPAT9 | 1-acylglycerol-3-phosphate O-acyltransferase 9 [Source: HGNC Symbol; Acc: HGNC: 28157] |
| ENSG00000225814 | 1.57236046 | 0 | 5 | GRPEL2P2 | GrpE-like 2, mitochondrial (*E. coli*) pseudogene 2 [Source: HGNC Symbol; Acc: HGNC: 41970] |
| ENSG00000172572 | 1.01708765 | 0 | 5 | PDE3A | phosphodiesterase 3A, cGMP-inhibited [Source: HGNC Symbol; Acc: HGNC: 8778] |
| ENSG00000107282 | 1.0986938 | 0 | 5 | APBA1 | amyloid beta (A4) precursor protein-binding, family A, member 1 [Source: HGNC Symbol; Acc: HGNC: 578] |
| ENSG00000171877 | 1.0590391 | 0 | 5 | FRMD5 | FERM domain containing 5 [Source: HGNC Symbol; Acc: HGNC: 28214] |
| ENSG00000151623 | 1.83557493 | 0 | 5 | NR3C2 | nuclear receptor subfamily 3, group C, member 2 [Source: HGNC Symbol; Acc: HGNC: 7979] |
| ENSG00000189184 | 1.39874706 | 0 | 5 | PCDH18 | protocadherin 18 [Source: HGNC Symbol; Acc: HGNC: 14268] |
| ENSG00000187479 | 1.56424224 | 0 | 5 | C11orf96 | chromosome 11 open reading frame 96 [Source: HGNC Symbol; Acc: HGNC: 38675] |
| ENSG00000178726 | 1.31386114 | 0 | 5 | THBD | thrombomodulin [Source: HGNC Symbol; Acc: HGNC: 11784] |
| ENSG00000137193 | 2.05607477 | 0 | 5 | PIM1 | Pim-1 proto-oncogene, serine/threonine kinase [Source: HGNC Symbol; Acc: HGNC: 8986] |
| ENSG00000154734 | 1.08386589 | 0 | 5 | ADAMTS1 | ADAM metallopeptidase with thrombospondin type 1 motif, 1 [Source: HGNC Symbol; Acc: HGNC: 217] |
| ENSG00000143772 | 1.05692317 | 0 | 5 | ITPKB | inositol-trisphosphate 3-kinase B [Source: HGNC Symbol; Acc: HGNC: 6179] |
| ENSG00000140022 | 1.42852098 | 0 | 5 | STON2 | stonin 2 [Source: HGNC Symbol; Acc: HGNC: 30652] |
| ENSG00000181722 | 1.75771309 | 0 | 5 | ZBTB20 | zinc finger and BTB domain containing 20 [Source: HGNC Symbol; Acc: HGNC: 13503] |
| ENSG00000184058 | 2.32518737 | 0 | 5 | TBX1 | T-box 1 [Source: HGNC Symbol; Acc: HGNC: 11592] |
| ENSG00000043591 | 1.38727807 | 0 | 5 | ADRB1 | adrenoceptor beta 1 [Source: HGNC Symbol; Acc: HGNC: 285] |

TABLE 5-continued

| RNASeq results filtered for genes with at least 10 reads in one sample per set | | | | | |
|---|---|---|---|---|---|
| | Log (base 2) fold-change | | | | |
| Gene | UM101 vs. control | SB203580 vs. control | bin | Gene Symbol | Gene Name |
| ENSG00000126550 | 2.94676056 | 0 | 5 | HTN1 | histatin 1 [Source: HGNC Symbol; Acc: HGNC: 5283] |
| ENSG00000143867 | 1.2361215 | 0 | 5 | OSR1 | odd-skipped related transciption factor 1 [Source: HGNC Symbol; Acc: HGNC: 8111] |
| ENSG00000116833 | 1.34604824 | 0 | 5 | NR5A2 | nuclear receptor subfamily 5, group A, member 2 [Source: HGNC Symbol; Acc: HGNC: 7984] |
| ENSG00000166292 | 2.00173044 | 0 | 5 | TMEM100 | transmembrane protein 100 [Source: HGNC Symbol; Acc: HGNC: 25607] |
| ENSG00000188487 | 1.04413181 | 0 | 5 | INSC | inscuteable homolog (*Drosophila*) [Source: HGNC Symbol; Acc: HGNC: 33116] |
| ENSG00000176697 | 1.76616859 | 0 | 5 | BDNF | brain-derived neurotrophic factor [Source: HGNC Symbol; Acc: HGNC: 1033] |
| ENSG00000079102 | 1.5770273 | 0 | 5 | RUNX1T1 | runt-related transcription factor 1; translocated to, 1 (cyclin D-related) [Source: HGNC Symbol; Acc: HGNC: 1535] |
| ENSG00000162599 | 1.02633907 | 0 | 5 | NFIA | nuclear factor I/A [Source: HGNC Symbol; Acc: HGNC: 7784] |
| ENSG00000188763 | 1.52543754 | 0 | 5 | FZD9 | frizzled class receptor 9 [Source: HGNC Symbol; Acc: HGNC: 4047] |
| ENSG00000154639 | 1.36734426 | 0 | 5 | CXADR | coxsackie virus and adenovirus receptor [Source: HGNC Symbol; Acc: HGNC: 2559] |
| ENSG00000227946 | 1.24976159 | 0 | 5 | AC007383.3 | |
| ENSG00000143341 | 1.16130281 | 0 | 5 | HMCN1 | hemicentin 1 [Source: HGNC Symbol; Acc: HGNC: 19194] |
| ENSG00000237892 | 1.07996952 | 0 | 5 | KLF7-IT1 | KLF7 intronic transcript 1 (non-protein coding) [Source: HGNC Symbol; Acc: HGNC: 41355] |
| ENSG00000103522 | 1.30364536 | 0 | 5 | IL21R | interleukin 21 receptor [Source: HGNC Symbol; Acc: HGNC: 6006] |
| ENSG00000162630 | 1.457488 | 0 | 5 | B3GALT2 | UDP-Gal: betaGlcNAc beta 1,3-galactosyltransferase, polypeptide 2 [Source: HGNC Symbol; Acc: HGNC: 917] |
| ENSG00000106069 | 1.15244395 | 0 | 5 | CHN2 | chimerin 2 [Source: HGNC Symbol; Acc: HGNC: 1944] |
| ENSG00000169047 | 1.03338349 | 0 | 5 | IRS1 | insulin receptor substrate 1 [Source: HGNC Symbol; Acc: HGNC: 6125] |
| ENSG00000226476 | 1.25685284 | 0 | 5 | RP11-776H12.1 | |
| ENSG00000181016 | 1.30372056 | 0 | 5 | LSMEM1 | leucine-rich single-pass membrane protein 1 [Source: HGNC Symbol; Acc: HGNC: 22036] |
| ENSG00000121966 | 3.89708969 | 0 | 5 | CXCR4 | chemokine (C-X-C motif) receptor 4 [Source: HGNC Symbol; Acc: HGNC: 2561] |
| ENSG00000189143 | 1.4778446 | 0 | 5 | CLDN4 | claudin 4 [Source: HGNC Symbol; Acc: HGNC: 2046] |
| ENSG00000257642 | 2.54048396 | 0 | 5 | RP11-474B16.1 | |
| ENSG00000250271 | 2.3827306 | 0 | 5 | RP11-64D22.5 | |
| ENSG00000188483 | 1.76997593 | 0 | 5 | IER5L | immediate early response 5-like [Source: HGNC Symbol; Acc: HGNC: 23679] |

TABLE 5-continued

| RNASeq results filtered for genes with at least 10 reads in one sample per set | | | | | |
|---|---|---|---|---|---|
| | Log (base 2) fold-change | | | | |
| Gene | UM101 vs. control | SB203580 vs. control | bin | Gene Symbol | Gene Name |
| ENSG00000183775 | 1.04020782 | 0 | 5 | KCTD16 | potassium channel tetramerization domain containing 16 [Source: HGNC Symbol; Acc: HGNC: 29244] |
| ENSG00000107984 | 1.55122779 | 0 | 5 | DKK1 | dickkopf WNT signaling pathway inhibitor 1 [Source: HGNC Symbol; Acc: HGNC: 2891] |
| ENSG00000174514 | 0 | 1.18746783 | 6 | MFSD4 | major facilitator superfamily domain containing 4 [Source: HGNC Symbol; Acc: HGNC: 25433] |
| ENSG00000270379 | 0 | 1.09045988 | 6 | HEATR9 | HEAT repeat containing 9 [Source: HGNC Symbol; Acc: HGNC: 26548] |
| ENSG00000240859 | 0 | 1.36188025 | 6 | AC093627.10 | |
| ENSG00000236671 | 0 | 1.65509644 | 6 | PRKG1-AS1 | PRKG1 antisense RNA 1 [Source: HGNC Symbol; Acc: HGNC: 45029] |
| ENSG00000261707 | 0 | 1.15736629 | 6 | RP11-264M12.2 | |
| ENSG00000273669 | 0 | 3.69876021 | 6 | RP11-405M12.4 | |
| ENSG00000231345 | 0 | 1.35868618 | 6 | BEND3P1 | BEN domain containing 3 pseudogene 1 [Source: HGNC Symbol; Acc: HGNC: 45014] |
| ENSG00000134253 | 0 | 1.10224143 | 6 | TRIM45 | tripartite motif containing 45 [Source: HGNC Symbol; Acc: HGNC: 19018] |
| ENSG00000138336 | 0 | 1.76426632 | 6 | TET1 | tet methylcytosine dioxygenase 1 [Source: HGNC Symbol; Acc: HGNC: 29484] |
| ENSG00000120162 | 0 | 1.23378866 | 6 | MOB3B | MOB kinase activator 3B [Source: HGNC Symbol; Acc: HGNC: 23825] |
| ENSG00000171860 | 0 | 1.01814888 | 6 | C3AR1 | complement component 3a receptor 1 [Source: HGNC Symbol; Acc: HGNC: 1319] |
| ENSG00000167676 | 0 | 1.03160807 | 6 | PLIN4 | perilipin 4 [Source: HGNC Symbol; Acc: HGNC: 29393] |
| ENSG00000237234 | 0 | 1.66084244 | 6 | RP1-142L7.5 | |
| ENSG00000164124 | 0 | 1.05381028 | 6 | TMEM144 | transmembrane protein 144 [Source: HGNC Symbol; Acc: HGNC: 25633] |
| ENSG00000118513 | 0 | 1.12982301 | 6 | MYB | v-myb avian myeloblastosis viral oncogene homolog [Source: HGNC Symbol; Acc: HGNC: 7545] |
| ENSG00000091137 | 0 | 1.16699806 | 6 | SLC26A4 | solute carrier family 26 (anion exchanger), member 4 [Source: HGNC Symbol; Acc: HGNC: 8818] |
| ENSG00000198483 | 0 | 1.43532228 | 6 | ANKRD35 | ankyrin repeat domain 35 [Source: HGNC Symbol; Acc: HGNC: 26323] |
| ENSG00000237886 | 0 | 1.57281997 | 6 | LINC01573 | long intergenic non-protein coding RNA 1573 [Source: HGNC Symbol; Acc: HGNC: 51192] |
| ENSG00000174004 | 0 | 2.27602232 | 6 | NRROS | negative regulator of reactive oxygen species [Source: HGNC Symbol; Acc: HGNC: 24613] |
| ENSG00000185634 | 0 | 1.66433678 | 6 | SHC4 | SHC (Src homology 2 domain containing) family, member 4 [Source: HGNC Symbol; Acc: HGNC: 16743] |

TABLE 5-continued

RNASeq results filtered for genes with at least 10 reads in one sample per set

| Gene | Log (base 2) fold-change UM101 vs. control | SB203580 vs. control | bin | Gene Symbol | Gene Name |
|---|---|---|---|---|---|
| ENSG00000259886 | 0 | 1.17666464 | 6 | | |
| ENSG00000145358 | 0 | 1.32550219 | 6 | DDIT4L | DNA-damage-inducible transcript 4-like [Source: HGNC Symbol; Acc: HGNC: 30555] |
| ENSG00000269896 | 0 | 1.28838255 | 6 | RP4-740C4.5 | |
| ENSG00000135828 | 0 | 1.0837094 | 6 | RNASEL | ribonuclease L (2',5'-oligoisoadenylate synthetase-dependent) [Source: HGNC Symbol; Acc: HGNC: 10050] |
| ENSG00000259162 | 0 | 1.52667158 | 6 | RP11-203M5.6 | |
| ENSG00000279109 | −3.3403535 | 0 | 7 | AC008641.1 | Uncharacterized protein {ECO: 0000313\|Ensembl: ENSP00000485568} [Source: UniProtKB/TrEMBL; Acc: A0A096LPF4] |
| ENSG00000152778 | −1.0972226 | 0 | 7 | IFIT5 | interferon-induced protein with tetratricopeptide repeats 5 [Source: HGNC Symbol; Acc: HGNC: 13328] |
| ENSG00000128284 | −1.3050716 | 0 | 7 | APOL3 | apolipoprotein L, 3 [Source: HGNC Symbol; Acc: HGNC: 14868] |
| ENSG00000213886 | −4.0396114 | 0 | 7 | UBD | ubiquitin D [Source: HGNC Symbol; Acc: HGNC: 18795] |
| ENSG00000164116 | −1.5223055 | 0 | 7 | GUCY1A3 | guanylate cyclase 1, soluble, alpha 3 [Source: HGNC Symbol; Acc: HGNC: 4685] |
| ENSG00000137462 | −1.0020489 | 0 | 7 | TLR2 | toll-like receptor 2 [Source: HGNC Symbol; Acc: HGNC: 11848] |
| ENSG00000049249 | −2.1008906 | 0 | 7 | TNFRSF9 | tumor necrosis factor receptor superfamily, member 9 [Source: HGNC Symbol; Acc: HGNC: 11924] |
| ENSG00000169181 | −2.095598 | 0 | 7 | GSG1L | GSG1-like [Source: HGNC Symbol; Acc: HGNC: 28283] |
| ENSG00000162888 | −1.7912286 | 0 | 7 | C1orf147 | chromosome 1 open reading frame 147 [Source: HGNC Symbol; Acc: HGNC: 32061] |
| ENSG00000107201 | −1.2413536 | 0 | 7 | DDX58 | DEAD (Asp-Glu-Ala-Asp) box polypeptide 58 [Source: HGNC Symbol; Acc: HGNC: 19102] |
| ENSG00000179826 | −2.5133806 | 0 | 7 | MRGPRX3 | MAS-related GPR, member X3 [Source: HGNC Symbol; Acc: HGNC: 17980] |
| ENSG00000132109 | −1.2867007 | 0 | 7 | TRIM21 | tripartite motif containing 21 [Source: HGNC Symbol; Acc: HGNC: 11312] |
| ENSG00000215007 | −1.0078729 | 0 | 7 | DNAJA1P3 | DnaJ (Hsp40) homolog, subfamily A, member 1 pseudogene 3 [Source: HGNC Symbol; Acc: HGNC: 39339] |
| ENSG00000204682 | −1.1628447 | 0 | 7 | CASC10 | cancer susceptibility candidate 10 [Source: HGNC Symbol; Acc: HGNC: 31448] |
| ENSG00000108688 | −1.8703428 | 0 | 7 | CCL7 | chemokine (C-C motif) ligand 7 [Source: HGNC Symbol; Acc: HGNC: 10634] |
| ENSG00000112096 | −1.0730214 | 0 | 7 | SOD2 | superoxide dismutase 2, mitochondrial [Source: HGNC Symbol; Acc: HGNC: 11180] |
| ENSG00000010379 | −2.697306 | 0 | 7 | SLC6A13 | solute carrier family 6 (neurotransmitter transporter), member 13 [Source: HGNC Symbol; Acc: HGNC: 11046] |
| ENSG00000169403 | −1.579388 | 0 | 7 | PTAFR | platelet-activating factor receptor [Source: HGNC Symbol; Acc: HGNC: 9582] |

TABLE 5-continued

RNASeq results filtered for genes with at least 10 reads in one sample per set

| Gene | Log (base 2) fold-change UM101 vs. control | SB203580 vs. control | bin | Gene Symbol | Gene Name |
|---|---|---|---|---|---|
| ENSG00000115604 | −3.2590591 | 0 | 7 | IL18R1 | interleukin 18 receptor 1 [Source: HGNC Symbol; Acc: HGNC: 5988] |
| ENSG00000133401 | −1.024655 | 0 | 7 | PDZD2 | PDZ domain containing 2 [Source: HGNC Symbol; Acc: HGNC: 18486] |
| ENSG00000095587 | −2.2510173 | 0 | 7 | TLL2 | tolloid-like 2 [Source: HGNC Symbol; Acc: HGNC: 11844] |
| ENSG00000134256 | −1.3577477 | 0 | 7 | CD101 | CD101 molecule [Source: HGNC Symbol; Acc: HGNC: 5949] |
| ENSG00000272463 | −1.1413394 | 0 | 7 | RP11-532F6.3 | |
| ENSG00000102794 | −1.5942464 | 0 | 7 | IRG1 | immunoresponsive 1 homolog (mouse) [Source: HGNC Symbol; Acc: HGNC: 33904] |
| ENSG00000223799 | −1.6341444 | 0 | 7 | IL10RB-AS1 | IL10RB antisense RNA 1 (head to head) [Source: HGNC Symbol; Acc: HGNC: 44303] |
| ENSG00000019582 | −1.1055825 | 0 | 7 | CD74 | CD74 molecule, major histocompatibility complex, class II invariant chain [Source: HGNC Symbol; Acc: HGNC: 1697] |
| ENSG00000121577 | −1.2357302 | 0 | 7 | POPDC2 | popeye domain containing 2 [Source: HGNC Symbol; Acc: HGNC: 17648] |
| ENSG00000215268 | −1.7373145 | 0 | 7 | LA16c-60G3.8 | |
| ENSG00000119121 | −1.4785767 | 0 | 7 | TRPM6 | transient receptor potential cation channel, subfamily M, member 6 [Source: HGNC Symbol; Acc: HGNC: 17995] |
| ENSG00000108576 | −1.2299055 | 0 | 7 | SLC6A4 | solute carrier family 6 (neurotransmitter transporter), member 4 [Source: HGNC Symbol; Acc: HGNC: 11050] |
| ENSG00000274818 | −1.8854991 | 0 | 7 | RP1-292L20.3 | |
| ENSG00000198133 | −1.9389698 | 0 | 7 | TMEM229B | transmembrane protein 229B [Source: HGNC Symbol; Acc: HGNC: 20130] |
| ENSG00000130477 | −1.2541053 | 0 | 7 | UNC13A | unc-13 homolog A (*C. elegans*) [Source: HGNC Symbol; Acc: HGNC: 23150] |
| ENSG00000266094 | −1.0579637 | 0 | 7 | RASSF5 | Ras association (RalGDS/AF-6) domain family member 5 [Source: HGNC Symbol; Acc: HGNC: 17609] |
| ENSG00000137571 | −1.0904993 | 0 | 7 | SLCO5A1 | solute carrier organic anion transporter family, member 5A1 [Source: HGNC Symbol; Acc: HGNC: 19046] |
| ENSG00000272512 | −1.5915514 | 0 | 7 | RP11-54O7.17 | |
| ENSG00000124391 | −1.7278326 | 0 | 7 | IL17C | interleukin 17C [Source: HGNC Symbol; Acc: HGNC: 5983] |
| ENSG00000136052 | −1.3272223 | 0 | 7 | SLC41A2 | solute carrier family 41 (magnesium transporter), member 2 [Source: HGNC Symbol; Acc: HGNC: 31045] |
| ENSG00000185245 | −1.9464332 | 0 | 7 | GP1BA | glycoprotein Ib (platelet), alpha polypeptide [Source: HGNC Symbol; Acc: HGNC: 4439] |
| ENSG00000203685 | −1.8061183 | 0 | 7 | C1orf95 | chromosome 1 open reading frame 95 [Source: HGNC Symbol; Acc: HGNC: 30491] |
| ENSG00000149654 | −1.331613 | 0 | 7 | CDH22 | cadherin 22, type 2 [Source: HGNC Symbol; Acc: HGNC: 13251] |
| ENSG00000230943 | −1.574129 | 0 | 7 | RP11-367G18.1 | |

TABLE 5-continued

| RNASeq results filtered for genes with at least 10 reads in one sample per set | | | | | |
|---|---|---|---|---|---|
| | Log (base 2) fold-change | | | | |
| Gene | UM101 vs. control | SB203580 vs. control | bin | Gene Symbol | Gene Name |
| ENSG00000215277 | −3.2333936 | 0 | 7 | RNF212B | ring finger protein 212B [Source: HGNC Symbol; Acc: HGNC: 20438] |
| ENSG00000112139 | −1.2861961 | 0 | 7 | MDGA1 | MAM domain containing glycosylphosphatidylinositol anchor 1 [Source: HGNC Symbol; Acc: HGNC: 19267] |
| ENSG00000143494 | −1.5135205 | 0 | 7 | VASH2 | vasohibin 2 [Source: HGNC Symbol; Acc: HGNC: 25723] |
| ENSG00000151883 | −1.1760751 | 0 | 7 | PARP8 | poly (ADP-ribose) polymerase family, member 8 [Source: HGNC Symbol; Acc: HGNC: 26124] |
| ENSG00000136514 | −1.9750242 | 0 | 7 | RTP4 | receptor (chemosensory) transporter protein 4 [Source: HGNC Symbol; Acc: HGNC: 23992] |
| ENSG00000106258 | −1.012592 | 0 | 7 | CYP3A5 | cytochrome P450, family 3, subfamily A, polypeptide 5 [Source: HGNC Symbol; Acc: HGNC: 2638] |
| ENSG00000243649 | −2.5551714 | 0 | 7 | CFB | complement factor B [Source: HGNC Symbol; Acc: HGNC: 1037] |
| ENSG00000164342 | −1.0290951 | 0 | 7 | TLR3 | toll-like receptor 3 [Source: HGNC Symbol; Acc: HGNC: 11849] |
| ENSG00000115956 | −2.3479537 | 0 | 7 | PLEK | pleckstrin [Source: HGNC Symbol; Acc: HGNC: 9070] |
| ENSG00000144476 | −1.7184658 | 0 | 7 | ACKR3 | atypical chemokine receptor 3 [Source: HGNC Symbol; Acc: HGNC: 23692] |
| ENSG00000157601 | −1.4173764 | 0 | 7 | MX1 | MX dynamin-like GTPase 1 [Source: HGNC Symbol; Acc: HGNC: 7532] |
| ENSG00000177409 | −1.1465499 | 0 | 7 | SAMD9L | sterile alpha motif domain containing 9-like [Source: HGNC Symbol; Acc: HGNC: 1349] |
| ENSG00000119917 | −1.8565474 | 0 | 7 | IFIT3 | interferon-induced protein with tetratricopeptide repeats 3 [Source: HGNC Symbol; Acc: HGNC: 5411] |
| ENSG00000271503 | −1.7683442 | 0 | 7 | CCL5 | chemokine (C-C motif) ligand 5 [Source: HGNC Symbol; Acc: HGNC: 10632] |
| ENSG00000117226 | −1.1447048 | 0 | 7 | GBP3 | guanylate binding protein 3 [Source: HGNC Symbol; Acc: HGNC: 4184] |
| ENSG00000163840 | −1.3311379 | 0 | 7 | DTX3L | deltex 3 like, E3 ubiquitin ligase [Source: HGNC Symbol; Acc: HGNC: 30323] |
| ENSG00000010030 | −1.2207673 | 0 | 7 | ETV7 | ets variant 7 [Source: HGNC Symbol; Acc: HGNC: 18160] |
| ENSG00000261884 | −1.3310986 | 0 | 7 | CTC-479C5.12 | Uncharacterized protein {ECO: 0000313\|Ensembl: ENSP00000463376} [Source: UniProtKB/TrEMBL; Acc: J3QL48] |
| ENSG00000152229 | −1.0179291 | 0 | 7 | PSTPIP2 | proline-serine-threonine phosphatase interacting protein 2 [Source: HGNC Symbol; Acc: HGNC: 9581] |
| ENSG00000100678 | −2.0514071 | 0 | 7 | SLC8A3 | solute carrier family 8 (sodium/calcium exchanger), member 3 [Source: HGNC Symbol; Acc: HGNC: 11070] |
| ENSG00000225194 | −2.4201688 | 0 | 7 | LINC00092 | long intergenic non-protein coding RNA 92 [Source: HGNC Symbol; Acc: HGNC: 31408] |

TABLE 5-continued

| RNASeq results filtered for genes with at least 10 reads in one sample per set | | | | | |
|---|---|---|---|---|---|
| | Log (base 2) fold-change | | | | |
| Gene | UM101 vs. control | SB203580 vs. control | bin | Gene Symbol | Gene Name |
| ENSG00000140968 | −1.1898419 | 0 | 7 | IRF8 | interferon regulatory factor 8 [Source: HGNC Symbol; Acc: HGNC: 5358] |
| ENSG00000006210 | −1.2182721 | 0 | 7 | CX3CL1 | chemokine (C-X3-C motif) ligand 1 [Source: HGNC Symbol; Acc: HGNC: 10647] |
| ENSG00000221963 | −1.1392138 | 0 | 7 | APOL6 | apolipoprotein L, 6 [Source: HGNC Symbol; Acc: HGNC: 14870] |
| ENSG00000130589 | −1.0673283 | 0 | 7 | HELZ2 | helicase with zinc finger 2, transcriptional coactivator [Source: HGNC Symbol; Acc: HGNC: 30021] |
| ENSG00000239713 | −1.6622438 | 0 | 7 | APOBEC3G | apolipoprotein B mRNA editing enzyme, catalytic polypeptide-like 3G [Source: HGNC Symbol; Acc: HGNC: 17357] |
| ENSG00000151023 | −1.0139189 | 0 | 7 | ENKUR | enkurin, TRPC channel interacting protein [Source: HGNC Symbol; Acc: HGNC: 28388] |
| ENSG00000187123 | −1.3193979 | 0 | 7 | LYPD6 | LY6/PLAUR domain containing 6 [Source: HGNC Symbol; Acc: HGNC: 28751] |
| ENSG00000253831 | −3.0507137 | 0 | 7 | ETV3L | ets variant 3-like [Source: HGNC Symbol; Acc: HGNC: 33834] |
| ENSG00000246130 | −3.0351799 | 0 | 7 | RP11-875O11.2 | |
| ENSG00000128335 | −1.8122079 | 0 | 7 | APOL2 | apolipoprotein L, 2 [Source: HGNC Symbol; Acc: HGNC: 619] |
| ENSG00000108702 | −4.9466198 | 0 | 7 | CCL1 | chemokine (C-C motif) ligand 1 [Source: HGNC Symbol; Acc: HGNC: 10609] |
| ENSG00000105963 | −1.2049889 | 0 | 7 | ADAP1 | ArfGAP with dual PH domains 1 [Source: HGNC Symbol; Acc: HGNC: 16486] |
| ENSG00000170075 | −1.4491156 | 0 | 7 | GPR37L1 | G protein-coupled receptor 37 like 1 [Source: HGNC Symbol; Acc: HGNC: 14923] |
| ENSG00000267607 | −1.2021234 | 0 | 7 | CTD-2369P2.8 | |
| ENSG00000142961 | −1.1266143 | 0 | 7 | MOB3C | MOB kinase activator 3C [Source: HGNC Symbol; Acc: HGNC: 29800] |
| ENSG00000159200 | −1.1629133 | 0 | 7 | RCAN1 | regulator of calcineurin 1 [Source: HGNC Symbol; Acc: HGNC: 3040] |
| ENSG00000185291 | −1.5031919 | 0 | 7 | IL3RA | interleukin 3 receptor, alpha (low affinity) [Source: HGNC Symbol; Acc: HGNC: 6012] |
| ENSG00000135917 | −1.3131434 | 0 | 7 | SLC19A3 | solute carrier family 19 (thiamine transporter), member 3 [Source: HGNC Symbol; Acc: HGNC: 16266] |
| ENSG00000179817 | −1.7239398 | 0 | 7 | MRGPRX4 | MAS-related GPR, member X4 [Source: HGNC Symbol; Acc: HGNC: 17617] |
| ENSG00000173918 | −1.1809051 | 0 | 7 | C1QTNF1 | C1q and tumor necrosis factor related protein 1 [Source: HGNC Symbol; Acc: HGNC: 14324] |
| ENSG00000198879 | −1.3578392 | 0 | 7 | SFMBT2 | Scm-like with four mbt domains 2 [Source: HGNC Symbol; Acc: HGNC: 20256] |
| ENSG00000272078 | −1.1495108 | 0 | 7 | RP4-734G22.3 | |
| ENSG00000269794 | −1.7476941 | 0 | 7 | AC010642.2 | |
| ENSG00000115919 | −1.2162129 | 0 | 7 | KYNU | kynureninase [Source: HGNC Symbol; Acc: HGNC: 6469] |
| ENSG00000255521 | −1.8970116 | 0 | 7 | RP4-607I7.1 | |

TABLE 5-continued

RNASeq results filtered for genes with at least 10 reads in one sample per set

| Gene | Log (base 2) fold-change UM101 vs. control | SB203580 vs. control | bin | Gene Symbol | Gene Name |
|---|---|---|---|---|---|
| ENSG00000173193 | −1.3401257 | 0 | 7 | PARP14 | poly (ADP-ribose) polymerase family, member 14 [Source: HGNC Symbol; Acc: HGNC: 29232] |
| ENSG00000183644 | −1.6099016 | 0 | 7 | C11orf88 | chromosome 11 open reading frame 88 [Source: HGNC Symbol; Acc: HGNC: 25061] |
| ENSG00000253522 | −1.2658724 | 0 | 7 | CTC-231O11.1 | |
| ENSG00000236453 | −1.8969845 | 0 | 7 | AC003092.1 | |
| ENSG00000131979 | −1.5762138 | 0 | 7 | GCH1 | GTP cyclohydrolase 1 [Source: HGNC Symbol; Acc: HGNC: 4193] |
| ENSG00000069493 | −2.1742062 | 0 | 7 | CLEC2D | C-type lectin domain family 2, member D [Source: HGNC Symbol; Acc: HGNC: 14351] |
| ENSG00000069696 | −1.1323561 | 0 | 7 | DRD4 | dopamine receptor D4 [Source: HGNC Symbol; Acc: HGNC: 3025] |
| ENSG00000175356 | −1.3984803 | 0 | 7 | SCUBE2 | signal peptide, CUB domain, EGF-like 2 [Source: HGNC Symbol; Acc: HGNC: 30425] |
| ENSG00000128165 | −1.1779326 | 0 | 7 | ADM2 | adrenomedullin 2 [Source: HGNC Symbol; Acc: HGNC: 28898] |
| ENSG00000166856 | −1.1992337 | 0 | 7 | GPR182 | G protein-coupled receptor 182 [Source: HGNC Symbol; Acc: HGNC: 13708] |
| ENSG00000199161 | −1.616849 | 0 | 7 | MIR126 | microRNA 126 [Source: HGNC Symbol; Acc: HGNC: 31508] |
| ENSG00000050730 | −1.9873165 | 0 | 7 | TNIP3 | TNFAIP3 interacting protein 3 [Source: HGNC Symbol; Acc: HGNC: 19315] |
| ENSG00000255750 | −1.8909724 | 0 | 7 | RP11-283G6.5 | |
| ENSG00000184530 | −2.3505853 | 0 | 7 | C6orf58 | chromosome 6 open reading frame 58 [Source: HGNC Symbol; Acc: HGNC: 20960] |
| ENSG00000104883 | −1.3860147 | 0 | 7 | PEX11G | peroxisomal biogenesis factor 11 gamma [Source: HGNC Symbol; Acc: HGNC: 20208] |
| ENSG00000129521 | −2.7016498 | 0 | 7 | EGLN3 | egl-9 family hypoxia-inducible factor 3 [Source: HGNC Symbol; Acc: HGNC: 14661] |
| ENSG00000204482 | −1.2475769 | 0 | 7 | LST1 | leukocyte specific transcript 1 [Source: HGNC Symbol; Acc: HGNC: 14189] |
| ENSG00000115267 | −1.3445539 | 0 | 7 | IFIH1 | interferon induced with helicase C domain 1 [Source: HGNC Symbol; Acc: HGNC: 18873] |
| ENSG00000162692 | −2.1801821 | 0 | 7 | VCAM1 | vascular cell adhesion molecule 1 [Source: HGNC Symbol; Acc: HGNC: 12663] |
| ENSG00000261618 | −1.2864344 | 0 | 7 | RP11-79H23.3 | |
| ENSG00000101276 | −1.1705916 | 0 | 7 | SLC52A3 | solute carrier family 52 (riboflavin transporter), member 3 [Source: HGNC Symbol; Acc: HGNC: 16187] |
| ENSG00000064309 | −1.4651234 | 0 | 7 | CDON | cell adhesion associated, oncogene regulated [Source: HGNC Symbol; Acc: HGNC: 17104] |
| ENSG00000167371 | −1.4282411 | 0 | 7 | PRRT2 | proline-rich transmembrane protein 2 [Source: HGNC Symbol; Acc: HGNC: 30500] |
| ENSG00000101017 | −1.5583663 | 0 | 7 | CD40 | CD40 molecule, TNF receptor superfamily member 5 [Source: HGNC Symbol; Acc: HGNC: 11919] |

TABLE 5-continued

| RNASeq results filtered for genes with at least 10 reads in one sample per set | | | | | |
|---|---|---|---|---|---|
| | Log (base 2) fold-change | | | | |
| Gene | UM101 vs. control | SB203580 vs. control | bin | Gene Symbol | Gene Name |
| ENSG00000164400 | 0 | −1.63408281 | 8 | CSF2 | colony stimulating factor 2 (granulocyte-macrophage) [Source: HGNC Symbol; Acc: HGNC: 2434] |
| ENSG00000172602 | 0 | −1.15027449 | 8 | RND1 | Rho family GTPase 1 [Source: HGNC Symbol; Acc: HGNC: 18314] |
| ENSG00000174502 | 0 | −2.09273487 | 8 | SLC26A9 | solute carrier family 26 (anion exchanger), member 9 [Source: HGNC Symbol; Acc: HGNC: 14469] |
| ENSG00000234290 | 0 | −1.00067832 | 8 | AC116366.6 | |
| ENSG00000170961 | 0 | −2.64619793 | 8 | HAS2 | hyaluronan synthase 2 [Source: HGNC Symbol; Acc: HGNC: 4819] |
| ENSG00000110848 | 0 | −1.46706866 | 8 | CD69 | CD69 molecule [Source: HGNC Symbol; Acc: HGNC: 1694] |
| ENSG00000164512 | 0 | −1.20441285 | 8 | ANKRD55 | ankyrin repeat domain 55 [Source: HGNC Symbol; Acc: HGNC: 25681] |
| ENSG00000167034 | 0 | −1.10541745 | 8 | NKX3-1 | NK3 homeobox 1 [Source: HGNC Symbol; Acc: HGNC: 7838] |
| ENSG00000105246 | 0 | −1.39394774 | 8 | EBI3 | Epstein-Barr virus induced 3 [Source: HGNC Symbol; Acc: HGNC: 3129] |
| ENSG00000145506 | 0 | −1.41815829 | 8 | NKD2 | naked cuticle homolog 2 (*Drosophila*) [Source: HGNC Symbol; Acc: HGNC: 17046] |
| ENSG00000127533 | 0 | −2.64266235 | 8 | F2RL3 | coagulation factor II (thrombin) receptor-like 3 [Source: HGNC Symbol; Acc: HGNC: 3540] |
| ENSG00000115008 | 0 | −2.15272028 | 8 | IL1A | interleukin 1, alpha [Source: HGNC Symbol; Acc: HGNC: 5991] |
| ENSG00000073282 | 0 | −1.31215479 | 8 | TP63 | tumor protein p63 [Source: HGNC Symbol; Acc: HGNC: 15979] |
| ENSG00000113196 | 0 | −1.61798433 | 8 | HAND1 | heart and neural crest derivatives expressed 1 [Source: HGNC Symbol; Acc: HGNC: 4807] |
| ENSG00000096996 | 0 | −1.40936482 | 8 | IL12RB1 | interleukin 12 receptor, beta 1 [Source: HGNC Symbol; Acc: HGNC: 5971] |
| ENSG00000275582 | 0 | −1.05575947 | 8 | RP4-681N20.5 | |
| ENSG00000244476 | 0 | −1.23492596 | 8 | ERVFRD-1 | endogenous retrovirus group FRD, member 1 [Source: HGNC Symbol; Acc: HGNC: 33823] |
| ENSG00000165685 | 0 | −1.10987961 | 8 | TMEM52B | transmembrane protein 52B [Source: HGNC Symbol; Acc: HGNC: 26438] |
| ENSG00000172331 | 0 | −1.20450079 | 8 | BPGM | 2,3-bisphosphoglycerate mutase [Source: HGNC Symbol; Acc: HGNC: 1093] |
| ENSG00000198846 | 0 | −1.42254609 | 8 | TOX | thymocyte selection-associated high mobility group box [Source: GNC Symbol; Acc: HGNC: 18988] |
| ENSG00000258521 | 0 | −1.0229865 | 8 | RP11-638I2.9 | |
| ENSG00000279133 | 0 | −1.46999903 | 8 | RP11-342K2.1 | |
| ENSG00000121905 | 0 | −2.21994573 | 8 | HPCA | hippocalcin [Source: HGNC Symbol; Acc: HGNC: 5144] |
| ENSG00000232810 | 0 | −1.4782116 | 8 | TNF | tumor necrosis factor [Source: HGNC Symbol; Acc: HGNC: 11892] |
| ENSG00000178882 | 0 | −1.71201963 | 8 | FAM101A | family with sequence similarity 101, member A [Source: HGNC Symbol; Acc: HGNC: 27051] |

TABLE 5-continued

| RNASeq results filtered for genes with at least 10 reads in one sample per set | | | | | |
|---|---|---|---|---|---|
| | Log (base 2) fold-change | | | | |
| Gene | UM101 vs. control | SB203580 vs. control | bin | Gene Symbol | Gene Name |
| ENSG00000173391 | 0 | −1.01327133 | 8 | OLR1 | oxidized low density lipoprotein (lectin-like) receptor 1 [Source: HGNC Symbol; Acc: HGNC: 8133] |
| ENSG00000257671 | 0 | −1.03664909 | 8 | RP3-416H24.1 | |
| ENSG00000269826 | 0 | −1.64046441 | 8 | RP11-158I3.3 | |
| ENSG00000176907 | 0 | −1.2182476 | 8 | C8orf4 | chromosome 8 open reading frame 4 [Source: HGNC Symbol; Acc: HGNC: 1357] |
| ENSG00000165478 | 0 | −1.21164831 | 8 | HEPACAM | hepatic and glial cell adhesion molecule [Source: HGNC Symbol; Acc: HGNC: 26361] |
| ENSG00000175746 | 0 | −1.57742953 | 8 | C15orf54 | chromosome 15 open reading frame 54 [Source: HGNC Symbol; Acc: HGNC: 33797] |
| ENSG00000187848 | 0 | −2.24446361 | 8 | P2RX2 | purinergic receptor P2X, ligand gated ion channel, 2 [Source: HGNC Symbol; Acc: HGNC: 15459] |

Figure 6:
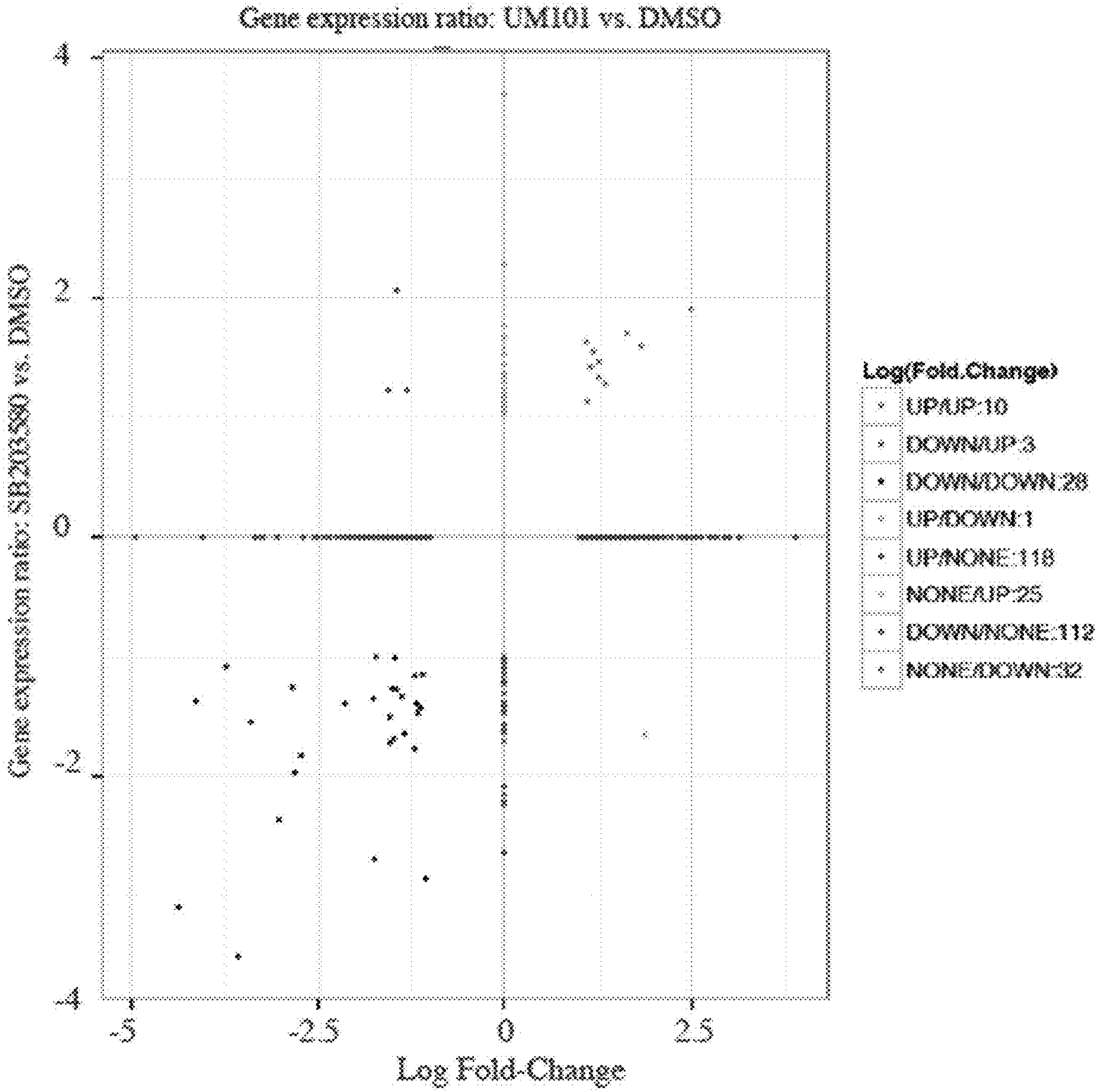
FIG. 6 is a quadrant map of RNASeq analysis. Genes with at least 10 reads in one sample per set and at least 2-fold increase with TNFα are shown. The key refers to the direction of change in UM101-treated cells/SB203580-treated cells vs. DMSO-treated cells.

List of genes modified by SB203580 or UM101 (see also FIG. 6); Bin number refers to gene expression response pattern:
1 = increased expression with both inhibitors
5 = increased with UM101, unchanged with SB203580
2 = decreased with UM101, increased with SB203580
6 = unchanged with UM101, increased with SB203580
3 = decreased expression with both inhibitors
7 = decreased with UM101, unchanged with SB203580
4 = increased with UM101, decreased with SB203580
8 = unchanged with UM101, decreased with SB203580

SB203580 inhibited expression of 61 TNFα-induced genes, 28 of which were also inhibited by U101 (Table 6, Table 5, FIG. 6). SB203580 increased expression of 38 genes, 10 of which were also increased by UM. Of the 28 genes inhibited by both SB203580 and UM101, 22 coded for known proteins, including IL-183, CCL17, MMNP9, TDO1, CXCL5, 10 and 11, hyaluronan synthase-3, MUC4, and PLA2 (Table 6). Of the 33 genes inhibited by SB203580 but not UM101, 24 coded for known proteins, including GM-CSF, IL-1α, TNFα, IL-12 receptor-β1, and hyaluronan synthase-2 (Table 6).

TABLE 6

| Effect of SB203580 and UM101 in HMVECLs on TNFα-induced genes [1] | | | |
|---|---|---|---|
| Gene Symbol | Gene name | LOG fold-change SB203580 vs. DMSO | LOG fold-change UM101 vs. DMSO |
| Genes inhibited by both SB203580 and UM101 | | | |
| PRRG4 | proline rich Gla 4 | −1.782580534 | −1.198488233 |
| TSLP | thymic stromal lymphopoietin | −1.651439594 | −1.336652511 |
| CCL17 | chemokine (C-C motif) ligand 17 | −1.834143455 | −2.730309773 |
| EXOC3L4 | exocyst complex component 3-like 4 | −1.479163179 | −1.160471021 |
| MMP9 | matrix metallopeptidase 9 | −1.157091348 | −1.091179627 |
| IDO1 | indoleamine 2,3-dioxygenase 1 | −3.510632932 | −3.567987354 |
| CXCL10 | chemokine (C-X-C motif) ligand 10 | −3.100915562 | −4.369836708 |
| CD200 | CD200 | −1.729285649 | −1.538155406 |
| SLC15A3 | solute carrier family 15, member 3 | −1.00338842 | −1.73105887 |
| VDR | Vitamin D receptor | −1.16718631 | −1.19731694 |
| IL1B | Interleukin-1β | −1.401586926 | −1.172530543 |
| GPR88 | G protein-coupled receptor 88 | −1.397083754 | −2.150599176 |
| CD207 | CD207 (langerin) | −1.547757288 | −3.382437255 |
| TCHH | trichohyalin | −1.504958085 | −1.547665316 |
| HAS3 | hyaluronan synthase 3 | −1.43377734 | −1.124339564 |
| GBP1P1 | guanylate binding protein 1 | −1.363287203 | −1.755706078 |
| MUC4 | Mucin-4 | −2.859491876 | −1.057315692 |
| ELOVL7 | ELOVL fatty acid elongase 7 | −1.340933369 | −1.381063226 |
| CXCL11 | chemokine (C-X-C motif) ligand 11 | −1.377905942 | −4.136354868 |
| GBP4 | guanylate binding protein 4 | −1.259283076 | −2.835947907 |
| PLA1A | phospholipase A1 member A | −1.27452433 | −1.500633356 |
| CXCL5 | chemokine (C-X-C motif) ligand 5 | −1.017427849 | −1.468307731 |

TABLE 6-continued

Effect of SB203580 and UM101 in HMVECLs on TNFα-induced genes [1]

| Gene Symbol | Gene name | LOG fold-change SB203580 vs. DMSO | LOG fold-change UM101 vs. DMSO |
|---|---|---|---|
| | Genes inhibited by SB203580 but not UM101 | | |
| CSF2 | GM-CSF | −1.634082807 | ns [2] |
| RND1 | Rho family GTPase 1 | −1.15027449 | ns |
| SLC26A9 | solute carrier family 26, member 9 | −2.092734866 | ns |
| HAS2 | hyaluronan synthase 2 | −2.646197932 | ns |
| CD69 | CD69 | −1.467068659 | ns |
| ANKRD55 | ankyrin repeat domain 55 | −1.204412851 | ns |
| NKX3-1 | NK3 homeobox 1 | −1.105417452 | ns |
| EBI3 | Epstein-Barr virus induced 3 | −1.393947741 | ns |
| NKD2 | naked cuticle homolog 2 | −1.418158287 | ns |
| F2RL3 | coagulation factor II receptor-like 3 | −2.642662346 | ns |
| IL1A | Interleukin-1alpha | −2.152720278 | ns |
| TP63 | Tumor protein 63 | −1.312154792 | ns |
| HAND1 | heart and neural crest derivatives expressed 1 | −1.617984328 | ns |
| IL12RB1 | interleukin 12 receptor, beta 1 | −1.409364824 | ns |
| ERVFRD-1 | endogenous retrovirus group FRD, member 1 | −1.234925956 | ns |
| TMEM52B | transmembrane protein 52B | −1.109879612 | ns |
| BPGM | 2,3-bisphosphoglycerate mutase | −1.204500786 | ns |
| TOX | thymocyte selection-associated high mobility group box | −1.422546092 | ns |
| HPCA | hippocalcin | −2.219945733 | ns |
| TNF | Tumor necrosis factor-alpha | −1.478211598 | ns |
| FAM101A | family with sequence similarity 101, member A | −1.712019627 | ns |
| OLR1 | oxidized low density lipoprotein receptor 1 | −1.013271327 | ns |
| HEPACAM | hepatic and glial cell adhesion molecule | −1.211648309 | ns |
| P2RX2 | purinergic receptor P2X | −2.244463614 | ns |

[1] HMVECLs were preincubated with either 0.4% DMSO, 10 μM SB20350, or 100 μM UM101 for 1 h, then stimulated with 10 ng/ml TNFα for 4 h and RNASeq performed.
[2] not significant The differentially expressed genes were further analyzed using PathwayNet and Ingenuity™ tools to identify the transcription factors and biological pathways regulated by the two inhibitors. PathwayNet analysis suggested that UM101 inhibits some of the SB203580-inhibited transcription factors (Stat-1, c-Fos, c-Jun, NFxB, p53, PPARy, and Spl), but not others (ATF1, ATF2, Elki, c/EBPP, USF1, SMAD3, FOXO1, and CREB via MSK1/2). Ingenuity™ analysis suggested that both SB203580 and UM101 inhibit the Dendritic Cell Maturation, Triggering Receptor Expressed on Myeloid cells-1 (TREM1), High Mobility Group Box 1 (HMGB1), and NFxB pathways and both increase Liver X-Receptor/Retinoid X-Receptor (LXR/RXR) activation, while only SB203580 inhibits IL-6, Acute Phase, and Cholecystokinin/Gastrin-mediated pathways (FIG. 3*a*). UM101 at 100 μM reduced expression of 115 genes and increased expression of 119 genes that were not modified by SB203580 (Table 5), which Ingenuity™ pathway analysis suggested reduced Toll-like receptor and Wnt/0-catenin signaling and increased Nitric Oxide in Cardiovascular Disease pathways (FIG. 3*b*).

Example 6: Comparing Effects of SB203580 and UM101 on p38 MAPK Substrate Phosphorylation Profile To assess whether UM101 selectively inhibits phosphorylation consistent with its target, HeLa cells were pretreated for 30 min with 10 μM SB203580, 50 μM UM101, or 0.1% DMSO vehicle control, then with the p38 activator, anisomycin (25 μg/ml) and phosphorylated MK2, and Stat-1 were analyzed by immunoblotting (FIG. 3*c*). Anisomycin-stimulated phosphorylation of MK2 and Stat-1 were reduced by both 10 μM SB203580 and 50 μM UM1010, but more so with SB203580.

Example 7: Analyzing Specific Binding of UM101 to p38α

DSF was used to analyze concentration-specific binding of UM101 to p38α and p38β. While SB203580 stabilized both p38α and p38β, UM101 only stabilized p38α (FIG. 3*d*). To confirm that UM101 bound the CADD-targeted pocket, DSF was used to compare UM101- and SB203580-binding to wild-type p38α and a p38α mutant with four of the ten target pocket amino acids (R49K/HL107-8TF/K165R) substituted (FIG. 3*e*). The mutant exhibited SB203580-binding that was identical to wild-type p38α, but no UM101-binding.

Selective binding of UM101 to the CADD-targeted pocket in p38α was confirmed using Saturation Transfer Difference (STD)-NMR. A 1D spectrum of UM101 in the presence of p38α is shown in FIG. 3*f* and the STD spectrum of the same sample is shown in FIG. 3*g*. The peaks in the 1D spectrum are labeled according to tentative peak assignments of UM101 in aqueous form, based on assignments of UM101 in 2 mM d6-DMSO, which were obtained from the use of 1D proton and $C_{13}$ and 2D-HMBC experiments. The shifts of the peaks in the STD spectrum correspond well to those of the 1D spectrum, thus indicating that protons in both aromatic rings of UM101 interact with p38α. In contrast, while the 1D spectra for UM101 with p380 and mutated p38α were similar to that of UM101/p38α (FIG. 3*h* and FIG. 3*j*), the interaction of UM101 with p380 and mutated p38α is much weaker, as indicated by the barely discernible peaks of the aromatic protons in the STD spectrum of UM101 with p380 (FIG. 3*i*) and mutated p38α (FIG. 3*k*).

Example 8: Synthetic Methods for Preparing Exemplary Compounds of the Invention

General Methods for Chemistry: All air or moisture sensitive reactions were performed under positive pressure of nitrogen with oven-dried glassware. Chemical reagents and anhydrous solvents are obtained from commercial sources and used as-is.

The p38α MAPK inhibitors of the invention can be prepared by methods generally known in the art. For example, compound UM101 can be prepared as depicted in Scheme 1. UM101 can be prepared in two steps from three commercially available fragments (Scheme 1), which facilitates its optimization. Acylation of 4-aminobenzaldehyde with 4-chlorobenzoyl chloride in the presence of diisopropylamine (DIPEA) generates an intermediate aldehyde. Subsequent reductive amination of the aldehyde with thiomorpholine 1,1-dioxide and Na-triacetoxyborohydride (NaBH$(OAc)_3$) affords UM101.

firmed that both its aromatic rings interact with the protein, hence modification of these rings will impact binding affinities. First, since the positively-charged (under physiological conditions) piperidine-type nitrogen of UM101 is predicted to interact with negatively-charged residues such as D112 and D168, will be retained in some embodiments. According to the FragMaps, aliphatic (e.g., cyclohexyl) or aromatic (e.g. furan) substituents off the central phenyl ring should enhance binding to the protein via interactions with V30, V38, A51, 184, L108, and L167. In addition, the presence of hydrogen bond acceptor maps overlapping with the aliphatic maps suggest that combined aliphatic/hydrogen bond acceptor groups, such as OEt, are incorporated ortho to the aniline nitrogen in some embodiments. Hydrogen bond donor (e.g. $NH_2$, OH) and/or acceptor groups (e.g. OMe, isoxazole) are incorporated into the ortho and meta positions of the peripheral chlorophenyl ring in some embodiments, which may be replaced with a chloropyridyl ring in other embodiments. These changes further increase compound solubility. Although the chlorine of the chlorophenyl ring interacts modestly with the protein as judged by SILCS GFE analysis in some embodiments, this site is also varied with alternative hydrophobic and more polar groups in other embodiments.

Scheme 1

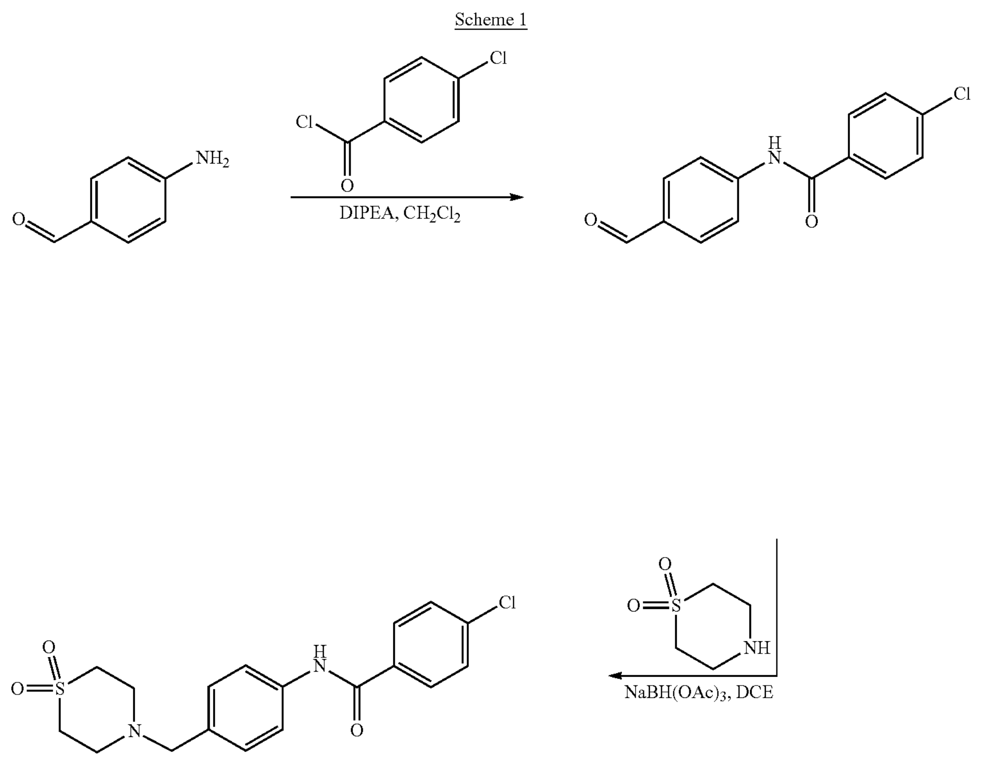

A focused structure-activity relationship (SAR) of UM101 and additional lead compounds is conducted to determine its pharmacophore and the information used to achieve its optimization, for example by feeding this information back into the CADD model to improve its predictability thereby facilitating subsequent design cycles. A summary of the proposed modifications to UM101 is shown in Scheme 2, which is driven by the SILCS molecular modeling, and addresses improvements in binding affinity and specificity, and enhancements in physicochemical properties. Importantly, the STD-NMR analysis of UM101 confirmed that both its aromatic rings interact with the protein, hence modification of these rings will impact binding affinities.

The trans-amide bond is modified to a rigid E-alkene in some embodiments, and a more flexible sulfonamide in other embodiments. The sulfone $SO_2$ group contributes −0.5 kcal/mol to binding based on SILCS GFE analysis, indicating that this region of the molecule can be exploited to optimize the molecule's physicochemical properties without compromising binding affinity in some embodiments. For example, the $SO_2$ group is replaced with a polar oxygen atom in some embodiments, and also an NMe group in other embodiments.

Scheme 2

Sulfone: interacts minimally with protein, therefore exploit to optimize physicochemical properties, e.g.:

Aniline ring: add aliphatic and aromatic groups; ortho to aniline also include hydrogen bond acceptors, e.g.

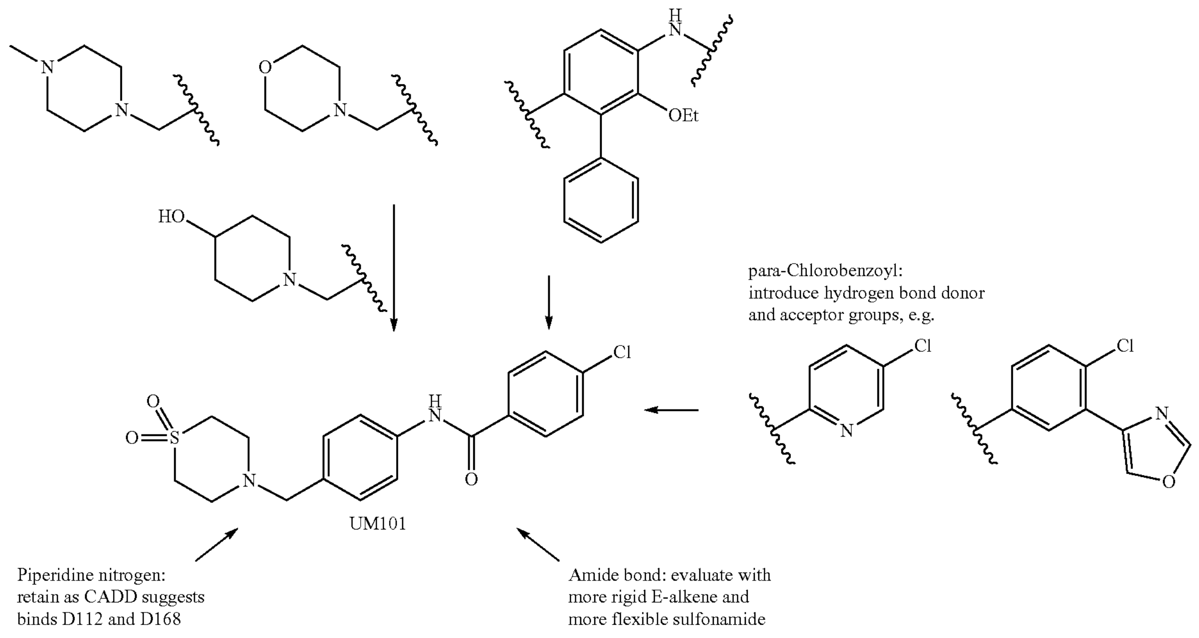

UM101

A number of patent and non-patent publications are cited herein in order to describe the state of the art to which this invention pertains. The entire disclosure of each of these publications is incorporated by reference herein.

While certain embodiments of the present invention have been described and/or exemplified above, various other embodiments will be apparent to those skilled in the art from the foregoing disclosure. The present invention is, therefore, not limited to the particular embodiments described and/or exemplified, but is capable of considerable variation and modification without departure from the scope and spirit of the appended claims.

Moreover, as used herein, the term "about" means that amounts, sizes, formulations, parameters, shapes and other quantities and characteristics are not and need not be exact, but may be approximate and/or larger or smaller, as desired, reflecting tolerances, conversion factors, rounding off, measurement error and the like, and other factors known to those of skill in the art. In general, an amount, size, formulation, parameter, shape or other quantity or characteristic is "about" or "approximate" whether or not expressly stated to be such.

Furthermore, the transitional terms "comprising", "consisting essentially of" and "consisting of", when used in the appended claims, in original and amended form, define the claim scope with respect to what unrecited additional claim elements or steps, if any, are excluded from the scope of the claim(s). The term "comprising" is intended to be inclusive or open-ended and does not exclude any additional, unrecited element, method, step or material. The term "consisting of" excludes any element, step or material other than those specified in the claim and, in the latter instance, impurities ordinary associated with the specified material(s). The term "consisting essentially of" limits the scope of a claim to the specified elements, steps or material(s) and those that do not materially affect the basic and novel characteristic(s) of the claimed invention. All compounds, compositions, formulations, and methods described herein that embody the present invention can, in alternate embodiments, be more specifically defined by any of the transitional terms "comprising," "consisting essentially of," and "consisting of."

REFERENCES

Wagner E F & Nebreda A R (2009) Signal integration by JNK and p38 MAPK pathways in cancer development. Nat Rev Cancer 9(8):537-549.

Thalhamer T, McGrath M A, & Harnett M M (2008) MAPKs and their relevance to arthritis and inflammation. Rheumatology (Oxford) 47(4):409-414.

Fisk M, Gajendragadkar P R, Maki-Petaja K M, Wilkinson I B, & Cheriyan J (2014) Therapeutic potential of p38 MAP kinase inhibition in the management of cardiovascular disease. Am J Cardiovasc Drugs 14(3):155-165.

Krementsov D N, Thornton™, Teuscher C, & Rincon M (2013) The emerging role of p38 mitogen-activated protein kinase in multiple sclerosis and its models. Mol Cell Biol 33(19):3728-3734.

Feng Y J & Li Y Y (2011) The role of p38 mitogen-activated protein kinase in the pathogenesis of inflammatory bowel disease. J Dig Dis 12(5):327-332.

Chung K F (2011) $p^{38}$ mitogen-activated protein kinase pathways in asthma and COPD. Chest 139(6):1470-1479.

Damarla M, et al. (2009) Mitogen activated protein kinase activated protein kinase 2 regulates actin polymerization and vascular leak in ventilator associated lung injury. PLoS One 4(2):e4600.

Shah N G, et al. (2012) Febrile-range hyperthermia augments reversible TNF-alpha-induced hyperpermeability in human microvascular lung endothelial cells. International journal of hyperthermia: the official journal of European Society for Hyperthermic Oncology, North American Hyperthermia Group 28(7):627-635.

Tulapurkar M E, et al. (2012) Febrile-range hyperthermia modifies endothelial and neutrophilic functions to promote extravasation. American Journal of Respiratory Cell and Molecular Biology 46(6):807-814.

Damjanov N, Kauffman R S, & Spencer-Green GT (2009) Efficacy, pharmacodynamics, and safety of VX-702, a novel p38 MAPK inhibitor, in rheumatoid arthritis: results of two randomized, double-blind, placebo-controlled clinical studies. Arthritis Rheum 60(5):1232-1241.

Watz H, Barnacle H, Hartley B F, & Chan R (2014) Efficacy and safety of the p38 MAPK inhibitor losmapimod for patients with chronic obstructive pulmonary disease: a randomised, double-blind, placebo-controlled trial. Lancet Respir Med 2(1):63-72.

MacNee W, Allan R J, Jones I, De Salvo M C, & Tan L F (2013) Efficacy and safety of the oral p38 inhibitor PH-797804 in chronic obstructive pulmonary disease: a randomised clinical trial. Thorax 68(8):738-745.

Schreiber S, et al. (2006) Oral p38 mitogen-activated protein kinase inhibition with BIRB 796 for active Crohn's disease: a randomized, double-blind, placebo-controlled trial. Clin Gastroenterol Hepatol 4(3):325-334.

Pargellis C, et al. (2002) Inhibition of p38 MAP kinase by utilizing a novel allosteric binding site. Nat Struct Biol 9(4):268-272.

Davidson W, et al. (2004) Discovery and characterization of a substrate selective p38alpha inhibitor. Biochemistry 43(37):11658-11671.

Hendriks B S, Seidl K M, & Chabot J R (2010) Two additive mechanisms impair the differentiation of 'substrate-selective' p38 inhibitors from classical p38 inhibitors in vitro. BMC Syst Biol 4:23.

Marber M S, Molkentin J D, & Force T (2010) Developing small molecules to inhibit kinases unkind to the heart: p38 MAPK as a case in point. Drug Discov Today Dis Mech 7(2):e123-e127.

Beardmore V A, et al. (2005) Generation and characterization of p38beta (MAPK11) gene-targeted mice. Mol Cell Biol 25(23):10454-10464.

O'Keefe S J, et al. (2007) Chemical genetics define the roles of p38alpha and p38beta in acute and chronic inflammation. J Biol Chem 282(48):34663-34671.

Ferrari G, et al. (2012) TGF-beta1 induces endothelial cell apoptosis by shifting VEGF activation of p38(MAPK) from the prosurvival p38beta to proapoptotic p38alpha. Mol Cancer Res 10(5):605-614.

Liu H, Yanamandala M, Lee T C, & Kim J K (2014) Mitochondrial p38beta and manganese superoxide dismutase interaction mediated by estrogen in cardiomyocytes. PLoS One 9(1):e85272.

Ananieva O, et al. (2008) The kinases MSK1 and MSK2 act as negative regulators of Toll-like receptor signaling. Nat Immunol 9(9):1028-1036.

Kim C, et al. (2008) The kinase p38 alpha serves cell type-specific inflammatory functions in skin injury and coordinates pro- and anti-inflammatory gene expression. Nat Immunol 9(9):1019-1027.

Cheriyan J, et al. (2011) Inhibition of p38 mitogen-activated protein kinase improves nitric oxide-mediated vasodilatation and reduces inflammation in hypercholesterolemia. Circulation 123(5):515-523.

Tanoue T, Adachi M, Moriguchi T, & Nishida E (2000) A conserved docking motif in MAP kinases common to substrates, activators and regulators. Nat Cell Biol 2(2): 110-116.

Tanoue T, Maeda R, Adachi M, & Nishida E (2001) Identification of a docking groove on ERK and p38 MAP kinases that regulates the specificity of docking interactions. Embo J 20(3):466-479.

Tzarum N, Komornik N, Ben Chetrit D, Engelberg D, & Livnah O (2013) DEF pocket in p38alpha facilitates substrate selectivity and mediates autophosphorylation. The Journal of Biological Chemistry 288(27):19537-19547.

ter Haar E, Prabhakar P, Liu X, & Lepre C (2007) Crystal structure of the p38 alpha-MAPKAP kinase 2 heterodimer. J Biol Chem 282(13):9733-9739.

Pan Y, Huang N, Cho S, & MacKerell A D, Jr. (2003) Consideration of molecular weight during compound selection in virtual target-based database screening. J Chem Inf Comput Sci 43(1):267-272.

Butina D (1999) Unsupervised Data Base Clustering on Daylight's Fingerprint and Tanimoto Similarity: A Fast and Automated Way to Cluster Small and Large Data Sets. J. Chem. Inf. Comput. Sci. 39:747-750.

Godden J W, Stahura F L, & Bajorath J (2005) Anatomy of fingerprint search calculations on structurally diverse sets of active compounds. Journal of chemical information and modeling 45(6):1812-1819.

Oashi T, Ringer A L, Raman E P, & Mackerell A D (2011) Automated selection of compounds with physicochemical properties to maximize bioavailability and druglikeness. Journal of chemical information and modeling 51(1):148-158.

Niesen F H, Berglund H, & Vedadi M (2007) The use of differential scanning fluorimetry to detect ligand interactions that promote protein stability. Nat Protoc 2(9):2212-2221.

Rice P, et al. (2005) Febrile-range Hyperthermia Augments Neutrophil Accumulation and Enhances Lung Injury in Experimental Gram-negative Bacterial Pneumonia. J. Immunol. 174:3676-3685.

Jiang M Z, et al. (2005) Effects of antioxidants and NO on TNF-alpha-induced adhesion molecule expression in human pulmonary microvascular endothelial cells. Respir Med 99(5):580-591.

Viemann D, et al. (2006) TNF induces distinct gene expression programs in microvascular and macrovascular human endothelial cells. J Leukoc Biol 80(1):174-185.

Vivoli M, Novak H R, Littlechild J A, & Harmer N J (2014) Determination of protein-ligand interactions using differential scanning fluorimetry. J Vis Exp (91):51809.

Hancock C N, et al. (2005) Identification of novel extracellular signal-regulated kinase docking domain inhibitors. J Med Chem 48(14):4586-4595.

Burkhard K, Smith S, Deshmukh R, MacKerell A D, Jr., & Shapiro P (2009) Development of extracellular signal-regulated kinase inhibitors. Curr Top Med Chem 9(8): 678-689.

Godl K, et al. (2003) An efficient proteomics method to identify the cellular targets of protein kinase inhibitors. Proceedings of the National Academy of Sciences of the United States of America 100(26):15434-15439.

Mayer M & Meyer B (2001) Group epitope mapping by saturation transfer difference NMR to identify segments of a ligand in direct contact with a protein receptor. J Am Chem Soc 123(25):6108-6117.

Zhong W, et al. (2014) Activation of the MAPK11/12/13/14 ($p^{38}$ MAPK) pathway regulates the transcription of autophagy genes in response to oxidative stress induced by a novel copper complex in HeLa cells. Autophagy 10(7):1285-1300.

Hu J, et al. (2014) Global analysis of phosphorylation networks in humans. Biochim Biophys Acta 1844(1 Pt B):224-231.

Zhao J, et al. (2015) Granulocyte/macrophage colony-stimulating factor attenuates endothelial hyperpermeability after thermal injury. Am J Transl Res 7(3):474-488.

Best R B, et al. (2012) Optimization of the additive CHARMM all-atom protein force field targeting improved sampling of the backbone phi, psi and side-chain chi(1) and chi(2) dihedral angles. J Chem Theory Comput 8(9):3257-3273.

Vanommeslaeghe K, et al. (2010) CHARMM general force field: A force field for drug-like molecules compatible with the CHARMM all-atom additive biological force fields. J Comput Chem 31(4):671-690.

Phillips J C, et al. (2005) Scalable molecular dynamics with NAMD. J. Comput. Chem. 26:1781-1802.

Foster T J, MacKerell A D, Jr., & Guvench O (2012) Balancing target flexibility and target denaturation in computational fragment-based inhibitor discovery. J Comput Chem 33(23):1880-1891.

Karpen M E, Tobias D J, & Brooks C L, 3rd (1993) Statistical clustering techniques for the analysis of long molecular dynamics trajectories: analysis of 2.2-ns trajectories of YPGDV. Biochemistry 32(2):412-420.

Zhong S & MacKerell A D, Jr. (2007) Binding response: a descriptor for selecting ligand binding site on protein surfaces. Journal of chemical information and modeling 47(6):2303-2315.

DesJarlais R L, Sheridan R P, Dixon J S, Kuntz I D, & Venkataraghavan R (1986) Docking flexible ligands to macromolecular receptors by molecular shape. Journal of Medicinal Chemistry 29(11):2149-2153.

Kuntz I D, Blaney J M, Oatley S J, Langridge R, & Ferrin T E (1982) A geometric approach to macromolecule-ligand interactions. Journal of Molecular Biology 161(2): 269-288.

Makino S & Kuntz I D (1997) Automated Flexible Ligand Docking Method and Its Application for Database Search. Journal of Computational Chemistry 18:1812-1825.

Pan Y, Huang N, Cho S, & MacKerell A D, Jr. (2003) Consideration of molecular weight during compound selection in virtual target-based database screening. J Chem Inf Comput Sci 43(1):267-272.

Lipinski C A (2000) Drug-like properties and the causes of poor solubility and poor permeability. J Pharmacol Toxicol Methods 44(1):235-249.

Gong P, et al. (2008) TLR4 signaling is coupled to SRC family kinase activation, tyrosine phosphorylation of zonula adherens proteins, and opening of the paracellular pathway in human lung microvascular endothelia. The Journal of Biological Chemistry 283(19):13437-13449.

Liu A, et al. (2012) TRAF6 protein couples Toll-like receptor 4 signaling to Src family kinase activation and opening of paracellular pathway in human lung microvascular endothelia. The Journal of Biological Chemistry 287(20): 16132-16145.

Hasday J D, et al. (2001) Exposure to febrile temperature modifies endothelial cell response to tumor necrosis factor-a. J. Appl. Physiol. 90:90-98.

Sakarya S, et al. (2004) Mobilization of neutrophil sialidase activity desialylates the pulmonary vascular endothelial surface and increases resting neutrophil adhesion to and migration across the endothelium. Glycobiology 14(6): 481-494.

Livak K J & Schmittgen T D (2001) Analysis of relative gene expression data using real-time quantitative PCR and the 2(−Delta Delta C(T)) Method. Methods 25(4): 402-408.

Gupta A, et al. (2013) Toll-like receptor agonists and febrile range hyperthermia synergize to induce heat shock protein 70 expression and extracellular release. The Journal of Biological Chemistry 288(4):2756-2766.

Kotlyarov, A. et al. MAPKAP kinase 2 is essential for LPS-induced TNF-alpha biosynthesis. Nat Cell Biol 1, 94-97, (1999).

Neininger, A. et al. MK2 targets AU-rich elements and regulates biosynthesis of tumor necrosis factor and interleukin-6 independently at different post-transcriptional levels. *J Biol Chem* 277, 3065-3068, (2002).

Shi, J. X., Su, X., Xu, J., Zhang, W. Y. & Shi, Y. MK2 posttranscriptionally regulates TNF-alpha-induced expression of ICAM-1 and IL-8 via tristetraprolin in human pulmonary microvascular endothelial cells. *Am J Physiol Lung Cell Mol Physiol* 302, L793-799, (2012).

Wolfson, R. K., Chiang, E. T. & Garcia, J. G. HMGB1 induces human lung endothelial cell cytoskeletal rearrangement and barrier disruption. *Microvasc Res* 81, 189-197, (2011).

Hannigan, M. O. et al. Abnormal migration phenotype of mitogen-activated protein kinase-activated protein kinase 2−/− neutrophils in Zigmond chambers containing formyl-methionyl-leucyl-phenylalanine gradients. *J Immunol* 167, 3953-3961, (2001).

Trempolec, N., Dave-Coll, N. & Nebreda, A. R. SnapShot: $p^{38}$ MAPK substrates. *Cell* 152, 924-924 e921, (2013).

Cuadrado, A. & Nebreda, A. R. Mechanisms and functions of p38 MAPK signalling. *The Biochemical journal* 429, 403-417, (2010).

Hayes, S. A., Huang, X., Kambhampati, S., Platanias, L. C. & Bergan, R. C. p38 MAP kinase modulates Smad-dependent changes in human prostate cell adhesion. *Oncogene* 22, 4841-4850, (2003).

Hammaker, D. & Firestein, G. S. "Go upstream, young man": lessons learned from the p38 saga. *Ann Rheum Dis* 69 Suppl 1, i77-82, (2010).

Zhang, J., Shen, B. & Lin, A. Novel strategies for inhibition of the p38 MAPK pathway. *Trends Pharmacol Sci* 28, 286-295, (2007).

Raman, E. P., Yu, W., Guvench, O. & Mackerell, A. D. Reproducing crystal binding modes of ligand functional groups using Site-Identification by Ligand Competitive Saturation (SILCS) simulations. *Journal of chemical information and modeling* 51, 877-896, (2011).

Boston, S. R. et al. Characterization of ERK docking domain inhibitors that induce apoptosis by targeting Rsk-1 and caspase-9. *BMC Cancer* 11, 7, (2011).

Irwin, J. J., Sterling, T., Mysinger, M. M., Bolstad, E. S. & Coleman, R. G. ZINC. a free tool to discover chemistry for biology. *J Chem Inf Model* 52, 1757-1768, (2012).

Guvench, O. & MacKerell, A. D., Jr. Computational fragment-based binding site identification by ligand competitive saturation. *PLoS computational biology* 5, e1000435, (2009).

Raman, E. P., Yu, W., Lakkaraju, S. K. & Mackerell, A. D., Jr. Inclusion of Multiple Fragment Types in the Site Identification by Ligand Competitive Saturation (SILCS) Approach. *Journal of chemical information and modeling* 53, 3384-3398, (2013).

Ekins, S., Boulanger, B., Swaan, P. W. & Hupcey, M. A. Towards a new age of virtual ADME/TOX and multidimensional drug discovery. *J Comput Aided Mol Des* 16, 381-401, (2002).

Ekins, S. et al. Progress in predicting human ADME parameters in silico. *J Pharmacol Toxicol Methods* 44, 251-272, (2000).

Oprea, T. I., Davis, A. M., Teague, S. J. & Leeson, P. D. Is there a difference between leads and drugs? A historical perspective. *J Chem Inf Comput Sci* 41, 1308-1315, (2001).

Cerchietti, L. C. et al. A small-molecule inhibitor of BCL6 kills DLBCL cells in vitro and in vivo. *Cancer Cell* 17, 400-411, (2010).

Chen, I. J. et al. Identification of HIV-1 integrase inhibitors via three-dimensional database searching using ASV and HIV-1 integrases as targets. *Bioorgan Med Chem* 8, 2385-2398, (2000).

Chen, X. et al. Rational design of human DNA ligase inhibitors that target cellular DNA replication and repair. *Cancer research* 68, 3169-3177, (2008).

Furci, L. M. et al. Inhibition of the bacterial heme oxygenases from *Pseudomonas aeruginosa* and *Neisseria meningitidis*: Novel antimicrobial targets. *Journal of Medicinal Chemistry* 50, 3804-3813, (2007).

Huang, N., Nagarsekar, A., Xia, G. J., Hayashi, J. & MacKerell, A. D. Identification of non-phosphate-containing small molecular weight inhibitors of the tyrosine kinase p56 Lck SH2 domain via in silico screening against the pY+3 binding site. *Journal of Medicinal Chemistry* 47, 3502-3511, (2004).

Markowitz, J. et al. Identification and characterization of small molecule inhibitors of the calcium-dependent S100B-p53 tumor suppressor interaction. *Journal of Medicinal Chemistry* 47, 5085-5093, (2004).

Yu, B. et al. Targeting Protein Tyrosine Phosphatase SHP2 for the Treatment of PTPN11-Associated Malignancies. *Mol Cancer Ther* 12, 1738-1748, (2013).

Hasday, J. et al. Febrile-Range Hyperthermia Augments Pulmonary Neutrophil Recruitment and Amplifies Pulmonary Oxygen Toxicity. *Am J. Pathol.* 162, 2005-2017, (2003).

Chen, W. H., Kang, T. J., Bhattacharjee, A. K. & Cross, A. S. Intranasal administration of a detoxified endotoxin vaccine protects mice against heterologous Gram-negative bacterial pneumonia. *Innate Immun* 14, 269-278, (2008).

Feng, C. et al. Neuraminidase reprograms lung tissue and potentiates lipopolysaccharide-induced acute lung injury in mice. *Journal of immunology* 191, 4828-4837, (2013).

Aqvist, J., Medina, C. & Samuelsson, J. E. A new method for predicting binding affinity in computer-aided drug design. *Protein Eng* 7, 385-391, (1994).

Chen, X., Rusinko, A., 3rd, Tropsha, A. & Young, S. S. Automated pharmacophore identification for large chemical data sets. *J Chem Inf Comput Sci* 39, 887-896, (1999).

Feig, M. & Brooks, C. L., 3rd. Recent advances in the development and application of implicit solvent models in biomolecule simulations. *Curr Opin Struct Biol* 14, 217-224, (2004).

Lee, M. S., Feig, M., Salsbury, F. R., Jr. & Brooks, C. L., 3rd. New analytic approximation to the standard molecular volume definition and its application to generalized Born calculations. *J Comput Chem* 24, 1348-1356, (2003).

Qui, D., Shenkin, P. S., Hollinger, F. P. & Still, W. C. The GB/SA Continuum Model for Solvation. A Fast Analytical Method for the Calculation of Approximate Born Radii. *J. Phys. Chem. A* 101, 3005-3014, (1997).

Frese, C. K. et al. Unambiguous phosphosite localization using electron-transfer/higher-energy collision dissociation (EThcD). *J Proteome Res* 12, 1520-1525, (2013).

Swaney, D. L., McAlister, G. C. & Coon, J. J. Decision tree-driven tandem mass spectrometry for shotgun proteomics. *Nat Methods* 5, 959-964, (2008).

Saba, J., Dutta, S., Hemenway, E. & Viner, R. Increasing the productivity of glycopeptides analysis by using higher-energy collision dissociation-accurate mass-product-dependent electron transfer dissociation. *Int J Proteomics* 2012, 560391, (2012).

Distler, U. et al. Drift time-specific collision energies enable deep-coverage data-independent acquisition proteomics. *Nat Methods* 11, 167-170, (2014).

Williamson, J. C. et al. High-performance hybrid Orbitrap mass spectrometers for quantitative proteome analysis: Observations and implications. *Proteomics* 16, 907-914, (2016).

Cox, J. et al. Accurate proteome-wide label-free quantification by delayed normalization and maximal peptide ratio extraction, termed MaxLFQ. *Mol Cell Proteomics* 13, 2513-2526, (2014).

Li, X. et al. Quantifying Kinase-specific Phosphorylation Stoichiometry Using Stable Isotope Labeling In a Reverse In-gel Kinase Assay. *Anal Chem*, (2016).

Wang, Z. et al. The structure of mitogen-activated protein kinase p38 at 2.1-A resolution. *Proc Natl Acad Sci USA* 94, 2327-2332, (1997).

Barker, J. J. et al. Fragment-based identification of Hsp90 inhibitors. *ChemMedChem* 4, 963-966, (2009).

Chang, C. I., Xu, B. E., Akella, R., Cobb, M. H. & Goldsmith, E. J. Crystal structures of MAP kinase p38 complexed to the docking sites on its nuclear substrate MEF2A and activator MKK3b. *Mol Cell* 9, 1241-1249, (2002).

Wang, Z. et al. Structural basis of inhibitor selectivity in MAP kinases. *Structure* 6, 1117-1128, (1998).

Watterson, D. M. et al. Development of Novel Chemical Probes to Address CNS Protein Kinase Involvement in Synaptic Dysfunction. *PLoS One* 8, e66226, (2013).

White, A., Pargellis, C. A., Studts, J. M., Werneburg, B. G. & Farmer, B. T., 2nd. Molecular basis of MAPK-activated protein kinase 2:p38 assembly. *Proc Natl Acad Sci USA* 104, 6353-6358, (2007).

Zhang, Y. Y., Wu, J. W. & Wang, Z. X. A distinct interaction mode revealed by the crystal structure of the kinase p38alpha with the MAPK binding domain of the phosphatase MKP5. *Sci Signal* 4, ra88, (2011).

Leavitt, S. & Freire, E. Direct measurement of protein binding energetics by isothermal titration calorimetry. *Curr Opin Struct Biol* 11, 560-566, (2001).

DeNardo, B. D. et al. Quantitative phosphoproteomic analysis identifies activation of the RET and IGF-1R/IR signaling pathways in neuroblastoma. *PLoS One* 8, e82513, (2013).

Soderholm, S., Hintsanen, P., Ohman, T., Aittokallio, T. & Nyman, T. A. PhosFox: a bioinformatics tool for peptide-level processing of LC-MS/MS-based phosphoproteomic data. *Proteome Sci* 12, 36, (2014).

Adams, P. D. & Parker, P. J. Activation of mitogen-activated protein (MAP) kinase by a MAP kinase-kinase. *J Biol Chem* 267, 13135-13137, (1992).

Boersema, P. J., Raijmakers, R., Lemeer, S., Mohammed, S. & Heck, A. J. Multiplex peptide stable isotope dimethyl labeling for quantitative proteomics. *Nat Protoc* 4, 484-494, (2009).

Lanning, M. E. et al. Structure-based design of N-substituted 1-hydroxy-4-sulfamoyl-2-naphthoates as selective inhibitors of the Mcl-1 oncoprotein. *Eur J Med Chem* 113, 273-292, (2016).

Jung, K. Y. et al. Structural modifications of (Z)-3-(2-aminoethyl)-5-(4-ethoxybenzylidene)thiazolidine-2,4-dione that improve selectivity for inhibiting the proliferation of melanoma cells containing active ERK signaling. *Org Biomol Chem* 11, 3706-3732, (2013).

Jiang, Q. et al. Febrile Core Temperature is Essential for Optimal Host Defense in Bacterial Peritonitis. Infect. Immun. 68, 1265-1270, (2000).

Jiang, Q., DeTolla, L., Kalvakolanu, I., Fitzgerald, B. & Hasday, J. D. Fever upregulates expression of pyrogenic cytokines in endotoxin-challenged mice. *Am. J. Physiol.* 276, R1653-R1660, (1999).

Jiang, Q. et al. Febrile range temperature modifies early systemic TNFα expression in mice challenged with bacterial endotoxin. *Infect. Immun.* 67, 1539-1546, (1999).

Workman, P. et al. Guidelines for the welfare and use of animals in cancer research. *Br J Cancer* 102, 1555-1577, (2010).

Dai, B. et al. Extracellular Signal-Regulated Kinase Positively Regulates the Oncogenic Activity of MCT-1 in Diffuse Large B-Cell Lymphoma. *Cancer Research* 69, 7835-7843, (2009).

Fandy, T., Abdallah, I., Khayat, M., Colby, D. & Hassan, H. In Vitro Characterization of Transport and Metabolism of the Alkaloids: Vincamine, Vinpocetine and Eburnamonine. *Cancer Chemother Pharmacol* in press, (2015).

Yu, M. et al. Simultaneous determination of L-tetrahydropalmatine and cocaine in human plasma by simple UPLC-FLD method: application in clinical studies. *J Chromatogr B Analyt Technol Biomed Life Sci* 965, 39-44, (2014).

Mason, C. W. et al. Characterization of the transport, metabolism, and pharmacokinetics of the dopamine D3 receptor-selective fluorenyl- and 2-pyridylphenyl amides developed for treatment of psychostimulant abuse. *J Pharmacol Exp Ther* 333, 854-864, (2010).

It is claimed:

1. A method of treating an inflammatory disease in a patient comprising administering to a patient in need of such treatment a therapeutically effective amount of a compound having the formula:

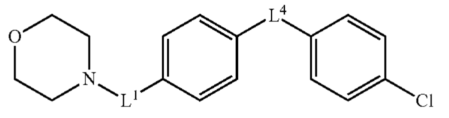

wherein, $L^1$ is selected from $—CH_2—$, $—C(CH_3)_2—$, and $—C(CH_2CH_2)—$; and $L^4$ is selected from —NHCO—, —CONH—, $—SO_2NH—$, $—NHSO_2—$, and —CH═CH—.

2. The method of claim 1, wherein administering comprises orally administering.

3. The method of claim 1, wherein administering comprises administering a dosage form comprising the compound, wherein the dosage form is selected from a controlled-release oral dosage form, a sustained-release oral dosage form, an extended-release oral dosage form, or a combination of any of the foregoing.

4. The method of claim 1, wherein the inflammatory disease is selected from rheumatoid arthritis, a cardiovascular disease, multiple sclerosis, inflammatory bowel disease, inflammatory bowel diseases, chronic obstructive pulmonary disease, asthma, acute respiratory distress syndrome, and acute lung injury.

5. The method of claim 1, wherein the inflammatory disease is acute respiratory distress syndrome.

6. A method of treating Alzheimer's disease, psoriasis, atherosclerosis, pain, multiple sclerosis, or glomerulosclerosis in a patient comprising administering to a patient in need of such treatment a therapeutically effective amount of a compound having the formula:

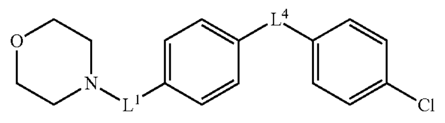

wherein, $L^1$ is selected from $—CH_2—$, $—C(CH_3)_2—$, and $—C(CH_2CH_2)—$; and $L^4$ is selected from —NHCO—, —CONH—, $—SO_2NH—$, $—NHSO_2—$, and —CH═CH—.

7. The method of claim 6, wherein administering comprises orally administering.

8. The method of claim 6, wherein administering comprises administering a dosage form comprising the compound, wherein the dosage form is selected from a controlled-release oral dosage form, a sustained-release oral dosage form, an extended-release oral dosage form, or a combination of any of the foregoing.

9. A method of treating cancer in a patient comprising administering to a patient in need of such treatment a therapeutically effective amount of a compound having the formula:

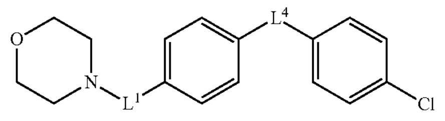

wherein, $L^1$ is selected from $—CH_2—$, $—C(CH_3)_2—$, and $—C(CH_2CH_2)—$; and $L^4$ is selected from —NHCO—, —CONH—, $—SO_2NH—$, $—NHSO_2—$, and —CH═CH—.

10. The method of claim 9, wherein administering comprises orally administering the pharmaceutical composition is for oral administration.

11. The method of claim 9, wherein administering comprises administering a dosage form comprising the compound, wherein the dosage form is selected from a controlled-release oral dosage form, a sustained-release oral dosage form, an extended-release oral dosage form, or a combination of any of the foregoing.

12. The method of claim 9, wherein the cancer is associated with dysregulation of the p38α MAPK protein.

13. The method of claim 9, wherein the cancer is treatable by inhibiting the p38α MAPK protein.

14. The method of claim 9, wherein the cancer overexpresses the p38α MAPK protein.

* * * * *